(12) United States Patent
Madison et al.

(10) Patent No.: US 7,172,892 B2
(45) Date of Patent: Feb. 6, 2007

(54) NUCLEIC ACID MOLECULES ENCODING SERINE PROTEASE CVSP14, THE ENCODED POLYPEPTIDES AND METHODS BASED THEREON

(75) Inventors: Edwin L. Madison, San Diego, CA (US); Jiunn-Chern Yeh, San Diego, CA (US)

(73) Assignee: Dendreon Corporation, San Diego, CA (US)

( * ) Notice: Subject to any disclaimer, the term of this patent is extended or adjusted under 35 U.S.C. 154(b) by 0 days.

(21) Appl. No.: 10/104,271

(22) Filed: Mar. 20, 2002

(65) Prior Publication Data

US 2003/0181658 A1    Sep. 25, 2003

Related U.S. Application Data

(60) Provisional application No. 60/278,166, filed on Mar. 22, 2001.

(51) Int. Cl.
  C12N 9/64       (2006.01)
  C12N 15/57      (2006.01)
  C12N 15/62      (2006.01)
  C12N 15/79      (2006.01)
  G01N 33/53      (2006.01)

(52) U.S. Cl. .......... 435/226; 435/7.1; 435/7.72; 435/69.1; 435/69.7; 436/809; 536/23.2

(58) Field of Classification Search .......... 435/69.1, 435/7.9, 23, 417, 226; 530/350
See application file for complete search history.

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |
| 3,630,200 A | 12/1971 | Higuchi | 128/260 |
| 3,645,090 A | 2/1972 | Mochizuki et al. | 58/58 |
| 3,843,443 A | 10/1974 | Fishman | 195/63 |
| 3,845,770 A | 11/1974 | Theeuwes et al. | 128/260 |
| 3,916,899 A | 11/1975 | Theeuwes et al. | 128/260 |
| 3,940,475 A | 2/1976 | Gross | 424/1 |
| 4,006,117 A | 2/1977 | Merrifield et al. | 260/45.9 NP |
| 4,008,719 A | 2/1977 | Theeuwes et al. | 128/260 |
| 4,179,337 A | 12/1979 | Davis et al. | 435/181 |
| 4,244,721 A | 1/1981 | Gupta et al. | 65/31 |
| 4,301,144 A | 11/1981 | Iwashita et al. | 424/78 |
| 4,496,689 A | 1/1985 | Mitra | 525/54.1 |
| 4,507,230 A | 3/1985 | Tam et al. | 260/112.5 R |
| 4,522,811 A | 6/1985 | Eppstein et al. | 514/2 |
| 4,640,835 A | 2/1987 | Shimizu et al. | 424/94 |
| 4,670,517 A | 6/1987 | Shimizu et al. | 514/6 |
| 4,687,610 A | 8/1987 | Vassilatos | 264/211.14 |
| 4,769,027 A | 9/1988 | Baker et al. | 424/493 |
| 4,791,192 A | 12/1988 | Nakagawa et al. | 530/399 |
| 4,908,405 A | 3/1990 | Bayer et al. | 525/61 |
| 4,946,778 A | 8/1990 | Ladner et al. | 435/69.6 |
| 4,952,496 A | 8/1990 | Studier et al. | 435/91 |
| 4,980,286 A | 12/1990 | Morgan et al. | 435/172.3 |
| 5,059,595 A | 10/1991 | Le Grazie | 424/468 |
| 5,073,543 A | 12/1991 | Marshall et al. | 514/21 |
| 5,120,548 A | 6/1992 | McClelland et al. | 424/473 |
| 5,215,899 A | 6/1993 | Dattagupta | 435/6 |
| 5,225,539 A | 7/1993 | Winter | 530/387.3 |
| 5,270,170 A | 12/1993 | Schatz et al. | 435/7.37 |
| 5,292,814 A | 3/1994 | Bayer et al. | 525/243 |
| 5,304,482 A | 4/1994 | Sambrook et al. | 435/226 |
| 5,338,665 A | 8/1994 | Schatz et al. | 435/6 |
| 5,354,566 A | 10/1994 | Addesso et al. | 426/9 |
| 5,389,449 A | 2/1995 | Afeyan et al. | 428/523 |
| 5,436,128 A | 7/1995 | Harpold et al. | 435/6 |
| 5,482,848 A | 1/1996 | Dickson et al. | 435/219 |
| 5,486,602 A | 1/1996 | Sambrook et al. | 536/23.2 |
| 5,534,418 A | 7/1996 | Evans et al. | 435/69.1 |
| 5,550,042 A | 8/1996 | Sambrook et al. | 435/172.1 |
| 5,571,696 A | 11/1996 | Evans et al. | 435/69.1 |
| 5,589,154 A | 12/1996 | Anderson | 424/1.41 |
| 5,591,767 A | 1/1997 | Mohr et al. | 514/413 |
| 5,597,705 A | 1/1997 | Evans et al. | 435/69.1 |
| 5,612,474 A | 3/1997 | Patel | 536/27.14 |
| 5,639,476 A | 6/1997 | Oshlack et al. | 424/468 |
| 5,643,578 A | 7/1997 | Robinson et al. | 424/210.1 |

(Continued)

FOREIGN PATENT DOCUMENTS

EP       0257352       3/1987

(Continued)

OTHER PUBLICATIONS

Seffernick et al., 2001, "Melamine deaminase and atrazine chlorohydrolase: 98 percent identical but functionally different", Journal of Biochemistry, vol. 183, pp. 2405-2410.*

(Continued)

*Primary Examiner*—Nashaat T. Nashed
*Assistant Examiner*—William W. Moore
(74) *Attorney, Agent, or Firm*—Fish & Richardson P.C.; Stephanie Seidman

(57) ABSTRACT

Provided herein are polypeptides designated CVSP14 polypeptides that exhibit protease activity as a single chain or as an activated two chain form. Methods using the polypeptides to identify compounds that modulate the protease activity thereof are provided. The polypeptides also serve as tumor markers.

30 Claims, No Drawings

U.S. PATENT DOCUMENTS

| | | | |
|---|---|---|---|
| 5,674,533 A | 10/1997 | Santus et al. | 424/493 |
| 5,710,004 A | 1/1998 | Evans et al. | 435/6 |
| 5,728,564 A | 3/1998 | Sambrook et al. | 435/215 |
| 5,733,566 A | 3/1998 | Lewis | 424/426 |
| 5,767,174 A | 6/1998 | Nakagawa et al. | 523/217 |
| 5,792,625 A | 8/1998 | Persico et al. | 435/7.21 |
| 5,795,872 A | 8/1998 | Ricigliano et al. | 514/44 |
| 5,804,410 A | 9/1998 | Yamaoka et al. | 435/69.1 |
| 5,861,274 A | 1/1999 | Evans et al. | 435/69.1 |
| 5,866,413 A | 2/1999 | Sambrook et al. | 435/320.1 |
| 5,902,723 A | 5/1999 | Dower et al. | 435/6 |
| 5,925,525 A | 7/1999 | Fodor et al. | 435/6 |
| 5,972,616 A | 10/1999 | O'Brien et al. | 435/6 |
| 6,121,238 A | 9/2000 | Dower et al. | 514/13 |
| 6,270,988 B1 | 8/2001 | Brinkmann et al. | 435/69.1 |
| 6,294,663 B1 | 9/2001 | O'Brien et al. | 536/23.5 |
| 6,323,332 B1 | 11/2001 | Fukuda et al. | 536/23.2 |
| 6,337,072 B1 | 1/2002 | Ford et al. | 424/198.1 |
| 6,365,391 B1 | 4/2002 | Webster et al. | 435/183 |
| 6,541,234 B1* | 4/2003 | Bryan | 435/221 |
| 6,541,235 B1* | 4/2003 | Bryan | 435/221 |
| 2002/0019006 A1* | 2/2002 | Yuan et al. | 435/6 |
| 2002/0037857 A1 | 3/2002 | Semple et al. | 514/19 |
| 2002/0064856 A1* | 5/2002 | Plowman et al. | 435/226 |
| 2002/0107266 A1 | 8/2002 | Lim-Wilby et al. | 514/339 |
| 2002/0160962 A1 | 10/2002 | Saksena et al. | 514/19 |
| 2002/0165376 A1* | 11/2002 | Walke et al. | 536/23.2 |
| 2003/0008372 A1 | 1/2003 | Madison et al. | 435/226 |
| 2003/0050251 A1 | 3/2003 | Semple et al. | 514/19 |
| 2003/0077697 A1 | 4/2003 | Gerlack et al. | 435/69.1 |
| 2003/0119168 A1 | 6/2003 | Madison et al. | 435/226 |
| 2003/0134298 A1 | 7/2003 | Madison et al. | 435/6 |
| 2003/0134794 A1 | 7/2003 | Madison et al. | 514/12 |
| 2003/0143219 A1 | 7/2003 | Madison et al. | 424/94.67 |
| 2003/0153014 A1* | 8/2003 | Shen et al. | 435/7.9 |
| 2003/0166851 A1 | 9/2003 | Madison et al. | 530/350 |
| 2003/0170630 A1 | 9/2003 | Alsobrook et al. | 435/6 |
| 2003/0175938 A1 | 9/2003 | Shi et al. | 435/183 |
| 2003/0186329 A1 | 10/2003 | Madison et al. | 435/7.1 |
| 2003/0232349 A1 | 12/2003 | Delegeane et al. | 435/226 |
| 2003/0235900 A1 | 12/2003 | Madison et al. | 435/226 |
| 2004/0001801 A1 | 1/2004 | Madison et al. | 424/85.1 |

FOREIGN PATENT DOCUMENTS

| | | |
|---|---|---|
| EP | 0320308 B1 | 6/1989 |
| EP | 0462207 B1 | 3/1990 |
| EP | 0613683 A1 | 7/1994 |
| EP | 0613683 B1 | 7/1994 |
| EP | 1029921 A1 | 8/2000 |
| EP | 1033401 | 9/2000 |
| EP | 1182207 A2 | 2/2002 |
| JP | 0037195 | 2/2000 |
| JP | 0078990 | 3/2000 |
| WO | 8603840 | 3/1986 |
| WO | 8809810 | 12/1988 |
| WO | 8910134 | 11/1989 |
| WO | 9010649 | 9/1990 |
| WO | 9011364 | 10/1990 |
| WO | 9013678 | 11/1990 |
| WO | 9206180 | 4/1992 |
| WO | 9206203 | 4/1992 |
| WO | 9220316 | 11/1992 |
| WO | 9222635 | 12/1992 |
| WO | 9314188 | 7/1993 |
| WO | 9320221 | 10/1993 |
| WO | 9325221 | 12/1993 |
| WO | 9408598 | 4/1994 |
| WO | 9417784 | 8/1994 |
| WO | 9511755 | 5/1995 |
| WO | 9523222 | 8/1995 |
| WO | 9534326 | 12/1995 |
| WO | 9630353 | 10/1996 |
| WO | 9721690 | 6/1997 |
| WO | 9739021 | 10/1997 |
| WO | 9747314 | 12/1997 |
| WO | 9821320 | 5/1998 |
| WO | 9917790 | 4/1999 |
| WO | 9832619 | 7/1999 |
| WO | 9936550 | 7/1999 |
| WO | 9942120 | 8/1999 |
| WO | 9946281 | 9/1999 |
| WO | 0012708 | 3/2000 |
| WO | 0050061 | 8/2000 |
| WO | 0052044 | 9/2000 |
| WO | 0053756 | 9/2000 |
| WO | 0055124 | 9/2000 |
| WO | 0068247 | 11/2000 |
| WO | 0078961 | 12/2000 |
| WO | 0104141 | 1/2001 |
| WO | 0127624 A2 | 4/2001 |
| WO | 0129058 | 4/2001 |
| WO | 0136351 A2 | 5/2001 |
| WO | 0136604 A2 | 5/2001 |
| WO | 0136645 A2 | 5/2001 |
| WO | 0146407 A1 | 6/2001 |
| WO | 0149864 | 7/2001 |
| WO | 0154477 A2 | 8/2001 |
| WO | 0155301 A2 | 8/2001 |
| WO | 0155441 A2 | 8/2001 |
| WO | 0157194 A2 | 8/2001 |
| WO | 0168848 | 9/2001 |
| WO | 0175067 A2 | 10/2001 |
| WO | WO 01/98468 A2 * | 12/2001 |
| WO | 0200860 | 1/2002 |
| WO | 0206453 A2 | 1/2002 |
| WO | 0208251 | 1/2002 |
| WO | 02008187 | 1/2002 |
| WO | 0214349 A2 | 2/2002 |
| WO | 0220475 | 3/2002 |
| WO | 0220475 A2 | 3/2002 |
| WO | 0226947 A2 | 4/2002 |
| WO | 02048097 | 6/2002 |
| WO | 02072786 | 9/2002 |
| WO | 02077263 | 10/2002 |
| WO | 02077267 A2 | 10/2002 |
| WO | 02092841 | 11/2002 |
| WO | 02095007 | 11/2002 |
| WO | 03004681 | 1/2003 |
| WO | 03031585 | 4/2003 |
| WO | 03044179 | 5/2003 |
| WO | WO 03/104391 | 12/2003 |
| WO | WO 04/005471 | 1/2004 |

OTHER PUBLICATIONS

Database EMBL, Accession No. W22987, "Human Serine Protease 67", XP002169836 abstract, Oct. 8, 1997; abstract of Japan, 1997(10), Oct. 31, 1997; abstract Japan 09 149790, Jun. 10, 1997.

Database EMBL, Accession No. AAY41710, "Human PRO168 protein sequence", *Genentech Inc.*, XP002175683 abstract, Dec. 7, 1999; PCT 99 46281 A, *Genentech Inc.*, Sep. 16, 1999.

Database EMBL, Accession No. AAZ34033, "Human PRO618 nucleotide sequence", *Genentech Inc.*, XP002175684 abstract, Dec. 7, 1999; PCT 99 46281 A, *Genentech Inc.*, Sep. 16, 1999.

Database EMBL, Accession No. AAZ33949, "Human PRO382 nucleotide sequence", *Genentech Inc.*, XP002175685 abstract, Dec. 7, 1999; PCT 99 46281 A, *Genentech Inc.*, Sep. 16, 1999.

Database EMBL, Accession No. AAY41694, "Human PRO382 protein sequence", *Genentech Inc.*, XP002175687 abstract, Dec. 7, 1999; PCT 99 46281 A, *Genentech Inc.*, Sep. 16, 1999.

Database EMBL, Accession No. AI469095, "tm06c09.x1 Homo sapiens cDNA clone IMAGE:2155792", XP002175686 abstract, Mar. 17, 1999.

Database EMBL Accession No. AF064819, Oct. 28, 1999, J.C. Lang and D.E. Schuller: "Homo sapiens serine protease DESC1 MRNA", XP002166624, abstract.
Database EMBL Accession No. R78581, Jun. 10, 1995, L. Hillier et al.: "yi73c10.r1 Soares placenta Nb2HP Homo sapiens cDNA clone", XP002166677, abstract.
Database EMBL Accession No. Y99414, Aug. 8, 2000, "Human PRO1461", XP002166625, abstract.
Derwent# 007409639, WPI Acc. No. 1988-043574/198807 for European Patent Application No. EP 257352, "Determining free portion of e.g. thyroxine in presence of binder—by reaction with antibody which does not effect bound-unbound equilibrium,".
Fernandez et al., "N-Succinyl-(β-alanyl-Lalanyl-L-leucyl)doxorubicin: An Extracellularly Tumor-Activated Prodrug Devoid of Intravenous Acute Toxicity," *J. Med. Chem.* 44(22): 3750-3753 (2001).
Harris et al., "Rapid and general profiling of protease specificity by using combinatorial fluorogenic substrate libraries," *Proc Natl Acad Sci USA* 97(14): 7754-7759 (2000).
La Vallie et al., "Cloning and Functional Expression of a cDNA Encoding the Catalytic Subunit of Bovine Enterokinase," *J. Biol. Chem.* 268(31):23311-23327 (1993).
Lee, Sheau-Ling et al., "Activation of hepatocyte growth factor and urokinase/plasminogen activator by matriptase, an epithelial membrane serine protease," *J. Biol. Chem.* 275(47): 36720-36725 (2000).
Liu et al., "Eradication of large colon tumor xenografts by targeted delivery of maytansinoids," *Proc Natl Acad Sci USA* 93: 8618-8623 (1996).
Lu et al., "Bovine Proenteropeptidase Is Activated by Trypsin, and the Specificity of Enteropeptidase Depends on the Heavy Chain," *J. Biol. Chem.* 272(50):31293-31300 (1997).
Rao et al., "Partial Characterization of Matrix-Associated Serine Protease Inhibitors from Human Skin Cells," *J. Invest. Dermatol.* 104(3):379-383, (1995).
Pastan et al., "Recombinant Toxins for Cancer Treatment," *Science* 254:1173-1177 (1991).
Schmidt et al., "Targeted inhibition of tumour cell growth by a bispecific single-chain toxin containing an antibody domain and TGFα," *Cancer* 74:853-862 (1996).
Trouet et al., "Extracellularly Tumor-activated Prodrugs for the Selective Chemotherapy of Cancer: Application to Doxorubicin and Preliminary *in Vitro* and *in Vivo* Studies," *Cancer Research* 61:2843-2846 (2001).
Abraham et al., "Immunochemical Identification of the Serine Protease Inhibitor $\alpha_1$-Antichymotrypsin in the Brain Amyloid Deposits of Alzheimer's Disease", *Cell*, 52:487-501 (1988).
Adams et al., "The *c-myc* oncogene driven by immunoglobulin enhancers induces lymphoid malignancy in transgenic mice", *Nature*, 318:533-538 (1985).
Alam et al., "Reporter Genes: Application to the Study of Mammalian Gene Transcription", *Anal. Biochem.*, 188:245-254 (1990).
Alexander et al., "Expression of the *c-myc* Oncogene under Control of an Immunoglobulin Enhancer in Eµ-*myc* Transgenic Mice", *Mol. Cell Biol.*, 7(4):1436-1444 (1987).
Alonso et al., "Effects of synthetic urokinase inhibitors on local invasion and metastasis in a murine mammary tumor model", *Breast Cancer Res. Treat.*, 40:209-223 (1996).
Avery et al., "Systemic Amiloride Inhibits Experimentally Induced Neovascularization", *Arch. Ophthalmol.*, 108:1474-1476 (1990).
Bains et al., "Effects of LEX032, a novel recombinant serine protease inhibitor, on $N^G$-nitro-L-arginine methyl ester induced leukocyte-endothelial cell", *Eur. J. Pharmacol.*, 356:67-72 (1998).
Baker et al., "A Scintillation Proximity Assay for UDP-GalNAc:Polypeptide, N-Acetylgalactosaminyltransferase", *Anal. Biochem.*, 239:20-24 (1996).
Bannwarth et al., "Global Phosphorylation Of Peptides Containing Oxidation-Sensitive Amino-Acids", *Bioorganic & Medicinal Chem. Lett.*, 6(17):2141-2146 (1996).
Bartel et al., "Isolation of New Ribozymes from a Large Pool of Random Sequences", *Science*, 261:1411-1418 (1993).

Bassell-Duby et al., "Tyrosine 67 in the Epidermal Growth Factor-like Domain of Tissue-type Plasminogen Activator Is Important for Clearance by a Specific Hepatic Receptor", *J. Biol Chem*, 267(14):9668-9677 (1992).
Batra et al., "Insertion of Constant Region Domains of Human $IgG_1$ Into CD4-PE40 Increases Its Plasma Half-life", *Molecular Immunol.*, 30(4):379-386 (1993).
Baum et al., "Development of a Scintillation Proximity Assay for Human Cytomegalovirus Protease Using $^{33}$Phosphorous", *Anal. Biochem.*, 237:129-134 (1996).
Baumbach et al., "Protein Purification Using Affinity Ligands Deduced from Peptide Libraries", *BioPharm.*, May ed., 24-35 (1992).
Beck et al., "Identification of Efficiently Cleaved Substrates for HIV-1 Protease Using a Phage Display Library and Use in Inhibitor Development", *Virology*, 274(2):391-401 (2000).
Benoist et al., "*In vivo* sequence requirements of the SV40 early promoter region", *Nature*, 290:304-310 (1981).
Benton et al., "Screening λgt Recombinant Clones by Hybridization to Single Plaques in situ", *Science*, 196:180-182 (1977).
Berg et al., "Long-Chain Polystyrene-Grafted Polyethylene Film Matrix: A New Support for Solid-Phase Peptide Synthesis", *J. Am. Chem. Soc.*, 111:8024-8026 (1989).
Berg et al., Book: "Peptide Synthesis on Polystyrene-Grafted Polyethylene Sheets", *Pept. Proc. 20th Eur. Pept. Symp.*, Jung, G. et al., Eds, pp. 196-198 (1988).
Berg et al., Book: "Polystyrene-Grafted Polyethylene: Design of Film and Felt Matrices for Solid-Phase Peptide Synthesis", *Innovation Perspect. Solid Phase Synth. Collect. Pap.*, Int. Sympl, 1st Epton, Roger, Ed., pp. 453-459 (1990).
Berger et al., "Structure of the mouse gene for the serine protease inhibitor neuroserpin (PI12)", *Gene*, 214:25-33 (1998).
Bernstein et al., "Role for a bidentate ribonuclease in the initiation step of RNA interference", *Nature*, 409:363-366 (2001).
Billström et al., "The Urokinase Inhibitor p-Aminobenzamidine Inhibits Growth of a Human Prostate Tumor in SCID Mice", *Int. J. Cancer*, 61:542-547 (1995).
Blaney et al., "Computational approaches for combinatorial library design and molecular diversity analysis", *Curr. Opin. Chem. Biol.*, 1:54-59 (1997).
Blanton et al., "Characterization of a native and recombinant *Schistosoma haematobium* serine protease inhibitor gene product", *Mol. Biochem. Parasitol.*, 63:1-11 (1994).
Bock et al., "Isolation of Human Blood Coagulation α-Factor $X_a$ by Soybean Trypsin Inibitor-Sepharose Chromatography and Its Active-Site Titration with Fluorescein Mono-p-guanidinoberizoate", *ARCH Biochem Biophy*, 273(2):375-388 (1989).
Bock et al., "Selection of single-stranded DNA molecules that bind and inhibit human thrombin", *Nature*, 355:564-566 (1992).
Boesen et al., "Circumvention of chemotherapy-induced myelosuppression by transfer of the *mdr1* gene", 6:291-302 (1994).
Borman, S., "Scientists Refine Understanding Of Protein Folding And Design", *Chem. Eng. News*, 2(12):29-35 (1996).
Boublik et al., "Eukaryotic Virus Display: Engineering the Major Surface Glycoprotein of the *Autographa californica* Nuclear Polyhedrosis Virus (AcNPV) for the Presentation of Foreign Proteins on the Virus Surface", *Bio/Technol.*, 13:1079-1084 (1995).
Bourinbaiar et al., "Effect of Serine Protease Inhibitor, N-α-Tosyl-L-lysyl-Chloromethyl Ketone (TLCK), on Cell-Mediated and Cell-Free HIV-1 Spread", *Cell. Immuno.*, 155:230-236 (1994).
Bout et al., "Lung Gene Therapy: *In Vivo* Adenovirus-Mediated Gene Transfer to Rhesus Monkey Airway Epithelium", *Human Gene Therapy*, 5:3-10 (1994).
Braunwalder et al., "Application of Scintillating Microtiter Plates to Measure Phosphopeptide Interactions with the GRB2-SH2 Binding Domain", *J. Biomol. Screening*, 1(1):23-26 (1996).
Brenner et al., "Encoded combinatorial chemistry", *Proc. Natl. Acad. Sci. USA*, 89:5381-5383 (1982).
Brinster et al., "Regulation of metallothionein-thymidine kinase fusion plasmids injected into mouse eggs", *Nature*, 296:39-42 (1982).

Brooks et al., "Use of the 10-Day-Old Chick Embryo Model for Studying Angiogenesis", *Methods in Molecular Biology*, 129:257-269 (1999).

Bunin et al., "A General and Expedient Method for the Solid-Phase Synthesis of 1,4-Benzodiazepine Derivatives", *J. Am. Chem. Soc.*, 114:10997-10998 (1992).

Bunin et al., "The combinatorial synthesis and chemical and biological evaluation of a 1.4-benzodiazepine library", *Proc. Natl. Acad. Sci. USA*, 91:4708-4712 (1994).

Butz et al., "Immunization and Affinity Purification of Antibodies Using Resin-Immobilized Lysine-Branched Synthetic Peptides", *Peptide Res.*, 7(1):20-23 (1994).

Caflisch et al., "Computational combinatorial chemistry for de novo ligand design: Review and assessment", *Perspectives in Drug Discovery and Design*, 3:51-84 (1995).

Capecchi et al., "Altering the Genome by Homologous Recombination", *Science*, 244:1288-1292 (1989).

Carrillo et al., "The Multiple Sequence Alignment Problem in Biology", *SIAM J Appl Math*, 48(5):1073-1082 (1988).

Chen et al., "Analogous Organic Synthesis of Small-Compound Libraries: Validation of Combinatorial Chemistry in Small-Molecule Synthesis", *J. Am. Chem. Soc.*, 116:2661-2662 (1994).

Chen et al., "IL-1β Induces Serine Protease Inhibitor 3 (SPI-3) Gene Expression in Rat Pancreatic β-Cells. Detection by Differential display of Messenger RNA", *CYTOKINE*, 11(11):856-862 (1999).

Chen et al., "Interaction of Phosphorylated FcγΕRIγ Immunoglobulin Receptor Tyrosine Activation Motif-based Peptides with Dual and Single SH2 Domains of $p72^{syk}$", *J. Biol. Chem.*, 271(41):25308-25315 (1996).

Cheng et al., "Sequence-Selective Peptide Binding with a Peptido-A,B-*trans*-steroidal Receptor Selected from an Encoded Combinatorial Receptor Library", *J. Am. Chem. Soc.*, 118:1813-1812 (1996).

Chu et al., "Using Affinity Capillary Electrophoresis To Identify the Peptide in a Peptide Library that Binds Most Tightly to Vancomycin", *J. Org. Chem.*, 58:648-652 (1993).

Chuang et al., "Specific and heritable genetic interference by double-stranded RNA in *Arabidopsis thaliana*", *PNAS*, 97(9):4985-4990 (2000).

Clackson et al., "Making antibody fragments using phage display libraries", *Nature*, 352:624-628 (1991).

Cline et al., "Perspectives for Gene Therapy: Inserting New Genetic Information into Mammalian Cells by Physical Techniques and Viral Vectors", *Pharmac. Ther.*, 29:69-92 (1985).

Clowes et al., "Long-Term Biological Response of Injured Rat Carotid Artery Seeded with Smooth Muscle Cells Expressing Retrovirally Introduced Human Genes", *J. Clin. Invest.*, 93:644-651 (1994).

Cole et al., in *Monoclonal Antibodies and Cancer Therapy*, "The EBV-Hybridoma Technique and Its Application to Human Lung Cancer", Alan R. Liss, Inc., pp. 77-96 (1985).

Combs et al., "Protein Structure-Based Combinatorial Chemistry: Discovery of Non-Peptide Binding Elements to Src SH3 Domain", *J. Am. Chem. Soc.*, 118:287-288 (1996).

Coombs et al., "Revisting Catalysis by Chymotrypsin Family Serine Proteases Using Peptide Substrates and Inhibitors with Unnatural Main Chains", *J. Biol. Chem.*, 274(34):24074-24079 (1999).

Coombs et al., "Substrate specificity of prostate-specific antigen (PSA)", *Chem. Biol.*, 5(9):475-488 (1998).

Coombs et al., "Directing Sequence-Specific Proteolysis to New Targets. The Influence Of Loop Size And Target Sequence Of Selective Proteolysis By Tissue-Type Plasminogen Activator And Urokinase-Type Plasminogen Activator", *J. Biol. Chem.*, 273(8):4323-4328 (1998).

Coombs et al., "Distinct Mechanisms Contribute to Stringent Substrate Specificity of Tissue-type Plasminogen Activator", *J. Biol. Chem.*, 271(8):4461-4467 (1996).

Cote et al., "Generation of human monoclonal antibodies reactive with cellular antigens", *Proc. Natl. Acad. Sci. USA*, 80:2026-2030 (1983).

Cotten et al., "Receptor-Mediated Transport of DNA into Eukaryotic Cells", *Meth. Enzymol.*, 218:619-644 (1993).

Crowley et al., "Prevention of metastasis by inhibition of the urokinase receptor", *Proc. Natl. Acad. Sci. USA*, 90:5021-5025 (1993).

Cumber et al., "Structural Features of the Antibody-A Chain Linkage that Influences the Activity and Stability of Ricin A Chain Immunotoxins", *Bioconj. Chem.*, 3:397-401 (1992).

*Current Protocols in Molecular Biology*, Book: Chapter 16, John Wiley & Sons, Inc. (1990).

*Current Protocols in Molecular Biology*, Book: Chapter 10, John Wiley & Sons, Inc. (2001).

Cwirla et al., "Peptides on phage: A vast library of peptides for identifying ligands", *Proc. Natl. Acad. Sci. USA*, 87:6378-6382 (1990).

De Boer et al., "The *tac* promoter: A functional hybrid derived from the *trp* and *lac* promoters", *Proc. Natl. Acad. Sci. USA*, 80:21-25 (1983).

Delaria et al., "Characterization of Placental Bikunin, a Novel Human Serine Protease Inhibitor", *J. Biol. Chem.*, 272(18):12209-12214 (1997).

Devlin et al., "Random Peptide Libraries: A Source of Specific Protein Binding Molecules", *Science*, 249:404-406 (1990).

DeWitt et al., "Diversomers: An approach to nonopeptide, nonligomeric chemical diversity", *Proc. Natl. Acad. Sci. USA*, 90:6909-6913 (1993).

Dexter et al., "Conditions Controlling the proliferation of Haemopoietic Stem Cells In Vitro", *J. Cell. Physiol.*, 91:335-344 (1976).

Ding et al., "Origins of the specificity of tissue-type plasminogen activator", *Proc. Natl. Acad. Sci. USA*, 92(17):7627-7631 (1995).

Dower et al., "The Search for Molecular Diversity (II): Recombinant and Synthetic Randomized Peptide Libraries", *An. Rep. Med. Chem.*, 26:271-280 (1991).

Dryjanski et al., "N-Tosyl-L-phenylalanine Chloromethyl Ketone, a Serine Protease Inhibitor, Identifies Glutamate 398 at the Coenzyme-Binding Site of Human Aldehyde Dehydrogenase. Evidence for a Second "Naked Anion" at the Active Site", *Biochem.*, 37(40):14151-14156 (1998).

Dufer et al., "Differential Effect of the Serine Protease Inhibitor Phenyl Methyl Sulfonyl Fluoride on Cytochemically Detectable Esterases in Human Leucocytes and Platelets", *Scand. J. Haematol.*, 32(1):25-32 (1984).

Eck et al., "Structure of TNF-α: Implications for Receptor Binding", *J. Biol. Chem.*, 26:17605 (1989).

Eck et al., "The Structure of Tumor Necrosis Factor-α at 2.6 Å Resolution", *J Biol Chem*, 264(29):17595-17605 (1989).

Ecker et al., "Combinatorial Drug Discovery: Which Methods Will Produce the Greatest Value?", *Bio/Technol.*, 13:351-360 (1995).

Edwards et al., "Inhibition of elastase by a synthetic cotton-bound serine protease inhibitor: in vitro kinetics and inhibitor release", *Wound Repair Regen.*, 7(2):106-118 (1999).

Eichler et al., "Identification of Substrate-Analog Trypsin Inhibitors through the Screening of Synthetic Peptide Combinatorial Libraries", *Biochem.*, 32:11035-11041 (1993).

Elbashir et al., "Duplexed of 21-nucleotide RNAs mediate RNA interference in cultured mammalian cells", *Nature*, 411:494-498 (2001).

Elbashir et al., "RNA interference is mediated by 21- and 22-nucleotide RNAs", *Genes & Develop*, 15:188-200 (2001).

Ellington et al., "*In vitro* selection of RNA molecules that bind specific ligands", *Nature*, 346:818-822 (1990).

Erickson et al., "Design, Activity, and 2.8 Å Crystal Structure of a $C_2$ Symmetric Inhibitor Complexed to HIV-1 Protease", *Science*, 249:527-533 (1990).

Erickson et al., Book: *The Proteins*, "Solid-Phase Peptide Synthesis", vol. II, Neurath H., Hill, R.L. Eds., Academic Press, New York, pp. 255-257 (1976).

Evans et al., "Design of Nonpeptidal Ligands for a Peptide Receptor: Cholecystokinin Antagonists", *J. Med. Chem.*, 30:1229-1239 (1987).

Farley et al., "Cloning and sequence analysis of rat hepsin, a cell surface serine proteinase", *BioChem. Biophys. Acta*, 1173:350-352 (1993).

Fattom et al., "Comparative Immunogenicity of Conjugates Composed of the *Staphylococcus aureus* Type 8 Capsular Polysaccharide Bound to Carrier Proteins by Adipic Acid Dihydrazide or N-Succinimidyl-3-(2-Pyridyldithio)propionate", *Infection & Immun.*, 60(1):584-589 (1992).

Fauchere, "Elements for the Rational Design of Peptide Drugs", *Adv. Drug Res.*, 15:29-69 (1986).

Fay et al., "Platelets inhibit fibrinolysis in vitro by both plasminogen activator inhibitor dependent and -independent mechanisms", *Blood*, 83(2):351-356 (1994).

Felici, F., "Selection of Antibody Ligands from a Large Library of Oligopeptides Expressed on a Multivalent Exposition Vector", *J. Mol. Biol.*, 222:301-310 (1991).

Feinstein et al., "Thrombin, Collagen and A23187 Stimulated Endogenous Platelet Arachidonate Metabolism: Differential Inhibition by PGE., Local Anesthetics and a Serine-Protease Inhibitor", *Prostaglandins*, 14(6):1075-1093 (1977).

Fire et al., "Potent and specific genetic interference by double-stranded RNA in *Caenorhabditis elegans*", *Nature*, 391:806-811 (1998).

Fire, A., "RNA-triggered gene silencing", *Trens in Genetics*, 15(9):358-363 (1999).

Fodor et al., "Light-Directed, Spatially Addressable Parallel Chemical Synthesis", *Science*, 251:767-773 (1991).

Forney et al., "Interaction of the human Serine Protease Inhibitor α-1-Antitrypsin with *Cryptosporidium Parvum*", *J. Parasitol.*, 82(3):496-502 (1996).

Franceschini et al., "Polysialyltransferase ST8Sia II (STX) polysialylates all of the major isoforms of NCAM and facilitates neurite outgrowth", *Glycobiol*, 11(3):231-239 (2001).

Francisco et al., "Transport and anchoring of β-lactamase to the external surface of *Escherichia coli*", *Proc. Natl. Acad. Sci. USA*, 89:2713-2717 (1992).

Friedrich et al., "Catalytic Domain Structures of MT-SP1/Matriptase, a Matrix-degrading Transmembrane Serine Proteinase", *J Bio Chem*, 277(3):2160-2168 (2002).

Fujise et al., "A tissue plasminogen activator/P-selectin fusion protein is an effective thrombolytic agent", *Circulation*, 95(3):715-722 (1997).

Gallop et al., "Applications of Combinatorial Technologies to Drug Discovery. 1. Background and Peptide Combinatorial Libraries", *J. Med. Chem.*, 37(9):1233-1251 (1994).

Gante, "Peptidomimetics-tailored Enzyme Inhibitors", *Angew. Chem. Int. Ed. Engl.*, 33:1699-1720 (1994).

Garcia et al., "The *E. coli* dnaY Gene Encodes an Arginine Transfer RNA", *Cell 45*: 453-459 (1986).

Gardner et al., "The complete nucleotide sequence of an infectious clone of cauliflower mosaic virus by M13mp7 shotgun sequencing", *Nucleic Acids. Res.*, 9(12):2871-2888 (1981).

Gautier et al., "α-DNA IV: α-anomeric and β-anomeric tetrathymidylates covalently linked to intercalating oxazolopyridocarbazole. Synthesis, physicochemical properties and poly (rA) binding", *Nucl. Acids Res.*, 15:6625-6641 (1987).

Gavazzi et al., "Responsiveness of sympathetic and sensory iridial nerves to NGF treatment in young and aged rats", *Neurobiol. of Aging*, 22:287-297 (2001).

Georgiou et al., "Practical applications of engineering Gram-negative bacterial cell surfaces", *TIBTECH*, 11:6-10 (1993).

Gething et al., "Variants of human tissue-type plasminogen activator that lack specific structural domains of the heavy chain", *EMBO J.*, 7(9):2731-2740 (1988).

Geysen et al., "Use of peptide synthesis to probe viral antigens for epitopes to a resolution of a single amino acid", *Proc. Natl. Acad. Sci. USA*, 81:3998-4002 (1984).

Ghendler et al., "Schistosoma mansoni: Isolation and Characterization of Smpi56, a Novel Serine Protease Inhibitor", *Exp. Parasitol.*, 78:121-131 (1994).

Gilbert et al., "Useful Proteins from Recombinant Bacteria", *Scientific American*, 242):79-94 (1980).

Glaser et al., "Antibody Engineering by Condon-Based Mutagenesis in a Filamentous Phage Vector System", *J. Immunol.*, 149(12):3903-3913 (1992).

Goldmacher et al., "Photoactivation of Toxin Conjugates", *Bioconj. Chem.*, 3:104-107 (1992).

Goldspiel et al., "Human gene therapy", *Clinical Frontiers, Clinical Pharmacy*, 12:488-505 (1993).

Gonzalez et al., "Voltage Sensing by Fluorescence Resonance Energy Transfer in Single Cells", *Biophys. J.*, 69:1272-1280 (1995).

Gram et al., "*In vitro* selection and affinity maturation of antibodies from a naive combinatorial immunoglobulin library", *Proc. Natl. Acad. Sci. USA*, 89:3576-3580 (1992).

Grosschedl et al., "Introduction of a μ Immunoglobulin Gene into the Mouse Germ Line: Specific Expression in Lymphoid Cells and Synthesis of Functional Antibody", *Cell*, 38:647-658 (1984).

Grossman et al., "Retroviruses: delivery vehicle to the liver", *Curr. Opin. in Genetics and Devel.*, 3:110-114 (1993).

Grunstein et al., "Colony hybridization: A method for the isolation of cloned DNAs that contain a specific gene", *Proc. Natl. Acad. Sci. USA*, 72(10):3961-3965 (1975).

Hamdaoui et al., "Purification of a Novel, Heat-Stable Serine Protease Inhibitor Protein from Ovaries of the Desert Locust, *Schistocerca gregaria*", *Biochem. Biophys. Res. Commun.*, 238:357-360 (1997).

Hameed et al., "3,4-Dichloroisocoumarin Serine Protease Inhibitor Induces DNA Fragmentation and Apoptosis in susceptible Target Cells", *DCI and Apoptosis, Proc. Soc. Exp. Biol. Med.*, 219(2):132-137 (1998).

Hamilton et al., "A Species of Small Antisense RNA in Post-transcriptional Gene Silencing in Plants", *Science*, 286:950-952 (1999).

Hammer et al., "Diversity of Alpha-Fetoprotein Gene Expression in Mice Is Generated by a Combination of Separate Enhancer Elements", *Science*, 235:53-58 (1987).

Hammond et al., "An RNA-directed nuclease mediates post-transcriptional gene silencing in *Drosophila* cell", *Nature*, 404:293-296 (2000).

Hammond et al., "Post-Transcriptional Gene Silencing by Double-Stranded RNA", *Nature*, 2:110-119 (2001).

Han et al., "Liquid-Phase Combinatorial Synthesis", *Proc. Natl. Acad. Sci. USA*, 92:6419-6423 (1995).

Hanahan, D., "Heritable formation of pancreatic β-cell tumours in transgenic mice expressing recombinant insulin/simian virus 40 oncogenes", *Nature*, 315:115-122 (1985).

Harper et al., "Reaction of Serine Proteases with Substituted Isocoumarins: Discovery of 3,4-Dichloroisocoumarin, a New General Mechanism Based Serine Protease Inhibitor" *Biochem.*, 24:1831-1841 (1985).

Hazum et al., A Photocleavable Protecting Group for the Thiol Function of Cysteine Department of Organic Chemistry, The Weizmann Institute of Science Rehovot, Israel, *Pept., Proc. Eur. Pept. Symp.*, 16th, Brunfeldt, K (Ed) pp. 105-110 (1981).

Herrera-Estrella et al., "Expression of chimeric genes transferred into plant cells using a Ti-plasmid-derived vector", *Nature*, 303:209-213 (1984).

Herrera-Estrella et al., "Light-inducible and chloroplast-associated expression of a chimeric gene introduced into *Nicotiana tabacum* using a Ti plasmid vector", *Nature*, 310:115-120 (1984).

Hervio et al., "Negative selectivity and the evolution of protease cascades: the specificity of plasmin for peptide and protein substrates", *Chem. Biol.*, 7(6):443-452 (2000).

Hesse et al., "Effects of the Serine Protease Inhibitor Gabexate Mesilate on Purified Pancreatic Phospholipase $A_2$", *Pharmacol. Res. Commun.*, 16(7):637-645 (1984).

Hill et al., "A new intracellular serine protease inhibitor expressed in the rat pituitary gland complexes with granzyme B", *FEBS Lett.*, 440:361-364 (1998).

Hiwasa et al., "Potent growth-suppressive activity of a serine protease inhibitor, ONO-3403, toward malignant human neuroblastoma cell lines", *Cancer Lett.*, 126:221-225 (1998).

Holmes, "Primary Structure of Human $\alpha_2$-Antiplasmin, a serine Protease Inhibitor (Serpin)", *J. Biol. Chem.*, 262(4):1659-1664 (1987).

Holstein et al., "The primitive metazoan *Hydra* expresses antistasin, a serine protease inhibitor of vertebrate blood coagulation: cDNA cloning, cellular localisation and development regulation", *FEBS Lett.*, 309(3):288-292 (1992).

Hoogenboom, et al., "Multi-Subunit Proteins on the Surface of Filamentous Phage: Methodologies for Displaying Antibody (Fab) Heavy and Light Chains", *Nucleic Acids Res.*, 19(15):4133-4137 (1991).

Hooper et al., "Type II Transmembrane Serine Proteases", *J. Biol. Chem.*, 276:857-860 (2001).

Houenou et al., "A serine protease inhibitor, protease nexin I, rescues motoneurons from naturally occurring and axotomy-induced cell death", *Proc. Natl. Acad. Sci. USA*, 92:895-899 (1995).

Houghten et al., "Generation and use of synthetic peptide combinatorial libraries for basic research and drug discovery", *Nature*, 354:84-86 (1991).

Houghten, et al., "General method for the rapid solid-phase synthesis of large numbers of peptides: specificity of antigen-antibody interaction at the level of individual amino acids", *Proc. Natl. Acad. Sci. USA*, 82:5131-5135 (1985).

Houghten et al., "The Use of Synthetic Peptide Combinatorial Libraries for the Identification of Bioactive Peptides", *Bio Techniques*, 313:412-421 (1992).

Houghten, et al., "The Use Of Synthetic Peptide Combinatorial Libraries For The Determination Of Peptide Ligands In Radio-Receptor Assays-Opioid-Peptides", *Bioorg. Med. Chem. Lett.*, 3(3):405-412 (1993).

Hruby et al., "Emerging approaches in the molecular design of receptor-selective peptide ligands: conformational, topographical and dynamic considerations", *Biochem J.*, 268:249-262 (1990).

Huang, et al., "Discovery of new ligand binding pathways in myoglobin by random mutagenesis", *Nature Struct. Biol.*, 1(4):226-229 (1994).

Huang et al., "Serine protease inhibitor TPCK prevents Taxol-induced cell death and blocks c-Raf-1 and Bcl-2 phosphorylation in human breast carcinoma cells", *Oncogene*, 18:3431-3439 (1999).

Hunkapiller et al., "A microchemical facility for the analysis and synthesis of genes and proteins", *Nature*, 310:105-111 (1984).

Huse et al., "Generation of a Large Combinatorial Library of the Immunoglobulin Repertoire in Phage Lambda", *Science*, 246:1275-1281 (1989).

Huston et al., "Protein engineering of antibody binding sites: Recovery of specific activity in an anti-digoxin single-chain Fv analogue produced in *Escherichia coli*", *Proc. Natl. Acad. Sci. USA* 85:5879-5883 (1988).

Hutchison et al., "Mutagenesis at a Specific Position in a DNA Sequence", *J Biol Chem*, 253(18):6551-6560 (1978).

Iijima et al., "Stage-Specific Inhibition of *Xenopus* Embryogenesis by Aprotinin, a Serine Protease Inhibitor", *J. Biochem.* (Tokyo), 126:912-916 (1999).

Inoue et al., "Sequence-dependent hydrolysis of RNA using modified oligonucleotide splints and RNase H", *FEBS Lett.* 215(2):327-330 (1987).

Inoue et al., "Synthesis and hybridization studies on two complementary nonal(2'-O-methyl)ribonucleotides", *Nucl. Acids Res.* 15(15):6131-6148 (1987).

IUPAC-IUB, "Commission on Biochemical Nomenclature Abbreviated Nomenclature of Synthetic Polypeptides (Polymerized Amino Acids)", *Biochem.*, 11(5):942-944 (1972).

Jacquinet et al. "Cloning, genomic organization, chromosomal assignment and expression of a novel mosaic serine proteinase: epitheliasin", *FEBS Lett.*, 468:93-100 (2000).

Jameson et al., "Fluorescence Anisotropy Applied to Biomolecular Interactions", *Methods Enzymol.*, 246:283-300 (1995).

Janda, K.D., "New Strategies for the Design of Catalytic Antibodies", *Biotechnol. Prog.*, 6:178-181 (1990).

Jankun et al., "Inhibitors of Urokinase Reduce Size of Prostate Cancer Xenografts in Severe Combined Immunodeficient Mice", *Canc. Res.*, 57:559-563 (1997).

Jessop et al., "Effects of Serine Protease Inhibitor, Tame, on IL-1β in LPS-Stimulated Human Monocytes: Relationship Between Synthesis and Release of a 33-kDa Precursor and the 17-kDa Biologically Active Species", *Inflammation*, 17(5):613-631 (1993).

Jolley, "Fluorescence Polarization Assays for the Detection of Proteases and Their Inhibitors", *J. Biomol. Screening*, 1(1)33-38 (1996).

Jung et al., "Multiple Peptide Synthesis Methods and Their Applications", *Angew. Chem. Int. Ed. Engl.*, 31(4):367-383 (1992).

Kalaria et al., "Serine Protease Inhibitor Antithrombin III and Its Messenger RNA in the Pathogenesis of alzheimer's Disease", *Am. J. Pathol.*, 143(3):886-893 (1993).

Kaminogo et al., "Combination of Serine Protease Inhibitor FUT-175 and Thromboxane Synthetase Inhibitor OKY-046 Decreases Cerebral Vasospasm in Patients with Subarachnoid Hemorrhage", *Neurol. Med. Chir.* (Tokyo), 38:704-709 (1998).

Kang et al., "Antibody redesign by chain shuffling from random combinatorial immunoglobulin libraries", *Proc. Natl. Acad. Sci. USA*, 88:11120-11123 (1991).

Kawaguchi et al., "Purification and the Cloning of hepatocyte Growth Factor Activator Inhibitor Type 2, a Kunitz-type serine Protease Inhibitor", *J. Biol. Chem.*, 272(44):27558-27564 (1997).

Kay et al., An M13 phage library displaying random 38-amino-acid-peptides as a source of novel sequences with affinity to selected targets genes, *Gene*, 128:59-65 (1993).

Ke et al., "Distinguishing the Specificities of Closely Related Proteases. Role of P3 In Substrate And Inhibitor Discrimination Between-type Plasminogen Activator And Urokinase", *J. Biol. Chem.*, 272(26):16603-16609 (1997).

Ke et al., "Rapid and efficient site-directed mutagenesis by single-tube 'megaprimer' PCR method", *Nucl. Acids Res.*, 25(16):3371-3372 (1997).

Ke et al., "Identification of a Hydrophobic Exosite on Tissue Type Plasminogen Activator That Modulates Specificity for Plasminogen", *J. Biol. Chem.*, 272(3):1811-1816 (1997).

Ke et al., "Optimal Subsite Occupancy and Design of a Selective Inhibitor of Urokinase", *J. Biol. Chem.*, 272(33):20456-20462 (1997).

Kelsey et al., "Species- and tissue-specific expression of human $\alpha_1$-antitrypsin in transgenic mice", *Genes and Devel.*, 1:161-171 (1987).

Kennedy et al., "Immobilized Enzymes", Book: vol. 66, Chapter 7, *Solid Phase Biochemistry. Analytical and Synthetic Aspects*, John Wiley & Sons, Inc., New York, pp. 253-391 (1993).

Kent et al., "Preparation and Properties of tert-Butyloxycarbonylaminoacyl-4-(oxymethyl)phenylacetamidomethyl-(Kel F-g-styrene) Resin, an Insoluble, Noncrosslinked Support for Solid Phase Peptide Synthesis", *J. Chem.*, 17:243-247 (1978).

Kiem et al., "Retrovirus-Mediated Gene Transduction Into Canine Peripheral Blood Repopulating Cells", *Blood*, 83(6):1467-1473 (1994).

Kim et al. "Cloning and chromosomal mapping of a gene isolated from thymic stromal cells encoding a new mouse type II membrane serine protease, epithin, containing four LDL receptor modules and two CUB", *Immunogenetics*, 49:420-428 (1999).

Kim et al., "A Cysteine-Rich Serine Protease Inhibitor (Guamerin II) from the Non-Blood Sucking Leech *Whitmania Edentula*: Biochemical Characterization and Amino Acid Sequence Analysis", *J. Enzym. Inhib.*, 10:81-91 (1996).

Kitamoto et al., "Enterokinase, the initiator of intestinal digestion, is a mosaic protease composed of a distinctive assortment of domains", *Proc. Natl. Acad. Sci. USA*, 91:7588-7592 (1994).

Kitamoto et al., "cDNA Sequence and Chromosomal Localization of Human Enterokinase, the Proteolytic of Trypsinogen", *Biochem.*, 34(14):4562-4568 (1995).

Kleine et al., "Lipopeptide-Polyoxythylene Conjugates as Mitogens and Adjuvants", *Immunobiol.*, 190:53-66 (1994).

Kobayashi et al., "Inhibition of Metastasis of Lewis Lung Carcinoma by a Synthetic Peptide within Growth Factor-like Domain of Urokinase in the Experimental and Spontaneous Metastasis Model", *Int. J. Canc.*, 57:727-733 (1994).

Kodo et al., "Antibody Synthesis by Bone Marrow Cells In Vitro following Primary and Booster Tetanus Toxoid Immunization in Humans", *J. Clin. Invest.*, 73:1377-1384 (1984).

Köhler et al., "Continuous cultures of fused cells secreting antibody of predefined specificity", *Nature*, 526:495-497 (1975).

Koller et al., "Inactivating the β₂-microglobulin locus in mouse embryonic stem cells by homologous recombinant", *Proc. Natl. Acad. Sci. USA* 86:8932-8935 (1989).

Kollias et al., "Regulated Expression of Human ᴬγ-, β-, and Hybrid γβ-Globin Genes in Transgenic Mice: Manipulation of the Development Expression Patterns", *Cell*, 46:89-94 (1986).

Kozak, "Structural Features in Eukaryotic mRNAs That Modulate the Initiation of Translation", *J. Biol. Chem.*, 266(30):19867-19870 (1991).

Kozarsky et al., "Gene therapy: adenovirus vectors", *Genetics and Development*, 3:499-503 (1993).

Kozbor et al., "The production of monoclonal antibodies from human lymphocytes", *Immunology Today* 4(3):72-79 (1983).

Krumlauf et al., "Developmental Regulation of α-Fetoprotein Genes in Transgenic Mice", *Mol. Cell. Biol.*, 5(7):1639-1648 (1985).

Ladurner et al., "Glutamine, Alanine or Glycine Repeats Inserted into the Loop of a Protein Have Minimal Effects on Stability and Folding Rate", *J. Mol. Biol.*, 273:330-337 (1997).

Lam, K.S., "Application of combinatorial library methods in cancer research and drug discovery", *Anti-Cancer Drug Des.*, 12:145-167 (1997).

Lam et al., A new type of synthetic peptide library for identifying ligand-binding activity, *Nature*, 354:82-84 (1991); (published errata appear in *Nature*, 358:434 (1992) and *Nature*, 360:768 (1992).

Lebl et al., "One Bead One Structure Combinatorial Libraries", *Biopolymerse (Pept. Sci.)*, 37:177-198 (1995).

Le Cam et al., "Growth Hormone-Mediated Transcriptional Activation of the Rat Serine Protease Inhibitor 2.1 Gene Involves Both Interleukin-1 β-Sensitive and -Insensitive Pathways", *Biochem. Biophys. Res. Commun.*, 253(2):311-314 (1998).

Leder et al., "Consequences of Widespread Deregulation of the c-*myc* Gene in Transgenic Mice: Multiple Neoplasms and Normal Development", *Cell*, 45:485-495 (1986).

Lemaitre et al., "Specific antiviral activity of a poly(L-lysine)-conjugated oligodeoxyribonucleotide sequence complementary to vesicular stomatitis virus N protein mRNA initiation site", *Proc. Natl. Acad. Sci. USA*, 84:648-652 (1987).

Lerner et al., "Antibodies without Immunization", *Science*, 258:1313-1314 (1992).

Lerner et al., "High Throughput Screen for Inhibitors of Bacterial DNA Topoisomerase I Using the Scintillation Proximity Assay", *J. Biomol. Screening*, 1(3):135-143 (1996).

Letsinger et al., "Cholesteryl-conjugated oligonucleotides: Synthesis, properties, and activity as inhibitors of replication of human immunodeficiency virus in cell culture", *Proc. Natl. Acad. Sci. USA*, 86:6553-6556 (1989).

Leytus et al., "A Novel Trypsin-like Serine Protease (Hepsin) with a Putative Transmembrane domain Expressed by Human Liver and Hepatoma Cells", *Biochem.*, 27:1067-1074 (1988).

Li et al., "Minimization of a Polypeptide Hormone", *Science*, 270:1657-1660 (1995).

Light et al., "Phophads: Antibody-Phage-lkaline Phosphatase Conjugates For One Step Elisa s Without Immunization", *Bioorg. Med. Chem. Lett.*, 2(9):1073-1078 (1992).

Lin et al., "Molecular Cloning of cDNA for Matriptase, a Matrix-degrading Serine Protease with Trypsin-like Activity", *J. Biol. Chem.*, 274(26):18231-18236 (1999).

Lin et al., "Purification and Characterization of a Complex Containing Matriptase and a Kunitz-type Serine Protease Inhibitor from Human Milk", *J. Biol. Chem.*, 274(26):18237-18242 (1999).

Lindmark et al., "Pulmonary Function in Middle-aged Women with Heterozygous Deficiency of the Serine Protease Inhibitor Alpha-antichymotrypsin", *Am. Rev. Respir. Des.*, 141:884-888 (1990).

Little et al., "Bacterial surface presentation of proteins and peptides: an alternative to phage technology?", *Trends Biotechnol.*, 11:3-5 (1993).

Liu et al., "Identification of a Novel Serine Protease-like Gene, the Expression of Which Is Down-Regulated during Breast Cancer Progression", *Cancer Res.*, 56:3371-3379 (1996).

Liu et al., "Matrix Localization of Tissue Factor Pathway Inhibitor-2/Matrix-Associated Serine Protease Inhibitor (TFPI-2/MSPI) Involves Arginine-Mediated Ionic Interactions wih Heparin and Dermatan Sulfate: Heparin Accelerates the Activity of TFPI-2/MSPI toward Plasmin", *Arch. Biochem. Biophys.*, 370(1):112-118 (1999).

Loeffler et al., "Gene Transfer into Primary and Established Mammalian Cell Lines with Lipopolyamine-Coated DNA", *Meth. Enzymol.*, 217:599-618 (1993).

Loh et al., "Night Functional Dependency Index", *JAGS*, 49:1395-1396 (2001).

Lundqvist et al., Original Research Papers, "The serine protease inhibitor diisopropylfluorophosphate inhibits neutrophil NADPH-oxidase activity induced by the calcium ionophore ionomycin and serum opsonised yeast particles", *Inflamm. Res.*, 44(12):510-517 (1995).

Luthman et al., "Peptides and Peptidomimetics", Book: *A Textbook of Drug Design and Development*, 2nd Ed., Harwood Academic Publishers, 14:386-406 (1996).

Lynch et al., "A Fluorescence Polarization Based Src-SH2 Binding Assay", *Anal. Biochem.*, 247:77-82 (1997).

Maake et al., "The Growth Hormone Dependent Serine Protease Inhibitor, Spi 2.1 Inhibits the Des (1-3) Insulin-Like Growth Factor-I Generating Protease", *Endocrinology*, 138(12):5630-5636 (1997).

MacDonald, R.J., "Expression of the Pancreatic Elastase I Gene in Transgenic Mice", *Hepatol.*, Suppl. 7(1):42S-51S (1987).

Madison E.L., "Substrate Specificity of Tissue Type Plasminogen Activator", *Adv. Exp. Med. Biol.*, 425:109-121 (1997).

Madison et al., "Substrate Specificity of Tissue Type Plasminogen Activator. Characterization Of The Fibrin Specificity Of t-PA For Plasminogen", *J. Biol. Chem.*, 270(13):7558-7562 (1995).

Madison E.L., "Studies of Serpins Unfold at a Feverish Pace", *J. Clin. Invest.*, 94(6):2174-2175 (1994).

Madison et al., "Converting Tissue Plasminogen Activator to a Zymogen: A Regulatory Triad of ASP-His-Ser", *Science*, 262(5132):419-421 (1993).

Madison, E.L., "Probing Structure/Function Relationships of Tissue-type Plasminogen Activator by Site Specific Mutagenesis", *Fibrinolysis*, 81(Suppl. 1):221-236 (1994).

Madison et al., "Probing Structure-Function Relationships of Tissue-Type Plasminogen Activator by Oligonucleotide-Mediated Site-Specific Mutagenesis", *Methods Enzymol.*, 223:249-271 (1993).

Madison et al., "A vector, pSHT, for the expression and secretion of protein domains in mammalian cells", *Gene*, 121(1):179-180 (1992).

Madison et al., "Restoration of Serine Protease-Inhibitor Interaction by Protein Engineering", *J. Biol. Chem.*, 265(35):21423-21426 (1990).

Madison et al., "Amino acid residues that affect interaction of tissue-type plasminogen activator with plasminogen activator inhibitor 1", *Proc. Natl. Acad. Sci. USA*, 87(9):3530-3533 (1990).

Madison et al., "Serpin-resistant mutants of human tissue type plasminogen activator", *Nature*, 339(6227):721-724 (1989).

Magram et al., "Developmental regulation of a cloned adult β-globin gene in transgenic mice", *Nature*, 315:338-340 (1985).

Marks et al., "By-Passing Immunization. Human Antibodies from V-Gene Libraries Displayed on Phage", *J. Mol. Biol.*, 222:581-597 (1991).

Marlor et al., "Identification and Cloning of Human Placental Bikunin, a Novel Serine Protease Inhibitor Containing Two Kunitz Domains", *J. Biol. Chem.*, 272(18):12202-12208 (1997).

Mason et al., "The Hypogonadal Mouse, Reproductive Functions Restored by Gene Therapy", *Science* 234:1372-1378 (1986).

Mastrangeli et al., "Diversity of Airway Epithelial Cell Targets for In Vivo Recombinant Adenovirus-mediated Gene Transfer", *J. Clin. Invest.* 91:225-234 (1993).

Matrisian et al., "Stromelysin/transin and tumor progression", *Cancer Biol.*, 1:107-115 (1990).

Matsushima et al., "Structural Characterization of Porcine Enteropeptidase", *J. Biol. Chem.*, 269(31):19976-19982 (1994).

Matthews et al., "Substrate Phage: Selection of Protease Substrates by Monovalent Phage Display", *Science*, 260:1113-1117 (1993).

McCafferty et al., "Phage Enzymes: Expression and Affinity Chromatography of Functional Alkaline Phosphatase on the Surface of Bacteriophage", *Protein Eng.*, 4(8):955-961 (1991).

McDonald, "Thrombopoietin. Its Biology, clinical Aspects, and Possibilities", *Am. J. of Pediatric Hematology/Oncology*, 14(1):8-21 (1992).

Mc Donnell et al., "Stromelysin in tumor progression and metastasis", *Cancer and Metastasis Reviews*, 9:305-319 (1990).

McPhalen et al., "Preliminary Crystallographic Data for the Serine Protease Inhibitor CI-2 from Barley Seeds", *J. Mol. Biol.*, 168:445-447 (1983).

Mellgren et al., "The Influence of a Serine Protease Inhibitor, Nafamostat Mesilate, on Plasma Coagulation, and Platelet Activation during Experimental Extracorporeal Life Support (ECLS)", *Thromb. Haemost.*, 79:342-347 (1998).

Menger et al., "Phosphatase Catalysis Developed Via Combinatorial Organic Chemistry", *J. Org. Chem.*, 60:6666-6667 (1995).

Merrifield, R.B., "Solid Phase Peptide Synthesis. I. The Synthesis of a Tetrapeptide", *J. Am. Chem. Soc.*, 85:2149-2154 (1963).

Merrifield, R.B., "Solid Phase Peptide Synthesis. III. An Improved Synthesis of Bradykinin", *Biochemistry*, 3(9):1385-1390 (1964).

Miller et al., "Use of Retroviral Vectors for Gene Transfer and Expression", *Meth. Enzymol.* 217:581-599 (1993).

Min et al., "Urokinase Receptor Antagonists Inhibit Angiogenesis and Primary Tumor Growth in Syngeneic Mice", *Canc. Res.*, 56:2428-2433 (1996).

Mitchell et al., "Preparation of Aminomethyl-Polystyrene Resin By Direct Amidomethylation", *Tetrahedron Lett.*, 42:3795-3798 (1976).

Mitchell et al., "A New Synthetic Route to *tert*-Butyloxycarbonylaminoacyl-4-(oxymethyl)phenylacetamidomethyl-resin, an Improved Support for solid-Phase Peptide Synthesis", *J. Org. Chem.*, 43(14):2845-2852 (1978).

Modha et al., "An association between schistosomes and contrapsin, a mouse serine protease inhibitor (serpin)", *Parasitology*, 96:99-109 (1988).

Monfardini et al., "A Branched Monomethoxypoly(ethylene glycol) for Protein Modification", *Bioconjugate Chem.*, 6(1):62-69 (1995).

Morgan et al., "Human Gene Therapy", *Annu. Rev. Biochem.*, 62:191-217 (1993).

Morgan et al., "Approaches to the Discovery of Non-Peptide Ligands for Peptide receptors and Peptidases", Book : *Annu. Rep. Med. Chem.*, Chapter 26, Section IV, 24:243-252 (1989).

Morrison et al., "Chimeric human antibody molecules: Mouse antigen-binding domains with human constant region domains", *Proc. Natl. Acad. Sci. USA*, 81:6851-6855 (1984).

Mosbach, K., "Introduction", *Methods in Enzymol.*, 44:3-7 (1976).

Mosbach et al., "Immobilization Techniques", Section II, *Methods in Enzymol.*, 44:53-65 (1976).

Mosbach et al., "Multistep Enzyme Systems", Section VII, *Methods in Enzymol.*, 44:453-479 (1976).

Mosbach et al., "Immobilized Coenzymes", Section X, *Methods in Enzymol.*, 44:859-887 (1976).

Moser et al., "Bdellastasin, a serine protease inhibitor of the antistasin family from the medical leech (*Hirudo medicinalis*)", *Eur. J. Biochem.*, 253:212-220 (1998).

Mulligan, "The Basic Science of Gene Therapy", *Science*, 260:926-932 (1993).

Nakabo et al., "Lysis of leukemic cells by human macrophages; inhibition by 4-(2-aminoethyl)-benzenesulfonyl fluoride (AEBSF), a serine protease inhibitor", *J. Leukoc. Biol.*, 60:328-336 (1996).

NCBI Protein NP 004253.
NCBI Nucleotide T30338.
NCBI Nucleotide U77054.
NCBI Nucleotide U81291.
NCBI Nucleotide AC012228.
NCBI Nucleotide AF133086.
NCBI Nucleotide AF042822.
NCBI Nucleotide NM_016425.
NCBI Nucleotide AF113596.
NCBI Nucleotide U75329.
NCBI Nucleotide X70900.
NCBI Nucleotide M18930.
NCBI Nucleotide AF030065.
NCBI Nucleotide AF118224.
NCBI Nucleotide AB002134.
NCBI Nucleotide U09860.
NCBI Nucleotide AB013874.
NCBI Nucleotide AF133845.

Neuberger et al., "Recombinant antibodies possessing novel effector functions", *Nature*, 312:604-608 (1984).

Newton et al., "Angiogenin Single-Chain Immunofusions: Influence of Peptide Linkers and Spacers between Fusion Protein Domains", *Biochemistry*, 35:545-553 (1996).

Nicolaou et al., "Radiofrequency Encoded Combinatorial Chemistry", *Angew. Chem. Int. Ed. Engl.*, 34(20):2289-2291 (1995).

Niimi et al., "A *Drosophila* gene encoding multiple splice variants of Kazal-type serine protease inhibitor-like proteins with potential destinations of mitochondria, cytosol and the secretory pathway", *Eur. J. Biochem.*, 266:282-292 (1999).

Nogrady, "Pro-Drugs and Soft Drugs", Book: *Medicinal Chemistry A Biochemical Approach*, Oxford University Press, NY, pp. 388-394 (1985).

Ohkoshi et al., "Effects of Serine Protease Inhibitor FOY-305 and Heparin on the Growth of Squa,ous Cell Carcinoma", *Anticancer Res.*, 13:963-966 (1993).

Oldenburg et al., "Peptide Ligands for A Sugar-Binding Protein Isolated from a Random Peptide Library", *Proc. Natl. Acad. Sci. USA*, 89:5393-5397 (1992).

Ong et al., "Biosynthesis of HNK-1 Glycans on O-Linked Oligonsaccharides Attached to the Neural Cell Adhesion Molecule (NCAM)", *J Biochem*, 277(20):18182-18190 (2002).

O'Reilly, "The preclinical evaluation of angiogenesis inhibitors", *Investigational New Drugs*, 15:5-13 (1997).

Ornitz et al., "Elastase I Promoter Directs Expression of Human Growth Hormone and SV40 T Antigen Genes to Pancreatic Acinar Cells in Transgenic Mice", *Cold Spring Harbor Symp. Quant. Biol.* 50:399-409 (1986).

Orth et al., "Complexes of tissue-type plasminogen activator and its serpin inhibitor plasminogen-activator inhibitor type 1 are internalized by means of the low density lipoprotein receptor-related protein/$\alpha_2$-macroglobulin receptor", *Proc. Natl. Acad. Sci. USA*, 89(16):7422-7426 (1992).

Ossowski, "In Vivo Invasion of Modified Chorioallantoic Membrane by Tumor Cells: the Role of Cell Surface-bound Urokinase", *J. Cell Biol.*, 107(6, Pt. 1):2437-2445 (1988).

Osterwalder et al., "Neuroserpin, an axonally secreted serine protease inhibitor", *EMBO J.*, 15(12):2944-2953 (1996).

Padwa et al., "Photoelimination of a $\beta$-Keto Sulfide with a Low-Lying $\Pi$—$\Pi$ Triplet State", *J. Org. Chem.*, 36(23):3550-2552 (1971).

Palencia et al., "Determination of Activable Proacrosin/Acrosin in Bovine Sperm Using an Irreversible Isocoumarin Serine Inhibitor Protease Inhibitor", *Biol. Reprod.*, 55:536-542 (1996).

Paoloni-Giacobino, "Cloning the TMPRSS2 Gene, Which Encodes a Novel Serine Protease with Transmembrane, LDLRA, and SRCR Domains and Maps to 21q22.3", et al., *Genomics*, 44:309-320 (1997).

Parmley et al., "Antibody-Selectable Filamentous fd Phage Vectors: Affinity Purification of Target Genes", *Genes*, 73:305-318 (1988).

Parodi et al., "Gabexate Mesilate, A New Synthetic Serine Protease Inhibitor: A Pilot Clinical Trial in Valvular Heart Surgery", *J. Cardiothorac. Vasc. Anesth.*, 10(2):235-237 (1996).

Paul et al., "Characterization of three transcriptional repressor sites within the 3' untranslated region of the rat serine protease inhibitor 2.3 gene", *Eur. J. Biochem.*, 254(3):538-546 (1998).

*PIERCE Catalog*, ImmunoTechnology Catalog & Handbook, 1992-1993.

Pinilla et al., "Review of the Utility of Soluble Combinatorial Libraries", *Biopolymers*, 37:221-240 (1995).

Pinilla et al., "Synthetic peptide combinatorial libraries (SPCLs)—identification of the antigenic determinant of beta-endorphin recognized by monoclonal antibody-3E7", *Gene*, 128:71-76 (1993).

Pinkert et al., "An albumin enhancer located 10 kb upstream functions along with its promoter to direct efficient, liver-specific expression in transgenic mice", *Genes & Development*, 1:268-276 (1987).

Pistor et al., "Expression of Viral Hemagglutinin On the Surface of *E. coli.*", *Klin. Wochenschr.*, 66:110-116 (1988).

Pittelkow et al., "New Techniques for the In Vitro Culture of Human Skin Keratinocytes and Perspectives on Their Use for Grafting Patients With Extensive Burns", *Mayo Clinic Proc.*, 61:771-777 (1986).

Pollack et al., "Selective Chemical Catalysis by an Antibody", *Science*, 234:1570-1573 (1986).

Powers et al., "Protein Purification by Affinity Binding to Unilamellar Vesicles", *Biotechnol. Bioengineering*, 33:173-182 (1989).

Press Release: Corvas Company, "Corvas Advances Anti-Cancer Drug Discovery Program on a New Family Of Membrane-Bound Serine Proteases", Feb. 7, 2002.

Press Release: Corvas Company, "Corvas International to Present at CIBC World Markets Health Care Conference", Nov. 1, 2001.

Press Release: Corvas Company, "Corvas International to Present at Salomon Smith Barney 2001 Health Care Conference", Oct. 25, 2001.

Press Release: Corvas Company, "Corvas International to Present at Techvest's 3rd Annual Healthcare Conference", Oct. 18, 2001.

Press Release: Corvas Company, "Corvas and Dyax Collaborate on Serine Protease Inhibitors; New Approach to Treat Cancer", Sep. 20, 2001.

Press Release: Corvas Company, "Corvas Presents 3-D Molecular Structure of Matriptase, First Structural Insight Into New Class of Protease Cancer Targets", Aug. 27, 2001.

Press Release: Corvas Company, "Corvas International to Present at UBS Warburg Global Life Sciences Conference", Oct. 3, 2001.

Press Release: Corvas Company, "Corvas International to Present at the 9th Annual Investing in Biotechnology Conference in London", Jul. 6, 2001.

Press Release: Corvas Company, "Corvas International to Present at BIO 2001", Jun. 22, 2001.

Press Release: Corvas Company, "Corvas International to Present at Wells Fargo Van Kasper Growth Stock Conference", Jun. 14, 2001.

Press Release: Corvas Company, "Abgenix and Corvas From Collaboration to Develop Therapeutic Antibodies Against Cancer", May 14, 2002.

Rabbani et al., "Prevention of Prostate-cancer Metastasis *In Vivo* by a Novel Synthetic Inhibitor of Urokinase-type Plasminogen Activator (uPA)", *Int. J. Cancer*, 63:840-845 (1995).

Rao et al., "Extracellular Matrix-Associated Serine Protease Inhibitors (M, 33,000, and 27, 2000) Are Single-Gene Products with Differential Glycosation: cDNA Cloning of the 33-kDa Inhibitor Reveals Its Identity to Tissue Factor Pathway Inhibitor-2", *Arch. Biochem. Biophys.*, 335(1):82-92 (1996).

Rao et al., "HT-1080 Fibrosarcoma Cell Matrix Degradation and Invasion are Inhibited by the Matrix-Associated Serine Protease Inhibitor TFPI-2/33 kDa MSPI", *Int. J. Cancer*, 76:749-756 (1998).

Ravichandran et al., "Cryocrystallography of a Kunitz-type serine inhibitor: the 90 K structure of winged bean chymotrypsin inhibitor (WCI) at 2.13 Å resolution", *Acta Cryst.*, D55:1814-1821 (1999).

Readhead et al., "Expression of a Myelin Basic Gene in Transgenic Shiverer Mice: Correction of the Dysmyelinating Phenotype", *Cell*, 48:703-712 (1987).

Rheinwald, "Serial Cultivation of Normal Human Epidermal Keratinocytes", Chapter 15, *Meth. Cell Biol.*, vol. 21, 21A:229-254 (1980).

Rigler et al., "Fluorescence Correlations, Single Molecule Detection and Large Number Screening: Applications in Biotechnology", *J. Biotechnol.*, 41:177-186 (1995).

Rizo et al., "Constrained Peptides: Models of Bioactive Peptides and Protein Substructures", *An. Rev. Biochem.*, 61:387-418 (1992).

Roberts et al., "Unusual Amino/Acids in Peptide Synthesis", *The Peptides. Analysis, Synthesis, Biology*, Chapter 6, 5:341-449 (1983).

Robinson, "Gene therapy—proceeding from laboratory to clinic", *TIBTECH*, 11(5):155-215 (1993).

Roch et al., "Characterization of a 14 kDa Plant-related Serine Protease Inhibitor and Regulation of Cytotoxic Activity in Earthworm Coelomic Fluid", *Dev. Comp. Immunol.*, 22(1):1-12 (1998).

Rosenfeld et al., "In Vivo Transfer of the Human Cystic Fibrosis Transmembrane Conductance Regulator Gene to the Airway Epithelium", *Cell*, 68:143-155 (1992).

Rosenfeld et al., "Adenovirus-mediated Transfer of a Recombinant α1-Antirypsin Gene to the Lung Epithelium in Vivo", *Science*, 252:431-434 (1991).

Rusbridge et al., "3,4-Dichloroisocoumarin, a serine protease inhibitor, inactivates glycogen phosphorylase *b*", *FEBS Lett.*, 268(1):133-136 (1990).

Ryo et al., "Treatment of Post-Transfusion Graft-versus-Host Disease with Nafmostat Mesilate, a Serine Protease Inhibitor", *Vox Sang.*, 76:241-246 (1999).

Salmons et al., "Targeting of Retroviral Vectors for Gene Therapy", *Human Gene Therapy*, 4:129-141 (1993).

Sambrook et al., "Molecular Cloning", *A Laboratory Manual*, 2d Ed., Cold Spring Harbor Laboratory Press, Cold Spring Harbor, New York (1989), vol. 3, p. B12-B14.

Sarin et al., "Inhibition of acquired immunodeficiency syndrome virus by oligodeoxynucleoside methylphosphonates", *Proc. Natl. Acad. Sci. USA* 85:7448-7451 (1988).

Sarver et al., "Ribozymes as Potential Anti-HIV-1 Therapeutic Agents", *Science*, 247:1222-1225 (1990).

Sarvetnick et al., "Increasing the Chemical Potential of the Germ-Line Antibody Repertoire", *Proc. Natl. Acad. Sci. USA*, 90:4008-4011 (1993).

Sastry et al., "Cloning of the immunological repertoire in *Escherichia coli* for generation of monoclonal catalytic antibodies: Construction of a heavy chain variable region-specific cDNA library", *Proc. Natl. Acad. Sci. USA*, 86:5728-5732 (1989).

Sawada et al., "Prevention of Neointimal Formation by a Serine Protease Inhibitor, FUT-175, After Carotid Balloon Injury in Rats", *Stroke*, 30(3):644-650 (1999).

Scalia et al., "Beneficial Effects of LEX032, A Novel Recombinant Serine Protease Inhibitor, in Murine Traumatic Shock", *Shock*, 4(4):251-256 (1995).

Schultz, et al., "The Combinatorial Library: A Multifunctional Resource", *Biotechnol. Prog.*, 12(6):729-743 (1996).

Scott et al., "Searching for Peptide Ligands with an Epitope Library", *Science*, 249:386-390 (1990).

Scott et al., "Random peptide libraries", *Curr. Opin. Biotechnol.*, 5:40-48 (1994).

Scuderi, "Suppression of Human Leukocyte Tumor Necrosis Factor Secretion by the Serine Protease Inhibitor $_p$-Toluenesulfonyl-L-Arginine Methyl Ester (Tame)", *J. Immunol.*, 143(1):168-173 (1989).

Sears et al., "Engineering Enzymes for Bioorganic Synthesis: Peptide Bond Formation", *Biotechnol. Prog.*, 12:423-433 (1996).

Sekar et al., "Specificity of the Serine Protease Inhibitor, Phenylmethylsulfonyl Fluoride", *Biochem. Biophys. Res. Commun.*, 89(2):474-478 (1979).

Senda et al., "Treatment of Ulcerative Colitis with Camostat Mesilate, A Serine Protease Inhibitor", *Intern. Med.*, 32(4):350-354 (1993).

Senter et al., "Novel Photocleavable Protein Crosslinking Reagents and Their Use in the Preparation of Antibody-Toxin Conjugates", *Photochem. Photobiol.*, 42(3):231-237 (1985).

Seto et al., "Central Effect of Aprotinin, a Serine Protease Inhibitor, on Blood Pressure in Spontaneously Hypertensive and Wistar-Kyoto Rats", *Adv. Exp. Med. Biol.*, 247B:49-54 (1989).

Seto et al., "The Effect of Aprotinin (A Serine Protease Inhibitor) on Renal Function and Renin Release", *Hypertension*, 5(6):893-899 (1983).

Shani, M., "Tissue-specific expression of rat myosin light-chain 2 gene in transgenic", *Nature*, 314:283-286 (1985).

Sharp, P.A., "RNA interference_2001", *Genes & Develop.*, 15:485-490 (2001).

Shilo et al., "DNA sequences homologous to vertebrate oncogenes are conserved in *Drosophila melanogaster*", *Proc. Natl. Acad. Sci.*, 78(11):6789-6792 (1981).

Shimomura et al., "Hepatocyte Growth Factor Activator Inhibitor, a Novel Kunitz-type Serine-Protease Inhibitor", *J. Biol. Chem.*, 272(10):6370-6376 (1997).

Shiozaki et al., "Effect of FUT-187, Oral Serine Protease Inhibitor, on Inflammation in the Gastric Remnant", *Jpn. J. Cancer Chemother.*, 23(14):1971-1979 (1996).

Shohet et al., "Inhibitor-Resistant Tissue-Type Plasminogen Activator: An Improved Thrombolytic Agent In Vitro", *Thromb. Haemost.*, 71(1):124-128 (1994).

Silverman et al., "New assay technologies for high-throughput screening", *Curr. Opin. Chem. Biol.*, 2(3):397-403 (1998).

Simar-Blanchet et al., "Regulation of expression of the rat serine protease inhibitor 2.3 gene by glucocorticoids and interleukin-6. A complex and unusual interplay between positive and negative cis-acting elements", *Eur. J. Biochem.*, 236(2):638-648 (1996).

Simon et al., "Peptides: A modular approach to drug discovery", *Proc. Natl. Acad Sci. USA*, 89:9367-9371 (1992).

Sittampalam et al., "High-throughput screening: advances in assay technologies", *Curr. Opin. Chem. Biol.*, 1:384-391 (1997).

Smith et al., "Protein Loop Grafting to Construct a Variant of Tissue-type Plasminogen Activator That Binds Platelet Integrin αIIbβ3", *J. Biol. Chem.*, 270(51):30489-30490 (1995).

Smith et al., "Single-step purification of polypeptides expressed in *Escherichia coli* as fusions with glutathione S-transferase", *Gene* 67:31-40 (1988).

Sonatore et al., "The Utility of FK506-Binding Protein as a Fusion Partner in Scintillation Proximity Assays: Application to SH2 Domains", *Anal. Biochem.*, 240:289-297 (1996).

Spatola et al., vol. 7, Chapter 5, "Peptide Backbone Modifications: A Structure-Activity Analysis of Peptides Containing Amide Bond Surrogates Conformational Constraints, and Rela", in *Chemistry and Biochemistry of Amino Acids, Peptides and Proteins*, (Weinstein, Ed.), Marcel Dekkar, New York (1983).

Stack et al., "Tissue-Type Plasminogen Activator", *Molecular Basis of Thrombosis and Hemostasis*, pp. 479-494, Marcel Dekker, Inc., New York.

Stankiewicz et al., "3' Noncoding sequences of the *CTA 1* gene enhance expression of the recombinant serine protease inhibitor, CPTI II, in *Saccharomyces cerevisiae*", *Acta Biochim. Pol.*, 43(3):525-529 (1996).

Steele et al., "Pigment epithelium-derived factor: Neurotrophic activity and identification as a member of the serine protease inhibitor gene family", *Proc. Natl. Acad. Sci. USA*, 90(4):1526-1530 (1993).

Stein et al., "Physicochemical properties of phosphorothioate oligodeoxynucleotides", *Nucl. Acids Res.* 16(8):3209-3221 (1988).

Stemple et al., "Isolaton of a Stem Cell for Neurons and Gila from the Mammalian Neural Crest", *Cell* 71:973-985 (1992).

Still, W.C, "Discovery of Sequence-Selective Peptide Binding by Synthetic Receptors Using Encoded Combinatorial Libraries", *Acc. Chem. Res.*, 29:155-163 (1996).

Strandberg et al., "Variants of Tissue-type Plasminogen Activator with Substantially Enhanced Response and Selectivity toward Fibrin Co-factors", *J. Biol. Chem.*, 270(40):23444-23449 (1995).

Sucholeiki, I., "Solid-Phase Photochemical C-S Bond Cleavage Of Thioethers-A New Approach To The Solid-Phase Production Of Non-Peptide Molecules", *Tetrahedron Lttrs.*, 35:7307-7310 (1994).

Sullivan et al., "Development of a Scintillation Proximity Assay for Calcineurin Phosphatase Activity", *J. Biomol. Screening*, 2:19-23 (1997).

Swift et al., "Tissue-Specific Expression of the Rat Pancreatic Elastase I Gene in Transgenic Mice", *Cell*, 38:639-646 (1984).

Tachias et al., "Variants of Tissue-type Plasminogen Activator That Display Extraordinary Resistance to Inhibition by the Serpin Plasminogen Activator Inhibitor Type 1", *J. Biol. Chem.*, 272(23):14580-14585 (1997).

Tachias et al., "Converting Tissue-type Plasminogen Activator into a Zymogen. Important Role Of Lys156", *J. Biol. Chem.*, 272(1):28-31 (1997).

Tachias et al., "Converting Tissue-type Plasminogen Activator into a Zymogen", *J. Biol. Chem.*, 271(46):28749-28752 (1996).

Tachias et al., "Variants of Tissue-type Plasminogen Activator Which Display Substantially Enhanced Stimulation by Fibrin", *J. Biol. Chem.*, 270(31):18319-18322 (1995).

Takeda et al., "Construction of chimaeric processed immunoglobulin genes containing mouse variable and human constant region sequences", *Nature*, 314:452-454 (1985).

Takeuchi et al., "Reverse biochemistry: Use of macromolecular protease inhibitors to dissect complex biological processes and identify a membrane-type serine protease in epithelial cancer and normal tissue", *Proc. Natl. Acad. Sci. USA*, 96:11054-11061 (1999).

Takeuchi et al., "Cellular Localization of Membrane-type Serine Protease 1 and Identification of Protease-activated Receptor-2 and Single-chain Urokinase-type Plasminogen Activator as Substrates", *J. Biol. Chem*, 275(34):26333-26342 (2000).

Tanimoto et al., "Hepsin, a Cell Surface Serine Protease Identified in Hepatoma Cells, Is Overexpressed in Ovarian Cancer", *Cancer Res.*, 57:2884-2887 (1997).

Thompson et al., "Synthesis and Applications of Small Molecule Libraries", *Chem. Rev.*, 96:555-600 (1996).

Tietze et al., "Domino reactions for library synthesis of small molecules in combinatorial chemistry", *Curr. Opin. Chem. Biol.*, 2(3):363-371 (1998).

Tolstoshev, "Gene Therapy, Concepts, Current Trials and Future Directions", *Annu. Rev. Pharmacol. Toxicol.*, 32:573-596 (1993).

Tomita et al., "A Novel Low-Density Lipoprotein Receptor-Related Protein with Type II Membrane Protein-Like Structure Is Abundant in Heart", *J. Biochem.*, 124:784-789 (1998).

Tramontano et al., "Catalytic Antibodies", *Science*, 234:1566-1569 (1986).

Treadwell et al., "Cartilage Synthesizes the Serine Protease Inhibitor PAI-1: Support for the Involvement of Serine Proteases in Cartilage Remodeling", *J. Orthop. Res.*, 9(3):309-316 (1991).

Tsutsui et al., "Cross-linking of Proteins to DNA in Newly Synthesized Chromatin By Diisopropylfluorophosphate. A Serine Protease Inhibitor", *Biochem. Biophys. Res. Commun.*, 123(1):271-277 (1984).

Tuschl, T., "RNA Interference and Small Interfering RNAs", *CHEMBIOCHEM*, 2:239-245 (2001).

Tyle, P., "Iontophoretic Devices for Drug Delivery", *Pharmaceutical Res.*, 3(6):318-326 (1986).

van der Krol et al., "Modulation of Eukaryotic Gene Expression by Complementary RNA or DNA Sequences", *BioTech.*, 6(10):958-976 (1988).

Veber et al., "The design of metabolically-stable peptide analogs", *TINS*, pp. 392-396 (1985).

Vedejs et al., "A Method for Mild Photochemical Oxidation Conversion of Phenacyl Sulfides into Carbonyl Compounds", *J. Org. Chem.*, 49:573-575 (1984).

Villa-Komaroff et al., "A bacterial clone synthesizing proinsulin", *Proc. Natl. Acad. Sci. USA*, 75(8):3727-3731 (1978).

Vu et al., "Identification and cloning of the Membrane-associated Serine Protease, Hepsin, from Mouse Preimplantation Embryos", *J. Biol. Chem.*, 272(50):31315-31320 (1997).

Wagner et al., "Nucleotide sequence of the thymidine kinase gene of herpes simplex virus type 1", *Proc. Natl. Acad. Sci. USA*, 78(3):1441-1445 (1981).

Wallrapp et al., "A Novel Transmembrane Serine Protease (TMPRSS3) Overexpressed in Pancreatic Cancer", *Cancer*, 60:2602-2606 (2000).

Walsh et al., "Gene Therapy for Human Hemoglobinopathies", *Proc. Soc. Exp. Biol. Med.*, 204:289-300 (1993).

Wang et al., "Rapid Detection of the Two Common Mutations in Ashkenazi Jewish Patients with Mucolipidosis Type IV", *Genetic Testing*, 5(2):87-92 (2001).

Wang, S., "Solid Phase Synthetic of Protected Peptides via Photolytic Cleavage of the α-Methylphenacyl Ester Anchoring Linkage", *J. Org. Chem.*, 41(20):3258-3261 (1976).

Warren et al., "Spi-1: an hepatic serine protease inhibitor regulated by GH and other hormones", *Mol. Cell Endocrinol.*, 98(1):27-32 (1993).

Watson et al., "The Fine Structure of Bacterial and Phage Genes", Book: *Molecular Biology of the Gene*, 4th Ed., The Benjamin/ Cummings Pub. Co., 1:224 (1987).

Weaner et al., "Tritium Labeling Of N-Protected Amino Acids and Peptides Containing O-Alkyl-Tyrosyl Residues", Paper 22, *Synthesis and Applications of Isotopically Labelled Compounds*, Allen J., Ed., pp. 137-140 (1994).

Webber et al., "Prostate-specific Antigen, a Serine Protease, Facilitates Human Prostate Cancer Cell Invasion", *Clin Cancer Res.*, 1:1089-1094 (1995).

Wellhöner et al., "Uptake and Concentration of Bioactive Macromolecules by K562 Cells via the Transferrin Cycle Utilizing an Acid-labile Transferrin", *J. Biol. Chem.*, 266(7):4309-4314 (1991).

Werner et al., "Identification of a Protein-binding Surface by Differential Admide Hydrogen-exchange Measurements", *J. Mol. Biol.*, 225:873-889 (1992).

Whitlock et al., "Long-term culture of B lymphocytes and their precursors from murine bone marrow", *Proc. Natl. Acad. Sci. USA*, 79:3608-3612 (1982).

Whitlow et al., "An improved linker for single-chain Fv with reduced aggregation and enhanced proteolytic stability", *Protein Engineering*, 6(8):989-995 (1993).

Woodard et al., "Chymase-Directed Serine Protease Inhibitor That Reacts with a Single 30-kDa Granzyme and Blocks NK-Mediated Cytotoxicity", *J. Immunol.*, 153:5016-5025 (1994).

Wong, S.S., Book: Chapter 12, "Conjugation of Proteins to Solid Matrices", *Chemistry of Protein Conjugation and Cross Linking*, CRC Press, Inc., pp. 295-317 (1993).

Wrighton et al., "Small Peptides as Potent Mimetics of the Protein Hormone Erythroprotein", *Science*, 273:458-463 (1996).

Wu et al., "Delivery systems for gene therapy", *Biotherapy*, 3:87-95 (1991).

Wu et al., "Receptor-mediated *in Vitro* Gene Transformation by a Soluble DNA Carrier System", *J. Biol. Chem.*, 262(1):4429-4432 (1987).

Xing et al., "Prevention of Breast Cancer Growth, Invasion, and Metastasis by Antiestrogen Tamoxifen Alone or in Combination with Urokinase Inhibitor B-428", *Canc. Res.*, 57:3585-3593 (1997).

Xu et al., "The Crystal Structure of Bikunin from the Inter-α-Inhibitor Complex: A Serine Protease Inhibitor with Two Kunitz Domains", *J. Mol. Biol.*, 276(5):955-966 (1998).

Yahagi et al., "Complementary DNA Cloning and Sequencing of Rat Enteropeptidase and Tissue Distribution of Its mRNA", *Biochem. Biophys. Res. Commun.*, 219:806-812 (1996).

Yamamoto et al., "Identification of a Functional Promoter in the Long Terminal Repeat of Rous Sarcoma Virus", *Cell*, 22:787-797 (1980).

Yamaoka et al., "Cloning and Characterization of the cDNA for Human Airway Trypsin-like Protease", *J. Biol. Chem.*, 273(19):11895-11901 (1998).

Yamauchi et al., "Anti-Carinogenic Effects of a Serine Protease Inhibitor (FOY-305) through the Suppression of Neutral Serine Protease Activity During chemical Hepatocarcinogenesis in Rats", *Hiroshima J. Med. Sci.*, 36(1):81-87 (1987).

Yan et al., "Corin, a Mosaic Transmembrane Serine Protease Encoded by a Novel cDNA from Human Heart", *J. Biol. Chem.*, 274(21):14926-14935 (1999).

Yan et al., "Corin, a transmembrane cardiac serine protease, acts as a pro-atrial natriuretic peptide-converting enzyme", *PNAS*, 97(15):8525-8529 (2000).

Yanamoto et al., "Preventive Effect of Synthetic Serine Protease Inhibitor, FUT-175, on Cerebral Vasospasm in Rabbits", *Neurosurgery*, 30(3):351-357 (1992).

Yanamoto et al., "Therapeutic Trial of Cerebral Vasospasm with the Serine Protease Inhibitor, FUT-175, Administered in the Acute Stage after Subarachnoid Hemorrhage", *Neurosurgery*, 30(3):358-363 (1992).

Yang et al., "Ecotin: A Serine Protease Inhibitor with Two Distinct and Interacting Binding Sites", *J. Mol. Biol.*, 279:945-957 (1998).

Yen et al., "Synthesis of water-soluble copolymers containing photocleavable bonds", *Makromol. Chem.*, 190:69-82 (1989).

Yi et al., "Bikunin, a Serine Protease Inhibitor, is Present on the Cell Boundary of Epidermis", *J. Invest. Dermatol.*, 113(2):182-188 (1999).

York et al., "Combinatorial Mutagenesis of the Reactive Site Region in Plasminogen Activator Inhibitor I", *J. Biol. Chem.*, 266(13):8495-8500 (1991).

Yu et al., "Message of nexin 1, a serine protease inhibitor, is accumulated in the follicular papilla during anagen of the air cycle", *J. Cell Sci.*, 108:3867-3874 (1995).

Zallipsky, "Functionalized Poly(ethylene glycol) for Preparation of Biologically Relevant Conjugates", *Bioconjugate Chem.*, 6:150-165 (1995).

Zamore et al., "RNAi: Double-Stranded RNA Directs the ATP-Dependent Cleavage of mRNA at 21 to 23 Nucleotide Intervals", *Cell*, 101:25-33 (2000).

Zebedee et al., "Human Combinatorial Antibody Libraries to Hepatitis B Surface Antigen", *Proc. Natl. Acad. Sci. USA*, 89:3175-3179 (1992).

Zhang et al., "Distinct Contributions of Residue 192 to the Specificity of Coagulation and Fibrinolytic Serine Proteases", *J. Biol. Chem.*, 274(11):7153-7156 (1999).

Zhang et al., "Modeling *Pichia pastoris* Growth on Methanol and Optimizing the Production of a Recombinant Protein, the Heavy-Chain Fragment C of Botulinum Neurotoxin, Serotype A", *Biotechnol Bioengineering*, 70(1):1-8 (2000).

Zhou et al., "The Vaccinia Virus K2L Gene Encodes a Serine Protease Inhibitor Which Inhibits Cell-Cell Fusion", *Virology*, 189:678-686 (1992).
Zijlstra et al., "Germ-line transmission of a disrupted $\beta_2$-microglobulin gene produced by homologous recombination in embryonic stem cells", *Nature*, 342:435-438 (1989).
Zon, "Oligonucleotide Analogues as Potential Chemotherapeutic Agents", *Pharm. Res.*, 5(9):539-549 (1988).
Zuckermann et al., "Efficient Method for the Preparation of Peptoids [Oligo(N-substituted glycines)] by Submonomer Solid-Phase Synthesis", *J. Am. Chem. Soc.*, 114:10646-10647 (1992).
Zuckermann et al., "Identification of Highest-Affinity Ligands by Affinity Selection from Equimolar Peptide Mixtures Generated by Robotic Synthesis", *Proc. Natl. Acad. Sci. USA*, 89:4505-4509 (1992).
Bergstrom et al., "Binding of nonphysiological protein and peptide substrates to proteases: differences between urokinase-type plasminogen activator and trypsin and contributions to the evolution of regulated proteolysis", *Biochem.*, 42:5395-402 (2003).
U.S. Appl. No. 60/257,495, filed Dec. 21, 2000, Zerhusen et al.
Bork, P., "Powers and Pitfalls in Sequence Analysis: the 70% Hurdle," *Genome Research* 10:398-400 (2000).
Broun et al., "Catalytic Plasticity of Fatty Acid Modification Enzymes Underlying Chemical Diversity of Plant Lipids," *Science* 282:1315-1317 (1998).
Bryan, Philip N., "Protein engineering of subtilisin," *Biochimica et Biophysica Acta 1543*:203-222 (2000).
Lu et al., "Crystal Structure of Enteropeptide Light Chain Complexed with an Analog of the Trypsinogen Activation Peptide," *J. Mol. Biol.*, 292:361-373 (1999).
Ngo et al. "Computational Complexity, Protein Structure Prediction, and the Levinthan Paradox," Chapter 14 in *The Protein folding problem and tertiary structure prediction* Kenneth M. Merz, Jr. and Scott M. Le Grand (Eds.) Boston: Birkhäuser pp. 433-506 (1994).
Nienaber et al., "Re-engineering of Human Urokinase Provides a System for Structure-based Drug Design at High Resolution and Reveals a Novel Structural Subsite," *The Journal of Biological Chemistry*, 275 (10):7239-7248 (2000).
Sommerhoff, et al., "The structure of the human βII-tryptase tetramer: fo(u)r better or worse," *Proc Natl Acad Sci U.S.A.*, 96:10984-10991 (1999).
Van de Loo et al., "An oleate 12-hydroxylase from *Ricinus communis* L. is a fatty acyl desaturase homolog," *Proc. Natl. Acad. Sci. USA 92*:6743-6747 (1995).
Venekei et al., "Attempts to convert chymotrypsin to trypsin," *FEBS Letters 379*, 143-147 (1996).
Wikowski et al, "Conversion of a β-Ketoacyl Synthase to a Malonyl Decarboxylase by Replacement of the Active-Site Systeine with Glutamine," *Biochemistry 38*:11643-11650 (1999).
Xu et al., "Mutational Analysis of the Primary Substrate Specificity Pocket of Complement Factor B," *The Journal of Biological Chemistry*, 275 (1):378-385 (2000).
Altschul et al., "Basic Local Alignment Search Tool," *Journal of Molecular Biology*. 215: 403-410 (1990).
Atwell et al., "Selection for improved subtiligases by phage display," *Proceedings of the National Academy of Sciences USA 96*:9497-9502 (1999).
Bachovchin et al., "Catalytic mechanism of serine proteases: Reexamination of the pH dependence of the histidyl $^1J_{13C2-H}$ coupling constant in the catalytic triad of α-lytic protease," *Proceedings of the National Academy of Sciences 78*:7323-7326 (1981).

Benaud et al., "Regulation of the activity of matripase on epithelial cell surfaces by a blood-derived factor," *Eur. J. Biochem. 268*:1439-1447 (2001).

Carter et al., "Dissecting the catalytic triad of a serine protease," *Nature 332*:564-568 (1988).

Cheah et al., "Site-directed Mutagenesis Suggests Close Functional Relationship between a Human Rhinovirus 3C Cysteine Protease and Cellular Trypsine Proteases," *Journal of Biological Chemistry 265*:7180-7187 (1990).

Craik et al., "The Catalytic Role of the Active Site Aspartic Acid in Serine Proteases," *Science 237*:909-913 (1987).

Devereux et al., "A comprehensive set of sequence analysis programs for the VAX", *Nucleic Acids Research 12*(1):387-395 (1984).

Koshikawa et al. "Identification of one- and two-chain forms of trypsinogen 1 produced by a human gastric adenocarcinoma cell line," *Biochem. J. 303*:187-190 (1994).

Lu et al. "Bovine proenteropeptidase is activated by trypsin, and the specificity of enteropeptidase depends on the heavy chain," *J. Biol. Chem. 272*:31293-31300 (1997).

Pearson et al., "Improved Tools for Biological Sequence Comparison," *Proceedings of the National Academy of Sciences USA 85*:2444-2448 (1988).

Pearson et al., "Identifying distantly related protein sequences", *CABIOS Invited Review 13*(4):325-332 (1997).

Sprang et al., "The Three-Dimensional Structure of $Asn^{102}$ Mutant of Trypsin: Role of $Asp^{102}$ in Serine Protease Catalysis," *Science 237*:905-909 (1987).

Wells et al., "Designing substrate specificity by protein engineering of electrostatic interactions," *Proceedings of the National Academy of Sciences 84*:1219-1223 (1987).

\* cited by examiner

NUCLEIC ACID MOLECULES ENCODING SERINE PROTEASE CVSP14, THE ENCODED POLYPEPTIDES AND METHODS BASED THEREON

RELATED APPLICATIONS

Benefit of priority under 35 U.S.C. §119(e) is claimed to U.S. provisional application Ser. No. 60/278,166, filed Mar. 22, 2001, to Edwin L. Madison and Jiunn-Chern Yeh entitled "NUCLEIC ACID MOLECULES ENCODING A TRANSMEMBRANE SERINE PROTEASE 14, THE ENCODED PROTEINS AND METHODS BASED THEREON." The subject matter of this application is incorporated in its entirety by reference thereto.

FIELD OF INVENTION

Nucleic acid molecules that encode proteases and portions thereof, particularly protease domains are provided. Also provided are prognostic, diagnostic and therapeutic methods using the proteases and domains thereof and the encoding nucleic acid molecules.

BACKGROUND OF THE INVENTION AND OBJECTS THEREOF

Cancer is a leading cause of death in the United States, developing in one in three Americans; one of every four Americans dies of cancer. Cancer is characterized by an increase in the number of abnormal neoplastic cells, which proliferate to form a tumor mass, the invasion of adjacent tissues by these neoplastic tumor cells, and the generation of malignant cells that metastasize via the blood or lymphatic system to regional lymph nodes and to distant sites.

Among the hallmarks of cancer is a breakdown in the communication among tumor cells and their environment. Normal cells do not divide in the absence of stimulatory signals, and cease dividing in the presence of inhibitory signals. Growth-stimulatory and growth-inhibitory signals are routinely exchanged between cells within a tissue. In a cancerous, or neoplastic, state, a cell acquires the ability to "override" these signals and to proliferate under conditions in which normal cells do not grow.

In order to proliferate tumor cells acquire a number of distinct aberrant traits reflecting genetic alterations. The genomes of certain well-studied tumors carry several different independently altered genes, including activated oncogenes and inactivated tumor suppressor genes. Each of these genetic changes appears to be responsible for imparting some of the traits that, in the aggregate, represent the full neoplastic phenotype.

A variety of biochemical factors have been associated with different phases of metastasis. Cell surface receptors for collagen, glycoproteins such as laminin, and proteoglycans, facilitate tumor cell attachment, an important step in invasion and metastases. Attachment triggers the release of degradative enzymes which facilitate the penetration of tumor cells through tissue barriers. Once the tumor cells have entered the target tissue, specific growth factors are required for further proliferation. Tumor invasion and progression involves a complex series of events, in which tumor cells detach from the primary tumor, break down the normal tissue surrounding it, and migrate into a blood or lymphatic vessel to be carried to a distant site. The breaking down of normal tissue barriers is accomplished by the elaboration of specific enzymes that degrade the proteins of the extracellular matrix that make up basement membranes and stromal components of tissues.

A class of extracellular matrix degrading enzymes have been implicated in tumor invasion. Among these are the matrix metalloproteinases (MMP). For example, the production of the matrix metalloproteinase stromelysin is associated with malignant tumors with metastatic potential (see, e.g., McDonnell et al. (1990) *Smnrs. in Cancer Biology* 1:107–115; McDonnell et al. (1990) *Cancer and Metastasis Reviews* 9:309–319).

The capacity of cancer cells to metastasize and invade tissue is facilitated by degradation of the basement membrane. Several proteinase enzymes, including the MMPs, have been reported to facilitate the process of invasion of tumor cells. MMPs are reported to enhance degradation of the basement membrane, which thereby permits tumorous cells to invade tissues. For example, two major metalloproteinases having molecular weights of about 70 kDa and 92 kDa appear to enhance ability of tumor cells to metastasize.

Serine Proteases

Serine proteases (SPs) have been implicated in neoplastic disease progression. Most serine proteases, which are either secreted enzymes or are sequestered in cytoplasmic storage organelles, have roles in blood coagulation, wound healing, digestion, immune responses and tumor invasion and metastasis. A class of cell surface proteins designated type II transmembrane serine proteases, which are membrane-anchored proteins with additional extracellular domains, has been identified. As cell surface proteins, they are positioned to play a role in intracellular signal transduction and in mediating cell surface proteolytic events. Other serine proteases can be membrane bound and function in a similar manner. Others are secreted. Many serine proteases exert their activity upon binding to cell surface receptors, and, hence act at cell surfaces. Cell surface proteolysis is a mechanism for the generation of biologically active proteins that mediate a variety of cellular functions.

Serine proteases, including secreted and transmembrane serine proteases, have been implicated in processes involved in neoplastic development and progression. While the precise role of these proteases has not been elaborated, serine proteases and inhibitors thereof are involved in the control of many intra- and extracellular physiological processes, including degradative actions in cancer cell invasion, metastatic spread, and neovascularization of tumors, that are involved in tumor progression. It is believed that proteases are involved in the degradation of extracellular matrix (ECM) and contribute to tissue remodeling, and are necessary for cancer invasion and metastasis. The activity and/or expression of some proteases have been shown to correlate with tumor progression and development.

For example, a membrane-type serine protease MTSP1 (also called matriptase; see SEQ ID Nos. 1 and 2 from U.S. Pat. No. 5,972,616; and GenBank Accession No. AF118224; (1999) *J. Biol. Chem.* 274:18231–18236; U.S. Pat. No. 5,792,616; see, also Takeuchi (1999) *Proc. Natl. Acad. Sci. U.S.A.* 96:11054–1161) that is expressed in epithelial cancer and normal tissue (Takeucuhi et al. (1999) *Proc. Natl. Acad. Sci. USA* 96:11054–61) has been identified. Matriptase was originally identified in human breast cancer cells as a major gelatinase (see, U.S. Pat. No. 5,482,848), a type of matrix metalloprotease (MMP). It has been proposed that it plays a role in the metastasis of breast cancer. Matriptase also is expressed in a variety of epithelial tissues with high levels of activity and/or expression in the human gastrointestinal tract and the prostate. MTSPs, designated MTSP3, MTSP4, MTSP6 have been decribed in published International PCT application No. WO 01/57194, based in International PCT application No. PCT/US01/03471.

Prostate-specific antigen (PSA), a kallikrein-like serine protease, degrades extracellular matrix glycoproteins fibronectin and laminin, and, has been postulated to facilitate invasion by prostate cancer cells (Webber et al. (1995) *Clin. Cancer Res.* 1:1089–94). Blocking PSA proteolytic activity with PSA-specific monoclonal antibodies results in a dose-dependent decrease in vitro in the invasion of the reconstituted basement membrane Matrigel by LNCaP human prostate carcinoma cells which secrete high levels of PSA.

Hepsin, a cell surface serine protease identified in hepatoma cells, is overexpressed in ovarian cancer (Tanimoto et al. (1997) *Cancer Res.*, 57):2884–7). The hepsin transcript appears to be abundant in carcinoma tissue and is almost never expressed in normal adult tissue, including normal ovary. It has been suggested that hepsin is frequently overexpressed in ovarian tumors and therefore can be a candidate protease in the invasive process and growth capacity of ovarian tumor cells.

A serine protease-like gene, designated normal epithelial cell-specific 1 (NES1) (Liu et al., *Cancer Res.*, 56:3371–9 (1996)) has been identified. Although expression of the NES1 mRNA is observed in all normal and immortalized nontumorigenic epithelial cell lines, the majority of human breast cancer cell lines show a drastic reduction or a complete lack of its expression. The structural similarity of NES1 to polypeptides known to regulate growth factor activity and a negative correlation of NES1 expression with breast oncogenesis suggest a direct or indirect role for this protease-like gene product in the suppression of tumorigenesis.

Hence transmembrane and other serine proteases and other proteases appear to be involved in the etiology and pathogenesis of tumors. There is a need to further elucidate their role in these processes and to identify additional transmembrane proteases. Therefore, it is an object herein to provide serine protease proteins and nucleic acids encoding such proteases that are involved in the regulation of or participate in tumorigenesis and/or carcinogenesis. It is also an object herein to provide prognostic, diagnostic, therapeutic screening methods using such proteases and the nucleic acids encoding such proteases.

SUMMARY OF THE INVENTION

Provided herein is a protein designated CVSP14, including the protease domain thereof (see, e.g., SEQ ID Nos. 5, 6, 12 and 13). CVSP14 is a secreted serine protease. CVSP14 is highly expressed in androgen-independent prostate tumors and is expressed in other tumors. Hence, as a protease it can be involved in tumor progression. By virtue of its functional activity it can be a therapeutic or diagnostic target. The expression and/or activation (or reduction in level of expression or activation) of the expressed protein or zymogen form thereof can be used to monitor cancer and cancer therapy. For example, the expression of the this protein can be used to monitor prostate cancer and prostate cancer therapy.

The serine protease family includes members that are activated and/or expressed in tumor cells at different levels from non-tumor cells; and those from cells in which substrates therefor differ in tumor cells from non-tumor cells or otherwise alter the specificity or activity of the serine protease (SP). The serine protease provided herein, designated herein as CVSP14, is a secreted protease. The protease domain and full-length protein, including the zymogen and activated forms, and uses thereof are also provided. Proteins encoded by splice variants are also provided. Nucleic acid molecules encoding the proteins and protease domains are also provided. The protease domain of a CVSP14 is set forth in SEQ ID No. 6; the sequence of a full length protein is set forth in SEQ ID No. 13. The sequences of encoding nucleic acid molecules are set forth in SEQ ID Nos. 5 and 12, respectively.

CVSP14 is expressed as a secreted protein and may bind to cell surface receptors and function as a cell-surface bound protease, such as by binding thereto or by dimerization or multimerization with a membrane-bound or receptor-bound protein.

Also provided herein are nucleic acid molecules that encode SP proteins and the encoded proteins. In particular, nucleic acid molecules encoding CVSP14 from animals, including splice variants thereof are provided. The encoded proteins are also provided. Also provided are functional domains thereof. For example, the SP protease domains, portions thereof, and muteins thereof are from or based on animal SPs, including, but are not limited to, rodent, such as mouse and rat; fowl, such as chicken; ruminants, such as goats, cows, deer, sheep; ovine, such as pigs; and humans.

The protease domain for use in the methods and assay provided herein does not have to result from activation, which produces a two chain activated product, but rather is a single chain polypeptide where the N-terminus includes the sequence ↓ILGG. Such polypeptides, although not the result of activation and not two-chain forms, exhibit proteolytic (catalytic) activity. These protease domain polypeptides are used in assays to screen for agents that modulate the activity of the CVSP14.

Such assays are also provided herein. In exemplary assays, the effects of test compounds on the ability of the full length or along at least about 70%, 80% or 90% of the full length of the single chain, two chain activated form, or a protease domain, which is a single chain or a two chain activated form, of CVSP14 to proteolytically cleave a known substrate, typically a fluorescently, chromogenically or otherwise detectably labeled substrate, are assessed. Agents, generally compounds, particularly small molecules, that modulate the activity of the protein (full length or protease domain either single or two chain forms thereof) are candidate compounds for modulating the activity of the CVSP14. The protease domains and full length proteins also can be used to produce two-chain and single-chain protease-specific antibodies. The protease domains provided herein include, but are not limited to, the single chain region having an N-terminus at the cleavage site for activation of the zymogen, through the C-terminus, or C-terminal truncated portions thereof that exhibit proteolytic activity as a single-chain polypeptide in in vitro proteolysis assays, of any family member, including CVSP14, such as from a mammal, including human, that, for example, is expressed or activity in tumor cells at different levels from non-tumor cells.

Also provided are muteins of the single chain protease domain of CVSP14 particularly muteins in which the Cys residue (residue no. 26 in SEQ ID No. 6) in the protease domain that is free (i.e., does not form disulfide linkages with any other Cys residue in the protease domain) is substituted with another amino acid substitution, generally with a substitution that does not eliminate the activity of interest, and muteins in which a glycosylation site(s) is eliminated. Muteins in which other substitutions in which catalytic activity is retained are also contemplated (see, e.g., Table 1, for exemplary amino acid substitutions).

Hence, provided herein is a member of the family of serine proteases designated CVSP14, and functional domains, especially protease (or catalytic) domains thereof, muteins and other derivatives and analogs thereof. Also provided herein are nucleic acids encoding the CVSP14.

The nucleic acid and amino acid sequences of CVSP14 are set forth in SEQ ID Nos. 5 and 6. Nucleic acid molecules that encode a single-chain protease domain or catalytically active portion thereof and also those that encode the full-length CVSP14 (SEQ ID Nos. 12 and 13) are provided. Single amino acid changes are contemplated; for example peptides in which there is an Arg in place of a Gly are provided. Nucleic acid molecules that encode a single-chain protease domain or catalytically active portion thereof and also those that encode the full-length CVSP14 are provided. Also provided are nucleic acid molecules that hybridize to such CVSP14 encoding nucleic acid along their full length or along at least about 70%, 80% or 90% of the full length and encode the full length or a truncated portion thereof, such as without the signal sequence or a protease domain or catalytically active portion thereof are provided. Hybridization is typically performed under conditions of at least low, generally at least moderate, and often high stringency.

Additionally provided herein are antibodies that specifically bind to the CVSP14 and inhibit the activity thereof. Included are antibodies that specifically bind to the protein or protease domain, including to the single and/or two chain forms thereof. Among the antibodies are two-chain-specific antibodies, and single-chain specific antibodies and neutralizing antibodies. Antibodies that specifically bind to the CVSP14, particularly the single chain protease domain, the zymogen and activated form are also provided herein. Antibodies that specifically bind to the two-chain and/or single-chain form of CVSP14 are provided. The antibodies include those that specifically bind to the two-chain or single-chain form of the protease domain and/or the full-length protein.

Further provided herein are prognostic, diagnostic, therapeutic screening methods using CVSP14 and the nucleic acids encoding CVSP14. Also provided are transgenic non-human animals bearing inactivated genes encoding the CVSP and bearing the genes encoding the CVSP14 under non-native or native promotor control are provided. Such animals are useful in animal models of tumor initiation, growth and/or progression models.

Provided herein are members of a family of serine proteases (SPs) that are expressed in certain tumor or cancer cells such lung, prostate, colon and breast cancers. In particular, it is shown herein, that CVSP14 is expressed in lung carcinoma, leukemia and cervical carcinoma as well as in certain normal cells and tissues (see e.g., EXAMPLES for tissue-specific expression profile). CVSP14 can also be a marker for breast, prostate and colon cancer.

SPs are of interest because they appear to be expressed and/or activated at different levels in tumor cells from normal cells, or have functional activity that is different in tumor cells from normal cells, such as by an alteration in a substrate therefor, or a cofactor. CVSP14 is of interest because it is expressed or is active in tumor cells. Hence the CVSP14 provided herein can serve as diagnostic markers for certain tumors. The level of activated CVSP14 can be diagnostic of prostate, uterine, lung or colon cancer or leukemia or other cancer.

Also provided herein are methods of modulating the activity of the CVSP14 and screening for compounds that modulate, including inhibit, antagonize, agonize or otherwise alter the activity of the CVSP14. Of particular interest is the protease domain of CVSP14 that includes the catalytic portion of the protein.

CVSP14 polypeptides, including, but not limited to splice variants thereof, and nucleic acids encoding CVSPs, and domains, derivatives and analogs thereof are provided herein. Single chain protease domains that contain the N-terminii that are generated by activation of the zymogen form of CVSP14 are also provided. The cleavage site for the protease domain is at amino acid 52 (R↓IGGS)(see SEQ ID Nos. 12 and 13).

Also provided are plasmids containing any of the nucleic acid molecules provided herein. Cells containing the plasmids are also provided. Such cells include, but are not limited to, bacterial cells, yeast cells, fungal cells, plant cells, insect cells and animal cells. In addition to cells and plasmids containing nucleic acid encoding the CVSP14 polypeptide, methods of expression of the encoded polypeptide are provided. In order to achieve expression of the protease domain, the nucleic acid encoding the signal sequence is removed. The protein is expressed in the inclusion bodies. The CVSP14 protease domain was then isolated from the inclusion bodies and treated under conditions whereby proper refolding occurred. Hence also provided are methods for producing active CVSP14 protease domain.

Also provided is a method of producing CVSP14 by growing the above-described cells under conditions whereby the CVSP14 is expressed by the cells, and recovering the expressed CVSP14 polypeptide. Methods for isolating nucleic acid encoding other CVSP14s are also provided.

Also provided are cells, generally eukaryotic cells, such as mammalian cells and yeast cells, in which the CVSP14 polypeptide is expressed by the cells. Such cells to which the secreted protein can bind are used in drug screening assays to identify compounds that modulate the activity of the CVSP14 polypeptide. These assays include in vitro binding assays, and transcription based assays in which signal transduction mediated directly or indirectly, such as via activation of pro-growth factors, by the CVSP14 or cleavage products thereof is assessed.

Further provided herein are prognostic, diagnostic and therapeutic screening methods using the CVSP14 and the nucleic acids encoding CVSP14. In particular, the prognostic, diagnostic and therapeutic screening methods are used for preventing, treating, or for finding agents useful in preventing or treating, tumors or cancers such as lung carcinoma, colon adenocarcinoma and ovarian carcinoma.

Also provided are methods for screening for compounds that modulate the activity of CVSP14. The compounds are identified by contacting them with the CVSP14 or protease domain thereof and a substrate for the CVSP14. A change-in the amount of substrate cleaved in the presence of the compounds compared to that in the absence of the compound indicates that the compound modulates the activity of the CVSP14. Such compounds are selected for further analyses or for use to modulate the activity of the CVSP14, such as inhibitors or agonists. The compounds also can be identified by contacting the substrates with a cell that binds to a CVSP14 or catalytically active portion thereof.

Also provided herein are modulators of the activity of CVSP14, especially the modulators obtained according to the screening methods provided herein. Such modulators can have use in treating cancerous conditions and other neoplastic conditions.

Pharmaceutical composition containing the protease domain and/or full-length or other domain of a CVSP14 polypeptide are provided herein in a pharmaceutically acceptable carrier or excipient are provided herein.

Also provided are articles of manufacture that contain CVSP14 polypeptide and protease domains of CVSP14 in single chain forms or activated forms. The articles contain a) packaging material; b) the polypeptide (or encoding nucleic acid), particularly the single chain protease domain thereof; and c) a label indicating that the article is for using in assays for identifying modulators of the activities of a CVSP14 polypeptide is provided herein.

Conjugates containing a) a CVSP14 polypeptide or protease domain in single chain from; and b) a targeting agent linked to the CVSP directly or via a linker, wherein the agent facilitates: i) affinity isolation or purification of the conjugate; ii) attachment of the conjugate to a surface; iii) detection of the conjugate; or iv) targeted delivery to a selected tissue or cell, is provided herein. The conjugate can contain a plurality of agents linked thereto. The conjugate can be a chemical conjugate; and it can be a fusion protein.

In another embodiment, the targeting agent is a protein or peptide fragment. The protein or peptide fragment can include a protein binding sequence, a nucleic acid binding sequence, a lipid binding sequence, a polysaccharide binding sequence, or a metal binding sequence.

Methods of diagnosing a disease or disorder characterized by detecting an aberrant level of a CVSP14 in a subject is provided. The method can be practiced by measuring the level of the DNA, RNA, protein or functional activity of the CVSP14. An increase or decrease in the level of the DNA, RNA, protein or functional activity of the CVSP, relative to the level of the DNA, RNA, protein or functional activity found in an analogous sample not having the disease or disorder (or other suitable control) is indicative of the presence of the disease or disorder in the subject or other relative any other suitable control.

Combinations are provided herein. The combination can include: a) an inhibitor of the activity of a CVSP14; and b) an anti-cancer treatment or agent. The CVSP inhibitor and the anti-cancer agent can be formulated in a single pharmaceutical composition or each is formulated in a separate pharmaceutical composition. The CVSP14 inhibitor can be an antibody or a fragment or binding portion thereof made against the CVSP14, such as an antibody that specifically binds to the protease domain, an inhibitor of CVSP14 production, or an inhibitor of CVSP14 membrane-localization or an inhibitor of CVSP14 activation. Other CVSP14 inhibitors include, but are not limited to, an antisense nucleic acid or double-stranded RNA (dsRNA), such as RNAi, encoding the CVSP14 or portions thereof, particularly a portion of the protease domain, a nucleic acid encoding at least a portion of a gene encoding the CVSP14 with a heterologous nucleotide sequence inserted therein such that the heterologous sequence inactivates the biological activity encoded CVSP14 or the gene encoding it. The portion of the gene encoding the CVSP14 typically flanks the heterologous sequence to promote homologous recombination with a genomic gene encoding the CVSP14.

Also, provided are methods for treating or preventing a tumor or cancer in a mammal by administering to a mammal an effective amount of an inhibitor of a CVSP14, whereby the tumor or cancer is treated or prevented. The CVSP14 inhibitor used in the treatment or for prophylaxis is administered with a pharmaceutically acceptable carrier or excipient. The mammal treated can be a human. The treatment or prevention method can additionally include administering an anti-cancer treatment or agent simultaneously with or subsequently or before administration of the CVSP14 inhibitor.

Also provided is a recombinant non-human animal in which an endogenous gene of a CVSP14 has been deleted or inactivated by homologous recombination or other recombination events or insertional mutagenesis of the animal or an ancestor thereof. A recombinant non-human animal is provided herein, where the gene of a CVSP14 is under control of a promoter that is not the native promoter of the gene or that is not the native promoter of the gene in the non-human animal or where the nucleic acid encoding the CVSP14 is heterologous to the non-human animal and the promoter is the native or a non-native promoter or the CVSP14 is on an extrachromosomal element, such as a plasmid or artificial chromosome. Transgenic non-human animals bearing the genes encoding the CVSP14 and bearing inactivated genes encoding CVSP14, particularly under a non-native promotor control or on an exogenous element, such as a plasmid or artificial chromosome, are additionally provided herein.

Also provided are methods of treatments of tumors by administering a prodrug that is activated by CVSP14 that is expressed or active in tumor cells, particularly those in which its functional activity in tumor cells is greater than in non-tumor cells. The prodrug is administered and, upon administration, active CVSP14 cleaves the prodrug and releases active drug in the vicinity of the tumor cells. The active anti-cancer drug accumulates in the vicinity of the tumor. This is particularly useful in instances in which CVSP14 is expressed or active in greater quantity, higher level or predominantly in tumor cells compared to other cells.

Also provided are methods of identifying a compound that binds to the single-chain or two-chain form of CVSP14, by contacting a test compound with a both forms; determining to which form the compound binds; and if it binds to a form of CVSP14, further determining whether the compound has at least one of the following properties:

(i) inhibits activation of the single-chain zymogen form of CVSP14;

(ii) inhibits activity of the two-chain or single-chain form; and (iii) inhibits dimerization of the protein.

The forms can be full length or truncated forms, including but not limited to, the protease domain resulting from cleavage at the RI activation site or from expression of the protease domain or catalytically active portions thereof.

Also provided are methods of diagnosing the presence of a pre-malignant lesion, a malignancy, or other pathologic condition in a subject, by obtaining a biological sample from the subject; exposing it to a detectable agent that binds to a two-chain or single-chain form of CVSP14, where the pathological condition is characterized by the presence or absence of the two-chain or single-chain form.

Methods of inhibiting tumor invasion or metastasis or treating a malignant or pre-malignant condition by administering an agent that inhibits activation of the zymogen form of CVSP14 or an activity of the activated form are provided. The conditions include, but are not limited to, a condition, such as a tumor, of the breast, cervix, prostate, lung, ovary or colon.

Methods for monitoring tumor progression and/or therapeutic effectiveness are also provided. The levels of activation or expression of CVSP14 or the protease domain thereof are assessed, and the change in the level, reflects tumor progression and/or the effectiveness of therapy. Generally, as the tumor progresses the amount of CVSP14 in a body tissue or fluid sample increases; effective therapy reduces the level.

DETAILED DESCRIPTION OF THE INVENTION

A. Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such indentifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

As used herein, serine protease refers to a diverse family of proteases wherein a serine residue is involved in the hydrolysis of proteins or peptides. The serine residue can be part of the catalytic triad mechanism, which includes a serine, a histidine and an aspartic acid in the catalysis, or be part of the hydroxyl/ε-amine or hydroxyl/α-amine catalytic dyad mechanism, which involves a serine and a lysine in the catalysis. Of particular interest are SPs of mammalian, including human, origin. Those of skill in this art recognize that, in general, single amino acid substitutions in non-essential regions of a polypeptide do not substantially alter biological activity (see, e.g., Watson et al. (1987) *Molecular Biology of the Gene,* 4th Edition, The Bejacmin/Cummings Pub. co., p.224).

As used herein, "transmembrane serine protease (MTSP)" refers to a family of transmembrane serine proteases that share common structural features as described herein (see, also Hooper et al. (2001) *J. Biol. Chem.* 276:857–860). Thus, reference, for example, to "MTSP" encompasses all proteins encoded by the MTSP gene family, including but are not limited to: MTSP3, MTSP4, MTSP6, MTSP7 or an equivalent molecule obtained from any other source or that has been prepared synthetically or that exhibits the same activity. Other MTSPs include, but are not limited to, corin, enterpeptidase, human airway trypsin-like protease (HAT), MTSP1, TMPRSS2, and TMPRSS4. Sequences of encoding nucleic molecules and the encoded amino acid sequences of exemplary MTSPs and/or domains thereof are set forth, for example in U.S. application Ser. No. 09/776,191 (SEQ ID Nos. 1–12, 49, 50 and 61–72 therein, published as International PCT application No. WO 01/57194). The term also encompass MTSPs with amino acid substitutions that do not substantially alter activity of each member, and also encompasses splice variants thereof. Suitable substitutions, including, although not necessarily, conservative substitutions of amino acids, are known to those of skill in this art and can be made without eliminating the biological activity, such as the catalytic activity, of the resulting molecule.

As used herein, a "protease domain of a CVSP" refers to a domain of CVSP that exhibits proteolytic activity and shares homology and structural features with the chymotrypsin/trypsin family protease domains. Hence it is at least the minimal portion of the domain that exhibits proteolytic activity as assessed by standard in vitro assays. Those of skill in this art recognize that such protease domain is the portion of the protease that is structurally equivalent to the trypsin or chymotrypsin fold. Contemplated herein are such protease domains and catalytically active portions thereof. Also provided are truncated forms of the protease domain that include the smallest fragment thereof that acts catalytically as a single chain form.

As used herein, the catalytically active domain of a CVSP refers to the protease domain. Reference to the protease domain of a CVSP includes refers to the single chain form of the protein. If the two-chain form or both is intended, it is so-specified. The zymogen form of each protein is a single chain, which is converted to the active two chain form by activation cleavage.

As used herein a protease domain of a CVSP14, whenever referenced herein, includes at least one or all of or any combination of or a catalytically active portion of:

a polypeptide encoded by the sequence of nucleotides set forth in SEQ ID No. 5;

a polypeptide encoded by a sequence of nucleotides that hybridizes under conditions of low, moderate or high stringency to the sequence of nucleotides set forth in SEQ ID No. 5;

a polypeptide that comprises the sequence of amino acids set forth in SEQ ID No. 6;

a polypeptide that comprises a sequence of amino acids having at least about 60%, 70%, 80%, 90% or about 95% sequence identity with the sequence of amino acids set forth in SEQ ID No. 6; and/or a protease domain of a splice variant of the CVSP14.

The CVSP14 can be from any animal, particularly a mammal, and includes but are not limited to, humans, rodents, fowl, ruminants and other animals. The full length zymogen or two-chain activated form is contemplated or any domain thereof, including the protease domain, which can be a two-chain activated form, or a single chain form.

By active form is meant a form active in vivo and/or in vitro. As described herein, the protease domain also can exist as a two-chain form. It is shown herein that, at least in vitro, the single chain forms of the SPs and the catalytic domains or proteolytically active portions thereof (typically C-terminal truncations) thereof exhibit protease activity. Hence provided herein are isolated single chain forms of the protease domains of SPs and their use in in vitro drug screening assays for identification of agents that modulate the activity thereof.

As used herein, activation cleavage refers to the cleavage of the protease at the N-terminus of the protease domain (in this instance between $R_{55}$ and $I_{56}$; with reference to SEQ ID Nos. 12 and 13). By virtue of the Cys—Cys pairing between the a Cys outside the protease domain (in this instance $C_{37}$) and a Cys in the protease domain (in this instance $Cys_{166}$), upon cleavage the resulting polypeptide has two chains ("A" chain and the "B" chain, which is the protease domain). Cleavage can be effected by another protease or autocatalytically.

As used herein, a two-chain form of the protease domain refers to a two-chain form that is formed from the two-chain form of the protease in which the Cys pairing between, in this instance, $Cys_{37}$ and $Cys_{166}$, which links the protease domain to the remainder of the polypeptide, the "A" chain. A two chain protease domain form refers to any form in which the "remainder of the polypeptide", i.e., "A" chain, is shortened and includes at least up to $Cys_{37}$.

As used herein a CVSP14, whenever referenced herein, includes at least one or all of or any combination of:
- a polypeptide encoded by the sequence of nucleotides set forth in SEQ ID No. 12;
- a polypeptide encoded by a sequence of nucleotides that hybridizes under conditions of low, moderate or high stringency to the sequence of nucleotides set forth in SEQ ID No. 12;
- a polypeptide that comprises the sequence of amino acids set forth in SEQ ID No. 13;
- a polypeptide that comprises a sequence of amino acids having at least about 60%, 70%, 80%, 90% or about 95% sequence identity with the sequence of amino acids set forth in SEQ ID No. 6 or 13; and/or
- a splice variant of the CVSP14.

The CVSP14 polypeptide includes the sequence of amino acids set forth in SEQ ID No. 13. Smaller portions thereof that retain protease activity are contemplated. The protease domain thereof is set forth in SEQ ID No. 6. The protease domains of CVSPs vary in size and constitution, including insertions and deletions in surface loops. They retain conserved structure, including at least one of the active site triad, primary specificity pocket, oxyanion hole and/or other features of serine protease domains of proteases. Thus, for purposes herein, the protease domain is a portion of a CVSP, as defined herein, and is homologous to a domain of other CVSP. As with the larger class of enzymes of the chymotrypsin (S1) fold (see, e.g., Internet accessible MEROPS data base), the CVSPs protease domains share a high degree of amino acid sequence identity. The His, Asp and Ser residues necessary for activity are present in conserved motifs. The activation site, whose cleavage creates the N-terminus of protease domain in the two-chain forms has a conserved motif and readily can be identified.

CVSPs of interest include those that are activated and/or expressed in tumor cells at different levels, typically higher, from non-tumor cells; and those from cells in which substrates therefor differ in tumor cells from non-tumor cells or differ with respect to substrates, co-factors or receptors, or otherwise alter the activity or specificity of the CVSP.

As used herein, a human protein is one encoded by nucleic acid, such as DNA, present in the genome of a human, including all allelic variants and conservative variations as long as they are not variants found in other mammals.

As used herein, a "nucleic acid encoding a protease domain or catalytically active portion of a SP" shall be construed as referring to a nucleic acid encoding only the recited single chain protease domain or active portion thereof, and not the other contiguous portions of the SP as a continuous sequence.

As used herein, catalytic activity refers to the activity of the SP as a serine protease. Function of the SP refers to its function in tumor biology, including promotion of or involvement in initiation, growth or progression of tumors, and also roles in signal transduction. Catalytic activity refers to the activity of the SP as a protease as assessed in in vitro proteolytic assays that detect proteolysis of a selected substrate.

As used herein, a zymogen is an inactive precursor of a proteolytic enzyme. Such precursors are generally larger, although not necessarily larger than the active form. With reference serine proteases zymogens are converted to active enzymes by specific cleavage, including catalytic and autocatalytic cleavage, or binding of an activating co-factor, which generates the mature active enzyme. A zymogen, thus, is an enzymatically inactive protein that is converted to a proteolytic enzyme by the action of an activator.

As used herein, "disease or disorder" refers to a pathological condition in an organism resulting from, e.g., infection or genetic defect, and characterized by identifiable symptoms.

As used herein, neoplasm (neoplasia) refers to abnormal new growth, and thus means the same as tumor, which can be benign or malignant. Unlike hyperplasia, neoplastic proliferation persists even in the absence of the original stimulus.

As used herein, neoplastic disease refers to any disorder involving cancer, including tumor development, growth, metastasis and progression.

As used herein, cancer refers to a general term for diseases caused by any type of malignant tumor.

As used herein, malignant, as applies to tumors, refers to primary tumors that have the capacity of metastasis with loss of growth control and positional control.

As used herein, an anti-cancer agent (used interchangeable with "anti-tumor or anti-neoplastic agent") refers to any agents used in the anti-cancer treatment. These include any agents, when used alone or in combination with other compounds, that can alleviate, reduce, ameliorate, prevent, or place or maintain in a state of remission of clinical symptoms or diagnostic markers associated with neoplastic disease, tumor and cancer, and can be used in methods, combinations and compositions provided herein. Non-limiting examples of anti-neoplastic agents include anti-angiogenic agents, alkylating agents, antimetabolite, certain natural products, platinum coordination complexes, anthracenediones, substituted ureas, methylhydrazine derivatives, adrenocortical suppressants, certain hormones, antagonists and anti-cancer polysaccharides.

As used herein, a splice variant refers to a variant produced by differential processing of a primary transcript of genomic nucleic acid, such as DNA, that results in more than one type of mRNA. Splice variants of SPs are provided herein.

As used herein, angiogenesis is intended to broadly encompass the totality of processes directly or indirectly involved in the establishment and maintenance of new vasculature (neovascularization), including, but not limited to, neovascularization associated with tumors.

As used herein, anti-angiogenic treatment or agent refers to any therapeutic regimen and compound, when used alone or in combination with other treatment or compounds, that can alleviate, reduce, ameliorate, prevent, or place or maintain in a state of remission of clinical symptoms or diagnostic markers associated with undesired and/or uncontrolled angiogenesis. Thus, for purposes herein an anti-angiogenic agent refers to an agent that inhibits the establishment or maintenance of vasculature. Such agents include, but are not limited to, anti-tumor agents, and agents for treatments of other disorders associated with undesirable angiogenesis, such as diabetic retinopathies, restenosis, hyperproliferative disorders and others.

As used herein, non-anti-angiogenic anti-tumor agents refer to anti-tumor agents that do not act primarily by inhibiting angiogenesis.

As used herein, pro-angiogenic agents are agents that promote the establishment or maintenance of the vasculature. Such agents include agents for treating cardiovascular disorders, including heart attacks and strokes.

As used herein, undesired and/or uncontrolled angiogenesis refers to pathological angiogenesis wherein the influence of angiogenesis stimulators outweighs the influence of angiogenesis inhibitors. As used herein, deficient angiogenesis refers to pathological angiogenesis associated with disorders where there is a defect in normal angiogenesis resulting in aberrant angiogenesis or an absence or substantial reduction in angiogenesis.

As used herein, the protease domain of an SP protein refers to the protease domain of an SP that exhibits proteolytic activity. Hence it is at least the minimal portion of the protein that exhibits proteolytic activity as assessed by standard assays in vitro. It refers, herein, to a single chain form and also the two chain activated form (where the two chain form is intended it will be so-noted). Exemplary protease domains include at least a sufficient portion of sequences of amino acids set forth in SEQ ID No. 6 (encoded by nucleotides in SEQ ID No. 5) to exhibit protease activity.

Also contemplated are nucleic acid molecules that encode a polypeptide that has proteolytic activity in an in vitro proteolysis assay and that have at least 60%, 70%, 80%, 90% or about 95% sequence identity with the full length of a protease domain of a CVSP14 polypeptide, or that hybridize along their full length or along at least about 70%, 80% or 90% of the full length to a nucleic acids that encode a protease domain, particularly under conditions of moderate, generally high, stringency.

For the protease domains, residues at the N-terminus can be critical for activity. It is shown herein that the protease domain of the single chain form of the CVSP14 protease is catalytically active. Hence the protease domain generally requires the N-terminal amino acids thereof for activity; the C-terminus portion can be truncated. The amount that can be removed can be determined empirically by testing the polypeptide for protease activity in an in vitro assay that assesses catalytic cleavage.

Hence smaller portions of the protease domains, particularly the single chain domains, thereof that retain protease activity are contemplated. Such smaller versions generally are C-terminal truncated versions of the protease domains. The protease domains vary in size and constitution, including insertions and deletions in surface loops. Such domains exhibit conserved structure, including at least one structural feature, such as the active site triad, primary specificity pocket, oxyanion hole and/or other features of serine protease domains of proteases. Thus, for purposes herein, the protease domain is a single chain portion of a CVSP14, as defined herein, but is homologous in its structural features and retention of sequence of similarity or homology the protease domain of chymotrypsin or trypsin. The polypeptide exhibits proteolytic activity as a single chain.

As used herein, by homologous means about greater than 25% nucleic acid sequence identity, such as 25% 40%, 60%, 70%, 80%, 90% or 95%. If necessary the percentage homology will be specified. The terms "homology" and "identity" are often used interchangeably. In general, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073). By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid or or along at least about 70%, 80% or 90% of the full length nucleic acid molecule of interest. Also contemplated are nucleic acid molecules that contain degenerate codons in place of codons in the hybridizing nucleic acid molecule.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Atschul, S. F., et al, *J Molec Biol* 215:403 (1990); Guide to Huge Computers, Martin J. Bishop, ed., Academic Press, San Diego, 1994, and Carillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., ATLAS OF PROTEIN SEQUENCE AND STRUCTURE, National Biomedical Research Foundation, pp. 353–358 (1979); (2) a penalty of 3.0 for each gap and an additional 0.10 penalty for each symbol in each gap; and (3) no penalty for end gaps. Therefore, as used herein, the term "identity" represents a comparison between a test and a reference polypeptide or polynucleotide.

As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions. At the level of homologies or identities above about 85–90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, animals include any animal, such as, but are not limited to, goats, cows, deer, sheep, rodents, pigs and humans. Non-human animals, exclude humans as the contemplated animal. The SPs provided herein are from any source, animal, plant, prokaryotic and fungal. Most CVSP14s are of animal origin, including mammalian origin.

As used herein, genetic therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy can also be used to deliver nucleic acid encoding a gene product that replaces a defective gene or supplements a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy can also involve delivery of an inhibitor or repressor or other modulator of gene expression.

As used herein, heterologous nucleic acid is nucleic acid that (if DNA encodes RNA) and proteins that are not normally produced in vivo by the cell in which it is expressed or that mediates or encodes mediators that alter expression of endogenous nucleic acid, such as DNA, by affecting transcription, translation, or other regulatable biochemical processes. Heterologous nucleic acid, such as DNA, can also be referred to as foreign nucleic acid, such as DNA. Any nucleic acid, such as DNA, that one of skill in the art would recognize or consider as heterologous or foreign to the cell in which is expressed is herein encompassed by heterologous nucleic acid; heterologous nucleic acid includes exogenously added nucleic acid that is also expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed.

Hence, herein heterologous nucleic acid or foreign nucleic acid, includes a nucleic acid molecule not present in the exact orientation or position as the counterpart nucleic acid molecule, such as DNA, found in the genome. It can also refer to a nucleic acid molecule from another organism or species (i e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease.

As used herein, recitation that a polypeptide consists essentially of the protease domain means that the only SP portion of the polypeptide is a protease domain or a catalytically active portion thereof. The polypeptide can optionally, and generally will, include additional non-SP-derived sequences of amino acids.

As used herein, cancer or tumor treatment or agent refers to any therapeutic regimen and/or compound that, when used alone or in combination with other treatments or compounds, can alleviate, reduce, ameliorate, prevent, or place or maintain in a state of remission of clinical symptoms or diagnostic markers associated with deficient angiogenesis.

As used herein, domain refers to a portion of a molecule, e.g., proteins or the encoding nucleic acids, that is structurally and/or functionally distinct from other portions of the molecule.

As used herein, protease refers to an enzyme catalyzing hydrolysis of proteins or peptides. It includes the zymogen form and activated forms thereof. For clarity reference to protease refers to all forms, and particular forms will be specifically designated. For purposes herein, the protease domain includes single and two chain forms of the protease domain of an SP protein. For CVSP14 the protease domain also includes two chain forms of the protease domain.

As used herein, nucleic acids include DNA, RNA and analogs thereof, including protein nucleic acids (PNA) and mixture thereof. Nucleic acids can be single or double-stranded. When referring to probes or primers, optionally labeled, with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous of sequence complementary to or identical a gene of interest. Probes and primers can be 10, 20, 30, 50, 100 or more nucleic acids long.

As used herein, nucleic acid encoding a fragment or portion of an SP refers to a nucleic acid encoding only the recited fragment or portion of SP, and not the other contiguous portions of the SP.

As used herein, operative linkage of heterologous nucleic to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame. Thus, operatively linked or operationally associated refers to the functional relationship of nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it can be necessary to remove, add or alter 5' untranslated portions of the clones to eliminate extra, potential inappropriate alternative translation initiation (i.e., start) codons or other sequences that can interfere with or reduce expression, either at the level of transcription or translation. Alternatively, consensus ribosome binding sites (see, e.g., Kozak J. Biol. Chem. 266:19867–19870 (1991)) can be inserted immediately 5' of the start codon and can enhance expression. The desirability of (or need for) such modification can be empirically determined.

As used herein, a sequence complementary to at least a portion of an RNA, with reference to antisense oligonucleotides, means a sequence having sufficient complementarily to be able to hybridize with the RNA, generally under moderate or high stringency conditions, forming a stable duplex; in the case of double-stranded SP antisense nucleic acids, a single strand of the duplex DNA (or dsRNA) can thus be tested, or triplex formation can be assayed. The ability to hybridize depends on the degree of complementarily and the length of the antisense nucleic acid. Generally, the longer the hybridizing nucleic acid, the more base mismatches with a SP encoding RNA it can contain and still form a stable duplex (or triplex, as the case can be). One skilled in the art can ascertain a tolerable degree of mismatch by use of standard procedures to determine the melting point of the hybridized complex.

For purposes herein, amino acid substitutions can be made in any of SPs and protease domains thereof provided that the resulting protein exhibits protease activity. Muteins can be made by making conservative amino acid substitutions and also non-conservative amino acid substitutions. For example, amino acid substitutions the desirably alter properties of the proteins can be made. In one embodiment, mutations that prevent degradation of the polypeptide can be made. Many proteases cleave after basic residues, such as R and K; to eliminate such cleavage, the basic residue is replaced with a non-basic residue. Interaction of the protease with an inhibitor can be blocked while retaining catalytic activity by effecting a non-conservative change at the site interaction of the inhibitor with the protease. Receptor binding can be altered without altering catalytic activity.

Amino acid substitutions contemplated include conservative substitutions, such as those set forth in Table 1, which do not eliminate proteolytic activity. As described herein, substitutions that alter properties of the proteins, such as removal of cleavage sites and other such sites are also contemplated; such substitutions are generally non-conservative, but can be readily effected by those of skill in the art.

Suitable conservative substitutions of amino acids are known to those of skill in this art and can be made generally without altering the biological activity, for example enzymatic activity, of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p.224). Also included within the definition, is the catalytically active fragment of an SP, particularly a single chain protease portion. Conservative amino acid substitutions are made, for example, in accordance with those set forth in TABLE 1 as follows:

TABLE 1

| Original residue | Conservative substitution |
| --- | --- |
| Ala (A) | Gly; Ser, Abu |
| Arg (R) | Lys, orn |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val; Met; Nle; Nva |
| Leu (L) | Ile; Val; Met; Nle; Nv |
| Lys (K) | Arg; Gln; Glu |
| Met (M) | Leu; Tyr; Ile; NLe Val |
| Ornitine | Lys; Arg |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met; Nle; Nv |

Other substitutions are also permissible and can be determined empirically or in accord with known conservative substitutions.

As used herein, Abu is 2-aminobutyric acid; Orn is ornithine.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, a probe or primer based on a nucleotide sequence disclosed herein, includes at least 10, 14, typically at least 16 contiguous sequence of nucleotides of SEQ ID No. 5, and probes of at least 30, 50 or 100 contiguous sequence of nucleotides of SEQ ID No. 5. The length of the probe or primer for unique hybridization is a function of the complexity of the genome of interest.

As used herein, amelioration of the symptoms of a particular disorder by administration of a particular pharmaceutical composition refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double-stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double-stranded DNA, inhibition of RNA synthesis (transcription) occurs. The resulting inhibition of translation and/or transcription leads to an inhibition of the synthesis of the protein encoded by the sense strand. Antisense nucleic acid molecule typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest, for example, nucleic acid encoding a single chain protease domain of an SP.

As used herein, an array refers to a collection of elements, such as antibodies, containing three or more members. An addressable array is one in which the members of the array are identifiable, typically by position on a solid phase support. Hence, in general the members of the array are immobilized on discrete identifiable loci on the surface of a solid phase.

As used herein, antibody refers to an immunoglobulin, whether natural or partially or wholly synthetically produced, including any derivative thereof that retains the specific binding ability the antibody. Hence antibody includes any protein having a binding domain that is homologous or substantially homologous to an immunoglobulin binding domain. Antibodies include members of any immunoglobulin claims, including IgG, IgM, IgA, IgD and IgE.

As used herein, antibody fragment refers to any derivative of an antibody that is less then full length, retaining at least a portion of the full-length antibody's specific binding ability. Examples of antibody fragments include, but are not limited to, Fab, Fab', F(ab)$_2$, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain ($V_H$) and one variable light domain linked by noncovalent interactions.

As used herein, a dsFV refers to an Fv with an engineered intermolecular disulfide bond, which stabilizes the $V_H$-$V_L$ pair.

As used herein, an F(ab)$_2$ fragment is an antibody fragment that results from digestion of an immunoglobulin with pepsin at pH 4.0–4.5; it can be recombinantly produced to produce the equivalent fragment.

As used herein, Fab fragments is an antibody fragment that results from digestion of an immunoglobulin with papain; it can be recombinantly produced to produce the equivalent fragment.

As used herein, scFVs refer to antibody fragments that contain a variable light chain ($V_L$) and variable heavy chain ($V_H$) covalently connected by a polypeptide linker in any order. The linker is of a length such that the two variable domains are bridged without substantial interference. Included linkers are (Gly-Ser)$_n$ residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, diabodies are dimeric scFV; diabodies typically have shorter peptide linkers than scFvs, and they generally dimerize.

As used herein, production by recombinant means by using recombinant DNA methods means the use of the well known methods of molecular biology for expressing proteins encoded by cloned DNA.

As used herein the term assessing is intended to include quantitative and qualitative determination in the sense of obtaining an absolute value for the activity of an SP, or a domain thereof, present in the sample, and also of obtaining an index, ratio, percentage, visual or other value indicative of the level of the activity. Assessment can be direct or indirect and the chemical species actually detected need not of course be the proteolysis product itself but can for example be a derivative thereof or some further substance.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein the biological activity of a luciferase is its oxygenase activity whereby, upon oxidation of a substrate, light is produced.

As used herein, functional activity refers to a polypeptide or portion thereof that displays one or more activities associated with a full-length (complete) protein. Functional activities include, but are not limited to, biological activity, catalytic or enzymatic activity, antigenicity (ability to bind to or compete with a polypeptide for binding to an anti-polypeptide antibody), immunogenicity, ability to form multimers, the ability to specifically bind to a receptor or ligand for the polypeptide.

As used herein, a conjugate refers to the compounds provided herein that include one or more SPs, including a CVSP14, particularly single chain protease domains thereof, and one or more targeting agents. These conjugates include those produced by recombinant means as fusion proteins, those produced by chemical means, such as by chemical coupling, through, for example, coupling to sulfhydryl groups, and those produced by any other method whereby at least one SP, or a domain thereof, is linked, directly or indirectly via linker(s) to a targeting agent.

As used herein, a targeting agent, is any moiety, such as a protein or effective portion thereof, that provides specific binding of the conjugate to a cell surface receptor, which, can internalize the conjugate or SP portion thereof. A targeting agent can also be one that promotes or facilitates, for example, affinity isolation or purification of the conjugate; attachment of the conjugate to a surface; or detection of the conjugate or complexes containing the conjugate.

As used herein, an antibody conjugate refers to a conjugate in which the targeting agent is an antibody.

As used herein, derivative or analog of a molecule refers to a portion derived from or a modified version of the molecule.

As used herein, an effective amount of a compound for treating a particular disease is an amount that is sufficient to ameliorate, or in some manner reduce the symptoms associated with the disease. Such amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

As used herein equivalent, when referring to two sequences of nucleic acids means that the two sequences in question encode the same sequence of amino acids or equivalent proteins. When equivalent is used in referring to two proteins or peptides, it means that the two proteins or peptides have substantially the same amino acid sequence with only amino acid substitutions (such, as but not limited to, conservative changes such as those set forth in Table 1, above) that do not substantially alter the activity or function of the protein or peptide. When equivalent refers to a property, the property does not need to be present to the same extent (e.g., two peptides can exhibit different rates of the same type of enzymatic activity), but the activities are usually substantially the same. Complementary, when referring to two nucleotide sequences, means that the two sequences of nucleotides are capable of hybridizing, typically with less than 25%, 15%, 5% or 0% mismatches between opposed nucleotides. If necessary the percentage of complementarity will be specified. Typically the two molecules are selected such that they will hybridize under conditions of high stringency.

As used herein, an agent that modulates the activity of a protein or expression of a gene or nucleic acid either decreases or increases or otherwise alters the activity of the protein or, in some manner up- or down-regulates or otherwise alters expression of the nucleic acid in a cell.

As used herein, inhibitor of the activity of an SP encompasses any substances that prohibit or decrease production, post-translational modification(s), maturation, or membrane localization of the SP or any substances that interferes with or decreases the proteolytic efficacy of thereof, particularly of a single chain form in an in vitro screening assay.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis can be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, pharmaceutically acceptable salts, esters or other derivatives of the conjugates include any salts, esters or derivatives that can be readily prepared by those of skill in this art using known methods for such derivatization and that produce compounds that can be administered to animals or humans without substantial toxic effects and that either are pharmaceutically active or are prodrugs.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound is regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

As used herein, a drug identified by the screening methods provided herein refers to any compound that is a candidate for use as a therapeutic or as a lead compound for the design of a therapeutic. Such compounds can be small molecules, including small organic molecules, peptides, peptide mimetics, antisense molecules or dsRNA, such as RNAi, antibodies, fragments of antibodies, recombinant antibodies and other such compound which can serve as drug candidate or lead compound.

As used herein, a peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art. For example the methylene bioisostere $CH_2S$ has been used as an amide replacement in enkephalin analogs (see, e.g., Spatola (1983) pp. 267–357 in *Chemistry and Biochemistry of Amino Acids, Peptides, and Proteins*, Weistein, Ed. volume 7, Marcel Dekker, New York). Morphine, which can be administered orally, is a compound that is a peptidomimetic of the peptide endorphin. For purposes herein, cyclic peptides are included among pepidomimetics.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences can be cis acting or can be responsive to trans acting factors. Promoters, depending upon the nature of the regulation, can be constitutive or regulated. Exemplary promoters contemplated for use in prokaryotes include the bacteriophage T7 and T3 promoters.

As used herein, a receptor refers to a molecule that has an affinity for a given ligand. Receptors can be naturally-occurring or synthetic molecules. Receptors can also be referred to in the art as anti-ligands. As used herein, the receptor and anti-ligand are interchangeable. Receptors can be used in their unaltered state or as aggregates with other species. Receptors can be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest can be investigated; determination of a sequence that mimics an antigenic epitope can lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, including polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant (see, e.g., U.S. Pat. No. 5,215,899);

e) hormone receptors: determination of the ligands that bind with high affinity to a receptor is useful in the development of hormone replacement therapies; for example, identification of ligands that bind to such receptors can lead to the development of drugs to control blood pressure; and f) opiate receptors: determination of ligands that bind to the opiate receptors in the brain is useful in the development of less-addictive replacements for morphine and related drugs.

As used herein, sample refers to anything which can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein: stringency of hybridization in determining percentage mismatch is as follows:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Those of skill in this art know that the washing step selects for stable hybrids and also know the ingredients of SSPE (see, e.g., Sambrook, E. F. Fritsch, T. Maniatis, in: *Molecular Cloning, A Laboratory Manual*, Cold Spring Harbor Laboratory Press (1989), vol. 3, p. B.13, see, also, numerous catalogs that describe commonly used laboratory solutions). SSPE is pH 7.4 phosphate-buffered 0.18 NaCl. Further, those of skill in the art recognize that the stability of hybrids is determined by $T_m$, which is a function of the sodium ion concentration and temperature ($T_m=81.5°$ C.$-16.6(\log_{10}[Na^+])+0.41(\%$ G+C$)-600/l)$), so that the only parameters in the wash conditions critical to hybrid stability are sodium ion concentration in the SSPE (or SSC) and temperature.

It is understood that equivalent stringencies can be achieved using alternative buffers, salts and temperatures. By way of example and not limitation, procedures using conditions of low stringency are as follows (see also Shilo and Weinberg, *Proc. Natl. Acad. Sci. USA* 78:6789–6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7).

Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65–68° C. and reexposed to film. Other conditions of low stringency which can be used are well known in the art (e.g., as employed for cross-species hybridizations).

By way of example and not way of limitation, procedures using conditions of moderate stringency include, for example, but are not limited to, procedures using such conditions of moderate stringency are as follows: Filters containing DNA are pretreated for 6 hours at 55° C. in a solution containing 6×SSC, 5× Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 hours at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 hour in a solution containing 2×SSC, 0.1% SDS.

By way of example and not way of limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art.

The term substantially identical or homologous or similar varies with the context as understood by those skilled in the relevant art and generally means at least 60% or 70%, preferably means at least 80%, more preferably at least 90%, and most preferably at least 95% identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, target cell refers to a cell that expresses an SP in vivo.

As used herein, test substance (or test compound) refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on an SP, particularly a single chain form that includes the protease domain or a sufficient portion thereof for activity, as determined by an in vitro method, such as the assays provided herein.

As used herein, the terms a therapeutic agent, therapeutic regimen, radioprotectant, chemotherapeutic mean conventional drugs and drug therapies, including vaccines, which are known to those skilled in the art. Radiotherapeutic agents are well known in the art.

As used herein, treatment means any manner in which the symptoms of a condition, disorder or disease are ameliorated or otherwise beneficially altered. Treatment also encompasses any pharmaceutical use of the compositions herein.

As used herein, vector (or plasmid) refers to discrete elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, protein binding sequence refers to a protein or peptide sequence that is capable of specific binding to other protein or peptide sequences generally, to a set of protein or peptide sequences or to a particular protein or peptide sequence.

As used herein, epitope tag refers to a short stretch of amino acid residues corresponding to an epitope to facilitate subsequent biochemical and immunological analysis of the epitope tagged protein or peptide. Epitope tagging is achieved by including the sequence of the epitope tag to the protein-encoding sequence in an appropriate expression vector. Epitope tagged proteins can be affinity purified using highly specific antibodies raised against the tags.

As used herein, metal binding sequence refers to a protein or peptide sequence that is capable of specific binding to metal ions generally, to a set of metal ions or to a particular metal ion.

As used herein, a combination refers to any association between two or among more items.

As used herein, a composition refers to a any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, an agent is said to be randomly selected when the agent is chosen randomly without considering the specific sequences involved in the association of a protein alone or with its associated substrates, binding partners, etc. An example of randomly selected agents is the use a chemical library or a peptide combinatorial library, or a growth broth of an organism or conditioned medium.

As used herein, an agent is said to be rationally selected or designed when the agent is chosen on a non-random basis which takes into account the sequence of the target site and/or its conformation in connection with the agent's action. As described in the Examples, there are proposed binding sites for serine protease and (catalytic) sites in the protein having SEQ ID NO:3 or SEQ ID NO:4. Agents can be rationally selected or rationally designed by utilizing the peptide sequences that make up these sites. For example, a rationally selected peptide agent can be a peptide whose amino acid sequence is identical to the ATP or calmodulin binding sites or domains.

For clarity of disclosure, and not by way of limitation, the detailed description is divided into the subsections that follow.

B. CVSP14 Polypeptides, Muteins, Derivatives and Analogs thereof SPs

The serine proteases (SPs) are a family of proteins found in mammals and also other species. SPs that share a number of common structural features as described herein. The proteolytic domains share sequence homology including conserved His, Asp, and Ser residues necessary for catalytic activity that are present in conserved motifs. These SPs are synthesized as zymogens, and activated to two chain forms by specific cleavage.

The SP family can be target for therapeutic intervention and also can serve as diagnostic markers for tumor initiation, development, growth and/or progression. As discussed, members of this family are involved in proteolytic processes that are implicated in tumor development, growth and/or progression. This implication is based upon their functions as proteolytic enzymes in extracellular matrix degradation and remodelling and growth and pro-angiogenic factor activation. In addition, their levels of expression or level of activation or their apparent activity resulting from substrate levels or alterations in substrates and levels thereof differs in tumor cells and non-tumor cells in the same tissue. Hence, protocols and treatments that alter their activity, such as their proteolytic activities and roles in signal transduction, and/or their expression, such as by contacting them with a compound that modulates their activity and/or expression, could impact tumor development, growth and/or progression. Also, in some instances, the level of activation and/or expression can be altered in tumors, such as pancreas, stomach, uterus, lung, colon and cervical cancers, and also breast, prostate or leukemias. The SP, thus, can serve as a diagnostic marker for tumors.

In other instances the SP protein can exhibit altered activity by virtue of a change in activity or expression of a co-factor therefor or a substrate therefor. Detection of the SPs, particularly the protease domains, in body fluids, such as serum, blood, saliva, cerebral spinal fluid, synovial fluid and interstitial fluids, urine, sweat and other such fluids and secretions, can serve as a diagnostic tumor marker. In particular, detection of higher levels of such polypeptides in a subject compared to a subject known not to have any neoplastic disease or compared to earlier samples from the same subject, can be indicative of neoplastic disease in the subject.

Provided is a family member designated CVSP14. It is shown herein, that the CVSP14s provided herein are serine proteases that are expressed and/or activated in certain tumors; hence their activation or expression can serve as a diagnostic marker for tumor development, growth and/or progression. The CVSP14 is also provided for use as a drug target and used in screening assays, including those exemplified herein. It is shown herein that the single chain proteolytic domain can function in vitro and, hence is useful in in vitro assays for identifying agents that modulate the activity of members of this family. In addition the two-chain form or the full-length or truncated forms thereof, such as forms in which the signal peptide is removed can also be used in such assays.

In certain embodiments, the CVSP14 polypeptide is detectable in a body fluid at a level that differs from its level in body fluids in a subject not having a tumor. In other embodiments, the polypeptide is present in a tumor; and a substrate or cofactor for the polypeptide is expressed at levels that differ from its level of expression in a non-tumor cell in the same type of tissue.

CVSP14

Provided are substantially purified CVSP14 zymogens, activated two chain forms, single chain protease domains and two chain protease domains. A full-length CVSP14 polypeptide, including the signal sequence, is set forth in SEQ ID Nos. 12 and 13. The signal sequence can be cleaved upon expression or prior to expression.

Also provided is a substantially purified protein including a sequence of amino acids that has at least 60%, 70%, 80%, 90% or about 95%, identity to the CVSP14 where the percentage identity is determined using standard algorithms and gap penalties that maximize the percentage identity. A human CVSP14 polypeptide is exemplified, although other mammalia CVSP14 polypeptides are contemplated. Splice variants of the CVSP14, particularly those with a proteolytically active protease domain, are contemplated herein.

In other embodiments, substantially purified polypeptides that include a protease domain of a CVSP14 polypeptide or a catalytically active portion thereof, but that do not include the entire sequence of amino acids set forth in SEQ ID No. 13 are provided. Among these are polypeptides that include a sequence of amino acids that has at least 60%, 70%, 80%, 90%, 95% or 100% sequence identity to SEQ ID No. 6.

Provided are substantially purified CVSP14 polypeptides and functional domains thereof, including catalytically active domains and portions, that have at least about 60%, 70%, 80%, 90% or about 95% sequence identity with a protease domain that includes the sequence of amino acids set forth in SEQ ID No. 6 or a catalytically active portion thereof or with a protease that includes the sequence of amino acids set forth in SEQ ID No. 13 and domains thereof.

With reference to SEQ ID No. 13, the protease activation cleavage site is between $R_{55}$ and $I_{56}$; the catalytic triad based upon homology is $H_{96}$, $D_{146}$, $S_{244}$; there is a potential N-glycosylation site at $N_{108}VT$; Cys pairing is predicted to be between $C_{37}$–$C_{166}$, which links the protease domain to the remainder of the polypeptide, $C_{180}$–$C_{250}$, $C_{211}$–$C_{229}$ and $C_{240}$–$C_{269}$. Hence $C_{166}$ is a free Cys in the protease domain, which also can be provided as a two chain molecule. It is shown herein, however, that the single chain form is proteolytically active.

Also provided are polypeptides that are encoded by the nucleic acid molecules provided herein. Included among those polypeptides are the CVSP14 protease domain or a polypeptide with amino acid changes such that the specificity and protease activity is not eliminated and is retained at least 10%, 20%, 30%, 40%, 50%, 60%, 70%, 80%, 90% or remains substantially unchanged. In particular, a substantially purified mammalian SP protein is provided that includes a serine protease catalytic domain and can additionally include other domains. The CVSP14 can form homodimers and can also form heterodimers with some other protein, such as a membrane-bound protein.

The domains, fragments, derivatives or analogs of a CVSP14 that are functionally active are capable of exhibiting one or more functional activities associated with the CVSP14 polypeptide, such as serine protease activity, immunogenicity and antigenicity, are provided.

Antigenic epitopes that contain at least 4, 5, 6, 7, 8, 9, 10, 11, 12, 13, 14, 15, 20, 25, 30, 40, 50, and typically 10–15 amino acids of the CVSP14 polypeptide are provided. These antigenic epitopes are used, for example, to raise antibodies. Antibodies specific for each epitope or combinations thereof and for single and two-chain forms are also provided.

Muteins and Derivatives of CVSP14 Polypeptides

Full-length CVSP14, zymogen and activated forms thereof and CVSP14 protease domains, portions thereof, and muteins and derivatives of such polypeptides are provided. Among the derivatives are those based on animal CVSP14s, including, but are not limited to, rodent, such as mouse and rat; fowl, such as chicken; ruminants, such as goats, cows, deer, sheep; ovine, such as pigs; and humans. For example, CVSP14 derivatives can be made by altering their sequences by substitutions, additions or deletions. CVSP14 derivatives include, but are not limited to, those containing, as a primary amino acid sequence, all or part of the amino acid sequence of CVSP14, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence can be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid (see, e.g., Table 1). Muteins of the CVSP14 or a domain thereof, such as a protease domain, in which up to about 10%, 20%, 30%, 40%, 50%, 60%, 70%, 80%, 85%, 90% or 95% of the amino acids are replaced with another amino acid are provided. Generally such muteins retain at least about 10%, 20%, 30%, 40%, 50%, 60%, 70%, 80% or 90% of the protease activity the unmutated protein.

Muteins in which one or more of the Cys residues, particularly, a residue that is paired in the activated two form, but unpaired in the protease domain alone (i.e., the Cys at residue position 26 (see SEQ ID Nos. 5 and 6) in the protease domain), is/are replaced with any amino acid, typically, although not necessarily, a conservative amino acid residue, such as Ser, are contemplated. Muteins of CVSP14, particularly those in which Cys residues, such as the Cys in the single chain protease domain, is replaced with another amino acid that does not eliminate the activity, are provided.

Muteins of the protein are also provided in which amino acids are replaced with other amino acids. Among the muteins are those in which the Cys residues, is/are replaced typically although not necessarily, with a conservative amino acid residues, such as a serine. Such muteins are also provided herein. Muteins in which 10%, 20%, 30%, 35%, 40%, 45%, 50% or more of the amino acids are replaced but the resulting polypeptide retains at least about 10%, 20%, 30%, 35%, 40%, 45%, 50%, 60%, 70%, 80%, 90% or 95% of the catalytic activity as the unmodified form for the same substrate.

Protease Domains

Isolated, substantially pure proteases that include the protease domains or catalytically active portions thereof as single chain forms of SPs are provided. The protease domains can be included in a longer protein, and such longer protein is optionally the CVSP14 zymogen.

Provided herein are isolated substantially pure single polypeptides that contain the protease domain of a CVSP14 as a single chain. The CVSP14 provided herein is expressed or activated by or in tumor cells, typically at a level that differs from the level in which they are expressed by the non-tumor cell of the same type. Hence, for example, if the SP is expressed by a prostate or ovarian tumor cell, to be of interest herein with respect to ovarian or prostate cancer, it an expression, extent of activation or activity that is different from that in non-tumor cells. CVSP14 is expressed in lung, colon, prostate, breast, uterine, ovarian and other tumor cells.

SP protease domains include the single chain protease domains of CVSP14. Provided are the protease domains or proteins that include a portion of an SP that is the protease domain of any SP, particularly a CVSP14. The protein can also include other non-SP sequences of amino acids, but includes the protease domain or a sufficient portion thereof to exhibit catalytic activity in any in vitro assay that assess such protease activity, such as any provided herein. Also provided are two chain activated forms of the full length protease and also two chain forms of the protease domain.

In an embodiment, the substantially purified SP protease is encoded by a nucleic acid that hybridizes to the a nucleic acid molecule containing the protease domain encoded by the nucleotide sequence set forth in SEQ. ID No. 5 under at least moderate, generally high, stringency conditions, such that the protease domain encoding nucleic acid thereof hybridizes along its full length or along at least about 70%, 80% or 90% of the full length. In other embodiments the substantially purified SP protease is a single chain polypeptide that includes substantially the sequence of amino acids set forth in SEQ ID No. 6, or a catalytically active portion thereof.

In particular, exemplary protease domains include at least a sufficient portion of sequences of amino acids set forth in SEQ ID No. 6 (encoded by nucleotides in SEQ ID No. 5) to exhibit protease activity in an assay provided herein.

The signal peptide (amino acids 1–25 of SEQ ID No. 13) is also provided. In addition the mature CVSP15 polypeptide with the signal sequence removed is provided.

As described below, all forms of the CVSP14, including the pro-polypeptide with the signal sequence, the mature polypeptide and catalytically active portions thereof, the protease domains and catalytically active portions thereof, two-chain and single chain forms of any of these proteins are provided herein and can be used in the screening assays and for preparing antibodies specific therefore. The expression, quantity and/or activation of the protein in tumor cells and body fluids can be diagnostic of disease or its absence.

Nucleic Acid Molecules, Vectors and Plasmids, Cells and Expression of CVSP14 Polyeptides Nucleic Acid Molecules Due to the degeneracy of nucleotide coding sequences, other nucleic sequences which encode substantially the same amino acid sequence as a CVSP14 gene can be used. These include but are not limited to nucleotide sequences comprising all or portions of CVSP14 genes that are altered by the substitution of different codons that encode the amino acid residue within the sequence, thus producing a silent change.

Also provided are nucleic acid molecules that hybridize to the above-noted sequences of nucleotides encoding CVSP14 at least at low stringency, at moderate stringency, and/or at high stringency, and that encode the protease domain and/or the full length protein or other domains of a CVSP14 or a splice variant or allelic variant thereof.

Generally the molecules hybridize under such conditions along their full length (or along at least about 70%, 80% or 90% of the full length) for at least one domain and encode at least one domain, such as the protease domain, of the polypeptide. In particular, such nucleic acid molecules include any isolated nucleic fragment that encodes at least one domain of a serine protease, that (1) contains a sequence of nucleotides that encodes the protease or a functionally active, such as catalytically active, domain thereof, and (2) is selected from among:

(a) a sequence of nucleotides that encodes the protease or a domain thereof includes a sequence of nucleotides set forth in SEQ ID Nos. 5 or 12;

(b) a sequence of nucleotides that encodes such portion or the full length protease and hybridizes under conditions of moderate or high stringency, generally to nucleic acid that is complementary to a mRNA transcript present in a mammalian cell that encodes such protein or fragment thereof;

(c) a sequence of nucleotides that encodes a serine protease or domain thereof that includes a sequence of amino acids encoded by such portion or the full length open reading frame;

(d) a sequence of nucleotides that encodes the serine protease that includes a sequence of amino acids encoded by a sequence of nucleotides that encodes such subunit and hybridizes under conditions of high stringency to DNA that is complementary to the mRNA transcript;

(e) a sequence of nucleotides that encodes a splice variant of any of (a)–(d); and (f) a sequence of nucleotides that includes degenerate codons of all or a portion of any of (a)–(e).

The isolated nucleic acid fragment is DNA, including genomic or cDNA, or is RNA, or can include other components, such as protein nucleic acid. The isolated nucleic acid can include additional components, such as heterologous or native promoters, and other transcriptional and translational regulatory sequences, these genes can be linked to other genes, such as reporter genes or other indicator genes or genes that encode indicators.

The CVS14s provided herein are encoded by a nucleic acid that includes sequence encoding a protease domain that exhibits proteolytic activity and that hybridizes to a nucleic acid molecule including the sequence of nucleotides set forth in SEQ ID No. 5, typically under moderate, generally under high stringency, conditions and generally along the full length of the protease domain or along at least about 70%, 80% or 90% of the full length. Splice variants are also provided herein.

In a specific embodiment, a nucleic acid that encodes a CVSP, designated CVSP14 is provided. In particular, the nucleic acid includes the sequence of nucleotides set forth in SEQ ID No. 5 or a portion there of that encodes a catalytically active polypeptide. Also provided are nucleic acid molecules that hybridize under conditions of at least low stringency, generally moderate stringency, more typically high stringency to the SEQ ID No. 5 or degenerates thereof.

In one embodiment, the isolated nucleic acid fragment hybridizes to a nucleic acid molecule containing the nucleotide sequence set forth in SEQ ID No: 5 (or degenerates thereof) under high stringency conditions, in one embodiments contains the sequence of nucleotides set forth in SEQ ID Nos. 5 and 6). A full-length CVSP14 is set forth in SEQ ID No. 13 and is encoded by SEQ ID No. 12 or degenerates thereof.

Also contemplated are nucleic acid molecules that encode a single chain SP protease that have proteolytic activity in an in vitro proteolysis assay and that have at least 60%, 70%, 80%, 85%, 90% or 95% sequence identity with the full length of a protease domain of a CVSP14 polypeptide, or that hybridize along their full length or along at least about 70%, 80% or 90% of the full length to a nucleic acids that encode a protease domain, particularly under conditions of moderate, generally high, stringency. As above, the encoded polypeptides contain the protease as a single chain.

The isolated nucleic acids can contain least 10 nucleotides, 25 nucleotides, 50 nucleotides, 100 nucleotides, 150 nucleotides, or 200 nucleotides or more contiguous nucleotides of a CVSP14-encoding sequence, or a full-length SP coding sequence. In another embodiment, the nucleic acids are smaller than 35, 200 or 500 nucleotides in length. Nucleic acids that hybridize to or are complementary to a CVSP14-encoding nucleic acid molecule can be single or double-stranded. For example, nucleic acids are provided that include a sequence complementary to (specifically are the inverse complement of) at least 10, 25, 50, 100, or 200 nucleotides or the entire coding region of a CVSP14 encoding nucleic acid, particularly the protease domain thereof. For CVSP14 the full-length protein or a domain or active fragment thereof is also provided.

For each of the nucleic acid molecules, the nucleic acid can be DNA or RNA or PNA or other nucleic acid analogs or can include non-natural nucleotide bases. Also provided are isolated nucleic acid molecules that include a sequence of nucleotides complementary to the nucleotide sequence encoding an SP.

Probes, Primers, Antisense Oligonucleotides and dsRNA

Also provided are fragments thereof or oligonucleotides that can be used as probes or primers and that contain at least about 10, 14, 16 nucleotides, generally less than 1000 or less than or equal to 100, set forth in SEQ ID No. 5 (or the complement thereof); or contain at least about 30 nucleotides (or the complement thereof) or contain oligonucleotides that hybridize along their full length or along at least about 70%, 80% or 90% of the full length to any such fragments or oligonucleotides. The length of the fragments are a function of the purpose for which they are used and/or the complexity of the genome of interest. Generally probes and primers contain less than about 500, 150, 100 nucleotides.

Probes and primers derived from the nucleic acid molecules are provided, Such probes and primers contain at least 8, 14, 16, 30, 100 or more contiguous nucleotides with identity to contiguous nucleotides of a CVSP14. The probes and primers are optionally labelled with a detectable label, such as a radiolabel or a fluorescent tag, or can be mass differentiated for detection by mass spectrometry or other means.

Also provided is an isolated nucleic acid molecule that includes the sequence of molecules that is complementary to the nucleotide sequence encoding CVSP14 or the portion thereof. Double-stranded RNA (dsRNA), such as RNAi is also provided.

Plasmids, Vectors and Cells

Plasmids and vectors containing the nucleic acid molecules are also provided. Cells containing the vectors, including cells that express the encoded proteins are provided. The cell can be a bacterial cell, a yeast cell, a fungal cell, a plant cell, an insect cell or an animal cell. Methods for producing an SP or single chain form of the protease domain thereof by, for example, growing the cell under conditions whereby the encoded SP is expressed by the cell, and recovering the expressed protein, are provided herein. As noted, for CVSP14, the full-length zymogens and activated proteins and activated (two chain) protease and single chain protease domains are provided.

As discussed below, the CVSP14 polypeptide, and catalytically active portions thereof, can be expressed as a secreted protein using the native signal sequence or a heterologous signal. Alternatively, as exemplified, the protein can be expressed as inclusion bodies in the cytoplasm and isolated therefrom. The resulting protein can be treated to refold (see, e.g., EXAMPLE 1). It is shown herein that active protease domain can be produced by expression in inclusion bodies, isolation therefrom and denaturation followed by refolding.

C. Tumor Specificity and Tissue Expression Profiles

Each SP has a characteristic tissue expression profile; the SPs in particular, although not exclusively expressed or activated in tumors, exhibit characteristic tumor tissue expression or activation profiles. In some instances, SPs can have different activity in a tumor cell from a non-tumor cell by virtue of a change in a substrate or cofactor therefor or other factor that would alter the apparent functional activity of the SP. Hence each can serve as a diagnostic marker for particular tumors, by virtue of a level of activity and/or expression or function in a subject (i.e. a mammal, particularly a human) with neoplastic disease, compared to a subject or subjects that do not have the neoplastic disease. In addition, detection of activity (and/or expression) in a particular tissue can be indicative of neoplastic disease.

Circulating SPs in body fluids can be indicative of neoplastic disease. Secreted CVSP14 or activated CVSP14 is indicative of neoplastic disease. Also, by virtue of the activity and/or expression profiles of each, they can serve as therapeutic targets, such as by administration of modulators of the activity thereof, or, as by administration of a prodrug specifically activated by one of the SPs.

Tissue Expression Profiles CVSP14

The CVSP14 is expressed at high levels in an androgen-independent tumor cell line. The CVSP14 transcript was detected in normal kidney samples. CVSP14 signals were diminished in all the matched kidney tumor samples. Weak signals were detected in all three pairs of prostate normal/tumor cDNA samples. Weak signals were also detected in 3 of 9 normal breast samples. A weak signal was also detected in one of the 7 uterine tumors, but not in their normal tissue counterparts. Weak signals were also detected in two of the three normal lung tissue samples, but not in their matched tumor samples. Very weak signals can be seen in cDNA samples from various tumor cell lines, including HeLa cells, Burkitt's lymphoma Daudi cells, chronic myelogenous leukemia K562, promyelocytic leukemia HL-60 cells, melanoma G361 cells, lung carcinoma A549 cells, lymphoblastic leukemia MOLT-4 and colorectal adenocarcinoma SW480 cells.

Hence expression in certain cells, such as prostate cancer, can serve as a tumor marker; whereas in other tissues, such as kidney, the absence of expression or activation, can serve as a tumor marker.

D. Identification and Isolation of SP Protein Genes

The SP polpeptides, including CVSP14 polypeptides, or domains thereof, can be obtained by methods well known in the art for protein purification and recombinant protein expression. Any method known to those of skill in the art for identification of nucleic acids that encode desired genes can be used. Any method available in the art can be used to obtain a full length (i.e., encompassing the entire coding region) cDNA or genomic DNA clone encoding an SP protein. In particular, the polymerase chain reaction (PCR) can be used to amplify a sequence identified as being differentially expressed or encoding proteins activated at different levels in tumor and non-tumor cells or tissues, e.g., nucleic acids encoding a CVSP14 polypeptide (SEQ. NOs: 5, 6, 12 and 13), in a genomic or cDNA library. Oligonucleotide primers that hybridize to sequences at the 3' and 5' termini of the identified sequences can be used as primers to amplify by PCR sequences from a nucleic acid sample (RNA or DNA), typically a cDNA library, from an appropriate source (e.g., tumor or cancer tissue).

PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to amplify nucleic acid homologs (e.g., to obtain SP protein sequences from species other than humans or to obtain human sequences with homology to CVSP14 polypeptide) by allowing for greater or lesser degrees of nucleotide sequence similarity between the known nucleotide sequence and the nucleic acid homolog being isolated. For cross species hybridization, low or moderate stringency conditions are used. For same species hybridization, moderately or high stringency conditions generally are used. After successful amplification of the nucleic acid containing all or a portion of the identified SP protein sequence or of a nucleic acid encoding all or a portion of an SP protein homolog, that segment can be molecularly cloned and sequenced, and used as a probe to isolate a complete cDNA or genomic clone. This, in turn, permits the determination of the gene's complete nucleotide sequence, the analysis of its expression, and the production of its protein product for functional analysis. Once the nucleotide sequence is determined, an open reading frame encoding the SP protein gene protein product can be determined by any method well known in the art for determining open reading frames, for example, using publicly available computer programs for nucleotide sequence analysis. Once an open reading frame is defined, it is routine to determine the amino acid sequence of the protein encoded by the open reading frame. In this way, the nucleotide sequences of the entire SP protein genes as well as the amino acid sequences of SP protein proteins and analogs can be identified.

Any eukaryotic cell potentially can serve as the nucleic acid source for the molecular cloning of the SP protein gene. The nucleic acids can be isolated from vertebrate, mammalian, human, porcine, bovine, feline, avian, equine, canine, as well as additional primate sources, insects, plants, etc. The DNA can be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA can contain regulatory and intron DNA regions in addition to coding regions; clones derived from cDNA contains only exon sequences. Whatever the source, the gene should be molecularly cloned into a suitable vector for propagation of the gene.

In the molecular cloning of the gene from genomic DNA, DNA fragments are generated, some of which encode the desired gene. The DNA can be cleaved at specific sites using various restriction enzymes. Alternatively, one can use DNAse in the presence of manganese to fragment the DNA, or the DNA can be physically sheared, for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene can be accomplished in a number of ways. For example, a portion of the SP protein (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments can be screened by nucleic acid hybridization to the labeled probe (Benton and Davis, *Science* 196:180 (1977); Grunstein and Hogness, *Proc. Natl. Acad. Sci. U.S.A.* 72:3961 (1975)). Those DNA fragments with substantial homology to the probe hybridize. It is also possible to identify the appropriate fragment by restriction enzyme digestion(s) and comparison of fragment sizes with those expected according to a known restriction map if such is available or by DNA sequence analysis and comparison to the known nucleotide sequence of SP protein. Further selection can be carried out on the basis of the properties of the gene. Alternatively, the presence of the gene can be detected by assays based on the physical, chemical, or immunological properties of its expressed product. For example, cDNA clones, or DNA clones which hybrid-select the proper mRNA, can be selected which produce a protein that, e.g., has similar or identical electrophoretic migration, isoelectric focusing behavior, proteolytic digestion maps, antigenic properties, serine protease activity. If an anti-SP protein antibody is available, the protein can be identified by binding of labeled antibody to the putatively SP protein synthesizing clones, in an ELISA (enzyme-linked immunosorbent assay)-type procedure.

Alternatives to isolating the CVSP14 polypeptide genomic DNA include, but are not limited to, chemically synthesizing the gene sequence from a known sequence or making cDNA to the mRNA that encodes the SP protein. For example, RNA for cDNA cloning of the SP protein gene can be isolated from cells expressing the protein. The identified and isolated nucleic acids can then be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini. If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can comprise specific chemically synthesized oligonucleotides encoding restriction endonuclease recognition sequences. In an alternative method, the cleaved vector and SP protein gene can be modified by homopolymeric tailing. Recombinant molecules can be introduced into host cells via, for example, transformation, transfection, infection, electroporation and sonorporation, so that many copies of the gene sequence are generated.

In specific embodiments, transformation of host cells with recombinant DNA molecules that incorporate the isolated SP protein gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

E. Vectors, Plasmids and Cells that Contain Nucleic Acids Encoding an SP Protein or Protease Domain Thereof and Expression of SP Proteins Vectors and Cells For recombinant expression of one or more of the SP proteins, the nucleic acid containing all or a portion of the nucleotide sequence encoding the SP protein can be inserted into an appropriate expression vector, i.e., a vector that contains the necessary elements for the transcription and translation of the inserted protein coding sequence. The necessary transcriptional and translational signals also can be supplied by the native promoter for SP genes, and/or their flanking regions.

Also provided are vectors that contain nucleic acid encoding the SPs. Cells containing the vectors are also provided. The cells include eukaryotic and prokaryotic cells, and the vectors are any suitable for use therein.

Prokaryotic and eukaryotic cells, including endothelial cells, containing the vectors are provided. Such cells include bacterial cells, yeast cells, fungal cells, plant cells, insect cells and animal cells. The cells are used to produce an SP protein or protease domain thereof by growing the above-described cells under conditions whereby the encoded SP protein or protease domain of the SP protein is expressed by the cell, and recovering the expressed protease domain protein. For purposes herein, the protease domain can be secreted into the medium.

In one embodiment, the vectors include a sequence of nucleotides that encodes a polypeptide that has protease activity and contains all or a portion of only the protease domain, or multiple copies thereof, of an SP protein are provided. Also provided are vectors that comprise a sequence of nucleotides that encodes the protease domain and additional portions of an SP protein up to and including a full length SP protein, as well as multiple copies thereof, are also provided. The vectors can selected for expression of the SP protein or protease domain thereof in the cell or such that the SP protein is expressed as a secreted protein.

Alternatively, the vectors can include signals necessary for secretion of encoded proteins. When the protease domain is expressed the nucleic acid is linked to nucleic acid encoding a secretion signal, such as the *Saccharomyces cerevisiae* a mating factor signal sequence or a portion thereof, or the native signal sequence.

A variety of host-vector systems can be used to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of DNA fragments into a vector can be used to construct expression vectors containing a chimeric gene containing of appropriate transcriptional/translational control signals and protein coding sequences. These methods can include in vitro recombinant DNA and synthetic techniques and in vivo recombinants (genetic recombination). Expression of nucleic acid sequences encoding SP protein, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for SP protein. Promoters which can be used include but are not limited to the SV40 early promoter (Bernoist and Chambon, *Nature* 290:304–310 (1981)), the promoter contained in the 3' long terminal repeat of Rous sarcoma virus (Yamamoto et al. *Cell* 22:787–797 (1980)), the herpes thymidine kinase promoter (Wagner et al., *Proc. Natl. Acad. Sci. USA* 78:1441–1445 (1981)), the regulatory sequences of the metallothionein gene (Brinster et al., *Nature* 296:39–42 (1982)); prokaryotic expression vectors such as the β-lactamase promoter (Villa-Kamaroff et al., *Proc. Natl. Acad. Sci. USA* 75:3727–3731 1978)) or the tac promoter (DeBoer et al., *Proc. Natl. Acad. Sci. USA* 80:21–25 (1983)); see also "Useful Proteins from Recombinant Bacteria": in Scientific American 242:79–94 (1980)); plant expression vectors containing the nopaline synthetase promoter (Herrar-Estrella et al., *Nature* 303: 209–213 (1984)) or the cauliflower mosaic virus 35S RNA promoter (Garder et al., *Nucleic Acids Res.* 9:2871 (1981)), and the promoter of the photosynthetic enzyme ribulose bisphosphate carboxylase (Herrera-Estrella et al., *Nature* 310:115–120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 38:639–646 (1984); Ornitz et al., *Cold Spring Harbor Symp. Quant. Biol.* 50:399–409 (1986); MacDonald, *Hepatology* 7:425–515 (1987)); insulin gene control region which is active in pancreatic beta cells (Hanahan et al., *Nature* 315:115–122 (1985)), immunoglobulin gene control region which is active in lymphoid cells (Grosschedl et al., *Cell* 38:647–658 (1984); Adams et al., *Nature* 318:533–538 (1985); Alexander et al., *Mol. Cell Biol.* 7:1436–1444 (1987)), mouse mammary tumor virus control region which is active in testicular, breast, lymphoid and mast cells (Leder et al., *Cell* 45:485–495 (1986)), albumin gene control region which is active in liver (Pinckert et al., *Genes and Devel* 1:268–276 (1987)), alpha-fetoprotein gene control region which is active in liver (Krumlauf et al., *Mol. Cell. Biol.* 5:1639–1648 (1985); Hammer et al, *Science* 235:53–58 1987)), alpha-1 antitrypsin gene control region which is active in liver (Kelsey et al., *Genes and Devel.* 1:161–171 (1987)), beta globin gene control region which is active in myeloid cells (Mogram et al., *Nature* 315:338–340 (1985); Kollias et al., *Cell* 46:89–94 (1986)), myelin basic protein gene control region which is active in oligodendrocyte cells of the brain (Readhead et al., *Cell* 48:703–712 (1987)), myosin light chain-2 gene control region which is active in skeletal muscle (Sani, *Nature* 314:283–286 (1985)), and gonadotrophic releasing hormone gene control region which is active in gonadotrophs of the hypothalamus (Mason et al., *Science* 234:1372–1378 (1986)).

In a specific embodiment, a vector is used that contains a promoter operably linked to nucleic acids encoding an SP protein, or a domain, fragment, derivative or homolog, thereof, one or more origins of replication, and optionally, one or more selectable markers (e.g., an antibiotic resistance gene). Expression vectors containing the coding sequences, or portions thereof, of an SP protein, is made, for example, by subcloning the coding portions into the EcoRI restriction site of each of the three pGEX vectors (glutathione S-transferase expression vectors (Smith and Johnson, *Gene* 7:31–40 (1988)). This allows for the expression of products in the correct reading frame. Vectors and systems for expression of the protease domains of the SP proteins include the well known *Pichia* vectors (available, for example, from Invitrogen, San Diego, Calif.), particularly those designed for secretion of the encoded proteins. One exemplary vector is described in the EXAMPLES.

Plasmids for transformation of *E. coli* cells, include, for example, the pET expression vectors (see, U.S. Pat. No. 4,952,496; available from NOVAGEN, Madison, Wis.; see, also literature published by Novagen describing the system). Such plasmids include pET 11a, which contains the T7lac promoter, T7 terminator, the inducible *E. coli* lac operator, and the lac repressor gene; pET 12a–c, which contains the T7 promoter, T7 terminator, and the *E. coli* ompT secretion signal; and pET 15b and pET19b (NOVAGEN, Madison, Wis.), which contain a His-Tag™ leader sequence for use in purification with a His column and a thrombin cleavage site that permits cleavage following purification over the column; the T7-lac promoter region and the T7 terminator.

The vectors are introduced into host cells, such as *Pichia* cells and bacterial cells, such as *E. coli* and the proteins expressed therein. *Pichia* strains, which are known and readily available, include, for example, GS115. Bacterial hosts can contain chromosomal copies of DNA encoding T7 RNA polymerase operably linked to an inducible promoter, such as the lacUV promoter (see, U.S. Pat. No. 4,952,496). Such hosts include, but are not limited to, the lysogenic *E. coli* strain BL21 (DE3).

Expression and Production of Proteins

The SP domains, derivatives and analogs can be produced by various methods known in the art. For example, once a recombinant cell expressing an SP protein, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product.

The CVSP14 polypeptides can be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties can be evaluated using any suitable assay known in the art.

Alternatively, once an SP protein or its domain or derivative is identified, the amino acid sequence of the protein can be deduced from the nucleotide sequence of the gene which encodes it. As a result, the protein or its domain or derivative can be synthesized by standard chemical methods known in the art (e.g. see Hunkapiller et al, *Nature* 310:105–111 (1984)).

Manipulations of SP protein sequences can be made at the protein level. Also contemplated herein are SP protein proteins, domains thereof, derivatives or analogs or fragments thereof, which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In addition, domains, analogs and derivatives of an SP protein can be chemically synthesized. For example, a peptide corresponding to a portion of an SP protein, which includes the desired domain or which mediates the desired activity in vitro can be synthesized by use of a peptide synthesizer. Furthermore, if desired, nonclassical amino acids or chemical amino acid analogs can be introduced as a substitution or addition into the SP protein sequence. Non-classical amino acids include but are not limited to the D-isomers of the common amino acids, a-amino isobutyric acid, 4-aminobutyric acid, Abu, 2-aminobutyric acid, ϵ-Abu, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

In cases where natural products are suspected of having a mutation or are isolated from new species, the amino acid sequence of the SP protein isolated from the natural source, as well as those expressed in vitro, or from synthesized expression vectors in vivo or in vitro, can be determined from analysis of the DNA sequence, or alternatively, by direct sequencing of the isolated protein. Such analysis can be performed by manual sequencing or through use of an automated amino acid sequenator.

In particular, for expression of the protease domain of the CVSP14, it was found to be advantageous to express the protein intracellularly without a signal sequence, which results in accumulation or formation of inclusion bodies containing protease domain. The inclusion bodies are isolated, denatured, solublized and refolded protease domain, which is then activated by cleavage at the RI site (see, e.g., EXAMPLES).

Modifications

A variety of modification of the SP proteins and domains are contemplated herein. An SP-encoding nucleic acid molecule be modified by any of numerous strategies known in the art (Sambrook et al. (1989) *Molecular Cloning, A Laboratory Manual*, 2d ed., Cold Spring Harbor Laboratory, Cold Spring Harbor, N.Y.). The sequences can be cleaved at appropriate sites with restriction endonuclease(s), followed by further enzymatic modification if desired, isolated, and ligated in vitro. In the production of the gene encoding a domain, derivative or analog of SP, care should be taken to ensure that the modified gene retains the original translational reading frame, uninterrupted by translational stop signals, in the gene region where the desired activity is encoded.

Additionally, the SP-encoding nucleic acid molecules can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Also, as described herein muteins with primary sequence alterations, such as replacements of Cys residues and elimination of glycosylation sites are contemplated. Such mutations can be effected by any technique for mutagenesis known in the art, including, but not limited to, chemical mutagenesis and in vitro site-directed mutagenesis (Hutchinson et al., *J. Biol. Chem.* 253:6551–6558 (1978)), use of TAB® linkers (Pharmacia). In one embodiment, for example, an SP protein or domain thereof is modified to include a fluorescent label. In other specific embodiments, the SP protein is modified to have a heterofunctional reagent, such heterofunctional reagents can be used to crosslink the members of the complex.

The SP proteins can be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties can be evaluated using any suitable assay known in the art.

F. Screening Methods

The single chain protease domains, as shown herein, can be used in a variety of methods to identify compounds that modulate the activity thereof. For SPs that exhibit higher activity or expression in tumor cells, compounds that inhibit the proteolytic activity are of particular interest. For any SPs that are active at lower levels in tumor cells, compounds or agents that enhance the activity are potentially of interest. In all instances the identified compounds include agents that are candidate cancer treatments.

Several types of assays are exemplified and described herein. It is understood that the protease domains can be used in other assays. It is shown here, however, that the single chain protease domains exhibit catalytic activity. As such they are ideal for in vitro screening assays. They can also be used in binding assays.

The CVSP14 full length zymogens, activated enzymes, single and two chain protease domains are contemplated for use in any screening assay known to those of skill in the art, including those provided herein. Hence the following description, if directed to proteolytic assays is intended to apply to use of a single chain protease domain or a catalytically active portion thereof of any SP, including a CVSP14. Other assays, such as binding assays are provided herein, particularly for use with a CVSP14, including any variants, such as splice variants thereof.

1. Catalytic Assays for Identification of Agents that Modulate the Protease Activity of an SP Protein Methods for identifying a modulator of the catalytic activity of an SP, particularly a single chain protease domain or catalytically active portion thereof, are provided herein. The methods can be practiced by: a) contacting the CVSP14, a full-length zymogen or activated form, and particularly a single-chain domain thereof, with a substrate of the CVSP14 in the presence of a test substance, and detecting the proteolysis of the substrate, whereby the activity of the CVSP14 is assessed, and comparing the activity to a control. For example, the control can be the activity of the CVSP14 assessed by contacting a CVSP14, including a full-length zymogen or activated form, and particularly a single-chain domain thereof, particularly a single-chain domain thereof, with a substrate of the CVSP14, and detecting the proteolysis of the substrate, whereby the activity of the CVSP14 is assessed. The results in the presence and absence of the test compounds are compared. A difference in the activity indicates that the test substance modulates the activity of the CVSP14. Activators of activation are also contemplated; such assays are discussed below.

In one embodiment a plurality of the test substances are screened simultaneously in the above screening method. In another embodiment, the CVSP14 is isolated from a target cell as a means for then identifying agents that are potentially specific for the target cell.

In another embodiment, a test substance is a therapeutic compound, and whereby a difference of the CVSP14 activity measured in the presence and in the absence of the test substance indicates that the target cell responds to the therapeutic compound.

One method includes the steps of (a) contacting the CVSP14 polypeptide or protease domain thereof with one or a plurality of test compounds under conditions conducive to interaction between the ligand and the compounds; and (b) identifying one or more compounds in the plurality that specifically binds to the ligand.

Another method provided herein includes the steps of a) contacting a CVSP14 polypeptide or protease domain thereof with a substrate of the CVSP14 polypeptide, and detecting the proteolysis of the substrate, whereby the activity of the CVSP14 polypeptide is assessed; b) contacting the CVSP14 polypeptide with a substrate of the CVSP14 polypeptide in the presence of a test substance, and detecting the proteolysis of the substrate, whereby the activity of the CVSP14 polypeptide is assessed; and c) comparing the activity of the CVSP14 polypeptide assessed in steps a) and b), whereby the activity measured in step a) differs from the activity measured in step b) indicates that the test substance modulates the activity of the CVSP14 polypeptide.

In another embodiment, a plurality of the test substances are screened simultaneously. In comparing the activity of a CVSP14 polypeptide in the presence and absence of a test substance to assess whether the test substance is a modulator of the CVSP14 polypeptide, it is unnecessary to assay the activity in parallel, although such parallel measurement is typical. It is possible to measure the activity of the CVSP14 polypeptide at one time point and compare the measured activity to a historical value of the activity of the CVSP14 polypeptide.

For instance, one can measure the activity of the CVSP14 polypeptide in the presence of a test substance and compare with historical value of the activity of the CVSP14 polypeptide measured previously in the absence of the test substance, and vice versa. This can be accomplished, for example, by providing the activity of the CVSP14 polypeptide on an insert or pamphlet provided with a kit for conducting the assay.

Methods for selecting substrates for a particular SP are described in the EXAMPLES, and particular proteolytic assays are exemplified.

Combinations and kits containing the combinations optionally including instructions for performing the assays are provided. The combinations include a CVSP14 polypeptide and a substrate of the CVSP14 polypeptide to be assayed; and, optionally reagents for detecting proteolysis of the substrate. The substrates, which are can be chromogenic or fluorgenic molecules, including proteins, subject to proteolysis by a particular CVSP14 polypeptide, can be identified empirically by testing the ability of the CVSP14 polypeptide to cleave the test substrate. Substrates that are cleaved most effectively (i.e., at the lowest concentrations and/or fastest rate or under desirable conditions), are identified.

Additionally provided herein is a kit containing the above-described combination. The kit optionally includes instructions for identifying a modulator of the activity of a CVSP14 polypeptide. Any CVSP14 polypeptide is contemplated as target for identifying modulators of the activity thereof.

2. Binding Assays

Also provided herein are methods for identification and isolation of agents, particularly compounds that bind to CVSP14s. The assays are designed to identify agents that bind to the zymogen form, the single chain isolated protease domain (or a protein, other than a CVSP14 polypeptide, that contains the protease domain of a CVSP14 polypeptide), and to the activated form, including the activated form derived from the full length zymogen or from an extended protease domain. The identified compounds are candidates or leads for identification of compounds for treatments of tumors and other disorders and diseases involving aberrant angiogenesis. The CVSP14 polypeptides used in the methods include any CVSP14 polypeptide as defined herein, including the CVSP14 single chain protease domain or proteolytically active portion thereof.

A variety of methods are provided herein. These methods can be performed in solution or in solid phase reactions in which the CVSP14 polypeptide(s) or protease domain(s) thereof are linked, either directly or indirectly via a linker, to a solid support. Screening assays are described in the Examples, and these assays have been used to identify candidate compounds. For purposes herein, all binding assays described above are provided for CVSP14.

Methods for identifying an agent, such as a compound, that specifically binds to a CVSP14 single chain protease domain, a zymogen or full-length activated CVSP14 or two chain protease domain thereof are provided herein. The method can be practiced by (a) contacting the CVSP14 with one or a plurality of test agents under conditions conducive to binding between the CVSP14 and an agent; and (b) identifying one or more agents within the plurality that specifically binds to the CVSP14. For example, in practicing such methods the CVSP14 polypeptide is mixed with a potential binding partner or an extract or fraction of a cell under conditions that allow the association of potential binding partners with the polypeptide. After mixing, peptides, polypeptides, proteins or other molecules that have become associated with a CVSP14 are separated from the mixture. The binding partner that bound to the CVSP14 can then be removed and further analyzed. To identify and isolate a binding partner, the entire protein, for instance the entire disclosed protein of SEQ ID Nos. 6 can be used. Alternatively, a fragment of the protein can be used.

A variety of methods can be used to obtain cell extracts or body fluids, such as blood, serum, urine, sweat, synovial fluid, CSF and other such fluids. For example, cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the CVSP14 under conditions in which association of the protein with the binding partner can occur. A variety of conditions can be used, including conditions that resemble conditions found in the cytoplasm of a human cell. Features such as osmolarity, pH, temperature, and the concentration of cellular extract used, can be varied to optimize the association of the protein with the binding partner. Similarly, methods for isolation of molecules of interest from body fluids are known.

After mixing under appropriate conditions, the bound complex is separated from the mixture. A variety of techniques can be used to separate the mixture. For example, antibodies specific to a CVSP14 can be used to immunoprecipitate the binding partner complex. Alternatively, standard chemical separation techniques such as chromatography and density/sediment centrifugation can be used.

After removing the non-associated cellular constituents in the extract, the binding partner can be dissociated from the complex using conventional methods. For example, dissociation can be accomplished by altering the salt concentration or pH of the mixture.

To aid in separating associated binding partner pairs from the mixed extract, the CVSP14 can be immobilized on a solid support. For example, the protein can be attached to a nitrocellulose matrix or acrylic beads. Attachment of the protein or a fragment thereof to a solid support aids in separating peptide/binding partner pairs from other constituents found in the extract. The identified binding partners can be either a single protein or a complex made up of two or more proteins.

Alternatively, the nucleic acid molecules encoding the single chain proteases can be used in a yeast two-hybrid system. The yeast two-hybrid system has been used to identify other protein partner pairs and can readily be adapted to employ the nucleic acid molecules herein described.

Another in vitro binding assay, particularly for a CVSP14, uses a mixture of a polypeptide that contains at least the catalytic domain of one of these proteins and one or more candidate binding targets or substrates. After incubating the mixture under appropriate conditions, the ability of the CVSP14 or a polypeptide fragment thereof containing the catalytic domain to bind to or interact with the candidate substrate is assessed. For cell-free binding assays, one of the components includes or is coupled to a detectable label. The label can provide for direct detection, such as radioactivity, luminescence, optical or electron density, etc., or indirect detection such as an epitope tag, an enzyme, etc. A variety of methods can be employed to detect the label depending on the nature of the label and other assay components. For example, the label can be detected bound to the solid substrate or a portion of the bound complex containing the label can be separated from the solid substrate, and the label thereafter detected.

3. Detection of Signal Transduction

Secreted CVSPs, such as CVSP14, can be involved in signal transduction either directly by binding to or interacting with a cell surface receptor or indirectly by activating proteins, such as pro-growth factors that can initiate signal transduction. Assays for assessing signal transduction are well known to those of skill in the art, and can be adapted for use with the CVSP14 polypeptide.

Assays for identifying agents that affect or alter signal transduction mediated directly or indirectly, such as via activation of a pro-growth factor, by a CVSP14, particularly the full length or a sufficient portion to anchor the extracellular domain or a functional portion thereof of a CVSP on the surface of a cell are provided. Such assays, include, for example, transcription based assays in which modulation of a transduced signal is assessed by detecting an effect on an expression from a reporter gene (see, e.g., U.S. Pat. No. 5,436,128).

4. Methods for Identifying Agents that Modulate the Expression a Nucleic Acid Encoding a CVSP14

Another embodiment provides methods for identifying agents that modulate the expression of a nucleic acid encoding a CVSP14. Such assays use any available means of monitoring for changes in the expression level of the nucleic acids encoding a CVSP14.

In one assay format, cell lines that contain reporter gene fusions between the open reading frame of CVSP14 or a domain thereof, particularly the protease domain and any assayable fusion partner can be prepared. Numerous assayable fusion partners are known and readily available including the firefly luciferase gene and the gene encoding chloramphenicol acetyltransferase (Alam et al., *Anal. Biochem.* 188: 245–54 (1990)). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding a CVSP14.

Additional assay formats can be used to monitor the ability of the agent to modulate the expression of a nucleic acid encoding a CVSP14. For instance, mRNA expression can be monitored directly by hybridization to the nucleic acids. Cell lines are exposed to the agent to be tested under appropriate conditions and time and total RNA or mRNA is isolated by standard procedures (see, e.g., Sambrook et al. (1989) MOLECULAR CLONING: A LABORATORY MANUAL, 2nd Ed. Cold Spring Harbor Laboratory Press). Probes to detect differences in RNA expression levels between cells exposed to the agent and control cells can be prepared from the nucleic acids. It is typical, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes can be designed from the nucleic acids through methods known in the art. For instance, the G+C content of the probe and the probe length can affect probe binding to its target sequence. Methods to optimize probe specificity are commonly available (see, e.g., Sambrook et al. (1989) MOLECULAR CLONING: A LABORATORY MANUAL, 2nd Ed. Cold Spring Harbor Laboratory Press); and Ausubel et al. (1995) CURRENT PROTOCOLS IN MOLECULAR BIOLOGY, Greene Publishing Co., NY).

Hybridization conditions are modified using known methods (see, e.g., Sambrook et al. (1989) MOLECULAR CLONING: A LABORATORY MANUAL, 2nd Ed. Cold Spring Harbor Laboratory Press); and Ausubel et al. (1995) CURRENT PROTOCOLS IN MOLECULAR BIOLOGY, Greene Publishing Co., NY), as required for each probe. Hybridization of total cellular RNA or RNA enriched for polyA RNA can be accomplished in any available format. For instance, total cellular RNA or RNA enriched for polyA RNA can be affixed to a solid support, and the solid support exposed to at least one probe comprising at least one, or part of one of the nucleic acid molecules under conditions in which the probe specifically hybridizes. Alternatively, nucleic acid fragments comprising at least one, or part of one of the sequences can be affixed to a solid support, such as a porous glass wafer. The glass wafer can then be exposed to total cellular RNA or polyA RNA from a sample under conditions in which the affixed sequences specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the CVSP14 polypeptide, are identified.

In one format, the relative amounts of a protein between a cell population that has been exposed to the agent to be tested compared to an un-exposed control cell population can be assayed (e.g., a prostate cancer cell line, a lung cancer cell line, a colon cancer cell line or a breast cancer cell line). In this format, probes, such as specific antibodies, are used to monitor the differential expression or level of activity of the protein in the different cell populations or body fluiids. Cell lines or populations or body fluids are exposed to the agent to be tested under appropriate conditions and time. Cellular lysates or body fluids can be prepared from the exposed cell line or population and a control, unexposed cell line or population or unexposed body fluid. The cellular lysates or body fluids are then analyzed with the probe.

For example, N- and C-terminal fragments of the CVSP14 can be expressed in bacteria and used to search for proteins which bind to these fragments. Fusion proteins, such as His-tag or GST fusion to the N- or C-terminal regions of the CVSP14 can be prepared for use as a substrate. These fusion proteins can be coupled to, for example, Glutathione-Sepharose beads and then probed with cell lysates or body fluids. Prior to lysis, the cells or body fluids can be treated with a candidate agent which can modulate a CVSP14 or proteins that interact with domains thereon. Lysate proteins binding to the fusion proteins can be resolved by SDS-PAGE, isolated and identified by protein sequencing or mass spectroscopy, as is known in the art.

Antibody probes are prepared by immunizing suitable mammalian hosts in appropriate immunization protocols using the peptides, polypeptides or proteins if they are of sufficient length (e.g., 4, 5, 6, 7, 8, 9, 10, 11, 12, 13, 14, 15, 20, 25, 30, 35, 40 or more consecutive amino acids the CVSP14 polypeptide or if required to enhance immunogenicity, conjugated to suitable carriers. Methods for preparing immunogenic conjugates with carriers, such as bovine serum albumin (BSA), keyhole limpet hemocyanin (KLH), or other carrier proteins are well known in the art. In some circumstances, direct conjugation using, for example, carbodiimide reagents can be effective; in other instances linking reagents such as those supplied by Pierce Chemical Co., Rockford, Ill., can be desirable to provide accessibility to the hapten. Hapten peptides can be extended at either the amino or carboxy terminus with a Cys residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal amino acids of the CVSP14. Synthetic peptides can be as small as 1–3 amino acids in length, generally at least 4 or more amino acid residues long. The peptides can be coupled to KLH using standard methods and can be immunized into animals, such as rabbits or ungulate. Polyclonal antibodies can then be purified, for example using Actigel beads containing the covalently bound peptide.

While the polyclonal antisera produced in this way can be satisfactory for some applications, for pharmaceutical compositions, use of monoclonal preparations are generally used. Immortalized cell lines which secrete the desired monoclonal antibodies can be prepared using the standard method of Kohler et al., (*Nature* 256: 495–7 (1975)) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in vivo via ascites fluid. Of particular interest, are monoclonal antibodies that recognize the catalytic domain of the a CVSP14.

Additionally, the zymogen or two-chain form of the CVSP14 can be used to make monoclonal antibodies that recognize conformation epitopes. The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments are often used, especially in a therapeutic context, as these fragments are generally less immunogenic than the whole immunoglobulin.

The antibodies or fragments can also be produced. Regions that bind specifically to the desired regions of receptor also can be produced in the context of chimeras with multiple species origin.

Agents that are assayed in the above method can be randomly selected or rationally selected or designed.

The agents can be, as examples, peptides, small molecules, and carbohydrates. A skilled artisan can readily recognize that there is no limit as to the structural nature of the agents.

The peptide agents can be prepared using standard solid phase (or solution phase) peptide synthesis methods, as is known in the art. In addition, the DNA encoding these peptides can be synthesized using commercially available oligonucleotide synthesis instrumentation and produced recombinantly using standard recombinant production systems. The production using solid phase peptide synthesis is necessitated if non-gene-encoded amino acids are to be included.

G. Assay Formats and Selection of Test Substances that Modulate at Least One Activity of a CVSP14 Polypeptide Methods for identifying agents that modulate at least one activity of a CVSP14 are provided. The methods include phage display and other methods for assessing alterations in the activity of a CVSP14. Such methods or assays can use any means of monitoring or detecting the desired activity. A variety of formats and detection protocols are known for performing screening assays. Any such formats and protocols can be adapted for identifying modulators of CVSP14 polypeptide activities. The following includes a discussion of exemplary protocols.

1. High Throughput Screening Assays

Although the above-described assay can be conducted where a single CVSP14 polypeptide is screened, and/or a single test substance is screened in one assay, the assay typically is conducted in a high throughput screening mode, i.e., a plurality of the SP proteins are screened against and/or a plurality of the test substances are screened simultaneously (See generally, *High Throughput Screening: The Discovery of Bioactive Substances* (Devlin, Ed.) Marcel Dekker, 1997; Sittampalam et al., *Curr. Opin. Chem. Biol.*, 1:384–91 (1997); and Silverman et al., *Curr. Opin. Chem. Biol.*, 2:397–403 (1998)). For example, the assay can be conducted in a multi-well (e.g., 24-, 48-, 96-, 384-, 1536-well or higher density), chip or array format.

High-throughput screening (HTS) is the process of testing a large number of diverse chemical structures against disease targets to identify "hits" (Sittampalam et al., *Curr. Opin. Chem. Biol.*, 1:384–91 (1997)). Current state-of-the-art HTS operations are highly automated and computerized to handle sample preparation, assay procedures and the subsequent processing of large volumes of data.

Detection technologies employed in high-throughput screens depend on the type of biochemical pathway being investigated (Sittampalam et al., *Curr. Opin. Chem. Bio.*, 1:384–91 (1997)). These methods include, radiochemical methods, such as the scintillation proximity assays (SPA), which can be adapted to a variety of enzyme assays (Lerner et al., *J. Biomol. Screening*, 1:135–143 (1996); Baker et al., *Anal. Biochem.*, 239:20–24 (1996); Baum et al., *Anal. Biochem.*, 237:129–134 (1996); and Sullivan et al., *J. Biomol. Screening* 2:19–23 (1997)) and protein-protein interaction assays (Braunwalder et al., *J. Biomol. Screening* 1:23–26 (1996); Sonatore et al., *Anal. Biochem.* 240:289–297 (1996); and Chen et al., *J. Biol. Chem.* 271: 25308–25315 (1996)), and non-isotopic detection methods, including but are not limited to, calorimetric and luminescence detection methods, resonance energy transfer (RET) methods, time-resolved fluorescence (HTRF) methods, cell-based fluorescence assays, such as fluorescence resonance energy transfer (FRET) procedures (see, e.g., Gonzalez et al., *Biophys. J.*, 69:1272–1280 (1995)), fluorescence polarization or anisotropy methods (see, e.g., Jameson et al., *Methods Enzymol.* 246:283–300 (1995); Jolley, *J. Biomol. Screening* 1:33–38 (1996); Lynch et al., *Anal. Biochem.*

247:77–82 (1997)), fluorescence correlation spectroscopy (FCS) and other such methods.

2. Test Substances

Test compounds, including small molecules, antibodies, proteins, nucleic acids, peptides, and libraries and collections thereof, can be screened in the above-described assays and assays described below to identify compounds that modulate the activity of a CVSP14 polypeptide. Rational drug design methodologies that rely on computational chemistry can be used to screen and identify candidate compounds.

The compounds identified by the screening methods include inhibitors, including antagonists, and can be agonists Compounds for screening include any compounds and collections of compounds available, known or that can be prepared.

a. Selection of Compounds

Compounds can be selected for their potency and selectivity of inhibition of serine proteases, especially a CVSP14 polypeptide. As described herein, and as generally known, a target serine protease and its substrate are combined under assay conditions permitting reaction of the protease with its substrate. The assay is performed in the absence of test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells.

Typically candidate compounds have an $IC_{50}$ value of 100 nM or less as measured in an in vitro assay for inhibition of CVSP14 polypeptide activity. The test compounds also are evaluated for selectivity toward a serine protease. As described herein, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value for the target enzyme, e.g., CVSP14 polypeptide, and a higher $IC_{50}$ value or $EC_{50}$ value for other enzymes within the test panel (e.g., urokinase tissue plasminogen activator, thrombin, Factor Xa), is considered to be selective toward the target enzyme. Generally, a compound is deemed selective if its $IC_{50}$ value or $EC_{50}$ value in the target enzyme assay is at least one order of magnitude less than the next smallest $IC_{50}$ value or $EC_{50}$ value measured in the selectivity panel of enzymes.

Compounds are also evaluated for their activity in vivo. The type of assay chosen for evaluation of test compounds depends on the pathological condition to be treated or prevented by use of the compound, as well as the route of administration to be evaluated for the test compound.

For instance, to evaluate the activity of a compound to reduce tumor growth through inhibition of CVSP14 polypeptide, the procedures described by Jankun et al., *Canc. Res.* 57:559–563 (1997) to evaluate PAI-1 can be employed. Briefly, the ATCC cell lines DU145 and LnCaP are injected into SCID mice. After tumors are established, the mice are given test compound according to a dosing regime determined from the compound's in vitro characteristics. The Jankun et al. compound was administered in water. Tumor volume measurements are taken twice a week for about five weeks. A compound is deemed active if an animal to which the compound was administered exhibited decreased tumor volume, as compared to animals receiving appropriate control compounds.

Another in vivo experimental model designed to evaluate the effect of p-aminobenzamidine, a swine protease inhibitor, on reducing tumor volume is described by Billström et al., *Int. J. Cancer* 61:542–547 (1995).

To evaluate the ability of a compound to reduce the occurrence of, or inhibit, metastasis, the procedures described by Kobayashi et al. *Int. J. Canc.* 57:727–733d (1994) can be employed. Briefly, a murine xenograft selected for high lung colonization potential in injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1–6 or days 7–13 after tumor inoculation. The animals are sacrificed about three or four weeks after tumor inoculation, and the lung tumor colonies are counted. Evaluation of the resulting data permits a determination as to efficacy of the test compound, optimal dosing and route of administration.

The activity of the tested compounds toward decreasing tumor volume and metastasis can be evaluated in model described in Rabbani et al., *Int. J. Cancer* 63:840–845 (1995) to evaluate their inhibitor. There, Mat LyLu tumor cells were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al., *Canc. Res.* 57:3585–3593 (1997).

To evaluate the anti-angiogenesis activity of a compound, a rabbit cornea neovascularization model can be employed (see, e.g., Avery et al. (1990) *Arch. Ophthalmol.*, 108: 1474–147). Avery et al. describes anesthetizing New Zealand albino rabbits and then making a central corneal incision and forming a radial corneal pocket. A slow release prostaglandin pellet was placed in the pocket to induce neovascularization. Test compound was administered i.p. for five days, at which time the animals were sacrificed. The effect of the test compound is evaluated by review of periodic photographs taken of the limbus, which can be used to calculate the area of neovascular response and, therefore, limbal neovascularization. A decreased area of neovascularization as compared with appropriate controls indicates the test compound was effective at decreasing or inhibiting neovascularization.

An angiogenesis model used to evaluate the effect of a test compound in preventing angiogenesis is described by Min et al. *Canc. Res.* 56:2428–2433 (1996). C57BL6 mice receive subcutaneous injections of a Matrigel mixture containing bFGF, as the angiogenesis-inducing agent, with and without the test compound. After five days, the animals are sacrificed and the Matrigel plugs, in which neovascularization can be visualized, are photographed. An experimental animal receiving Matrigel and an effective dose of test compound exhibits less vascularization than a control animal or an experimental animal receiving a less- or non-effective does of compound.

An in vivo system designed to test compounds for their ability to limit the spread of primary tumors is described by Crowley et al., *Proc. Natl. Acad. Sci.* 90:5021–5025 (1993). Nude mice are injected with tumor cells (PC3) engineered to express CAT (chloramphenicol acetyltransferase). Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental modes designed to evaluate the inhibitory potential of a test serine protease inhibitors, using a tumor cell line F3II known to be highly invasive (see, e.g., Alonso et al., *Breast Canc. Res. Treat.* 40:209–223 (1996)). Alonso describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski in 1998 (*J. Cell Biol.* 107:2437–2445 (1988)), provides another method for evaluating the inhibitory activity of a test compound. In the CAM model, tumor cells invade through the chorioallantoic membrane containing CAM with tumor cells in the presence of several serine protease inhibitors results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's inhibitory activity. A compound having inhibitory activity correlates with less tumor invasion.

The CAM model is also used in a standard assay of angiogenesis (i.e., effect on formation of new blood vessels (Brooks et al. *Methods in Molecular Biology* 129:257–269 (1999)). According to this model, a filter disc containing an angiogenesis inducer, such as basic fibroblast growth factor (bFDG) is placed onto the CAM. Diffusion of the cytokine into the CAM induces local angiogenesis, which can be measured in several ways such as by counting the number of blood vessel branch points within the CAM directly below the filter disc. The ability of identified compounds to inhibit cytokine-induced angiogenesis can be tested using this model. A test compound can either be added to the filter disc that contains the angiogenesis inducer, be placed directly on the membrane or be administered systemically. The extent of new blood vessel formation in the presence and/or absence of test compound can be compared using this model. The formation of fewer new blood vessels in the presence of a test compound would be indicative of anti-angiogenesis activity. Demonstration of anti-angiogenesis activity for inhibitors of a CVSP14 polypeptide indicates a role in angiogenesis for that SP protein.

b. Known Serine Protease Inhibitors

Compounds for screening can be serine protease inhibitors, which can be tested for their ability to inhibit the activity of a CVSP14. Exemplary, serine protease inhibitors for use in the screening assays, include, but are not limited to: Serine Protease Inhibitor 3 (SPI-3) (Chen, et al. *Citokine*, 11:856–862 (1999)); Aprotinin (Iijima, R., et al., *J. Biochem.* (*Tokyo*) 126:912–916 (1999)); Kazal-type serine protease inhibitor-like proteins (Niimi, et al. *Eur. J. Biochem.*, 266: 282–292 (1999)); Kunitz-type serine protease inhibitor (Ravichandran, S., et al., *Acta Crystallogr. D. Biol. Crystallogr.*, 55:1814–1821 (1999)); Tissue factor pathway inhibitor-2/Matrix-associated serine rotease inhibitor (TFPI-2/MSPI), (Liu, Y. et al. *Arch. Biochem. Biophys.* 370:112–8 (1999)); Bukunin (Cui, C. Y. et al. *J. Invest. Dermatol.* 113:182–8 (1999)); Nafmostat mesilate (Ryo, R. et al. *Vox Sang.* 76:241–6 (1999)); TPCK (Huang et al. *Oncogene* 18:3431–3439 (1999)); A synthetic cotton-bound serine protease inhibitor (Edwards et al. *Wound Repair Regen.* 7:106–18 (1999)); FUT-175 (Sawada, M. et al. *Stroke* 30:644–50 (1999)); Combination of serine protease inhibitor FUT-0175 and thromboxane synthetase inhibitor OKY-046 (Kaminogo et al. *Neurol. Med. Chir.* (*Tokyo*) 38:704–8; discussion 708–9 (1998)); The rat serine protease inhibitor 2.1 gene (LeCam, A., et al., *Biochem. Biophys. Res. Commun.*, 253:311–4 (1998)); A new intracellular serine protease inhibitor expressed in the rat pituitary gland complexes with granzyme B (Hill et al. *FEBS Lett.* 440:361–4 (1998)); 3,4-Dichloroisocoumarin (Hammed et al. *Proc. Soc. Exp. Biol. Med.*, 219:132–7 (1998)); LEX032 (Bains et al. *Eur. J. Pharmacol.* 356:67–72 (1998)); N-tosyl-L-phenylalanine chloromethyl ketone (Dryjanski et al. *Biochemistry* 37:14151–6 (1998)); Mouse gene for the serine protease inhibitor neuroserpin (P112) (Berger et al. *Gene*, 214:25–33 (1998)); Rat serine protease inhibitor 2.3 gene (Paul et al. *Eur. J. Biochem.* 254:538–46 (1998)); Ecotin (Yang et al. *J. Mol. Biol.* 279:945–57 (1998)); A 14 kDa plant-related serine protease inhibitor (Roch et al. *Dev. Comp. Immunol.* 22(1):1–12 (1998)); Matrix-associated serine protease inhibitor TFPI-2/33 kDa MSPI (Rao et al. *Int. J. Cancer* 76:749–56 (1998)); ONO-3403 (Hiwasa et al. *Cancer Lett.* 126:221–5 (1998)); Bdellastasin (Moser et al. *Eur. J. Biochem.* 253:212–20 (1998)); Bikunin (Xu et al. *J. Mol. Biol.* 276:955–66 (1998)); Nafamostat mesilate (Meligren et al. *Thromb. Haemost.* 79:342–7 (1998)); The growth hormone dependent serine protease inhibitor, Spi 2.1 (Maake et al. *Endocrinology* 138:5630–6 (1997)); Growth factor activator inhibitor type 2, a Kunitz-type serine protease inhibitor (Kawaguchi et al. *J. Biol. Chem.*, 272:27558–64 (1997)); Heat-stable serine protease inhibitor protein from ovaries of the desert locust, *Schistocerga gregaria* (Hamdaoui et al. *Biochem. Biophys. Res. Commun.* 238:357–60 (1997)); Human placental Hepatocyte growth factor activator inhibitor, a Kunitz-type serine protease inhibitor (Shimomura et al. *J. Biol. Chem.* 272:6370–6 (1997)); FUT-187, oral serine protease inhibitor (Shiozaki et al. *Gan To Kaguku Ryoho*, 23(14): 1971–9 (1996)); Extracellular matrix-associated serine protease inhibitors (Mr 33,000, 31,000, and 27,000 (Rao, C. N., et al., *Arch. Biochem. Biophys.*, 335:82–92 (1996)); An irreversible isocoumarin serine protease inhibitor (Palencia, D. D., et al., *Biol. Reprod.*, 55:536–42 (1996)); 4-(2-aminoethyl)-benzenesulfonyl fluoride (AEBSF) (Nakabo et al. *J. Leukoc. Biol.* 60:328–36 (1996)); Neuroserpin (Osterwalder, T., et al., *EMBO J.* 15:2944–53 (1996)); Human serine protease inhibitor alpha-1-antitrypsin (Forney et al. *J. Parasitol.* 82:496–502 (1996)); Rat serine protease inhibitor 2.3 (Simar-Blanchet, A. E., et al., *Eur. J. Biochem.*, 236:638–48 (1996)); Gebaxate mesilate (parodi, F., et al., *J. Cardiothorac. Vasc. Anesth.* 10:235–7 (1996)); Recombinant serine protease inhibitor, CPTI II (Stankiewicz, M., et al., (*Acta Biochim. Pol.*, 43(3):525–9 (1996)); A cysteine-rich serine protease inhibitor (Guamerin II) (Kim, D. R., et al., *J. Enzym. Inhib.*, 10:81–91 (1996)); Diisopropylfluorophosphate (Lundqvist, H., et al., *Inflamm. Res.*, 44(12): 510–7 (1995)); Nexin 1 (Yu, D. W., et al., *J. Cell Sci.*, 108(Pt 12):3867–74 (1995)); LEX032 (Scalia, R., et al., *Shock*, 4(4):251–6 (1995)); Protease nexin I (Houenou, L. J., et al., *Proc. Natl. Acad. Sci. U.S.A.*, 92(3):895–9 (1995)); Chymase-directed serine protease inhibitor (Woodard S. L., et al., *J. Immunol.*, 153(11):5016–25 (1994)); N-alpha-tosyl-L-lysyl-chloromethyl ketone (TLCK) (Bourinbaiar, A. S., et al., *Cell Immunol.*, 155(1):230–6 (1994)); Smpi56 (Ghendler, Y., et al., *Exp. Parasitol.*, 78(2):121–31 (1994)); Schistosoma haematobium serine protease (Blanton, R. E., et al., *Mol. Biochem. Parasitol.*, 63(1):1–11 (1994)); Spi-1 (Warren, W. C., et al., *Mol. Cell Endocrinol.*, 98(1):27–32 (1993)); TAME (Jessop, J. J., et al., *Inflammation*, 17(5):613–31 (1993)); Antithrombin III (Kalaria, R. N., et al., *Am. J. Pathol.*, 143(3):886–93 (1993)); FOY-305 (Ohkoshi, M., et al., *Anticancer Res.*, 13(4):963–6 (1993)); Camostat mesilate (Senda, S., et al., *Intern. Med.*, 32(4):350–4 (1993)); Pigment epithelium-derived factor (Steele, F. R., et al., *Proc. Natl. Acad. Sci. U.S.A.*, 90(4):1526–30 (1993)); Antistasin (Holstein, T. W., et al., *FEBS Lett.*, 309(3):288–92 (1992)); The vaccinia virus K2L gene encodes a serine protease inhibitor (Zhou, J., et al., *Virology*, 189(2):678–86 (1992)); Bowman-Birk serine-protease inhibitor (Werner, M. H., et al., *J. Mol. Biol.*, 225(3):873–89 (1992); FUT-175 (Yanamoto, H., et al., *Neurosurgery*, 30(3):358–63 (1992)); FUT-175; (Yanamoto, H., et al., *Neurosurgery*, 30(3):351–6, discussion 356–7 (1992)); PAI-I (Yreadwell, B. V., et al., *J. Orthop. Res.*, 9(3):309–16 (1991)); 3,4-Dichloroisocoumarin (Rusbridge, N. M., et al., *FEBS Lett.*, 268(1):133–6 (1990)); Alpha 1-antichymotrypsin (Lindmark, B. E., et al., *Am. Rev. Respir. Des.*, 141(4 Pt 1):884–8 (1990)); P-toluenesulfonyl-L-arginine methyl ester (TAME) (Scuderi, P., *J. Immunol.*, 143(1):168–73 (1989)); Alpha 1-antichymotrypsin (Abraham, C. R., et al., *Cell*, 52(4):487–501 (1988)); Contrapsin (Modha, J., et al., *Parasitology*, 96 (Pt 1):99–109 (1988)); Alpha 2-antiplasmin (Holmes, W. E., et al., *J. Biol. Chem.*, 262(4):1659–64 (1987)); 3,4-dichloroisocoumarin (Harper, J. W., et al., *Biochemistry*, 24(8):1831–41 (1985)); Diisoprophylfluorophosphate (Tsutsui, K., et al., *Biochem. Biophys. Res. Commun.*, 123(1):271–7 (1984)); Gabexate mesilate (Hesse, B., et al., *Pharmacol. Res. Commun.*, 16(7):637–45 (1984)); Phenyl methyl sulfonyl fluoride (Dufer, J., et al., *Scand. J. Haematol.*, 32(11):25–32 (1984)); Protease inhibitor CI-2 (McPhalen, C. A., et al., *J. Mol. Biol.*, 168(2):445–7 (1983)); Phenylmethylsulfonyl fluoride (Sekar V., et al., *Biochem. Biophys. Res. Commun.*, 89(2):474–8 (1979)); PGE1 (Feinstein, M. D., et al., *Prostaglandine*, 14(6):1075–93 (1977).

C. Combinatorial Libraries and Other Libraries

The source of compounds for the screening assays, can be libraries, including, but are not limited to, combinatorial libraries. Methods for synthesizing combinatorial libraries and characteristics of such combinatorial libraries are known in the art (See generally, *Combinatorial Libraries: Synthesis, Screening and Application Potential* (Cortese Ed.) Walter de Gruyter, Inc., 1995; Tietze and Lieb, *Curr. Opin. Chem. Biol.*, 2(3):363–71 (1998); Lam, *Anticancer Drug Des.*, 12(3):145–67 (1997); Blaney and Martin, *Curr. Opin. Chem. Biol.*, 1(1):54–9 (1997); and Schultz and Schultz, *Biotechnol. Prog.*, 12(6):729–43 (1996)).

Methods and strategies for generating diverse libraries, primarily peptide- and nucleotide-based oligomer libraries, have been developed using molecular biology methods and/or simultaneous chemical synthesis methodologies (see, e.g., Dower et al., *Annu. Rep. Med. Chem.*, 26:271–280 (1991); Fodor et al., *Science*, 251:767–773 (1991); Jung et al., *Angew. Chem. Ind. Ed. Engl.*, 31:367–383 (1992); Zuckerman et al., *Proc. Natl. Acad. Sci. USA*, 89:4505–4509 (1992); Scott et al., *Science*, 249:386–390 (1990); Devin et al., *Science*, 249:404–406 (1990); Cwirla et al., *Proc. Natl. Acad. Sci. USA*, 87:6378–6382 (1990); and Gallop et al., *J. Medicinal Chemistry*, 37:1233–1251 (1994)). The resulting combinatorial libraries potentially contain millions of compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads (see, e.g., Lam et al., *Nature*, 354:82–84 (1991)) and cotton supports (see, e.g., Eichler et al., *Biochemistry* 32:11035–11041 (1993)); and methods in which the compounds are used in solution (see, e.g., Houghten et al., *Nature*, 354:84–86 (1991); Houghten et al., *BioTechniques*, 313:412–421 (1992); and Scott et al., *Curr. Opin. Biotechnol.*, 5:40–48 (1994)). There are numerous examples of synthetic peptide and oligonucleotide combinatorial libraries and there are many methods for producing libraries that contain non-peptidic small organic molecules. Such libraries can be based on basis set of monomers that are combined to form mixtures of diverse organic molecules or that can be combined to form a library based upon a selected pharmacophore monomer.

Either a random or a deterministic combinatorial library can be screened by the presently disclosed and/or claimed screening methods. In either of these two libraries, each unit of the library is isolated and/or immobilized on a solid support. In the deterministic library, one knows a priori a particular unit's location on each solid support. In a random library, the location of a particular unit is not known a priori although each site still contains a single unique unit. Many methods for preparing libraries are known to those of skill in this art (see, e.g., Geysen et al., *Proc. Natl. Acad. Sci. USA*, 81:3998–4002 (1984), Houghten et al., *Proc. Natl. Acad. Sci. USA*, 81:5131–5135 (1985)). Combinatorial library generated by the any techniques known to those of skill in the art are contemplated (see, e.g., Table 1 of Schultz and Schultz, *Biotechnol. Prog.*, 12(6):729–43 (1996)) for screening; Bartel et al., *Science*, 261:1411–1418 (1993); Baumbach et al. *BioPharm, (Can)*:24–35 (1992); Bock et al. *Nature*, 355:564–566 (1992); Borman, S., Combinatorial chemists focus on samII molecules molecular recognition, and automation, *Chem. Eng. News*, 2(12):29 (1996); Boublik, et al., Eukaryotic Virus Display: Engineering the Major Surface Glycoproteins of the Autographa California Nuclear Polyhedrosis Virus (ACNPV) for the Presentation of Foreign Proteins on the Virus Surface, *Bio/Technology*, 13:1079–1084 (1995); Brenner, et al., Encoded Combinatorial Chemistry, *Proc. Natl. Acad Sci. U.S.A.*, 89:5381–5383 (1992); Caflisch, et al., Computational Combinatorial Chemistry for De Novo Ligand Design: Review and Assessment, *Perspect. Drug Discovery Des.*, 3:51–84 (1995); Cheng, et al., Sequence-Selective Peptide Binding with a Peptido-A,B-trans-steroidal Receptor Selected from an Encoded Combinatorial Library, *J. Am. Chem. Soc.*, 118:1813–1814 (1996); Chu, et al., Affinity Capillary Electrophoresis to Identify the Peptide in A Peptide Library that Binds Most Tightly to Vancomycin, *J. Org. Chem.*, 58:648–652 (1993); Clackson, et al., Making Antibody Fragments Using Phage Display Libraries, *Nature*, 352:624–628 (1991); Combs, et al., Protein Structure-Based Combinatorial Chemistry: Discovery of Non-Peptide Binding Elements to Src SH3 Domain, *J. Am. Chem. Soc.*, 118:287–288 (1996); Cwirla, et al., Peptides On Phage: A Vast Library of Peptides for Identifying Ligands, *Proc. Natl. Acad. Sci. U.S.A.*, 87:6378–6382 (1990); Ecker, et al., Combinatorial Drug Discovery: Which Method will Produce the Greatest Value, *Bio/Technology*, 13:351–360 (1995); Ellington, et al., In Vitro Selection of RNA Molecules That Bind Specific Ligands, *Nature*, 346:818–822 (1990); Ellman, J. A., Variants of Benzodiazephines, *J. Am. Chem. Soc.*, 114:10997 (1992); Erickson, et al., *The Proteins*; Neurath, H., Hill, R. L., Eds.: Academic: New York, 1976; pp. 255–257; Felici, et al., *J. Mol. Biol.*, 222:301–310 (1991); Fodor, et al., Light-Directed, Spatially Addressable Parallel Chemical Synthesis, *Science*, 251:767–773 (1991); Francisco, et al., Transport and Anchoring of Beta-Lactamase to the External Surface of *E. Coli.*, *Proc. Natl. Acad. Sci. U.S.A.*, 89:2713–2717 (1992); Georgiou, et al., Practical Applications of Engineering Gram-Negative Bacterial Cell Surfaces, *TIBTECH*, 11:6–10 (1993); Geysen, et al., Use of peptide synthesis to probe viral antigens for epitopes to a resolution of a single amino acid, *Proc. Natl. Acad. Sci. U.S.A.*, 81:3998–4002 (1984); Glaser, et al., Antibody Engineering by Condon-Based Mutagenesis in a Filamentous Phage Vector System, *J. Immunol.*, 149:3903–3913 (1992); Gram, et al., In vitro selection and affinity maturation of antibodies from a naive combinatorial immunoglobulin library, *Proc. Natl. Acad. Sci.*, 89:3576–3580 (1992); Han, et al., Liquid-Phase Combinatorial Synthesis, *Proc. Natl. Acad. Sci. U.S.A.*, 92:6419–6423 (1995); Hoogenboom, et al., Multi-Subunit Proteins on the Surface of Filamentous Phage: Methodologies for Displaying Antibody (Fab) Heavy and Light Chains, *Nucleic Acids Res.*, 19:4133–4137 (1991); Houghten, et al., General Method for the Rapid Solid-Phase Synthesis of Large Numbers of Peptides: Specificity of Antigen-Antibody Interaction at the Level of Individual Amino Acids, *Proc. Natl. Acad. Sci. U.S.A.*, 82:5131–5135 (1985); Houghten, et al., The Use of Synthetic Peptide Combinatorial Libraries for the Determination of Peptide Ligands in Radio-Receptor Assays-Opiod-Peptides, *Bioorg. Med. Chem. Lett.*, 3:405–412 (1993); Houghten, et al., Generation and Use of Synthetic Peptide Combinatorial Libraries for Basic Research and Drug Discovery, *Nature*, 354:84–86 (1991); Huang, et al., Discovery of New Ligand Binding Pathways in Myoglobin by Random Mutagenesis, *Nature Struct. Biol.*, 1:226–229 (1994); Huse, et al., Generation of a Large Combinatorial Library of the Immunoglobulin Repertoire In Phage Lambda, *Science*, 246:1275–1281 (1989); Janda, K. D., New Strategies for the Design of Catalytic Antibodies, *Biotechnol. Prog.*, 6:178–181 (1990); Jung, et al., Multiple Peptide Synthesis Methods and Their Applications, *Angew. Chem. Int. Ed. Engl.*, 31:367–486 (1992); Kang, et al., Linkage of Recognition and Replication Functions By Assembling Combinatorial Antibody Fab Libraries Along Phage Surfaces, *Proc. Natl. Acad. Sci. U.S.A.*, 88:4363–4366 (1991 a); Kang, et al., Antibody Redesign by Chain Shuffling from Random Combinatorial Immunoglobulin Libraries, *Proc. Natl. Acad. Sci. U.S.A.*, 88:11120–11123 (1991 b); Kay, et al., An M13 Phage Library Displaying Random 38-Amino-Acid-Peptides as a Source of Novel Sequences with Affinity to Selected Targets Genes, *Gene*, 128:59–65 (1993); Lam, et al., A new type of synthetic peptide library for identifying ligand-binding activity, *Nature*, 354:82–84 (1991) (published errata apear in *Nature*, 358:434 (1992) and *Nature*, 360:768 (1992); Lebl, et al., One Bead One Structure Combinatorial Libraries, *Biopolymers (Pept. Sci.)*, 37:177–198 (1995); Lerner, et al., Antibodies without Immunization, *Science*, 258:1313–1314 (1992); Li, et al., Minimization of a Polypeptide Hormone, *Science*, 270:1657–1660 (1995); Light, et al., Display of Dimeric Bacterial Alkaline Phosphatase on the Major Coat Protein of Filamentous Bacteriophage, *Bioorg. Med. Chem. Lett.*, 3:1073–1079 (1992); Little, et al., Bacterial Surface Presentation of Proteins and Peptides: An Alternative to Phage Technology, *Trends Biotechnol.*, 11:3–5 (1993); Marks, et al., By-Passing Immunization. Human Antibodies from V-Gene Libraries Displayed on Phage, *J. Mol. Biol.*, 222:581–597 (1991); Matthews, et al., Substrate Phage: Selection of Protease Substrates by Monovalent Phage Display, *Science*, 260:1113–1117 (1993); McCafferty, et al., Phage Enzymes: Expression and Affinity Chromatography of Functional Alkaline Phosphatase on the Surface of Bacteriophage, *Protein Eng.*, 4:955–961 (1991); Menger, et al., Phosphatase Catalysis Developed Via Combinatorial Organic Chemistry, *J. Org. Chem.*, 60:6666–6667 (1995); Nicolaou, et al., *Angew. Chem. Int. Ed. Engl.*, 34:2289–2291 (1995); Oldenburg, et al., Peptide Ligands for A Sugar-Binding Protein Isolated from a Random Peptide Library, *Proc. Natl. Acad. Sci. U.S.A.*, 89:5393–5397 (1992); Parmley, et al., Antibody-Selectable Filamentous fd Phage Vectors: Affinity Purification of Target Genes, *Genes*, 73:305–318 (1988); Pinilla, et al., Synthetic Peptide Combinatorial Libraries (SPCLS)—Identification of the Antigenic Determinant of Beta-Endorphin Recognized by Monoclonal Antibody-3E7, *Gene*, 128:71–76 (1993); Pinilla, et al., Review of the Utility of Soluble Combinatorial Libraries, *Biopolymers*, 37:221–240 (1995); Pistor, et al., Expression of Viral Hemegglutinan On the Surface of *E. Coli.*, *Klin. Wochenschr.*, 66:110–116 (1989); Pollack, et al., Selective Chemical Catalysis by an Antibody, *Science*, 234:1570–1572 (1986); Rigler, et al., Fluorescence Correlations, Single Molecule Detection and Large Number Screening: Applications in Biotechnology, *J. Biotechnol*, 41:177–186 (1995); Sarvetnick, et al., Increasing the Chemical Potential of the Germ-Line Antibody Repertoire, *Proc. Natl. Acad. Sci. U.S.A.*, 90:4008–4011 (1993); Sastry, et al., Cloning of the Immunological Repertiore in *Escherichia Coli* for Generation of Monoclonal Catalytic Antibodies: Construction of a Heavy Chain Variable Region-Specific cDNA Library, *Proc. Natl. Acad. Sci. U.S.A.*, 86:5728–5732 (1989); Scott, et al., Searching for Peptide Ligands with an Epitope Library, *Science*, 249:386–390 (1990); Sears, et al., Engineering Enzymes for Bioorganic Synthesis: Peptide Bond Formation, *Biotechnol. Prog.*, 12:423–433 (1996); Simon, et. al., Peptides: A Modular Approach to Drug Discovery, *Proc. Natl. Acad. Sci. U.S.A.*, 89:9367–9371 (1992); Still, et al., Discovery of Sequence-Selective Peptide Binding by Synthetic Receptors Using Encoded Combinatorial Libraries, *Acc. Chem. Res.*, 29:155–163 (1996); Thompson, et al., Synthesis and Applications of Small Molecule Libraries, *Chem. Rev.*, 96:555–600 (1996); Tramontano, et al., Catalytic Antibodies, *Science*, 234:1566–1570 (1986); Wrighton, et al., Small Peptides as Potent Mimetics of the Protein Hormone Erythropoietin, *Science*, 273:458–464 (1996); York, et al., Combinatorial mutagenesis of the reactive site region in plasminogen activator inhibitor I, *J. Biol. Chem.*, 266:8595–8600 (1991); Zebedee, et al., Human Combinatorial Antibody Libraries to Hepatitis B Surface Antigen, *Proc. Natl. Acad. Sci. U.S.A.*, 89:3175–3179 (1992); Zuckerman, et al., Identification of Highest-Affinity Ligands by Affinity Selection from Equimolar Peptide Mixtures Generated by Robotic Synthesis, *Proc. Natl. Acad. Sci. U.S.A.*, 89:4505–4509 (1992).

For example, peptides that bind to a CVSP14 polypeptide or a protease domain of an SP protein can be identified using phage display libraries. In an exemplary embodiment, this method can include a) contacting phage from a phage library with the CVSP14 polypeptide or a protease domain thereof; (b) isolating phage that bind to the protein; and (c) determining the identity of at least one peptide coded by the isolated phage to identify a peptide that binds to a CVSP14 polypeptide.

H. Modulators of the Activity of CVSP14 Polypeptides

Provided herein are compounds, identified by screening or produced using the CVSP14 polypeptide or protease domain in other screening methods, that modulate the activity of a CVSP14. These compounds act by directly interacting with the CVSP14 polypeptide or by altering transcription or translation thereof. Such molecules include, but are not limited to, antibodies that specifically react with a CVSP14 polypeptide, particularly with the protease domain thereof, antisense nucleic acids or double-stranded RNA (dsRNA) such as RNAi, that alter expression of the CVSP14 polypeptide, antibodies, peptide mimetics and other such compounds.

1. Antibodies

Antibodies, including polyclonal and monoclonal antibodies, that specifically bind to the CVSP14 polypeptide provided herein, particularly to the single chain protease domains thereof or the activated forms of the full-length or protease domain or the zymogen form, are provided.

Generally, the antibody is a monoclonal antibody, and typically the antibody specifically binds to the protease domain of the CVSP14 polypeptide. In particular embodiments, antibodies to each of the single chain of the protease domain of CVSP14 are provided. Also provided are antibodies that specifically bind to any domain of CVSP14 and to two chain forms thereof.

The CVSP14 polypeptide and domains, fragments, homologs and derivatives thereof can be used as immunogens to generate antibodies that specifically bind such immunogens. Such antibodies include but are not limited to polyclonal, monoclonal, chimeric, single chain, Fab fragments, and an Fab expression library. In a specific embodiment, antibodies to human CVSP14 polypeptide are produced. In another embodiment, complexes formed from fragments of CVSP14 polypeptide, which fragments contain the serine protease domain, are used as immunogens for antibody production.

Various procedures known in the art can be used for the production of polyclonal antibodies to CVSP14 polypeptide, its domains, derivatives, fragments or analogs. For production of the antibody, various host animals can be immunized by injection with the native CVSP14 polypeptide or a synthetic version, or a derivative of the foregoing, such as a cross-linked CVSP14 polypeptide. Such host animals include but are not limited to rabbits, mice, rats, etc. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and corynebacterium parvum.

For preparation of monoclonal antibodies directed towards a CVSP14 polypeptide or domains, derivatives, fragments or analogs thereof, any technique that provides for the production of antibody molecules by continuous cell lines in culture can be used. Such techniques include but are not restricted to the hybridoma technique originally developed by Kohler and Milstein (*Nature* 256:495–497 (1975)), the trioma technique, the human B-cell hybridoma technique (Kozbor et al., *Immunology Today* 4:72 (1983)), and the EBV hybridoma technique to produce human monoclonal antibodies (Cole et al., in *Monoclonal Antibodies and Cancer Therapy*, Alan R. Liss, Inc., pp. 77–96 (1985)). In an additional embodiment, monoclonal antibodies can be produced in germ-free animals utilizing recent technology (PCT/US90/02545). Human antibodies can be used and can be obtained by using human hybridomas (Cote et al., *Proc. Natl. Acad. Sci. USA* 80:2026–2030 (1983)), or by transforming human B cells with EBV virus in vitro (Cole et al., in *Monoclonal Antibodies and Cancer Therapy*, Alan R. Liss, Inc., pp. 77–96 (1985)). Techniques developed for the production of "chimeric antibodies" (Morrison et al., *Proc. Natl. Acad. Sci. USA* 81:6851–6855 (1984); Neuberger et al., *Nature* 312:604–608 (1984); Takeda et al., *Nature* 314: 452–454 (1985)) by splicing the genes from a mouse antibody molecule specific for the CVSP14 polypeptide together with genes from a human antibody molecule of appropriate biological activity can be used.

Techniques described for the production of single chain antibodies (U.S. Pat. No. 4,946,778) can be adapted to produce CVSP14 polypeptide-specific single chain antibodies. An additional embodiment uses the techniques described for the construction of Fab expression libraries (Huse et al., *Science* 246:1275–1281 (1989)) to allow rapid and easy identification of monoclonal Fab fragments with the desired specificity for CVSP14 polypeptide or domains, derivatives, or analogs thereof. Non-human antibodies can be "humanized" by known methods (see, e.g., U.S. Pat. No. 5,225,539).

Antibody fragments that specifically bind to CVSP14 polypeptide or epitopes thereof can be generated by techniques known in the art. For example, such fragments include but are not limited to: the F(ab')2 fragment, which can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

In the production of antibodies, screening for the desired antibody can be accomplished by techniques known in the art, e.g., ELISA (enzyme-linked immunosorbent assay). To select antibodies specific to a particular domain of the CVSP14 polypeptide one can assay generated hybridomas for a product that binds to the fragment of the CVSP14 polypeptide that contains such a domain The foregoing antibodies can be used in methods known in the art relating to the localization and/or quantitation of CVSP14 polypeptide proteins, e.g., for imaging these proteins, measuring levels thereof in appropriate physiological samples, in, for example, diagnostic methods. In another embodiment, anti-CVSP14 polypeptide antibodies, or fragments thereof, containing the binding domain are used as therapeutic agents.

2. Peptides, Polypeptides and Peptide Mimetics

Provided herein are methods for identifying molecules that bind to and modulate the activity of SP proteins. Included among molecules that bind to SPs, particularly the single chain protease domain or catalytically active fragments thereof, are peptides, polypeptides and peptide mimetics, including cyclic peptides. Peptide mimetics are molecules or compounds that mimic the necessary molecular conformation of a ligand or polypeptide for specific binding to a target molecule such as a CVSP14 polypeptide. In an exemplary embodiment, the peptides, peptides, polypeptides and peptide mimetics or peptide mimetics bind to the protease domain of the CVSP14 polypeptide. Such peptides and peptide mimetics include those of antibodies that specifically bind to a CVSP14 polypeptide and, typically, bind to the protease domain of a CVSP14 polypeptide.

The peptides, polypeptides and peptide mimetics and peptide mimetics identified by methods provided herein can be agonists or antagonists of CVSP14 polypeptides.

Such peptides and peptide mimetics are useful for diagnosing, treating, preventing, and screening for a disease or disorder associated with CVSP14 polypeptide activity in a mammal. In addition, the peptides and peptide mimetics are useful for identifying, isolating, and purifying molecules or compounds that modulate the activity of a CVSP14 polypeptide, or specifically bind to a CVSP14 polypeptide, generally the protease domain of a CVSP14 polypeptide. Low molecular weight peptides and peptide mimetics can have strong binding properties to a target molecule, e.g., a CVSP14 polypeptide or the protease domain of a CVSP14 polypeptide.

Peptides, polypeptides and peptide mimetics that bind to CVSP14 polypeptides as described herein can be administered to mammals, including humans, to modulate CVSP14 polypeptide activity. Thus, methods for therapeutic treatment and prevention of neoplastic diseases comprise administering a peptide, polypeptides or peptide mimetic compound in an amount sufficient to modulate such activity are provided. Thus, also provided herein are methods for treating a subject having such a disease or disorder in which a peptide, polypeptides or peptide mimetic compound is administered to the subject in a therapeutically effective dose or amount.

Compositions containing the peptides, polypeptides or peptide mimetics can be administered for prophylactic and/or therapeutic treatments. In therapeutic applications, compositions can be administered to a patient already suffering from a disease, as described above, in an amount sufficient to cure or at least partially arrest the symptoms of the disease and its complications. Amounts effective for this use will depend on the severity of the disease and the weight and general state of the patient and can be empirically determined.

In prophylactic applications, compositions containing the peptides, polypeptides and peptide mimetics are administered to a patient susceptible to or otherwise at risk of a particular disease. Such an amount is defined to be a "prophylactically effective dose". In this use, the precise amounts again depend on the patient's state of health and weight.

Accordingly, the peptides, polypeptides and peptide mimetics that bind to a CVSP14 polypeptide can be used to prepare pharmaceutical compositions containing, as an active ingredient, at least one of the peptides or peptide mimetics in association with a pharmaceutical carrier or diluent. The compounds can be administered, for example, by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration (see, e.g., International PCT application Nos. WO 93/25221 and WO 94/17784; and European Patent Application 613,683).

Peptides, polypeptides and peptide mimetics that bind to CVSP14 polypeptides are useful in vitro as unique tools for understanding the biological role of CVSP14 polypeptides, including the evaluation of the many factors thought to influence, and be influenced by, the production of CVSP14 polypeptide. Such peptides, polypeptides and peptide mimetics are also useful in the development of other compounds that bind to and modulate the activity of a CVSP14 polypeptide, because such compounds provide important information on the relationship between structure and activity that should facilitate such development.

The peptides, polypeptides and peptide mimetics are also useful as competitive binders in assays to screen for new CVSP14 polypeptides or CVSP14 polypeptide agonists. In such assay embodiments, the compounds can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}I$ enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds can also include spacers or linkers in cases where the compounds are to be attached to a solid support.

Moreover, based on their ability to bind to a CVSP14 polypeptide, the peptides, polypeptides and peptide mimetics can be used as reagents for detecting CVSP14 polypeptides in living cells, fixed cells, in biological fluids, in tissue homogenates and in purified, natural biological materials. For example, by labelling such peptides, polypeptides and peptide mimetics, cells having CVSP14 polypeptides can be identified. In addition, based on their ability to bind a CVSP14 polypeptide, the peptides, polypeptides and peptide mimetics can be used in in situ staining, FACS (fluorescence-activated cell sorting), Western blotting, ELISA and other analytical protocols. Based on their ability to bind to a CVSP14 polypeptide, the peptides, polypeptides and peptide mimetics can be used in purification of CVSP14 polypeptide polypeptides or in purifying cells expressing the CVSP14 polypeptide polypeptides, e.g., a polypeptide encoding the protease domain of a CVSP14 polypeptide.

The peptides, polypeptides and peptide mimetics can also be used as commercial reagents for various medical research and diagnostic uses. The activity of the peptides and peptide mimetics can be evaluated either in vitro or in vivo in one of the numerous models described in McDonald (1992) *Am. J. of Pediatric Hematology/Oncology*, 14:8–21.

3. Peptide, Polypeptides and Peptide Mimetic Therapy

Peptide analogs are commonly used in the pharmaceutical industry as non-peptide drugs with properties analogous to those of the template peptide. These types of non-peptide compounds are termed "peptide mimetics" or "peptidomimetics" (Luthman et al., *A Textbook of Drug Design and Development*, 14:386–406, 2nd Ed., Harwood Academic Publishers (1996); Joachim Grante (1994) *Angew. Chem. Int. Ed. Engl.*, 33:1699–1720; Fauchere (1986) *J. Adv. Drug Res.*, 15:29; Veber and Freidinger (1985) *TINS*, p. 392; and Evans et al. (1987) *J. Med. Chem.* 30:1229). Peptide mimetics that are structurally similar to therapeutically useful peptides can be used to produce an equivalent or enhanced therapeutic or prophylactic effect. Preparation of peptidomimetics and structures thereof are known to those of skill in this art.

Systematic substitution of one or more amino acids of a consensus sequence with a D-amino acid of the same type (e.g., D-lysine in place of L-lysine) can be used to generate more stable peptides. In addition, constrained peptides containing a consensus sequence or a substantially identical consensus sequence variation can be generated by methods known in the art (Rizo et al. (1992) *An. Rev. Biochem.*, 61:387, incorporated herein by reference); for example, by adding internal cysteine residues capable of forming intramolecular disulfide bridges which cyclize the peptide.

Those skilled in the art appreciate that modifications can be made to the peptides and mimetics without deleteriously effecting the biological or functional activity of the peptide. Further, the skilled artisan would know how to design non-peptide structures in three dimensional terms, that mimic the peptides that bind to a target molecule, e.g., a CVSP14 polypeptide or, generally, the protease domain of CVSP14 polypeptides (see, e.g., Eck and Sprang (1989) *J. Biol. Chem.*, 26: 17605–18795).

When used for diagnostic purposes, the peptides and peptide mimetics can be labeled with a detectable label and, accordingly, the peptides and peptide mimetics without such a label can serve as intermediates in the preparation of labeled peptides and peptide mimetics. Detectable labels can be molecules or compounds, which when covalently attached to the peptides and peptide mimetics, permit detection of the peptide and peptide mimetics in vivo, for example, in a patient to whom the peptide or peptide mimetic has been administered, or in vitro, e.g., in a sample or cells. Suitable detectable labels are well known in the art and include, by way of example, radioisotopes, fluorescent labels (e.g., fluorescein), and the like. The particular detectable label employed is not critical and is selected to be detectable at non-toxic levels. Selection of the such labels is well within the skill of the art.

Covalent attachment of a detectable label to the peptide or peptide mimetic is accomplished by conventional methods well known in the art. For example, when the $^{125}$I radioisotope is employed as the detectable label, covalent attachment of $^{125}$I to the peptide or the peptide mimetic can be achieved by incorporating the amino acid tyrosine into the peptide or peptide mimetic and then iodinating the peptide (see, e.g., Weaner et al. (1994) *Synthesis and Applications of Isotopically Labelled Compounds*, pp. 137–140). If tyrosine is not present in the peptide or peptide mimetic, incorporation of tyrosine to the N or C terminus of the peptide or peptide mimetic can be achieved by well known chemistry. Likewise, $^{32}$P can be incorporated onto the peptide or peptide mimetic as a phosphate moiety through, for example, a hydroxyl group on the peptide or peptide mimetic using conventional chemistry.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labeling) of peptidomimetics should not substantially interfere with the desired biological or pharmacological activity of the peptidomimetic.

Peptides, polypeptides and peptide mimetics that can bind to a CVSP14 polypeptide or the protease domain of CVSP14 polypeptides and/or modulate the activity thereof, or exhibit CVSP14 polypeptide activity, can be used for treatment of neoplastic disease. The peptides, polypeptides and peptide mimetics can be delivered, in vivo or ex vivo, to the cells of a subject in need of treatment. Further, peptides which have CVSP14 polypeptide activity can be delivered, in vivo or ex vivo, to cells which carry mutant or missing alleles encoding the CVSP14 polypeptide gene. Any of the techniques described herein or known to the skilled artisan can be used for preparation and in vivo or ex vivo delivery of such peptides, polypeptides and peptide mimetics that are substantially free of other human proteins. For example, the peptides, polypeptides and peptide mimetics can be readily prepared by expression in a microorganism or synthesis in vitro.

The peptides or peptide mimetics can be introduced into cells, in vivo or ex vivo, by microinjection or by use of liposomes, for example. Alternatively, the peptides, polypeptides or peptide mimetics can be taken up by cells, in vivo or ex vivo, actively or by diffusion. In addition, extracellular application of the peptide, polypeptides or peptide mimetic can be sufficient to effect treatment of a neoplastic disease. Other molecules, such as drugs or organic compounds, that: 1) bind to a CVSP14 polypeptide or protease domain thereof; or 2) have a similar function or activity to an CVSP14 polypeptide or protease domain thereof, can be used in methods for treatment.

4. Rational Drug Design

The goal of rational drug design is to produce structural analogs of biologically active polypeptides or peptides of interest or of small molecules or peptide mimetics with which they interact (e.g., agonists and antagonists) in order to fashion drugs which are, e.g., more active or stable forms thereof; or which, for example, enhance or interfere with the function of a polypeptide in vivo (e.g., a CVSP14 polypeptide). In one approach, one first determines the three-dimensional structure of a protein of interest (e.g., a CVSP14 polypeptide or polypeptide having a protease domain) or, for example, of a CVSP14 polypeptide-ligand complex, by X-ray crystallography, by computer modeling or most typically, by a combination of approaches (see, e.g., Erickson et al. 1990). Also, useful information regarding the structure of a polypeptide can be gained by modeling based on the structure of homologous proteins. In addition, peptides can be analyzed by an alanine scan. In this technique, an amino acid residue is replaced by Ala, and its effect on the peptide's activity is determined. Each of the amino acid residues of the peptide is analyzed in this manner to determine the important regions of the peptide.

Also, a polypeptide or peptide that binds to a CVSP14 polypeptide or, generally, the protease domain of a CVSP14 polypeptide, can be selected by a functional assay, and then the crystal structure of this polypeptide or peptide can be determined. The polypeptide can be, for example, an antibody specific for a CVSP14 polypeptide or the protein domain of a CVSP14 polypeptide. This approach can yield a pharmacophore upon which subsequent drug design can be based. Further, it is possible to bypass the crystallography altogether by generating anti-idiotypic polypeptides or peptides, (anti-ids) to a functional, pharmacologically active polypeptide or peptide that binds to a CVSP14 polypeptide or protease domain of a CVSP14 polypeptide. As a mirror image of a mirror image, the binding site of the anti-ids is expected to be an analog of the original target molecule, e.g., a CVSP14 polypeptide or polypeptide having a CVSP14 polypeptide. The anti-id could then be used to identify and isolate peptides from banks of chemically or biologically produced banks of peptides. Selected peptides would then act as the pharmacophore.

Thus, one can design drugs which have, e.g., improved activity or stability or which act as modulators (e.g., inhibitors, agonists, antagonists) of CVSP14 polypeptide activity, and are useful in the methods, particularly the methods for diagnosis, treatment, prevention, and screening of a neoplastic disease. By virtue of the availability of cloned CVSP14 polypeptide sequences, sufficient amounts of the CVSP14 polypeptide polypeptide can be made available to perform such analytical studies as X-ray crystallography. In addition, the knowledge of the amino acid sequence of a CVSP14 polypeptide or the protease domain thereof, e.g., the protease domain encoded by the amino acid sequence of SEQ ID Nos. 5 and 6, can provide guidance on computer modeling techniques in place of, or in addition to, X-ray crystallography.

Methods of Identifying Peptides and Peptide Mimetics that Bind to CVSP14 Polypeptides Peptides having a binding affinity to the CVSP14 polypeptide polypeptides provided herein (e.g., a CVSP14 polypeptide or a polypeptide having a protease domain of a CVSP14 polypeptide) can be readily identified, for example, by random peptide diversity generating systems coupled with an affinity enrichment process. Specifically, random peptide diversity generating systems include the "peptides on plasmids" system (see, e.g., U.S. Pat. Nos. 5,270,170 and 5,338,665); the "peptides on phage" system (see, e.g., U.S. Pat. No. 6,121,238 and Cwirla, et al. (1990) *Proc. Natl. Acad. Sci. U.S.A.* 87:6378–6382); the "polysome system;" the "encoded synthetic library (ESL)" system; and the "very large scale immobilized polymer synthesis" system (see, e.g., U.S. Pat. No. 6,121,238; and Dower et al. (1991) *An. Rep. Med. Chem.* 26:271–280

For example, using the procedures described above, random peptides can generally be designed to have a defined number of amino acid residues in length (e.g., 12). To generate the collection of oligonucleotides encoding the random peptides, the codon motif (NNK)x, where N is nucleotide A, C, G, or T (equimolar; depending on the methodology employed, other nucleotides can be employed), K is G or T (equimolar), and x is an integer corresponding to the number of amino acids in the peptide (e.g., 12) can be used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

The random peptides can be presented, for example, either on the surface of a phage particle, as part of a fusion protein containing either the pIII or the pVIII coat protein of a phage fd derivative (peptides on phage) or as a fusion protein with the LacI peptide fusion protein bound to a plasmid (peptides on plasmids). The phage or plasmids, including the DNA encoding the peptides, can be identified and isolated by an affinity enrichment process using immobilized CVSP14 polypeptide polypeptide having a protease domain. The affinity enrichment process, sometimes called "panning," typically involves multiple rounds of incubating the phage, plasmids, or polysomes with the immobilized CVSP14 polypeptide polypeptide, collecting the phage, plasmids, or polysomes that bind to the CVSP14 polypeptide polypeptide (along with the accompanying DNA or mRNA), and producing more of the phage or plasmids (along with the accompanying LacI-peptide fusion protein) collected.

Characteristics of Peptides and Peptide Mimetics

Among the peptides, polypeptides and peptide mimetics for therapeutic application are those of having molecular weights from about 250 to about 8,000 daltons. If such peptides are oligomerized, dimerized and/or derivatized with a hydrophilic polymer (e.g., to increase the affinity and/or activity of the compounds), the molecular weights of such peptides can be substantially greater and can range anywhere from about 500 to about 120,000 daltons, generally from about 8,000 to about 80,000 daltons. Such peptides can contain 9 or more amino acids that are naturally occurring or synthetic (non-naturally occurring) amino acids. One skilled in the art can determine the affinity and molecular weight of the peptides and peptide mimetics suitable for therapeutic and/or diagnostic purposes (e.g., see Dower et al., U.S. Pat. No. 6,121,238).

The peptides can be covalently attached to one or more of a variety of hydrophilic polymers. Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives. When the peptide compounds are derivatized with such polymers, their solubility and circulation half-lives can be increased with little, if any, diminishment in their binding activity. The peptide compounds can be dimerized and each of the dimeric subunits can be covalently attached to a hydrophilic polymer. The peptide compounds can be PEGylated, i.e., covalently attached to polyethylene glycol (PEG).

5. Methods of Preparing Peptides and Peptide Mimetics

Peptides that bind to CVSP14 polypeptides can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology (see, e.g., Merrifield (1963) *J. Am. Chem. Soc.,* 85:2149, incorporated herein by reference.)

Using the "encoded synthetic library" or "very large scale immobilized polymer synthesis" systems (see, e.g., U.S. Pat. No. 5,925,525, and 5,902,723); the minimum size of a peptide with the activity of interest can be determined. In addition all peptides that form the group of peptides that differ from the desired motif (or the minimum size of that motif) in one, two, or more residues can be prepared. This collection of peptides then can be screened ability to bind to the target molecule, e.g., and CVSP14 polypeptide or, generally, the protease domain of a CVSP14 polypeptide. This immobilized polymer synthesis system or other peptide synthesis methods can also be used to synthesize truncation analogs and deletion analogs and combinations of truncation and deletion analogs of the peptide compounds.

These procedures can also be used to synthesize peptides in which amino acids other than the 20 naturally occurring, genetically encoded amino acids are substituted at one, two, or more positions of the peptide. For instance, naphthylalanine can be substituted for tryptophan, facilitating synthesis. Other synthetic amino acids that can be substituted into the peptides include L-hydroxypropyl, L-3,4-dihydroxy-phenylalanyl, d amino acids such as L-d-hydroxylysyl and D-d-methylalanyl, L-α-methylalanyl, β amino acids, and isoquinolyl. D amino acids and non-naturally occurring synthetic amino acids can also be incorporated into the peptides (see, e.g., Roberts et al. (1983) *Unusual Amino/Acids in Peptide Synthesis,* 5(6):341–449).

The peptides can also be modified by phosphorylation (see, e.g., W. Bannwarth et al. (1996) *Biorganic and Medicinal Chemistry Letters,* 6(17):2141–2146), and other methods for making peptide derivatives (see, e.g., Hruby et al. (1990) *Biochem. J.,* 268(2):249–262). Thus, peptide compounds also serve as a basis to prepare peptide mimetics with similar biological activity.

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis (see, e.g., Morgan et al. (1989) *An. Rep. Med. Chem.*, 24:243–252). Methods for preparing peptide mimetics modified at the N-terminal amino group, the C-terminal carboxyl group, and/or changing one or more of the amido linkages in the peptide to a non-amido linkage are known to those of skill in the art.

Amino terminus modifications include, but are not limited to, alkylating, acetylating and adding a carbobenzoyl group, forming a succinimide group (see, e.g., Murray et al. (1995) *Burger's Medicinal Chemistry and Drug Discovery, 5th ed., Vol. 1*, Manfred E. Wolf, ed., John Wiley and Sons, Inc.). C-terminal modifications include mimetics wherein the C-terminal carboxyl group is replaced by an ester, an amide or modifications to form a cyclic peptide.

In addition to N-terminal and C-terminal modifications, the peptide compounds, including peptide mimetics, can advantageously be modified with or covalently coupled to one or more of a variety of hydrophilic polymers. It has been found that when peptide compounds are derivatized with a hydrophilic polymer, their solubility and circulation half-lives can be increased and their immunogenicity is masked, with little, if any, diminishment in their binding activity. Suitable nonproteinaceous polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives. Generally, such hydrophilic polymers have an average molecular weight ranging from about 500 to about 100,000 daltons, including from about 2,000 to about 40,000 daltons and, from about 5,000 to about 20,000 daltons. The hydrophilic polymers also can have an average molecular weights of about 5,000 daltons, 10,000 daltons and 20,000 daltons.

Methods for derivatizing peptide compounds or for coupling peptides to such polymers have been described (see, e.g., Zallipsky (1995) *Bioconjugate Chem.*, 6:150–165; Monfardini et al. (1995) *Bioconjugate Chem.*, 6:62–69; U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 and WO 95/34326, all of which are incorporated by reference in their entirety herein).

Other methods for making peptide derivatives are described, for example, in Hruby et al. (1990), *Biochem J.*, 268(2):249–262, which is incorporated herein by reference. Thus, the peptide compounds also serve as structural models for non-peptidic compounds with similar biological activity. Those of skill in the art recognize that a variety of techniques are available for constructing compounds with the same or similar desired biological activity as a particular peptide compound but with more favorable activity with respect to solubility, stability, and susceptibility to hydrolysis and proteolysis (see, e.g., Morgan et al. (1989) *An. Rep. Med. Chem.*, 24:243–252, incorporated herein by reference). These techniques include replacing the peptide backbone with a backbone composed of phosphonates, amidates, carbamates, sulfonamides, secondary amines, and N-methylamino acids.

Peptide compounds can exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues can also be substituted with a homocysteine.

I. Conjugates

A conjugate, containing: a) a single chain protease domain (or proteolytically active portion thereof) of a CVSP14 polypeptide or a full length zymogen, activated form thereof, or two or single chain protease domain thereof; and b) a targeting agent linked to the CVSP14 polypeptide directly or via a linker, wherein the agent facilitates: i) affinity isolation or purification of the conjugate; ii) attachment of the conjugate to a surface; iii) detection of the conjugate; or iv) targeted delivery to a selected tissue or cell, is provided herein. The conjugate can be a chemical conjugate or a fusion protein mixture thereof.

The targeting agent can be a protein or peptide fragment, such as a tissue specific or tumor specific monoclonal antibody or growth factor or fragment thereof linked either directly or via a linker to a CVSP14 polypeptide or a protease domain thereof. The targeting agent can also be a protein or peptide fragment that contains a protein binding sequence, a nucleic acid binding sequence, a lipid binding sequence, a polysaccharide binding sequence, or a metal binding sequence, or a linker for attachment to a solid support. In a particular embodiment, the conjugate contains a) the CVSP14 or portion thereof, as described herein; and b) a targeting agent linked to the CVSP14 polypeptide directly or via a linker.

Conjugates, such as fusion proteins and chemical conjugates, of the CVSP14 polypeptide with a protein or peptide fragment (or plurality thereof) that functions, for example, to facilitate affinity isolation or purification of the CVSP14 polypeptide domain, attachment of the CVSP14 polypeptide domain to a surface, or detection of the CVSP14 polypeptide domain are provided. The conjugates can be produced by chemical conjugation, such as via thiol linkages, and can be produced by recombinant means as fusion proteins. In the fusion protein, the peptide or fragment thereof is linked to either the N-terminus or C-terminus of the CVSP14 polypeptide domain. In chemical conjugates the peptide or fragment thereof can be linked anywhere that conjugation can be effected, and there can be a plurality of such peptides or fragments linked to a single CVSP14 polypeptide domain or to a plurality thereof.

The targeting agent is for in vitro or in vivo delivery to a cell or tissue, and includes agents such as cell or tissue-specific antibodies, growth factors and other factors that bind to moieties expressed on specific cells; and other cell or tissue specific agents that promote directed delivery of a linked protein. The targeting agent can be one that specifically delivers the CVSP14 polypeptide to selected cells by interaction with a cell surface protein and internalization of conjugate or CVSP14 polypeptide portion thereof.

These conjugates are used in a variety of methods and are particularly suited for use in methods of activation of prodrugs, such as prodrugs that upon cleavage by the particular CVSP14, which is localized at or near the targeted cell or tissue, protein are cytotoxic. The prodrugs are administered prior to, or simultaneously with, or subsequently to the conjugate. Upon delivery to the targeted cells, the protease activates the prodrug, which then exhibits a therapeutic effect, such as a cytotoxic effect.

1. Conjugation

Conjugates with linked CVSP14 polypeptide domains can be prepared either by chemical conjugation, recombinant DNA technology, or combinations of recombinant expression and chemical conjugation. The CVSP14 polypeptide domains and the targeting agent can be linked in any orientation and more than one targeting agents and/or CVSP14 polypeptide domains can be present in a conjugate.

a. Fusion Proteins

Fusion proteins are proved herein. A fusion protein contains: a) one or a plurality of domains of a CVSP14 polypeptides and b) a targeting agent. The fusion proteins are generally produced by recombinant expression of nucleic acids that encode the fusion protein.

b. Chemical Conjugation

To effect chemical conjugation herein, the CVSP14 polypeptide domain is linked via one or more selected linkers or directly to the targeting agent. Chemical conjugation must be used if the targeted agent is other than a peptide or protein, such a nucleic acid or a non-peptide drug. Any means known to those of skill in the art for chemically conjugating selected moieties can be used.

2. Linkers

Linkers for two purposes are contemplated herein. The conjugates can include one or more linkers between the CVSP14 polypeptide portion and the targeting agent. Additionally, linkers are used for facilitating or enhancing immobilization of a CVSP14 polypeptide or portion thereof on a solid support, such as a microtiter plate, silicon or silicon-coated chip, glass or plastic support, such as for high throughput solid phase screening protocols.

Any linker known to those of skill in the art for preparation of conjugates can be used herein. These linkers are typically used in the preparation of chemical conjugates; peptide linkers can be incorporated into fusion proteins.

Linkers can be any moiety suitable to associate a domain of CVSP14 polypeptide and a targeting agent. Such linkers and linkages include, but are not limited to, peptidic linkages, amino acid and peptide linkages, typically containing between one and about 60 amino acids, more generally between about 10 and 30 amino acids, chemical linkers, such as heterobifunctional cleavable cross-linkers, including but are not limited to, N-succinimidyl (4-iodoacetyl)-aminobenzoate, sulfosuccinimydil (4-iodoacetyl)-aminobenzoate, 4-succinimidyl-oxycarbonyl-a-(2-pyridyidithio)toluene, sulfosuccinimidyl-6-[a-methyl-a-(pyridyidithiol)-toluamido]hexanoate, N-succinimidyl-3-(-2-pyridyldithio)-proprionate, succinimidyl 6[3-(-2-pyridyidithio)-proprionamido]hexanoate, sulfosuccinimidyl 6[3-(-2-pyridyldithio)-propionamido]hexanoate, 3-(2-pyridyldithio)-propionyl hydrazide, Ellman's reagent, dichlorotriazinic acid, and S-(2-thiopyridyl)-L-cysteine. Other linkers include, but are not limited to peptides and other moieties that reduce stearic hindrance between the domain of CVSP14 polypeptide and the targeting agent, intracellular enzyme substrates, linkers that increase the flexibility of the conjugate, linkers that increase the solubility of the conjugate, linkers that increase the serum stability of the conjugate, photocleavable linkers and acid cleavable linkers.

Other exemplary linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. *Molecular Immunol.*, 30:379–386 (1993)). In some embodiments, several linkers can be included in order to take advantage of desired properties of each linker.

Chemical linkers and peptide linkers can be inserted by covalently coupling the linker to the domain of CVSP14 polypeptide and the targeting agent. The heterobifunctional agents, described below, can be used to effect such covalent coupling. Peptide linkers can also be linked by expressing DNA encoding the linker and therapeutic agent (TA), linker and targeted agent, or linker, targeted agent and therapeutic agent (TA) as a fusion protein. Flexible linkers and linkers that increase solubility of the conjugates are contemplated for use, either alone or with other linkers are also contemplated herein.

a) Acid Cleavable, Photocleavable and Heat Sensitive Linkers

Acid cleavable linkers, photocleavable and heat sensitive linkers can also be used, particularly where it can be necessary to cleave the domain of CVSP14 polypeptide to permit it to be more readily accessible to reaction. Acid cleavable linkers include, but are not limited to, bismaleimideothoxy propane; and adipic acid dihydrazide linkers (see, e.g., Fattom et al. (1992) *Infection & Immun.* 60:584–589) and acid labile transferrin conjugates that contain a sufficient portion of transferrin to permit entry into the intracellular transferrin cycling pathway (see, e.g., Welhöner et al. (1991) *J. Biol. Chem.* 266:4309–4314).

Photocleavable linkers are linkers that are cleaved upon exposure to light (see, e.g., Goldmacher et al. (1992) *Bioconj. Chem.* 3:104–107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

b) Other Linkers for Chemical Conjugation

Other linkers, include trityl linkers, particularly, derivatized trityl groups to generate a genus of conjugates that provide for release of therapeutic agents at various degrees of acidity or alkalinity. The flexibility thus afforded by the ability to preselect the pH range at which the therapeutic agent is released allows selection of a linker based on the known physiological differences between tissues in need of delivery of a therapeutic agent (see, e.g., U.S. Pat. No.

5,612,474). For example, the acidity of tumor tissues appears to be lower than that of normal tissues.

c) Peptide Linkers

The linker moieties can be peptides. Peptide linkers can be employed in fusion proteins and also in chemically linked conjugates. The peptide typically has from about 2 to about 60 amino acid residues, for example from about 5 to about 40, or from about 10 to about 30 amino acid residues. The length selected depends upon factors, such as the use for which the linker is included.

Peptide linkers are advantageous when the targeting agent is proteinaceous. For example, the linker moiety can be a flexible spacer amino acid sequence, such as those known in single-chain antibody research. Examples of such known linker moieties include, but are not limited to, peptides, such as $(Gly_mSer)_n$ and $(Ser_mGly)_n$, in which n is 1 to 6, including 1 to 4 and 2 to 4, and m is 1 to 6, including 1 to 4, and 2 to 4, enzyme cleavable linkers and others.

Additional linking moieties are described, for example, in Huston et al., *Proc. Natl. Acad. Sci. U.S.A.* 85:5879–5883, 1988; Whitlow, M., et al., *Protein Engineering* 6:989–995, 1993; Newton et al., *Biochemistry* 35:545–553, 1996; A. J. Cumber et al., *Bioconj. Chem.* 3:397–401, 1992; Ladurner et al., *J. Mol. Biol.* 273:330–337, 1997; and U.S. Pat. No. 4,894,443. In some embodiments, several linkers can be included in order to take advantage of desired properties of each linker.

3. Targeting Agents

Any agent that facilitates detection, immobilization, or purification of the conjugate is contemplated for use herein. For chemical conjugates any moiety that has such properties is contemplated; for fusion proteins, the targeting agent is a protein, peptide or fragment thereof that is sufficient to effects the targeting activity. Contemplated targeting agents include those that deliver the CVSP14 polypeptide or portion thereof to selected cells and tissues. Such agents include tumor specific monoclonal antibodies and portions thereof, growth factors, such as FGF, EGF, PDGF, VEGF, cytokines, including chemokines, and other such agents.

4. Nucleic Acids, Plasmids and Cells

Isolated nucleic acid fragments encoding fusion proteins are provided. The nucleic acid fragment that encodes the fusion protein includes: a) nucleic acid encoding a protease domain of a CVSP14 polypeptide; and b) nucleic acid encoding a protein, peptide or effective fragment thereof that facilitates: i) affinity isolation or purification of the fusion protein; ii) attachment of the fusion protein to a surface; or iii) detection of the fusion protein. Generally, the nucleic acid is DNA.

Plasmids for replication and vectors for expression that contain the above nucleic acid fragments are also provided. Cells containing the plasmids and vectors are also provided. The cells can be any suitable host including, but are not limited to, bacterial cells, yeast cells, fungal cells, plant cells, insect cell and animal cells. The nucleic acids, plasmids, and cells containing the plasmids can be prepared according to methods known in the art including any described herein.

Also provided are methods for producing the above fusion proteins. An exemplary method includes the steps of growing, i.e. culturing the cells so that the proliferate, cells containing a plasmid encoding the fusion protein under conditions whereby the fusion protein is expressed by the cell, and recovering the expressed fusion protein. Methods for expressing and recovering recombinant proteins are well known in the art (See generally, *Current Protocols in Molecular Biology* (1998) § 16, John Wiley & Sons, Inc.) and such methods can be used for expressing and recovering the expressed fusion proteins.

The recovered fusion proteins can be isolated or purified by methods known in the art such as centrifugation, filtration, chromatograph, electrophoresis, immunoprecipitation, etc., or by a combination thereof (See generally, *Current Protocols in Molecular Biology* (1998) § 10, John Wiley & Sons, Inc.). Generally the recovered fusion protein is isolated or purified through affinity binding between the protein or peptide fragment of the fusion protein and an affinity binding moiety. As discussed in the above sections regarding the construction of the fusion proteins, any affinity binding pairs can be constructed and used in the isolation or purification of the fusion proteins. For example, the affinity binding pairs can be protein binding sequences/protein, DNA binding sequences/DNA sequences, RNA binding sequences/RNA sequences, lipid binding sequences/lipid, polysaccharide binding sequences/polysaccharide, or metal binding sequences/metal.

5. Immobilization and Supports or Substrates Therefor

In certain embodiments, where the targeting agents are designed for linkage to surfaces, the CVSP14 polypeptide can be attached by linkage such as ionic or covalent, non-covalent or other chemical interaction, to a surface of a support or matrix material. Immobilization can be effected directly or via a linker. The CVSP14 polypeptide can be immobilized on any suitable support, including, but are not limited to, silicon chips, and other supports described herein and known to those of skill in the art. A plurality of CVSP14 polypeptide or protease domains thereof can be attached to a support, such as an array (i.e., a pattern of two or more) of conjugates on the surface of a silicon chip or other chip for use in high throughput protocols and formats.

It is also noted that the domains of the CVSP14 polypeptide can be linked directly to the surface or via a linker without a targeting agent linked thereto. Hence chips containing arrays of the domains of the CVSP14 polypeptide.

The matrix material or solid supports contemplated herein are generally any of the insoluble materials known to those of skill in the art to immobilize ligands and other molecules, and are those that used in many chemical syntheses and separations. Such supports are used, for example, in affinity chromatography, in the immobilization of biologically active materials, and during chemical syntheses of biomolecules, including proteins, amino acids and other organic molecules and polymers. The preparation of and use of supports is well known to those of skill in this art; there are many such materials and preparations thereof known. For example, naturally-occurring support materials, such as agarose and cellulose, can be isolated from their respective sources, and processed according to known protocols, and synthetic materials can be prepared in accord with known protocols.

The supports are typically insoluble materials that are solid, porous, deformable, or hard, and have any required structure and geometry, including, but not limited to: beads, pellets, disks, capillaries, hollow fibers, needles, solid fibers, random shapes, thin films and membranes. Thus, the item can be fabricated from the matrix material or combined with it, such as by coating all or part of the surface or impregnating particles.

Typically, when the matrix is particulate, the particles are at least about 10–2000 μm, but can be smaller or larger, depending upon the selected application. Selection of the matrices is governed, at least in part, by their physical and chemical properties, such as solubility, functional groups, mechanical stability, surface area swelling propensity, hydrophobic or hydrophilic properties and intended use.

If necessary, the support matrix material can be treated to contain an appropriate reactive moiety. In some cases, the support matrix material already containing the reactive moiety can be obtained commercially. The support matrix material containing the reactive moiety can thereby serve as the matrix support upon which molecules are linked. Materials containing reactive surface moieties such as amino silane linkages, hydroxyl linkages or carboxysilane linkages can be produced by well established surface chemistry techniques involving silanization reactions, or the like. Examples of these materials are those having surface silicon oxide moieties, covalently linked to gamma-aminopropylsilane, and other organic moieties; N-[3-(triethyoxysilyl) propyl]phthelamic acid; and bis-(2-hydroxyethyl)aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art (e.g., the Tentagel® Resins are available with a multitude of functional groups, and are sold by Rapp Polymere, Tubingen, Germany; see, U.S. Pat. No. 4,908,405 and U.S. Pat. No. 5,292,814; see, also Butz et al., *Peptide Res.*, 7:20–23 (1994); and Kleine et al., *Immunobiol.*, 190:53–66 (1994)).

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene and others (see, Merrifield, *Biochemistry*, 3:1385–1390 (1964)), polyacrylamides, latex gels, polystyrene, dextran, polyacrylamides, rubber, silicon, plastics, nitrocellulose, celluloses, natural sponges. Of particular interest herein, are highly porous glasses (see, e.g., U.S. Pat. No. 4,244,721) and others prepared by mixing a borosilicate, alcohol and water.

Synthetic supports include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers (see, e.g., Merrifield, *Biochemistry*, 3:1385–1390 (1964); Berg et al., in *Innovation Perspect. Solid Phase Synth. Collect. Pap.*, Int. Symp., 1st, Epton, Roger (Ed), pp. 453–459 (1990); Berg et al., *Pept., Proc. Eur. Pept. Symp.*, 20th, Jung, G. et al. (Eds), pp. 196–198 (1989); Berg et al., *J. Am. Chem. Soc.*, 111:8024–8026 (1989); Kent et al., *Isr. J. Chem.*, 17:243–247 (1979); Kent et al., *J. Org. Chem.*, 43:2845–2852 (1978); Mitchell et al., *Tetrahedron Lett.*, 42:3795–3798 (1976); U.S. Pat. No. 4,507,230; U.S. Pat. No. 4,006,117; and U.S. Pat. No. 5,389,449). Such materials include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethyl-acrylate, polypropylene-co-methyl acrylate, polyethylene-co-vinyl acetate, polypropylene-co-vinyl acetate, and those containing acid anhydride groups such as polyethylene-co-maleic anhydride and polypropylene-co-maleic anhydride. Liposomes have also been used as solid supports for affinity purifications (Powell et al. *Biotechnol. Bioeng.*, 33:173 (1989)).

Numerous methods have been developed for the immobilization of proteins and other biomolecules onto solid or liquid supports (see, e.g., Mosbach, *Methods in Enzymology*, 44 (1976); Weetall, *Immobilized Enzymes, Antigens, Antibodies, and Peptides*, (1975); Kennedy et al., *Solid Phase Biochemistry, Analytical and Synthetic Aspects*, Scouten, ed., pp. 253–391 (1983); see, generally, Affinity Techniques. Enzyme Purification: *Part B. Methods in Enzymology*, Vol. 34, ed. W. B. Jakoby, M. Wilchek, Acad. Press, N.Y. (1974); and Immobilized Biochemicals and Affinity Chromatography, *Advances in Experimental Medicine and Biology*, vol. 42, ed. R. Dunlap, Plenum Press, N.Y. (1974)).

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art (see, e.g., the PIERCE CATALOG, ImmunoTechnology Catalog & Handbook, 1992–1993, which describes the preparation of and use of such reagents and provides a commercial source for such reagents; Wong, *Chemistry of Protein Conjugation and Cross Linking*, CRC Press (1993); see also DeWitt et al., *Proc. Natl. Acad. Sci. U.S.A.*, 90:6909 (1993); Zuckermann et al., *J. Am. Chem. Soc.*, 114:10646 (1992); Kurth et al., *J. Am. Chem. Soc.*, 116:2661 (1994); Ellman et al., *Proc. Natl. Acad. Sci. U.S.A.*, 91:4708 (1994); Sucholeiki, *Tetrahedron Lttrs.*, 35:7307 (1994); Su-Sun Wang, *J. Org. Chem.*, 41:3258 (1976); Padwa et al., *J. Org. Chem.*, 41:3550 (1971); and Vedejs et al., *J. Org. Chem.*, 49:575 (1984), which describe photosensitive linkers).

To effect immobilization, a composition containing the protein or other biomolecule is contacted with a support material such as alumina, carbon, an ion-exchange resin, cellulose, glass or a ceramic. Fluorocarbon polymers have been used as supports to which biomolecules have been attached by adsorption (see, U.S. Pat. No. 3,843,443; Published International PCT Application WO/86 03840).

J. Prognosis and Diagnosis

CVSP14 polypeptide proteins, domains, analogs, and derivatives thereof, and encoding nucleic acids (and sequences complementary thereto), and anti-CVSP14 polypeptide antibodies, can be used in diagnostics, particularly diagnosis of cervical cancer, colon or pancreatic cancers.

Such molecules can be used in assays, such as immunoassays, to detect, prognose, diagnose, or monitor various conditions, diseases, and disorders affecting CVSP14 polypeptide expression, or monitor the treatment thereof. For purposes herein, the presence of CVSP14s in body fluids or tumor tissues are of particular interest.

In particular, such an immunoassay is carried out by a method including contacting a sample derived from a patient with an anti-CVSP14 polypeptide antibody under conditions such that specific binding can occur, and detecting or measuring the amount of any specific binding by the antibody. Such binding of antibody, in tissue sections, can be used to detect aberrant CVSP14 polypeptide localization or aberrant (e.g., increased, decreased or absent) levels of CVSP14 polypeptide. In a specific embodiment, antibody to CVSP14 polypeptide can be used to assay in a patient tissue or serum sample for the presence of CVSP14 polypeptide where an aberrant level of CVSP14 polypeptide is an indication of a diseased condition.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

CVSP14 polypeptide genes and related nucleic acid sequences and subsequences, including complementary sequences, also can be used in hybridization assays. CVSP14 polypeptide nucleic acid sequences, or subsequences thereof containing about at least 8 nucleotides, generally 14 or 16 or 30 or more, generally less than 1000 or up to 100, continugous nucleotides can be used as hybridization probes. Hybridization assays can be used to detect, prognose, diagnose, or monitor conditions, disorders, or disease states associated with aberrant changes in CVSP14 polypeptide expression and/or activity as described herein. In particular, such a hybridization assay is carried out by a method by contacting a sample containing nucleic acid with a nucleic acid probe capable of hybridizing to CVSP14 polypeptide encoding DNA or RNA, under conditions such that hybridization can occur, and detecting or measuring any resulting hybridization.

In a specific embodiment, a method of diagnosing a disease or disorder characterized by detecting an aberrant level of a CVSP14 polypeptide in a subject is provided herein by measuring the level of the DNA, RNA, protein or functional activity of the CVSP14 polypeptide in a sample derived from the subject, wherein an increase or decrease in the level of the DNA, RNA, protein or functional activity of the CVSP14 polypeptide, relative to the level of the DNA, RNA, protein or functional activity found in an analogous sample not having the disease or disorder indicates the presence of the disease or disorder in the subject.

Kits for diagnostic use are also provided, that contain in one or more containers an anti-CVSP14 polypeptide antibody, and, optionally, a labeled binding partner to the antibody. Alternatively, the anti-CVSP14 polypeptide antibody can be labeled (with a detectable marker, e.g., a chemiluminescent, enzymatic, fluorescent, or radioactive moiety). A kit is also provided that includes in one or more containers a nucleic acid probe capable of hybridizing to SP protein-encoding RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art under appropriate reaction conditions of at least a portion of an SP protein-encoding nucleic acid. A kit can optionally further comprise in a container a predetermined amount of a purified CVSP14 polypeptide or nucleic acid, e.g., for use as a standard or control.

K. Pharmaceutical Compositions and Modes of Administration

1. Components of the Compositions

Pharmaceutical compositions containing the identified compounds that modulate the activity of a CVSP14 polypeptide are provided herein. Also provided are combinations of a compound that modulates the activity of a CVSP14 polypeptide and another treatment or compound for treatment of a neoplastic disorder, such as a chemotherapeutic compound.

The CVSP14 polypeptide modulator and the anti-tumor agent can be packaged as separate compositions for administration together or sequentially or intermittently. Alternatively, they can provided as a single composition for administration or as two compositions for administration as a single composition. The combinations can be packaged as kits.

a. CVSP14 Polypeptide Inhibitors

Any CVSP14 polypeptide inhibitors, including those described herein when used alone or in combination with other compounds, that can alleviate, reduce, ameliorate, prevent, or place or maintain in a state of remission of clinical symptoms or diagnostic markers associated with neoplastic diseases, including undesired and/or uncontrolled angiogenesis, can be used in the present combinations.

In one embodiment, the CVSP14 polypeptide inhibitor is an antibody or fragment thereof that specifically reacts with a CVSP14 polypeptide or the protease domain thereof, an inhibitor of the CVSP14 polypeptide production, an inhibitor of CVSP14 polypeptide membrane-localization, or any inhibitor of the expression of or, especially, the activity of a CVSP14 polypeptide.

b. Anti-Angiogenic Agents and Anti-Tumor Agents

Any anti-angiogenic agents and anti-tumor agents, including those described herein, when used alone or in combination with other compounds, that can alleviate, reduce, ameliorate, prevent, or place or maintain in a state of remission of clinical symptoms or diagnostic markers associated with undesired and/or uncontrolled angiogenesis and/or tumor growth and metastasis, particularly solid neoplasms, vascular malformations and cardiovascular disorders, chronic inflammatory diseases and aberrant wound repairs, circulatory disorders, crest syndromes, dermatological disorders, or ocular disorders, can be used in the combinations. Also contemplated are anti-tumor agents for use in combination with an inhibitor of a CVSP14 polypeptide.

C. Anti-Tumor Agents and Anti-Angiogenic Agents

The compounds identified by the methods provided herein or provided herein can be used in combination with anti-tumor agents and/or anti-angiogenesis agents.

2. Formulations and Route of Administration

The compounds herein and agents can be formulated as pharmaceutical compositions, typically for single dosage administration. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, can also be suitable as pharmaceutically acceptable carriers. These can be prepared according to methods known to those skilled in the art. For example, liposome formulations can be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration can be determined empirically by testing the compounds in known in vitro and in vivo systems, such as the assays provided herein.

The concentration of active compound in the drug composition depends on absorption, inactivation and excretion rates of the active compound, the physicochemical characteristics of the compound, the dosage schedule, and amount administered as well as other factors known to those of skill in the art.

Typically a therapeutically effective dosage is contemplated. The amounts administered can be on the order of 0.001 to 1 mg/ml, including about 0.005–0.05 mg/ml and about 0.01 mg/ml, of blood volume. Pharmaceutical dosage unit forms are prepared to provide from about 1 mg to about 1000 mg, including from about 10 to about 500 mg, and including about 25–75 mg of the essential active ingredient or a combination of essential ingredients per dosage unit form. The precise dosage can be empirically determined.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of the claimed compositions and combinations containing them.

Pharmaceutically acceptable derivatives include acids, salts, esters, hydrates, solvates and prodrug forms. The derivative is typically selected such that its pharmacokinetic properties are superior to the corresponding neutral compound.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the disorder for which treatment is contemplated. The concentration of active compound in the composition depends on absorption, inactivation, excretion rates of the active compound, the dosage schedule, amount administered, particular formulation as well as other factors known to those of skill in the art.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as Tween®, or dissolution in aqueous sodium bicarbonate. Derivatives of the compounds, such as prodrugs of the compounds can also be used in formulating effective pharmaceutical compositions. For ophthalmic indications, the compositions are formulated in an ophthalmically acceptable carrier. For the ophthalmic uses herein, local administration, either by topical administration or by injection are contemplated. Time release formulations are also desirable. Typically, the compositions are formulated for single dosage administration, so that a single dose administers an effective amount.

Upon mixing or addition of the compound with the vehicle, the resulting mixture can be a solution, suspension, emulsion or other composition. The form of the resulting mixture depends upon a number of factors, including the intended mode of administration and the solubility of the compound in the selected carrier or vehicle. If necessary, pharmaceutically acceptable salts or other derivatives of the compounds are prepared.

The compound is included in the pharmaceutically acceptable carrier in an amount sufficient to exert a therapeutically useful effect in the absence of undesirable side effects on the patient treated. It is understood that number and degree of side effects depends upon the condition for which the compounds are administered. For example, certain toxic and undesirable side effects are tolerated when treating life-threatening illnesses that would not be tolerated when treating disorders of lesser consequence.

The compounds also can be mixed with other active materials, that do not impair the desired action, or with materials that supplement the desired action known to those of skill in the art. The formulations of the compounds and agents for use herein include those suitable for oral, rectal, topical, inhalational, buccal (e.g., sublingual), parenteral (e.g., subcutaneous, intramuscular, intradermal, or intravenous), transdermal administration or any route. The most suitable route in any given case depends on the nature and severity of the condition being treated and on the nature of the particular active compound which is being used. The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art (see, e.g., Remington's Pharmaceutical Sciences, Mack Publishing Company, Easton, Pa., 15th Edition, 1975). The composition or formulation to be administered contains a quantity of the active compound in an amount sufficient to alleviate the symptoms of the treated subject.

Dosage forms or compositions containing active ingredient in the range of 0.005% to 100% with the balance made up from non-toxic carrier can be prepared. For oral administration, the pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art.

The pharmaceutical preparation can also be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

Formulations suitable for rectal administration can be presented as unit dose suppositories. These can be prepared by admixing the active compound with one or more conventional solid carriers, for example, cocoa butter, and then shaping the resulting mixture.

Formulations suitable for topical application to the skin or to the eye generally are formulated as an ointment, cream, lotion, paste, gel, spray, aerosol and oil. Carriers which can be used include vaseline, lanoline, polyethylene glycols, alcohols, and combinations of two or more thereof. The topical formulations can further advantageously contain 0.05 to 15 percent by weight of thickeners selected from among hydroxypropyl methyl cellulose, methyl cellulose, polyvinylpyrrolidone, polyvinyl alcohol, poly (alkylene glycols), poly/hydroxyalkyl, (meth)acrylates or poly(meth) acrylamides. A topical formulation is often applied by instillation or as an ointment into the conjunctival sac. It also can be used for irrigation or lubrication of the eye, facial sinuses, and external auditory meatus. It can also be injected into the anterior eye chamber and other places. The topical formulations in the liquid state can be also present in a hydrophilic three-dimensional polymer matrix in the form of a strip, contact lens, and the like from which the active components are released.

For administration by inhalation, the compounds for use herein can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

The compounds can be formulated for parenteral administration by injection, e.g., by bolus injection or continuous infusion. Formulations for injection can be presented in unit dosage form, e.g., in ampules or in multi-dose containers, with an added preservative. The compositions can be suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water or other solvents, before use.

Formulations suitable for transdermal administration can be presented as discrete patches adapted to remain in intimate contact with the epidermis of the recipient for a prolonged period of time. Such patches suitably contain the active compound as an optionally buffered aqueous solution of, for example, 0.1 to 0.2 M concentration with respect to the active compound. Formulations suitable for transdermal administration can also be delivered by iontophoresis (see, e.g., Pharmaceutical Research 3 (6), 318 (1986)) and typically take the form of an optionally buffered aqueous solution of the active compound.

The pharmaceutical compositions can also be administered by controlled release means and/or delivery devices (see, e.g., in U.S. Pat. Nos. 3,536,809; 3,598,123; 3,630,200; 3,845,770; 3,847,770; 3,916,899; 4,008,719; 4,687,610; 4,769,027; 5,059,595; 5,073,543; 5,120,548; 5,354,566; 5,591,767; 5,639,476; 5,674,533 and 5,733,566).

Desirable blood levels can be maintained by a continuous infusion of the active agent as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

The efficacy and/or toxicity of the CVSP14 polypeptide inhibitor(s), alone or in combination with other agents also can be assessed by the methods known in the art (See generally, O'Reilly, *Investigational New Drugs*, 15:5–13 (1997)).

The active compounds or pharmaceutically acceptable derivatives can be prepared with carriers that protect the compound against rapid elimination from the body, such as time release formulations or coatings.

Kits containing the compositions and/or the combinations with instructions for administration thereof are provided. The kit can further include a needle or syringe, typically packaged in sterile form, for injecting the complex, and/or a packaged alcohol pad. Instructions are optionally included for administration of the active agent by a clinician or by the patient.

Finally, the compounds or CVSP14 polypeptides or protease domains thereof or compositions containing any of the preceding agents can be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted.

L. Methods of Treatment

The compounds identified by the methods herein are used for treating or preventing neoplastic diseases in an animal, particularly a mammal, including a human, is provided herein. In one embodiment, the method includes administering to a mammal an effective amount of an inhibitor of a CVSP14 polypeptide, whereby the disease or disorder is treated or prevented.

In an embodiment, the CVSP14 polypeptide inhibitor used in the treatment or prevention is administered with a pharmaceutically acceptable carrier or excipient. The mammal treated can be a human. The inhibitors provided herein are those identified by the screening assays. In addition, antibodies and antisense nucleic acids or double-stranded RNA (dsRNA), such as RNAi, are contemplated.

The treatment or prevention method can further include administering an anti-angiogenic treatment or agent or anti-tumor agent simultaneously with, prior to or subsequent to the CVSP14 polypeptide inhibitor, which can be any compound identified that inhibits the activity of a CVSP14 polypeptide. Such compounds include small molecule modulators, an antibody or a fragment or derivative thereof containing a binding region thereof against the CVSP14 polypeptide, an antisense nucleic acid or double-stranded RNA (dsRNA), such as RNAi, encoding the CVSP14 polypeptide, and a nucleic acid containing at least a portion of a gene encoding the CVSP14 polypeptide into which a heterologous nucleotide sequence has been inserted such that the heterologous sequence inactivates the biological activity of at least a portion of the gene encoding the CVSP14 polypeptide, in which the portion of the gene encoding the CVSP14 polypeptide flanks the heterologous sequence to promote homologous recombination with a genomic gene encoding the CVSP14 polypeptide. In addition, such molecules are generally less than about 1000 nt long.

1. Antisense Treatment

In a specific embodiment, as described hereinabove, CVSP14 polypeptide function is reduced or inhibited by CVSP14 polypeptide antisense nucleic acids, to treat or prevent neoplastic disease. The therapeutic or prophylactic use of nucleic acids of at least six nucleotides that are antisense to a gene or cDNA encoding CVSP14 polypeptide or a portion thereof. A CVSP14 polypeptide "antisense" nucleic acid as used herein refers to a nucleic acid capable of hybridizing to a portion of a CVSP14 polypeptide RNA (generally mRNA) by virtue of some sequence complementarity, and generally under high stringency conditions. The antisense nucleic acid can be complementary to a coding and/or noncoding region of a CVSP14 polypeptide mRNA. Such antisense nucleic acids have utility as therapeutics that reduce or inhibit CVSP14 polypeptide function, and can be used in the treatment or prevention of disorders as described supra.

The CVSP14 polypeptide antisense nucleic acids are of at least six nucleotides and are generally oligonucleotides (ranging from 6 to about 150 nucleotides including 6 to 50 nucleotides). The antisense molecule can be complementary to all or a portion of the protease domain. For example, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide can include other appending groups such as peptides, or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci. U.S.A.* 84:648–652 (1987); PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., *BioTechniques* 6:958–976 (1988)) or intercalating agents (see, e.g., Zon, *Pharm. Res.* 5:539–549 (1988)).

The CVSP14 polypeptide antisense nucleic acid generally is an oligonucleotide, typically single-stranded DNA or RNA or an analog thereof or mixtures thereof. For example, the oligonucleotide includes a sequence antisense to a portion of human CVSP14 polypeptide. The oligonucleotide can be modified at any position on its structure with substituents generally known in the art.

The CVSP14 polypeptide antisense oligonucleotide can include at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide includes at least one modified sugar moiety selected from the group including but not limited to arabinose, 2-fluoroarabinose, xylulose, and hexose. The oligonucleotide can include at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide can be an a-anomeric oligonucleotide. An α-anomeric oligonucleotide forms specific double-stranded hybrids with complementary RNA in which the strands run parallel to each other (Gautier et al., *Nucl. Acids Res.* 15:6625–6641 (1987)).

The oligonucleotide can be conjugated to another molecule, e.g., a peptide, hybridization triggered cross-linking agent, transport agent and hybridization-triggered cleavage agent.

The oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

In a specific embodiment, the CVSP14 polypeptide antisense oligonucleotide includes catalytic RNA or a ribozyme (see, e.g., PCT International Publication WO 90/11364, published Oct. 4, 1990; Sarver et al., *Science* 247:1222–1225 (1990)). In another embodiment, the oligonucleotide is a 2'-O-methylribonucleotide (Inoue et al., *Nucl. Acids Res.* 15:6131–6148 (1987)), or a chimeric RNA-DNA analogue (Inoue et al., *FEBS Lett.* 215:327–330 (1987)). Alternatively, the oligonucleotide can be double-stranded RNA (dsRNA) such as RNAi.

In an alternative embodiment, the CVSP14 polypeptide antisense nucleic acid is produced intracellularly by transcription from an exogenous sequence. For example, a vector can be introduced in vivo such that it is taken up by a cell, within which cell the vector or a portion thereof is transcribed, producing an antisense nucleic acid (RNA). Such a vector would contain a sequence encoding the CVSP14 polypeptide antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the CVSP14 polypeptide antisense RNA can be by any promoter known in the art to act in mammalian, including human, cells. Such promoters can be inducible or constitutive. Such promoters include but are not limited to: the SV40 early promoter region (Bernoist and Chambon, *Nature* 290:304–310 (1981), the promoter contained in the 3' long terminal repeat of Rous sarcoma virus (Yamamoto et al., *Cell* 22:787–797 (1980), the herpes thymidine kinase promoter (Wagner et al., *Proc. Natl. Acad. Sci. U.S.A.* 78:1441–1445 (1981), the regulatory sequences of the metallothionein gene (Brinster et al., *Nature* 296: 39–42 (1982), etc.

The antisense nucleic acids include sequence complementary to at least a portion of an RNA transcript of a CVSP14 polypeptide gene, including a human CVSP14 polypeptide gene. Absolute complementarily is not required.

The amount of CVSP14 polypeptide antisense nucleic acid (dsRNA) that is effective in the treatment or prevention of neoplastic disease depends on the nature of the disease, and can be determined empirically by standard clinical techniques. Where possible, it is desirable to determine the antisense cytotoxicity in cells in vitro, and then in useful animal model systems prior to testing and use in humans.

2. RNA Interference

RNA interference (RNAi) (see, e.g. Chuang et al. (2000) *Proc. Natl. Acad. Sc. U.S.A.* 97:4985) can be employed to inhibit the expression of a gene encoding a CVSP14. Interfering RNA (RNAi) fragments, particularly double-stranded (ds) RNAi, can be used to generate loss-of-CVSP14 function. Methods relating to the use of RNAi to silence genes in organisms including, mammals, *C. elegans*, Drosophila and plants, and humans are known (see, e.g., Fire et al. (1998) *Nature* 391:806–811 Fire (1999) *Trends Genet.* 15:358–363; Sharp (2001) *Genes Dev.* 15:485–490; Hammond, et al. (2001) *Nature Rev. Genet.* 2:110–1119; Tuschl (2001) *Chem. Biochem.* 2:239–245; Hamilton et al. (1999) *Science* 286:950–952; Hammond et al. (2000) *Nature* 404: 293–296; Zamore et al. (2000) *Cell* 101:25–33; Bernstein et al. (2001) *Nature* 409: 363–366; Elbashir et al. (2001) *Genes Dev.* 15:188–200; Elbashir et al. (2001) *Nature* 411:494–498; International PCT application No. WO 01/29058; International PCT application No. WO 99/32619). Double-stranded RNA (dsRNA)-expressing constructs are introduced into a host, such as an animal or plant using, a replicable vector that remains episomal or integrates into the genome. By selecting appropriate sequences, expression of dsRNA can interfere with accumulation of endogenous mRNA encoding a CVSP14. RNAi also can be used to inhibit expression in vitro. Regions include at least about 21 (or 21) nucleotides that are selective (i.e. unique) for CVSP14 are used to prepare the RNAi. Smaller fragments of about 21 nucleotides can be transformed directly into cells; larger RNAi dsRNA molecules are generally introduced using vectors that encode them. dsRNA molecules are at least about 21 bp long or longer, such as 50, 100, 150, 200 and longer.

3. Gene Therapy

In an exemplary embodiment, nucleic acids that include a sequence of nucleotides encoding a CVSP14 polypeptide or functional domains or derivative thereof, are administered to promote CVSP14 polypeptide function, by way of gene therapy. Gene therapy refers to therapy performed by the administration of a nucleic acid to a subject. In this embodiment, the nucleic acid produces its encoded protein that mediates a therapeutic effect by promoting CVSP14 polypeptide function. Any of the methods for gene therapy available in the art can be used (see, Goldspiel et al., *Clinical Pharmacy* 12:488–505 (1993); Wu and Wu, *Biotherapy* 3:87–95 (1991); Tolstoshev, *An. Rev. Pharmacol. Toxicol.* 32:573–596 (1993); Mulligan, *Science* 260:926–932 (1993); and Morgan and Anderson, *An. Rev. Biochem.* 62:191–217 (1993); *TIBTECH* 11 (5):155–215 (1993). For example, one therapeutic composition for gene therapy includes a CVSP14 polypeptide-encoding nucleic acid that is part of an expression vector that expresses a CVSP14 polypeptide or domain, fragment or chimeric protein thereof in a suitable host. In particular, such a nucleic acid has a promoter operably linked to the CVSP14 polypeptide coding region, the promoter being inducible or constitutive, and, optionally, tissue-specific. In another particular embodiment, a nucleic acid molecule is used in which the CVSP14 polypeptide coding sequences and any other desired sequences are flanked by regions that promote homologous recombination at a desired site in the genome, thus providing for intrachromosomal expression of the SP protein nucleic acid (Koller and Smithies, *Proc. Natl. Acad. Sci. USA* 86:8932–8935 (1989); Zijlstra et al., *Nature* 342:435–438 (1989)).

Delivery of the nucleic acid into a patient can be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, *J. Biol. Chem.* 262:4429–4432 (1987)) (which can be used to target cell types specifically expressing the receptors), etc. In another embodiment, a nucleic acid-ligand complex can be formed in which the ligand is a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932–8935 (1989); Zijistra et al., *Nature* 342:435–438 (1989)).

In a specific embodiment, a viral vector that contains the CVSP14 polypeptide nucleic acid is used. For example, a retroviral vector can be used (see Miller et al., *Meth. Enzymol.* 217:581–599 (1993)). These retroviral vectors have been modified to delete retroviral sequences that are not necessary for packaging of the viral genome and integration into host cell DNA. The CVSP14 polypeptide nucleic acid to be used in gene therapy is cloned into the vector, which facilitates delivery of the gene into a patient. More detail about retroviral vectors can be found in Boesen et al., *Biotherapy* 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993) present a review of adenovirus-based gene therapy. Bout et al., *Human Gene Therapy* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431–434 (1991); Rosenfeld et al., *Cell* 68:143–155 (1992); and Mastrangeli et al., *J. Clin. Invest.* 91:225–234 (1993).

Adeno-associated virus (AAV) has also been proposed for use in gene therapy (Walsh et al., *Proc. Soc. Exp. Biol. Med.* 204:289–300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and can be used, provided that the necessary developmental and physiological functions of the recipient cells are not disrupted. The technique should provide for the stable transfer of the nucleic acid to the cell, so that the nucleic acid is expressible by the cell and generally heritable and expressible by its cell progeny.

The resulting recombinant cells can be delivered to a patient by various methods known in the art. In an embodiment, epithelial cells are injected, e.g., subcutaneously. In another embodiment, recombinant skin cells can be applied as a skin graft onto the patient. Recombinant blood cells (e.g., hematopoietic stem or progenitor cells) can be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., such as stem cells obtained from bone marrow, umbilical cord blood, peripheral blood, fetal liver, and other sources thereof.

For example, a cell used for gene therapy is autologous to the patient. In an embodiment in which recombinant cells are used in gene therapy, a CVSP14 polypeptide nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, *Cell* 71:973–985 (1992)).

Epithelial stem cells (ESCs) or keratinocytes can be obtained from tissues such as the skin and the lining of the gut by known procedures (Rheinwald, *Meth. Cell Bio.* 21A:229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, *Meth. Cell Bio.* 21A:229 (1980); Pittelkow and Scott, *Cano Clinic Proc.* 61:771 (1986)). If the ESCs are provided by a donor, a method for suppression of host versus graft reactivity (e.g., irradiation, drug or antibody administration to promote moderate immunosuppression) also can be used.

With respect to hematopoietic stem cells (HSC), any technique which provides for the isolation, propagation, and maintenance in vitro of HSC can be used in this embodiment. Techniques by which this can be accomplished include (a) the isolation and establishment of HSC cultures from bone marrow cells isolated from the future host, or a donor, or (b) the use of previously established long-term HSC cultures, which can be allogeneic or xenogeneic. Non-autologous HSC generally are used with a method of suppressing transplantation immune reactions of the future host/patient. In a particular embodiment, human bone marrow cells can be obtained from the posterior iliac crest by needle aspiration (see, e.g., Kodo et al., *J. Clin. Invest* 73:1377–1384 (1984)). For example, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., *J. Cell Physiol.* 91:335 (1977) or Witlock-Witte culture techniques (Witlock and Witte, *Proc. Natl. Acad. Sci. USA* 79:3608–3612 (1982)).

In a specific embodiment, the nucleic acid to be introduced for purposes of gene therapy includes an inducible promoter operably linked to the coding region, such that expression of the nucleic acid is controllable by controlling the presence or absence of the appropriate inducer of transcription.

3. Prodrugs

A method for treating tumors is provided. The method is practiced by administering a prodrug that is cleaved at a specific site by a CVSP14 to release an active drug. Upon contact with a cell that expresses CVSP14 activity, the prodrug is converted into an active drug. The prodrug can be a conjugate that contains the active agent, such as an anti-tumor drug, such as a cytotoxic agent, or other therapeutic agent (TA), linked to a substrate for the targeted CVSP14, such that the drug or agent is inactive or unable to enter a cell, in the conjugate, but is activated upon cleavage. The prodrug, for example, can contain an oligopeptide, typically a relatively short, less than about 10 amino acids peptide, that is proteolytically cleaved by the targeted CVSP14. Cytotoxic agents, include, but are not limited to, alkylating agents, antiproliferative agents and tubulin binding agents. Others include, vinca drugs, mitomycins, bleomycins and taxanes.

M. Animal Models

Transgenic animal models and animals, such as rodents, including mice an rats, cows, chickens, pigs, goats, sheep, gorillas and other primates, are provided herein. In particular, transgenic non-human animals that contain heterologous nucleic acid encoding a CVSP14 polypeptide or a transgenic animal in which expression of the polypeptide has been altered, such as by replacing or modifying the promoter region or other regulatory region of the endogenous gene are provided.

Such an animal can by produced by promoting recombination between an exogenous CVSP14 gene that could be over-expressed or mis-expressed, such as by expression under a strong promoter, via homologous or other recombination event. For example, transgenic animals can be produced by introducing the nucleic acid using vectors or other modes of gene delivery into a germline cell, such as an embryonic stem cell. Typically the nucleic acid is introduced, such as an embryonic stem cell, which is then injected by transforming embryo-derived stem (ES) cells with a vector containing the CVSP14 polypeptide-encoding nucleic acid followed by injecting the ES cells into a blastocyst, and implanting the blastocyst into a foster mother, followed by the birth of a transgenic animal. Generally introduction into a chromosome of the animal occurs by a recombination between the heterologous CVSP14-encoding nucleic acid and endogenous nucleic acid. The heterologous nucleic acid can be targeted to a specific chromosome. In some instances, knockout animals can be produced. Such an animal can be initially produced by promoting homologous recombination between a CVSP14 polypeptide gene in its chromosome and an exogenous CVSP14 polypeptide gene that has been rendered biologically inactive (typically by insertion of a heterologous sequence, e.g., an antibiotic resistance gene). In one embodiment, this homologous recombination is performed by transforming embryo-derived stem (ES) cells with a vector containing the insertionally inactivated CVSP14 polypeptide gene, such that homologous recombination occurs, followed by injecting the ES cells into a blastocyst, and implanting the blastocyst into a foster mother, followed by the birth of the chimeric animal ("knockout animal") in which a CVSP14 polypeptide gene has been inactivated (see Capecchi, *Science* 244:1288–1292 (1989)). The chimeric animal can be bred to produce homozygous knockout animals, which can then be used to produce additional knockout animals.

Knockout animals include, but are not limited to, mice, hamsters, sheep, pigs, cattle, and other non-human mammals. For example, a knockout mouse is produced. Such knockout animals are expected to develop or be predisposed to developing neoplastic diseases and thus can have use as animal models of such diseases e.g., to screen for or test molecules for the ability to treat or prevent such diseases or disorders. Such an animal can be initially produced by promoting homologous recombination between a CVSP14 gene in its chromosome and an exogenous CVSP14 polypeptide gene that would be over-expressed or mis-expressed (generally by expression under a strong promoter). In an embodiment, this homologous recombination is carried out by transforming embryo-derived stem (ES)

cells with a vector containing the over-expressed or mis-expressed CVSP14 polypeptide gene, such that homologous recombination occurs, followed by injecting the ES cells into a blastocyst, and implanting the blastocyst into a foster mother, followed by the birth of the chimeric animal in which a CVSP14 gene has been over-expressed or mis-expressed (see Capecchi, Science 244:1288–1292 (1989)). The chimeric animal can be bred to produce additional animals with over-expressed or mis-expressed CVSP14 polypeptide. Such animals include, but are not limited to, mice, hamsters, sheep, pigs, cattle and other non-human mammals. In a specific embodiment, a mouse with over-expressed or mis-expressed CVSP14 polypeptide is produced.

The following examples are included for illustrative purposes only and are not intended to limit the scope of the invention.

EXAMPLE 1

Identification of CVSP14

Preparation of Single Strand cDNA from Prostate Tumor Samples

The human prostate tumor CWR22R was grown on nude mice. CWR22R tissue was dissected and put into TRIZOL Reagent (Gibco BRL) and total RNA was purified according to the manufacturer's instructions. Poly $A^+$ RNA was further purified from total RNA using Oligotex mRNA mini Kit (Qiagen). Single strand cDNA was synthesized using SuperScript First-Strand Synthesis System (Gibco BRL). Either random hexamers or oligo(dT) was used to prime the first-strand cDNA synthesis.

Serine Protease Profiling by Degenerate Primer PCR

Serine protease domains were amplified using degenerate primers designed from the consensus sequences flanking the catalytic histidine (DSPP1) and the catalytic serine (DSPP2). The sequence of the sense primer (DSPP1) used is as follows (SEQ ID No. 7): 5'-TGG (GA)TI (ACG)TI (TA)(CG)I GCI (AG)CI CA(TC) TG-3' (nucleotides in parentheses represent equal molar mixtures and I represents deoxyinosine). The sequence of antisense primer (DSPP2) used is as follows (SEQ ID No. 8): 5'-IGG ICC ICC I(CG)(TA) (GA)TC ICC (TC)TI (AG)CA IG(TAC) (AG) TC-3'.

Random hexamer and oligo(dT) primed cDNA were used as templates for PCR reactions. PCR products were separated on agarose gels, and all products between 450- to 550-bp were extracted from the gels and subcloned into the pCR2.1-TOPO cloning vector (Invitrogen). Plasmids containing PCR-generated inserts were identified by electrophoresis of EcoR I digestion products on agarose gels. Plasmids containing 450–550 bp inserts were subjected to DNA sequencing. One of these clones contained a 474 bp insert that encoded a portion of the protease domain of a novel serine protease. This serine protease sequence is hereafter referred to as CVSP14.

Random hexamer and oligo(dT) primed cDNA were used as templates for PCR reactions. PCR products were separated on agarose gels, and all products between 450- to 550-bp were extracted from the gels and subcloned into the pCR2.1-TOPO cloning vector (Invitrogen). Plasmids containing PCR-generated inserts were identified by electrophoresis of EcoR I digestion products on agarose gels. Plasmids containing 450–550 bp inserts were subjected to DNA sequencing. One of these clones contained a 474 bp insert that encoded a portion of the protease domain of a serine protease, which is referred to as CVSP14 herein.

A BLAST search against the human genomic database htgs (Unfinished High Throughput Genomic Sequences) revealed that this sequence matches a genomic sequence AC012228 that is derived from human chromosome 11.

Cloning of cDNA Encoding the Protease Domain of CVSP14

ClonCapture cDNA Selection Kit (Clontech) was used to obtain cDNA encoding the CVSP14 protease domain. A biotinylated 474 bp partial cDNA clone for CVSP14 was generated by PCR using DSPP1 and DSPP2 primers in the presence of biotin-21-dUTP. The biotinylated product was gel purified and used as probe in RecA-mediated ClonCapture procedures. Human prostate adenocarcinoma cDNA library (Gibco BRL Cat. # 11597-010) was used as the cDNA source. The captured cDNAs were transformed into ElectroMAX DH10B cells by electroporation, and positive clones containing CVSP14 protease domain were identified by colony hybridization using a non-biotinylated DSPP1 and DSPP2 PCR product. Positive clones were verified by DNA sequencing. DNA sequencing analysis of four positive clones indicated that all clones contained cDNAs encoding the protease domain of a serine protease. The cDNA encoding CVSP14 protease domain is composed of 756 bp, which translates into 251-amino acids. BLAST analysis of the protein database indicated that this serine protease has highest homology to one of the serine protease domains of Xenopus oviductin (Genbank accession number U81291 and T30338) with 47% identity.

Cloning of Human CVSP14 Full-Length cDNA

To obtain the remaining 5' upstream cDNA of CVSP14, 5'-RACE reactions were performed on the human kidney RACE cDNA synthesized using GeneRacer Kit (Ambion, Cat. No. L1500-01). GeneRacer kit is specifically designed for full-length, RNA ligase-mediated rapid amplification of 5' and 3' cDNA ends (RLM-RACE). The first 5'-RACE reaction was performed by PCR using GeneRacer 5' primer with gene specific primers, GX-SP1-4AS, 5'-GTTAAGCG-GCCCCAGCCTGCAGTTGTAC-3' SEQ ID NO. The PCR products were purified from agarose gel.

A second nested PCR was then performed using GeneRacer 5' nested primer with gene specific primer GX-SP1-1AS, 5'-GCTCTCCTGGGTCTGTCTGGCTTAAGTC-3' SEQ ID NO. 19 (using first 5'-RACE product as template). The PCR products from RACE reactions, which were greater than 500 bp, were purified from agarose gel and subcloned into pCR2.1-TOPO cloning vector (Invitrogen, Carlsbad, Calif.). Colony hybridization was then performed to identify positive colonies containing CVSP14 sequence. An additional sequence of 279 bp was obtained from the second 5'-RACE products including an ATG start codon within a sequence of AAAACTATGAGT (SEQ ID NO. 20).

Nucleotide and Protein Sequence of the CVSP14

The nucleotide and Amino Acid sequences of Human CVSP14 are set forth below and in SEQ ID Nos. 12 and 13:

```
                GAT TCA CCA CGT CTT GGT TAA TGA ATA AAC TTG TTT TAA ATT GGC TTA TTG CTG

GTC TCT CAA GGC TTC CTA TTT TTG TTT GCT TTA GTC TCT CTA AAA TTT CAG GGA AAA ACT
115/1                                       145/11

ATG AGT CTC AAA ATG CTT ATA AGC AGG AAC AAG CTG ATT TTA CTA CTA GGA ATA GTC TTT
 M   S   L   K   M   L   I   S   R   N   K   L   I   L   L   L   G   I   V   F
175/21                                      205/31

TTT GAA CAA GGT AAA TCT GCA GCT CTT TCG CTC CCC AAA GCT CCC AGT TGT GGG CAG AGT
 F   E   Q   G   K   S   A   A   L   S   L   P   K   A   P   S   C   G   Q   S
235/41                                      265/51

CTG GTT AAG GTA CAG CCT TGG AAT TAT TTT AAC ATT TTC AGT CGC ATT CTT GGA GGA AGC
 L   V   K   V   Q   P   W   N   Y   F   N   I   F   S   R   I   L   C   C   S
295/61                                      325/71

CAA GTG GAG AAG GGT TCC TAT CCC TGG CAG GTA TCT CTG AAA CAA AGG CAG AAG CAT ATT
 Q   V   H   K   C   S   Y   P   W   Q   V   S   L   K   Q   R   Q   K   H   I
355/81                                      385/91

TGT GGA GGA AGC ATC GTC TCA CCA CAG TGG GTG ATC ACG GCG GCT CAC TGC ATT GCA AAC
 C   G   G   S   I   V   S   P   Q   W   V   I   T   A   A   H   C   I   A   N
415/101                                     445/111

AGA AAC ATT GTG TCT ACT TTG AAT GTT ACT GCT GGA GAG TAT GAC TTA AGC CAG ACA GAC
 R   N   I   V   S   T   L   N   V   T   A   C   H   Y   D   L   S   Q   T   D
475/121                                     505/131

CCA GGA GAG CAA ACT CTC ACT ATT GAA ACT GTC ATC ATA CAT CCA CAT TTC TCC ACC AAG
 P   C   E   Q   T   L   T   I   E   T   V   I   I   H   P   H   F   S   T   K
535/141                                     565/151

AAA CCA ATG GAC TAT GAT ATT GCC CTT TTG AAG ATG GCT GGA GCC TTC CAA TTT GGC CAC
 K   P   M   D   Y   D   I   A   L   L   K   M   A   G   A   F   Q   F   G   H
595/161                                     625/171

TTT GTG GGG CCC ATA TGT CTT CCA GAG CTG CGG GAG CAA TTT GAG GCT GGT TTT ATT TGT
 F   V   G   P   I   C   L   P   H   L   F   H   Q   F   H   A   C   F   I   C
655/181                                     685/191

ACA ACT GCA GGC TGG GGC CGC TTA ACT GAA GGT GGC GTC CTC TCA CAA GTC TTG CAG GAA
 T   T   A   G   W   G   R   L   T   E   G   G   V   L   S   Q   V   L   Q   E
715/201                                     745/211

GTG AAT CTG CCT ATT TTG ACC TGG GAA GAG TGT GTG GCA GCT CTG TTA ACA CTA AAG AGG
 V   N   L   P   I   L   T   W   E   E   C   V   A   A   L   L   T   K   R
775/221                                     805/231

CCC ATC AGT GGG AAG ACC TTT CTT TGC ACA GGT TTT CCT GAT GGA GGG AGA GAC GCA TGT
 P   I   S   G   K   T   F   L   C   T   G   F   P   D   G   G   R   D   A   C
835/241                                     865/251

CAG GGA GAT TCA GGA GGT TCA CTC ATG TGC CGG AAT AAG AAA GGG GCC TGG ACT CTG GCT
 Q   G   D   S   G   G   S   L   M   C   R   N   K   K   G   A   W   T   L   A
895/261                                     925/271

GGT GTG ACT TCC TGG GGT TTG GGC TGT GGT CGA GGC TGG AGA AAC AAT GTG AGG AAA AGT
 G   V   T   S   W   G   L   G   C   G   R   G   W   R   N   N   V   R   K   S
955/281                                     985/291

GAT CAA GGA TCC CCT GGG ATC TTC ACA GAC ATT AGT AAA GTG CTT TCC TGG ATC CAC GAA
 D   Q   G   S   P   G   I   F   T   D   I   S   K   V   L   S   W   I   H   E
1015/301                                    1045/311

CAC ATC CAA ACT GGT AAC TAA
 H   I   Q   T   G   N   *
*Underline indicates the signal peptide
```

Sequence Analysis and Domain Organization of CVSP14

The CVSP14 DNA and protein sequences were analyzed using DNA Strider (version 1.2). The ORF of CVSP14 is composed of 921 bp, which translate into a 306-amino acid protein. Protein sequence analysis using the SMART (Simple Modular Architecture Research Tool) program available on the internet at-smart.embl-heidelberg.de indicates that CVSP14 is a secreted serine protease with a signal peptide (amino acids 1–25) at the N-terminus followed by a trypsin-like serine protease domain (amino acids 55–306). The amino acid and nucleoide sequences are set forth in SEQ ID No. 12 and 13.

Gene Expression Profile of CVSP14 in Normal and Tumor Tissues

To obtain information regarding the gene expression profile of the CVSP14 transcript, PCR analysis was carried out on cDNA panels made from several human adult tissues (Clontech, Cat. #K1420-1), fetal tissues (Cat. #K1425-1)

and primary tumors (human tumor multiple tissue cDNA panel, catalog number K1522-1, CLONTECH) using CVSP14-specific primers GX-SP1-1 (SEQ ID No. 9) (5'-GACTTAAGCCAGACAGACCCAGGAGAGC-3') and GX-SP1-2AS (5'-TTGTGAGAGGACGCCACCTTCAGT-TAAGC-3') (SEQ ID No. 10).

After 35 PCR cycles, a DNA band (246 bp) of strong intensity, indicating high expression of CVSP14, was detected only in kidney cDNA. A DNA band of moderate intensity was seen in lung cDNA, and a weak band was seen in placenta cDNA. No detectable signal was observed in either fetal tissue or tumor cDNA. After 40 PCR cycles, additional signals can be detected in adult liver, pancreas, fetal heart, fetal lung, fetal skeletal muscle, fetal thymus, colon adenocarcinoma (CX-1), and pancreatic adenocarcinoma (GI-103).

A PCR product of 474 bp generated by DSPP1 and DSPP2 primers was used to probe a cDNA blot composed of cDNA synthesized from 68 human tumors and corresponding normal tissue from the same individual (catalog number 7840-1 human matched tumor/normal expression array; CLONTECH) as well as a dot blot composed of RNA extracted from 72 different human tissues (Human Multiple Tissue Expression (MTE) Array; Clontech, Palo Alto, Calif.; catalog no. 7776-1). Strong signals, indicating high expression of CVSP14, were detected in 6 of the 15 normal kidney cDNA samples and moderate to weak signals could also be detected in 8 additional normal kidney cDNA samples. CVSP14 signals were diminished in all the matched kidney tumor samples. Weak signals were detected in all three pairs of prostate normal/tumor cDNA samples. Weak signals were also detected in 3 of 9 normal breast samples. A weak signal was also detected in one of the 7 uterine tumors, but not in their normal tissue counterparts. Weak signals were also detected in two of the three normal lung tissue samples, but not in their matched tumor samples. Very weak signals can be seen in cDNA samples from various tumor cell lines, including HeLa cells, Burkitt's lymphoma Daudi cells, chronic myelogenous leukemia K562, promyelocytic leukemia HL-60 cells, melanoma G361 cells, lung carcinoma A549 cells, lymphoblastic leukemia MOLT-4 and colorectal adenocarcinoma SW480 cells.

The results of MTE analysis indicated that CVSP14 transcript is expressed moderately in lymph node and wealy in heart, stomach, duodenum, jejunum, ileum, ilocecum, colon (ascending, transverse, and descending), kidney, skeletal muscle, lung, placenta, liver, pancreas and salivary gland.

EXAMPLE 2

Expression of the Protease CVSP Domains

Nucleic acid encoding each the CVSP14 and protease domain thereof can be cloned into a derivative of the *Pichia pastoris* vector pPIC9K (available from Invitrogen; see SEQ ID NO. 11). Plasmid pPIC9K features include the 5' AOX1 promoter fragment at 1-948; 5' AOX1 primer site at 855-875; alpha-factor secretion signal(s) at 949-1218; alpha-factor primer site at 1152-1172; multiple cloning site at 1192-1241; 3' AOX1 primer site at 1327-1347; 3' AOX1 transcription termination region at 1253-1586; HIS4 ORF at 4514-1980; kanamycin resistance gene at 5743-4928; 3' AOX1 fragment at 6122-6879; ColE1 origin at 7961-7288; and the ampicillin resistance gene at 8966-8106. The plasmid is derived from pPIC9K by eliminating the XhoI site in the kanamycin resistance gene and the resulting vector is herein designated pPIC9Kx.

C122S Mutagenesis of the Protease Domain of CVSP14

The gene encoding the protease domain of CVSP14 was mutagenized by PCR SOE (PCR-based splicing by overlap extension) to replace the unpaired cysteine at position 122 (chymotrypsin numbering system; cysteine 166 in CVSP14 SEQ ID No. 13) with a serine. Two overlapping gene fragments, each containing the AGT codon for serine at position 166 were PCR amplified using the following primers: for the 5' gene fragment:

TCTCTCGAGAAAAGAATTCTTGGAG-GAAGCCAAGTGGAG (SEQ ID No. 14) and TTTGTGGGGCCCATAAGTCTTCCAGAGCTGCGG (SEQ ID No. 15); for the 3' gene fragment, ATTCGCGGC-CGCTTAGTTACCAGTTTGGATGTGTTCGTG (SEQ ID No. 16) and CCGCAGCTCTGGAAG ACTTATGGGCCCCACAAA (SEQ ID No. 17). The amplified gene fragments were purified on a 1% agarose gel, mixed and reamplified by PCR to produce the full length coding sequence for for the protease domain of CVSP14 C122S ($Cys_{166}$ Seq ID No 13; $Cys_{111}$ SEQ ID No. 6). This sequence was then cut with restriction enzymes NotI and XhoI, and ligated into vector pPic9KX.

Construction of CVSP14 Expression Vector cDNA encoding CVSP14 containing the C122S point mutation (i.e., CVSP14C122S, position $C_{166}$ in SEQ ID Nos. 12 and 13) was cloned from pPIC9Kx:CVSP14C122S. The primers CVSP14-5' GGAATTCCATATGAGCAGCG-GCCATATCGACGACGACGACAAAATTCT TGGAG-GAAGCCAAGTGGAG (containing a NdeI restriction site; SEQ ID No. 21) and CVSP14-3' CCGCTCGAGGTTAC-CAGTTTGGATGTGTTCGTGG (containing a XhoI restriction site; SEQ ID No. 22) were used to PCR amplify the human CVSP14 protease domain utilizing an enterokinase recognition sequence (DDDDK) for zymogen activation. Amplification was conducted in a total volume of 50 ul containing 20 mM tris-HCl (pH 8.75 at 25° C.), 10 mM KCl, 10 mM $(NH_4)_2SO_4$, 2 mM $MgSO_4$, 0.1% triton X-100, 0.1 mg/ml BSA, 0.2 mM dNTPs, 1.0 unit ACCUZYME DNA polymerase (Bioline USA, Inc., N.J.), and 100 pmol of primers. The reaction mixture was heated to 95° C. for 5 min, followed by 25 cycles of 95, 60, and 75° C. for 30 s each and a final extension of 75° C. for 2 min.

PCR products were purified using a QIAquick PCR purification kit (QIAGEN Inc., Chatsworth, Calif.). PCR products were doubly digested with 10 units NdeI and 10 units XhoI for 2 hrs at 37° C. The digested fragments were purified on a 1.4% agarose gel and stained with ethidium bromide. The band containing CVSP14 cDNA was excised and purified using a QIAEX II gel extraction kit (QIAGEN Inc., Chatsworth, Calif.). CVSP14 cDNA was then cloned into the NdeI and XhoI sites of the pET21 b expression vector (Novagen, Inc., Madison, Wis.) using standard methods. This vector allows the fusion of a C-terminal 6×HIS tag for purification by immobilized metal affinity chromatography (IMAC). Competent XL10 cells (Stratagene) were transformed with the pET21bCVSP14 vector and used to produce plasmid stocks. Proper insertion and DNA sequence were confirmed by fluorescent thermal dye DNA sequencing methods as well as restriction digests.

Protein Expression, Purification, and Refolding

Overexpression of the gene product was achieved in *E. coli* strain BL21(DE3) containing the dnaY plasmid for rare codon optimization (Garcia et. al. (1986) *Cell* 45:453–459; see, U.S. Pat. No. 6,270,988). 2×YT media (1L), supplemented with carbanicillin (50 ug/ml) and kanamycin (34 ug/ml), was inoculated with a 10 ml overnight culture and grown to a density of 0.6–1.0 OD600 before induction with 1M IPTG (1 mM final concentration). After 6 hours post-induction growth, cells were harvested by centrifugation (3000 g×20 minutes).

The cell pellet was resuspended in 50 mM $NaH_2PO_4$, 300 mM NaCl, 5% LADO, pH 7.4 (25 mL) supplemented with 5–10 mg lysozyme and 1U DNaseI to lyse the cells and shear the DNA. The resulting solution was then centrifuged at 48,000 g for 20 minutes. The supernatant was discarded and the inclusion body pellet was washed by homogenization with the lysis buffer followed by the lysis buffer minus detergent with centrifugation as described above between washes. The inclusion body pellet was then dissolved in 25 mL 6M GuHCl, 20 mM tris-HCl, 300 mM NaCl, 20 mM βMe, pH 8.0. This solution was then centrifuged at 48,000 g for 30 minutes to remove particulate matter.

The resulting solution was filtered through a 0.2 um syringe filter before loading onto 25 ml Ni-NTA resin (QIAGEN Inc., Chatsworth, Calif.) pre-equilibrated with 6M GuHCl, 20 mM tris-HCl, 300 mM NaCl, pH 8.0. The column was washed with two column volumes equilibration buffer followed by three column volumes 8M urea, 20 mM tris-HCl, 300 mM NaCl, pH 8.0. Purified inclusion bodies are then eluted with two column volumes 8M urea, 20 mM tris-HCl, 300 mM NaCl, 1M imidazole, pH 8.0.

CVSP14 was refolded by slowly adding the inclusion body mixture to 8 L 100 mM tris-HCl, 150 mM NaCl, 7.5 mM cysteine, 1 mM cystine, 0.5M arginine, 3 g/L cholic acid, pH 8.0 using a peristaltic pump. The refolding mixture was allowed to stir at 4° C. for 7 days or until thiol concentration was below 1 mM as detected by Ellman's reagent. The refolding solution was filtered through a 1 uM filter, concentrated by ultrafiltration and the buffer exchanged in PBS, 3 g/L cholic acid, pH 8.0.

Activation of CVSP14 was performed by the addition of 1–10 U/ml EKMax (Invitrogen, Carlsbad, Calif.) and incubation at 4° C. until the reaction was deemed complete (generally 4–8 days). Residual EKMax was removed by treating the solution with a small amount of ConA resin that binds the glycosylated enterokinase. Complete removal of EKMax was confirmed by measuring the activity of the solution towards a specific enterokinase fluorogenic substrate.

The resulting solution was screened for activity against a series of protease substrates; spec-tPa, spec-PL, spec-fXIIa (American Diagnostica), S-2239, S-2266 (Kabi Diagnostica), S-2586, S-2366, S-2444, S-2288, S-2251, S-2302, S-2765, S-2222, spec-TH (Chromogenix), and spec-fVIIa (Pentapharm). CVSP14 exhibited some activity towards a number of these substrates, but was most active towards S-2366 (DiaPharma, Westchester, Ohio).

EXAMPLE 3

Assays for Identification of Candidate Compounds that Modulate that Activity of a CVSP Assay for Identifying Inhibitors The ability of test compounds to act as inhibitors of catalytic activity of a CVSP14 can be assessed in an amidolytic assay. The inhibitor-induced inhibition of amidolytic activity by a recombinant CVSP or the protease domain portions thereof, can be measured by IC50 values in such an assay.

The protease domain of CVSP14 expressed as described above is assayed in Costar 96 well tissue culture plates (Corning N.Y.) for inhibition by various test compounds as follows. Approximately 1–10 nM protease is added without inhibitor, or with 100000 nM inhibitor and seven 1:6 dilutions into 1× direct buffer (29.2 mM Tris, pH 8.4, 29.2 mM Imidazole, 217 mM NaCl (100 μL final volume)), and allowed to incubate at room temperature for 30 minutes. 400 μM substrate S 2366 (L-pyroglutamyl-L-prolyl-L-arginine-p-nitroaniline hydrochloride; DiaPharma, Westchester, Ohio) is added and the reaction is monitored in a SpectraMAX Plus microplate reader (Molecular Devices, Sunnyvale Calif.) by following change in absorbance at 405 nm for 20 minutes at 37° C.

Identification of Substrates

Particular substrates for use in the assays can be identified empirically by testing substrates. The following list of substrates are exemplary of those that can be tested.

| Substrate name | Structure |
|---|---|
| S 2366 | pyroGlu-Pro-Arg-pNA.HCl |
| spectrozyme t-PA | $CH_3SO_2$-D-HHT-Gly-Arg-pNA.AcOH |
| N-p-tosyl-Gly-Pro-Arg-pNA | N-p-tosyl-Gly-Pro-Arg-pNA |
| Benzoyl-Val-Gly-Arg-pNA | Benzoyl-Val-Gly-Arg-pNA |
| Pefachrome t-PA | $CH_3SO_2$-D-HHT-Gly-Arg-pNA |
| S 2765 | N-α-Z-D-Arg-Gly-Arg-pNA.2HCl |
| S 2444 | pyroGlu-Gly-Arg-pNA.HCl |
| S 2288 | H-D-Ile-Pro-Arg-pNA.2HCl |
| spectrozyme UK | Cbo-L-(γ)Glu(α-t-BuO)-Gly-Arg-pNA.2AcOH |
| S 2302 | H-D-Pro-Phe-Arg-pNA.2HCl |
| S 2266 | H-D-Val-Leu-Arg-pNA.2HCl |
| S 2222 | Bz-Ile-Glu(g-OR)-Gly-Arg-pNA.HCl |
| | R = H(50%) and R = $CH_3$(50%) |
| Chromozyme PK | Benzoyl-Pro-Phe-Arg-pNA |
| S 2238 | H-D-Phe-Pip-Arg-pNA.2HCl |
| S 2251 | H-D-Val-Leu-Lys-pNA.2HCl |
| Spectrozyme Pl | H-D-Nle-HHT-Lys-pNA.2AcOH |
| | Pyr-Arg-Thr-Lys-Arg-AMC |
| | H-Arg-Gln-Arg-Arg-AMC |
| | Boc-Gln-Gly-Arg-AMC |
| | Z-Arg-Arg-AMC |

-continued

| Substrate name | Structure |
|---|---|
| Spectrozyme THE | H-D-HHT-Ala-Arg-pNA.2AcOH |
| Spectrozyme fXIIa | H-D-CHT-Gly-Arg-pNA.2AcOH |
| | CVS 2081-6 (MeSO$_2$-dPhe-Pro-Arg-pNA) |
| | Pefachrome fVIIa (CH$_3$SO$_2$-D-CHA-But-Arg-pNA) | pNA = para-nitranilide (chromogenic)

AMC=amino methyl coumarin (fluorescent)

If none of the above substrates are cleaved, a coupled assay, described above, can be used. Briefly, test the ability of the protease to activate and enzyme, such as plasminogen and trypsinogen. To perform these assays, the single chain protease is incubated with a zymogen, such as plasminogen or trypsinogen, in the presence of the a known substrate, such, lys-plasminogen, for the zymogen. If the single chain activates the zymogen, the activated enzyme, such as plasmin and trypsin, will degrade the substrate therefor.

EXAMPLE 4

Other Assays

These assays are described with reference to MTSP1, but such assays can be readily adapted for use with CVSP14.

Amidolytic Assay for Determining Inhibition of Serine Protease Activity of Matriptase or MTSP1

The ability of test compounds to act as inhibitors of rMAP catalytic activity was assessed by determining the inhibitor-induced inhibition of amidolytic activity by the MAP, as measured by IC$_{50}$ values. The assay buffer was HBSA (10 mM Hepes, 150 mM sodium chloride, pH 7.4, 0.1% bovine serum albumin). All reagents were from Sigma Chemical Co. (St. Louis, Mo.), unless otherwise indicated.

Two IC$_{50}$ assays (a) one at either 30-minutes or 60-minutes (a 30-minute or a 60-minute preincubation of test compound and enzyme) and (b) one at 0-minutes (no preincubation of test compound and enzyme) were conducted. For the IC$_{50}$ assay at either 30-minutes or 60-minutes, the following reagents were combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the rMAP (Corvas International) diluted in buffer, yielding a final enzyme concentration of 250 pM as determined by active site filtration. Following either a 30-minute or a 60-minute incubation at ambient temperature, the assay was initiated by the addition of 50 microliters of the substrate S-2765 (N-α-Benzyloxycarbonyl-D-arginyl-L-glycyl-L-arginine-p-nitroaniline dihydrochloride; DiaPharma Group, Inc.; Franklin, Ohio) to each well, yielding a final assay volume of 200 microliters and a final substrate concentration of 100 μM (about 4-times K$_m$). Before addition to the assay mixture, S-2765 was reconstituted in deionized water and diluted in HBSA. For the IC$_{50}$ assay at 0 minutes; the same reagents were combined: 50 microliters of HBSA, 50 microliters of the test compound, diluted (covering the identical concentration range) in HBSA (or HBSA alone for uninhibited velocity measurement), and 50 microliters of the substrate S-2765. The assay was initiated by the addition of 50 microliters of rMAP. The final concentrations of all components were identical in both IC$_{50}$ assays (at 30- or 60- and 0-minute).

The initial velocity of chromogenic substrate hydrolysis was measured in both assays by the change of absorbance at 405 nM using a Thermo Max® Kinetic Microplate Reader (Molecular Devices) over a 5 minute period, in which less than 5% of the added substrate was used. The concentration of added inhibitor, which caused a 50% decrease in the initial rate of hydrolysis was defined as the respective IC$_{50}$ value in each of the two assays (30- or 60-minutes and 0-minute).

In Vitro Enzyme Assays for Specificity Determination

The ability of compounds to act as a selective inhibitor of matriptase activity was assessed by determining the concentration of test compound that inhibits the activity of matriptase by 50%, (IC$_{50}$) as described in the above Example, and comparing IC$_{50}$ value for matriptase to that determined for all or some of the following serine proteases: thrombin, recombinant tissue plasminogen activator (rt-PA), plasmin, activated protein C, chymotrypsin, factor Xa and trypsin.

The buffer used for all assays was HBSA (10 mM HEPES, pH 7.5, 150 mM sodium chloride, 0.1% bovine serum albumin).

The assay for IC$_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for V$_o$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was used. The concentration of added inhibitor which caused a 50% decrease in the initial rate of hydrolysis was defined as the IC$_{50}$ value.

Thrombin (fIIa) Assay

Enzyme activity was determined using the chromogenic substrate, Pefachrome t-PA (CH$_3$SO$_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

IC$_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was used. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from DiaPharma Group (Franklin, Ohio). All substrates were reconstituted in deionized water prior to use. The final concentration of S-2765 was 250 µM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. *Arch. Biochem. Biophys.* 273:375–388 (1989)]. The enzyme was diluted into HBSA prior to assay in which the final concentration was 0.25 nM. Recombinant tissue plasminogen activator (rt-PA) Assay rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 (L-pyroglutamyl-L-prolyl-L-arginine-p-nitroaniline hydrochloride), which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzioxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3x-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Since modifications will be apparent to those of skill in this art, it is intended that this invention be limited only by the scope of the appended claims.

What is claimed is:

1. A substantially purified two chain protease comprising a CVSP14 protease domain having the sequence of amino acid residues set forth in SEQ ID No. 6.

2. The substantially purified protease of claim 1 that is a human protease.

3. The activated two chain protease of claim 1, wherein a free cysteine in the protease domain is replaced with another amino acid.

4. The protease of claim 3, wherein the cysteine is replaced by a conservative amino acid substitution.

5. The protease of claim 4, wherein the replacing amino acid is a serine.

6. A substantially purified protease that consists of the sequence of amino acid residues set forth in SEQ ID No. 6.

7. A substantially purified single chain or activated two chain CVSP14 protease that comprises a sequence of amino acids selected from the group consisting of:

(a) the sequence of amino acids encoded by the sequence of nucleotides set forth in SEQ ID No. 12; and (b) the sequence of amino acids set forth in SEQ ID No. 13.

8. The substantially purified CVSP14 protease of claim 7, that is a single chain protease consisting of the sequence of amino acids set forth in SEQ ID No. 12.

9. The substantially purified CVSP14 protease of claim 7, that is an activated two-chain protease consisting of the sequence of amino acids set forth in SEQ ID No. 12.

10. The substantially purified protease of claim 7 that is a human protease.

11. The substantially prurified protease of claim 7, wherein a free cysteine in the protease domain is replaced with another amino acid.

12. The polypeptide of claim 11, wherein the replacing amino acid is a serine.

13. A conjugate, comprising the protease of claim 1, and a targeting agent linked to the protease directly or via a linker.

14. The conjugate of claim 13, wherein the targeting agent permits
   i) affinity isolation or purification of the conjugate;
   ii) attachment of the conjugate to a surface;
   iii) detection of the conjugate; or
   iv) targeted delivery of the conjugate to a selected tissue or cell.

15. A conjugate, comprising the protease of claim 7, and a targeting agent linked to the protease directly or via a linker.

16. The conjugate of claim 15, wherein the targeting agent permits
   i) affinity isolation or purification of the conjugate;
   ii) attachment of the conjugate to a surface;
   iii) detection of the conjugate; or
   iv) targeted delivery of the conjugate to a selected tissue or cell.

17. A conjugate, comprising the protease of claim 9, and a targeting agent linked to the protease directly or via a linker.

18. The conjugate of claim 17, wherein the targeting agent permits
   i) affinity isolation or purification of the conjugate;
   ii) attachment of the conjugate to a surface;
   iii) detection of the conjugate; or
   iv) targeted delivery of the conjugate to a selected tissue or cell.

19. A solid support, comprising two or more proteases of claim 1 or claim 7 linked thereto either directly or via a linker.

20. The support of claim 19, wherein the proteases comprise an array.

21. The support of claim 20, wherein the array further comprises a plurality of different protease domains.

22. A method for identifying compounds that inhibit the protease activity of the activated two-chain protease of claim 1, comprising:
   contacting the protease of claim 1 with a substrate that is proteolytically cleaved by the protease, and, either simultaneously, before, or after, adding a test compound or plurality thereof;
   measuring the amount of substrate cleaved in the presence of the test compound; and,
   selecting test compounds that decrease the amount of substrate cleaved compared to a control,
   thereby identifying compounds that inhibit the activity of the protease.

23. The method of claim 22, wherein the test compounds are small molecules, peptides, peptidomimetics, natural products, antibodies or fragments thereof that inhibit the activity of the protease.

24. The method of claim 22, wherein the control measures the amount of substrate cleaved by the protease in the absence of the test compound.

25. The method of claim 22m wherein a plurality of the test compounds are screened simultaneously.

26. The method of claim 25, wherein a plurality of the proteases are linked to a solid support, either directly or via a linker.

27. The method of claim 26, wherein the proteases comprise an array.

28. The method of claim 22, wherein the protease consists of the sequence of amino acid residues set forth in SEQ ID No. 6.

29. A method for identifying compounds that inhibit the protease activity of the protease of claim 4, comprising:
   contacting the protease of claim 4 with a substrate that is proteolytically cleaved by the protease and, either simultaneously, before or after, adding a test compound or plurality thereof;
   measuring the amount of substrate cleaved in the presence of the test compound; and
   selecting compounds that change the amount of substrate cleaved compared to a control,
   thereby identifying compounds that inhibit the activity of the protease.

30. A method for identifying compounds that inhibit the protease activity of the protease of claim 9 comprising:
   contacting the protease of claim 9 with a substrate that is proteolytically cleaved by the protease, and, either simultaneously, before, or after, adding a test compound or plurality thereof;
   measuring the amount of substrate cleaved in the presence of the test compound; and,
   selecting test compounds that decrease the amount of substrate cleaved compared to a control,
   thereby identifying compounds that inhibit the activity of the protease.

* * * * *

UNITED STATES PATENT AND TRADEMARK OFFICE
CERTIFICATE OF CORRECTION

| | | |
|---|---|---|
| PATENT NO. | : 7,172,892 B2 | |
| APPLICATION NO. | : 10/104271 | |
| DATED | : February 6, 2007 | |
| INVENTOR(S) | : Edwin Madison and Jiunn-Chern Yey | |

It is certified that error appears in the above-identified patent and that said Letters Patent is hereby corrected as shown below:

IN THE TITLE PAGES:

Page 2, col. 2;

In Item (56) References Cited, in OTHER PUBLICATIONS:

in the Database EMBL, Accession No. AAY41710, please replace "PRO168" with: --PR0618--.

in the Database EMBL, Accession No. AAZ34033, please replace "PRO168" with: --PR0618--.

in the Database EMBL, Accession No. AAZ33949, please replace "PRO1382" with: --PR0382--.

in the Database EMBL, Accession No. AAY41694, please replace "PRO382" with: --PR0382--.

in the Database EMBL, Accession No. Y99414, please replace "PRO1461" with: --PR01461--.

in Stemple et al., please replace "Isolaton" with: --Isolation--.

Please replace claims 11, 12, 22, 25, 29 and 30 with the following claims:

Col. 133, lines 6-8;

--11. The substantially purified protease of claim 7, wherein a free cysteine in the protease domain is replaced with another amino acid.--

Col. 133, lines 9 and 10;

--12. The protease of claim 11, wherein the replacing amino acid is a serine.--

UNITED STATES PATENT AND TRADEMARK OFFICE
CERTIFICATE OF CORRECTION

| | |
|---|---|
| PATENT NO. | : 7,172,892 B2 |
| APPLICATION NO. | : 10/104271 |
| DATED | : February 6, 2007 |
| INVENTOR(S) | : Edwin Madison and Jiunn-Chern Yey |

It is certified that error appears in the above-identified patent and that said Letters Patent is hereby corrected as shown below:

Col. 133, lines 11-13;

--13. A conjugate, comprising:

the protease of claim 1, and a targeting agent linked to the protease directly or via a linker.--

Col. 133 and 134, lines 48-6;

--22. A method for identifying compounds that inhibit the protease activity of the activated two-chain protease of claim 1, comprising:

contacting the protease of claim 1 with a substrate that is proteolytically cleaved by the protease, and, either simultaneously, before, or after, adding a test compound or plurality thereof;

measuring the amount of substrate cleaved in the presence of the test compound; and, selecting test compounds that decrease the amount of substrate cleaved compared to a control, thereby identifying compounds that inhibit the activity of the protease.--

Col. 134, lines 14 and 15;

--25. The method of claim 22 wherein a plurality of the test compounds are screened simultaneously.--

UNITED STATES PATENT AND TRADEMARK OFFICE
CERTIFICATE OF CORRECTION

| | |
|---|---|
| PATENT NO. | : 7,172,892 B2 |
| APPLICATION NO. | : 10/104271 |
| DATED | : February 6, 2007 |
| INVENTOR(S) | : Edwin Madison and Jiunn-Chern Yey |

It is certified that error appears in the above-identified patent and that said Letters Patent is hereby corrected as shown below:

Col. 134, lines 24-35;

--29. A method for identifying compounds that inhibit the protease activity of the protease of claim 7, comprising:

contacting the protease of claim 7 with a substrate that is proteolytically cleaved by the protease, and, either simultaneously, before or after, adding a test compound or plurality thereof;

measuring the amount of substrate cleaved in the presence of the test compound; and selecting test compounds that decrease the amount of substrate cleaved compared to a control, thereby identifying compounds that inhibit the activity of the protease.--

Col. 134, lines 36-47;

--30. A method for identifying compounds that inhibit the protease activity of the protease of claim 9, comprising:

contacting the protease of claim 9 with a substrate that is proteolytically cleaved by the protease, and, either simultaneously, before, or after, adding a test compound or plurality thereof;

measuring the amount of substrate cleaved in the presence of the test compound; and,

UNITED STATES PATENT AND TRADEMARK OFFICE
CERTIFICATE OF CORRECTION

PATENT NO. : 7,172,892 B2
APPLICATION NO. : 10/104271
DATED : February 6, 2007
INVENTOR(S) : Edwin Madison and Jiunn-Chern Yey It is certified that error appears in the above-identified patent and that said Letters Patent is hereby corrected as shown below:

selecting test compounds that decrease the amount of substrate cleaved compared to a control, thereby identifying compounds that inhibit the activity of the protease.--

Signed and Sealed this

Twenty-seventh Day of May, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,172,892 B2 |
| APPLICATION NO. | : 10/104271 |
| DATED | : February 6, 2007 |
| INVENTOR(S) | : Edwin Madison and Jiunn-Chern Yey |

It is certified that error appears in the above-identified patent and that said Letters Patent is hereby corrected as shown below:

IN THE TITLE PAGES:

Page 2, col. 2;

In Item (56) References Cited, in OTHER PUBLICATIONS:

in the Database EMBL, Accession No. AAY41710, please replace "PRO168" with: --PR0618--.

in the Database EMBL, Accession No. AAZ34033, please replace "PRO168" with: --PR0618--.

in the Database EMBL, Accession No. AAZ33949, please replace "PRO1382" with: --PR0382--.

in the Database EMBL, Accession No. AAY41694, please replace "PRO382" with: --PR0382--.

in the Database EMBL, Accession No. Y99414, please replace "PRO1461" with: --PR01461--.

in Stemple et al., please replace "Isolaton" with: --Isolation--.

IN THE CLAIMS:

Please replace claims 11, 12, 13, 22, 25, 29 and 30 with the following claims:

Col. 133, lines 6-8;

--11. The substantially purified protease of claim 7, wherein a free cysteine in the protease domain is replaced with another amino acid.--

UNITED STATES PATENT AND TRADEMARK OFFICE
CERTIFICATE OF CORRECTION

| | |
|---|---|
| PATENT NO. | : 7,172,892 B2 |
| APPLICATION NO. | : 10/104271 |
| DATED | : February 6, 2007 |
| INVENTOR(S) | : Edwin Madison and Jiunn-Chern Yey |

It is certified that error appears in the above-identified patent and that said Letters Patent is hereby corrected as shown below:

Col. 133, lines 9 and 10;

--12. The protease of claim 11, wherein the replacing amino acid is a serine.--

Col. 133, lines 11-13;

--13. A conjugate, comprising:

the protease of claim 1, and a targeting agent linked to the protease directly or via a linker.--

Col. 133 and 134, lines 48-6;

--22. A method for identifying compounds that inhibit the protease activity of the activated two-chain protease of claim 1, comprising:

contacting the protease of claim 1 with a substrate that is proteolytically cleaved by the protease, and, either simultaneously, before, or after, adding a test compound or plurality thereof;

measuring the amount of substrate cleaved in the presence of the test compound; and, selecting test compounds that decrease the amount of substrate cleaved compared to a control, thereby identifying compounds that inhibit the activity of the protease.--

Col. 134, lines 14 and 15;

--25. The method of claim 22 wherein a plurality of the test compounds are screened simultaneously.--

UNITED STATES PATENT AND TRADEMARK OFFICE
CERTIFICATE OF CORRECTION

| | | |
|---|---|---|
| PATENT NO. | : 7,172,892 B2 | |
| APPLICATION NO. | : 10/104271 | |
| DATED | : February 6, 2007 | |
| INVENTOR(S) | : Edwin Madison and Jiunn-Chern Yey | |

It is certified that error appears in the above-identified patent and that said Letters Patent is hereby corrected as shown below:

Col. 134, lines 24-35;

--29. A method for identifying compounds that inhibit the protease activity of the protease of claim 7, comprising:

contacting the protease of claim 7 with a substrate that is proteolytically cleaved by the protease, and, either simultaneously, before or after, adding a test compound or plurality thereof;

measuring the amount of substrate cleaved in the presence of the test compound; and selecting compounds that decrease the amount of substrate cleaved compared to a control, thereby identifying compounds that inhibit the activity of the protease.--

Col. 134, lines 36-47;

--30. A method for identifying compounds that inhibit the protease activity of the protease of claim 9, comprising:

contacting the protease of claim 9 with a substrate that is proteolytically cleaved by the protease, and, either simultaneously, before, or after, adding a test compound or plurality thereof;

measuring the amount of substrate cleaved in the presence of the test compound; and,

UNITED STATES PATENT AND TRADEMARK OFFICE
CERTIFICATE OF CORRECTION

PATENT NO. : 7,172,892 B2
APPLICATION NO. : 10/104271
DATED : February 6, 2007
INVENTOR(S) : Edwin Madison and Jiunn-Chern Yey It is certified that error appears in the above-identified patent and that said Letters Patent is hereby corrected as shown below:

selecting test compounds that decrease the amount of substrate cleaved compared to a control, thereby identifying compounds that inhibit the activity of the protease.--

This certificate supersedes the Certificate of Correction issued May 27, 2008.

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 22

<210> SEQ ID NO 1
<211> LENGTH: 3147
<212> TYPE: DNA
<213> ORGANISM: Homo Sapien
<220> FEATURE:
<221> NAME/KEY: CDS
<222> LOCATION: (23)...(2589)
<223> OTHER INFORMATION: Nucleotide sequence encoding MTSP1
<300> PUBLICATION INFORMATION:
<301> AUTHORS: O'Brien, T.J. and Tanimoto, H.
<307> DATE: - -
<308> DATABASE ACCESSION NUMBER: GenBank #AR081724
<309> DATABASE ENTRY DATE: 2000-08-31
<310> PATENT DOCUMENT NUMBER: 5,972,616
<311> PATENT FILING DATE: 1998-02-20
<312> PUBLICATION DATE: 1999-10-26

<400> SEQUENCE: 1
tcaagagcgg cctcggggta cc atg ggg agc gat cgg gcc cgc aag ggc gga      52
```

```
                Met Gly Ser Asp Arg Ala Arg Lys Gly Gly
                 1               5                  10 ggg ggc ccg aag gac ttc ggc gcg gga ctc aag tac aac tcc cgg cac     100
Gly Gly Pro Lys Asp Phe Gly Ala Gly Leu Lys Tyr Asn Ser Arg His
             15                  20                  25 gag aaa gtg aat ggc ttg gag gaa ggc gtg gag ttc ctg cca gtc aac     148
Glu Lys Val Asn Gly Leu Glu Glu Gly Val Glu Phe Leu Pro Val Asn
             30                  35                  40 aac gtc aag aag gtg gaa aag cat ggc ccg ggg cgc tgg gtg gtg ctg     196
Asn Val Lys Lys Val Glu Lys His Gly Pro Gly Arg Trp Val Val Leu
             45                  50                  55 gca gcc gtg ctg atc ggc ctc ctc ttg gtc ttg ctg ggg atc ggc ttc     244
Ala Ala Val Leu Ile Gly Leu Leu Leu Val Leu Leu Gly Ile Gly Phe
             60                  65                  70 ctg gtg tgg cat ttg cag tac cgg gac gtg cgt gtc cag aag gtc ttc     292
Leu Val Trp His Leu Gln Tyr Arg Asp Val Arg Val Gln Lys Val Phe
 75              80                  85                  90 aat ggc tac atg agg atc aca aat gag aat ttt gtg gat gcc tac gag     340
Asn Gly Tyr Met Arg Ile Thr Asn Glu Asn Phe Val Asp Ala Tyr Glu
             95                  100                 105 aac tcc aac tcc act gag ttt gta agc ctg gcc agc aag gtg aag gac     388
Asn Ser Asn Ser Thr Glu Phe Val Ser Leu Ala Ser Lys Val Lys Asp
             110                 115                 120 gcg ctg aag ctg ctg tac agc gga gtc cca ttc ctg ggc ccc tac cac     436
Ala Leu Lys Leu Leu Tyr Ser Gly Val Pro Phe Leu Gly Pro Tyr His
             125                 130                 135 aag gag tcg gct gtg acg gcc ttc agc gag ggc agc gtc atc gcc tac     484
Lys Glu Ser Ala Val Thr Ala Phe Ser Glu Gly Ser Val Ile Ala Tyr
 140                 145                 150 tac tgg tct gag ttc agc atc ccg cag cac ctg gtg gag gag gcc gag     532
Tyr Trp Ser Glu Phe Ser Ile Pro Gln His Leu Val Glu Glu Ala Glu
 155                 160                 165                 170 cgc gtc atg gcc gag gag cgc gta gtc atg ctg ccc ccg cgg gcg cgc     580
Arg Val Met Ala Glu Glu Arg Val Val Met Leu Pro Pro Arg Ala Arg
             175                 180                 185 tcc ctg aag tcc ttt gtg gtc acc tca gtg gtg gct ttc ccc acg gac     628
Ser Leu Lys Ser Phe Val Val Thr Ser Val Val Ala Phe Pro Thr Asp
             190                 195                 200 tcc aaa aca gta cag agg acc cag gac aac agc tgc agc ttt ggc ctg     676
Ser Lys Thr Val Gln Arg Thr Gln Asp Asn Ser Cys Ser Phe Gly Leu
             205                 210                 215 cac gcc cgc ggt gtg gag ctg atg cgc ttc acc acg ccc ggc ttc cct     724
His Ala Arg Gly Val Glu Leu Met Arg Phe Thr Thr Pro Gly Phe Pro
 220                 225                 230 gac agc ccc tac ccc gct cat gcc cgc tgc cag tgg gcc ctg cgg ggg     772
Asp Ser Pro Tyr Pro Ala His Ala Arg Cys Gln Trp Ala Leu Arg Gly
 235                 240                 245                 250 gac gcc gac tca gtg ctg agc ctc acc ttc cgc agc ttt gac ctt gcg     820
Asp Ala Asp Ser Val Leu Ser Leu Thr Phe Arg Ser Phe Asp Leu Ala
             255                 260                 265 tcc tgc gac gag cgc ggc agc gac ctg gtg acg gtg tac aac acc ctg     868
Ser Cys Asp Glu Arg Gly Ser Asp Leu Val Thr Val Tyr Asn Thr Leu
             270                 275                 280 agc ccc atg gag ccc cac gcc ctg gtg cag ttg tgt ggc acc tac cct     916
Ser Pro Met Glu Pro His Ala Leu Val Gln Leu Cys Gly Thr Tyr Pro
             285                 290                 295 ccc tcc tac aac ctg acc ttc cac tcc tcc cag aac gtc ctg ctc atc     964
Pro Ser Tyr Asn Leu Thr Phe His Ser Ser Gln Asn Val Leu Leu Ile
 300                 305                 310
```

```
aca ctg ata acc aac act gag cgg cgg cat ccc ggc ttt gag gcc acc     1012
Thr Leu Ile Thr Asn Thr Glu Arg Arg His Pro Gly Phe Glu Ala Thr
315             320                 325                 330 ttc ttc cag ctg cct agg atg agc agc tgt gga ggc cgc tta cgt aaa     1060
Phe Phe Gln Leu Pro Arg Met Ser Ser Cys Gly Gly Arg Leu Arg Lys
                335                 340                 345 gcc cag ggg aca ttc aac agc ccc tac tac cca ggc cac tac cca ccc     1108
Ala Gln Gly Thr Phe Asn Ser Pro Tyr Tyr Pro Gly His Tyr Pro Pro
            350                 355                 360 aac att gac tgc aca tgg aac att gag gtg ccc aac aac cag cat gtg     1156
Asn Ile Asp Cys Thr Trp Asn Ile Glu Val Pro Asn Asn Gln His Val
        365                 370                 375 aag gtg agc ttc aaa ttc ttc tac ctg ctg gag ccc ggc gtg cct gcg     1204
Lys Val Ser Phe Lys Phe Phe Tyr Leu Leu Glu Pro Gly Val Pro Ala
    380                 385                 390 ggc acc tgc ccc aag gac tac gtg gag atc aat ggg gag aaa tac tgc     1252
Gly Thr Cys Pro Lys Asp Tyr Val Glu Ile Asn Gly Glu Lys Tyr Cys
395                 400                 405                 410 gga gag agg tcc cag ttc gtc gtc acc agc aac agc aac aag atc aca     1300
Gly Glu Arg Ser Gln Phe Val Val Thr Ser Asn Ser Asn Lys Ile Thr
                415                 420                 425 gtt cgc ttc cac tca gat cag tcc tac acc gac acc ggc ttc tta gct     1348
Val Arg Phe His Ser Asp Gln Ser Tyr Thr Asp Thr Gly Phe Leu Ala
            430                 435                 440 gaa tac ctc tcc tac gac tcc agt gac cca tgc ccg ggg cag ttc acg     1396
Glu Tyr Leu Ser Tyr Asp Ser Ser Asp Pro Cys Pro Gly Gln Phe Thr
        445                 450                 455 tgc cgc acg ggg cgg tgt atc cgg aag gag ctg cgc tgt gat ggc tgg     1444
Cys Arg Thr Gly Arg Cys Ile Arg Lys Glu Leu Arg Cys Asp Gly Trp
    460                 465                 470 gcc gac tgc acc gac cac agc gat gag ctc aac tgc agt tgc gac gcc     1492
Ala Asp Cys Thr Asp His Ser Asp Glu Leu Asn Cys Ser Cys Asp Ala
475                 480                 485                 490 ggc cac cag ttc acg tgc aag aac aag ttc tgc aag ccc ctc ttc tgg     1540
Gly His Gln Phe Thr Cys Lys Asn Lys Phe Cys Lys Pro Leu Phe Trp
                495                 500                 505 gtc tgc gac agt gtg aac gac tgc gga gac aac agc gac gag cag ggg     1588
Val Cys Asp Ser Val Asn Asp Cys Gly Asp Asn Ser Asp Glu Gln Gly
            510                 515                 520 tgc agt tgt ccg gcc cag acc ttc agg tgt tcc aat ggg aag tgc ctc     1636
Cys Ser Cys Pro Ala Gln Thr Phe Arg Cys Ser Asn Gly Lys Cys Leu
        525                 530                 535 tcg aaa agc cag cag tgc aat ggg aag gac gac tgt ggg gac ggg tcc     1684
Ser Lys Ser Gln Gln Cys Asn Gly Lys Asp Asp Cys Gly Asp Gly Ser
540                 545                 550 gac gag gcc tcc tgc ccc aag gtg aac gtc gtc act tgt acc aaa cac     1732
Asp Glu Ala Ser Cys Pro Lys Val Asn Val Val Thr Cys Thr Lys His
555                 560                 565                 570 acc tac cgc tgc ctc aat ggg ctc tgc ttg agc aag ggc aac cct gag     1780
Thr Tyr Arg Cys Leu Asn Gly Leu Cys Leu Ser Lys Gly Asn Pro Glu
                575                 580                 585 tgt gac ggg aag gag gac tgt agc gac ggc tca gat gag aag gac tgc     1828
Cys Asp Gly Lys Glu Asp Cys Ser Asp Gly Ser Asp Glu Lys Asp Cys
            590                 595                 600 gac tgt ggg ctg cgg tca ttc acg aga cag gct cgt gtt gtt ggg ggc     1876
Asp Cys Gly Leu Arg Ser Phe Thr Arg Gln Ala Arg Val Val Gly Gly
        605                 610                 615 acg gat gcg gat gag ggc gag tgg ccc tgg cag gta agc ctg cat gct     1924
Thr Asp Ala Asp Glu Gly Glu Trp Pro Trp Gln Val Ser Leu His Ala
620                 625                 630
```

| | |
|---|---|
| ctg ggc cag ggc cac atc tgc ggt gct tcc ctc atc tct ccc aac tgg<br>Leu Gly Gln Gly His Ile Cys Gly Ala Ser Leu Ile Ser Pro Asn Trp<br>635                    640                    645                    650 | 1972 |
| ctg gtc tct gcc gca cac tgc tac atc gat gac aga gga ttc agg tac<br>Leu Val Ser Ala Ala His Cys Tyr Ile Asp Asp Arg Gly Phe Arg Tyr<br>                    655                    660                    665 | 2020 |
| tca gac ccc acg cag tgg acg gcc ttc ctg ggc ttg cac gac cag agc<br>Ser Asp Pro Thr Gln Trp Thr Ala Phe Leu Gly Leu His Asp Gln Ser<br>            670                    675                    680 | 2068 |
| cag cgc agc gcc cct ggg gtg cag gag cgc agg ctc aag cgc atc atc<br>Gln Arg Ser Ala Pro Gly Val Gln Glu Arg Arg Leu Lys Arg Ile Ile<br>                    685                    690                    695 | 2116 |
| tcc cac ccc ttc ttc aat gac ttc acc ttc gac tat gac atc gcg ctg<br>Ser His Pro Phe Phe Asn Asp Phe Thr Phe Asp Tyr Asp Ile Ala Leu<br>700                    705                    710 | 2164 |
| ctg gag ctg gag aaa ccg gca gag tac agc tcc atg gtg cgg ccc atc<br>Leu Glu Leu Glu Lys Pro Ala Glu Tyr Ser Ser Met Val Arg Pro Ile<br>715                    720                    725                    730 | 2212 |
| tgc ctg ccg gac gcc tcc cat gtc ttc cct gcc ggc aag gcc atc tgg<br>Cys Leu Pro Asp Ala Ser His Val Phe Pro Ala Gly Lys Ala Ile Trp<br>                    735                    740                    745 | 2260 |
| gtc acg ggc tgg gga cac acc cag tat gga ggc act ggc gcg ctg atc<br>Val Thr Gly Trp Gly His Thr Gln Tyr Gly Gly Thr Gly Ala Leu Ile<br>            750                    755                    760 | 2308 |
| ctg caa aag ggt gag atc cgc gtc atc aac cag acc acc tgc gag aac<br>Leu Gln Lys Gly Glu Ile Arg Val Ile Asn Gln Thr Thr Cys Glu Asn<br>                    765                    770                    775 | 2356 |
| ctc ctg ccg cag cag atc acg ccg cgc atg atg tgc gtg ggc ttc ctc<br>Leu Leu Pro Gln Gln Ile Thr Pro Arg Met Met Cys Val Gly Phe Leu<br>780                    785                    790 | 2404 |
| agc ggc ggc gtg gac tcc tgc cag ggt gat tcc ggg gga ccc ctg tcc<br>Ser Gly Gly Val Asp Ser Cys Gln Gly Asp Ser Gly Gly Pro Leu Ser<br>795                    800                    805                    810 | 2452 |
| agc gtg gag gcg gat ggg cgg atc ttc cag gcc ggt gtg gtg agc tgg<br>Ser Val Glu Ala Asp Gly Arg Ile Phe Gln Ala Gly Val Val Ser Trp<br>                    815                    820                    825 | 2500 |
| gga gac ggc tgc gct cag agg aac aag cca ggc gtg tac aca agg ctc<br>Gly Asp Gly Cys Ala Gln Arg Asn Lys Pro Gly Val Tyr Thr Arg Leu<br>            830                    835                    840 | 2548 |
| cct ctg ttt cgg gac tgg atc aaa gag aac act ggg gta ta ggggccgggg<br>Pro Leu Phe Arg Asp Trp Ile Lys Glu Asn Thr Gly Val<br>                    845                    850                    855 | 2599 |
| ccacccaaat gtgtacacct gcggggccac ccatcgtcca ccccagtgtg cacgcctgca | 2659 |
| ggctggagac tggaccgctg actgcaccag cgcccccaga acatacactg tgaactcaat | 2719 |
| ctccagggct ccaaatctgc ctagaaaacc tctcgcttcc tcagcctcca aagtggagct | 2779 |
| gggaggtaga aggggaggac actggtggtt ctactgaccc aactgggggc aaaggtttga | 2839 |
| agacacagcc tccccgcca gccccaagct gggccgaggc gcgtttgtgt atatctgcct | 2899 |
| cccctgtctg taaggagcag cgggaacgga gcttcggagc ctcctcagtg aaggtggtgg | 2959 |
| ggctgccgga tctgggctgt ggggcccttg gccacgctc ttgaggaagc ccaggctcgg | 3019 |
| aggaccctgg aaaacagacg ggtctgagac tgaaattgtt ttaccagctc ccagggtgga | 3079 |
| cttcagtgtg tgtatttgtg taaatgggta aaacaattta tttcttttta aaaaaaaaaa | 3139 |
| aaaaaaaa | 3147 |

<210> SEQ ID NO 2

```
<211> LENGTH: 855
<212> TYPE: PRT
<213> ORGANISM: Homo Sapien

<400> SEQUENCE: 2

Met Gly Ser Asp Arg Ala Arg Lys Gly Gly Gly Pro Lys Asp Phe
 1               5                  10                  15

Gly Ala Gly Leu Lys Tyr Asn Ser Arg His Glu Lys Val Asn Gly Leu
                20                  25                  30

Glu Glu Gly Val Glu Phe Leu Pro Val Asn Asn Val Lys Lys Val Glu
                35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                    85                  90                  95

Thr Asn Glu Asn Phe Val Asp Ala Tyr Glu Asn Ser Asn Ser Thr Glu
                100                 105                 110

Phe Val Ser Leu Ala Ser Lys Val Lys Asp Ala Leu Lys Leu Leu Tyr
                115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Ala Glu Arg Val Met Ala Glu Glu
                165                 170                 175

Arg Val Val Met Leu Pro Pro Arg Ala Arg Ser Leu Lys Ser Phe Val
                180                 185                 190

Val Thr Ser Val Val Ala Phe Pro Thr Asp Ser Lys Thr Val Gln Arg
                195                 200                 205

Thr Gln Asp Asn Ser Cys Ser Phe Gly Leu His Ala Arg Gly Val Glu
                210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
                260                 265                 270

Ser Asp Leu Val Thr Val Tyr Asn Thr Leu Ser Pro Met Glu Pro His
                275                 280                 285

Ala Leu Val Gln Leu Cys Gly Thr Tyr Pro Pro Ser Tyr Asn Leu Thr
                290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
                340                 345                 350

Ser Pro Tyr Tyr Pro Gly His Tyr Pro Pro Asn Ile Asp Cys Thr Trp
                355                 360                 365

Asn Ile Glu Val Pro Asn Asn Gln His Val Lys Val Ser Phe Lys Phe
                370                 375                 380

Phe Tyr Leu Leu Glu Pro Gly Val Pro Ala Gly Thr Cys Pro Lys Asp
```

```
               385                 390                 395                 400
Tyr Val Glu Ile Asn Gly Glu Lys Tyr Cys Gly Arg Ser Gln Phe
                    405                 410                 415
Val Val Thr Ser Asn Ser Asn Lys Ile Thr Val Arg Phe His Ser Asp
                420                     425                 430
Gln Ser Tyr Thr Asp Thr Gly Phe Leu Ala Glu Tyr Leu Ser Tyr Asp
            435                     440                 445
Ser Ser Asp Pro Cys Pro Gly Gln Phe Thr Cys Arg Thr Gly Arg Cys
    450                     455                     460
Ile Arg Lys Glu Leu Arg Cys Asp Gly Trp Ala Asp Cys Thr Asp His
465                 470                     475                 480
Ser Asp Glu Leu Asn Cys Ser Cys Asp Ala Gly His Gln Phe Thr Cys
                485                     490                 495
Lys Asn Lys Phe Cys Lys Pro Leu Phe Trp Val Cys Asp Ser Val Asn
                500                 505                 510
Asp Cys Gly Asp Asn Ser Asp Glu Gln Gly Cys Ser Cys Pro Ala Gln
        515                 520                 525
Thr Phe Arg Cys Ser Asn Gly Lys Cys Leu Ser Lys Ser Gln Gln Cys
        530                 535                 540
Asn Gly Lys Asp Asp Cys Gly Asp Gly Ser Asp Glu Ala Ser Cys Pro
545                 550                 555                 560
Lys Val Asn Val Val Thr Cys Thr Lys His Thr Tyr Arg Cys Leu Asn
                565                 570                 575
Gly Leu Cys Leu Ser Lys Gly Asn Pro Glu Cys Asp Gly Lys Glu Asp
            580                 585                 590
Cys Ser Asp Gly Ser Asp Glu Lys Asp Cys Asp Cys Gly Leu Arg Ser
        595                 600                 605
Phe Thr Arg Gln Ala Arg Val Val Gly Gly Thr Asp Ala Asp Glu Gly
        610                 615                 620
Glu Trp Pro Trp Gln Val Ser Leu His Ala Leu Gly Gln Gly His Ile
625                 630                 635                 640
Cys Gly Ala Ser Leu Ile Ser Pro Asn Trp Leu Val Ser Ala Ala His
                645                 650                 655
Cys Tyr Ile Asp Asp Arg Gly Phe Arg Tyr Ser Asp Pro Thr Gln Trp
            660                 665                 670
Thr Ala Phe Leu Gly Leu His Asp Gln Ser Gln Arg Ser Ala Pro Gly
        675                 680                 685
Val Gln Glu Arg Arg Leu Lys Arg Ile Ile Ser His Pro Phe Phe Asn
        690                 695                 700
Asp Phe Thr Phe Asp Tyr Asp Ile Ala Leu Leu Glu Leu Glu Lys Pro
705                 710                 715                 720
Ala Glu Tyr Ser Ser Met Val Arg Pro Ile Cys Leu Pro Asp Ala Ser
                725                 730                 735
His Val Phe Pro Ala Gly Lys Ala Ile Trp Val Thr Gly Trp Gly His
                740                 745                 750
Thr Gln Tyr Gly Gly Thr Gly Ala Leu Ile Leu Gln Lys Gly Glu Ile
            755                 760                 765
Arg Val Ile Asn Gln Thr Thr Cys Glu Asn Leu Leu Pro Gln Gln Ile
        770                 775                 780
Thr Pro Arg Met Met Cys Val Gly Phe Leu Ser Gly Val Asp Ser
785                 790                 795                 800
Cys Gln Gly Asp Ser Gly Gly Pro Leu Ser Ser Val Glu Ala Asp Gly
                805                 810                 815
```

Arg Ile Phe Gln Ala Gly Val Val Ser Trp Gly Asp Gly Cys Ala Gln
    820                 825                 830

Arg Asn Lys Pro Gly Val Tyr Thr Arg Leu Pro Leu Phe Arg Asp Trp
        835                 840                 845

Ile Lys Glu Asn Thr Gly Val
    850                 855

<210> SEQ ID NO 3
<211> LENGTH: 3147
<212> TYPE: DNA
<213> ORGANISM: Homo Sapien
<220> FEATURE:
<221> NAME/KEY: CDS
<222> LOCATION: (1865)...(2590)
<223> OTHER INFORMATION: Nucleic acid sequence of protease domain of
      MTSP1

<400> SEQUENCE: 3

| | | | | | |
|---|---|---|---|---|---|
| tcaagagcgg | cctcggggta | ccatggggag | cgatcgggcc | cgcaagggcg | gagggggccc | 60 |
| gaaggacttc | ggcgcgggac | tcaagtacaa | ctcccggcac | gagaaagtga | atggcttgga | 120 |
| ggaaggcgtg | gagttcctgc | cagtcaacaa | cgtcaagaag | gtggaaaagc | atggcccggg | 180 |
| gcgctgggtg | gtgctggcag | ccgtgctgat | cggcctcctc | ttggtcttgc | tgggatcgg | 240 |
| cttcctggtg | tggcatttgc | agtaccggga | cgtgcgtgtc | cagaaggtct | tcaatggcta | 300 |
| catgaggatc | acaaatgaga | attttgtgga | tgcctacgag | aactccaact | ccactgagtt | 360 |
| tgtaagcctg | gccagcaagg | tgaaggacgc | gctgaagctg | ctgtacagcg | gagtcccatt | 420 |
| cctgggcccc | taccacaagg | agtcggctgt | gacggccttc | agcgagggca | gcgtcatcgc | 480 |
| ctactactgg | tctgagttca | gcatcccgca | gcacctggtg | gaggaggccg | agcgcgtcat | 540 |
| ggccgaggag | cgcgtagtca | tgctgccccc | gcgggcgcgc | tccctgaagt | cctttgtggt | 600 |
| cacctcagtg | gtggctttcc | ccacggactc | caaaacagta | cagaggaccc | aggacaacag | 660 |
| ctgcagcttt | ggcctgcacg | cccgcggtgt | ggagctgatg | cgcttcacca | cgcccggctt | 720 |
| ccctgacagc | ccctaccccg | ctcatgcccg | ctgccagtgg | gccctgcggg | gggacgccga | 780 |
| ctcagtgctg | agcctcacct | tccgcagctt | tgaccttgcg | tcctgcgacg | agcgcggcag | 840 |
| cgacctggtg | acggtgtaca | acaccctgag | ccccatggag | cccacgccc | tggtgcagtt | 900 |
| gtgtggcacc | taccctcct | cctacaacct | gaccttccac | tcctcccaga | acgtcctgct | 960 |
| catcacactg | ataaccaaca | ctgagcggcg | gcatcccggc | tttgaggcca | ccttcttcca | 1020 |
| gctgcctagg | atgagcagct | gtggaggccg | cttacgtaaa | gcccagggga | cattcaacag | 1080 |
| cccctactac | caggccact | acccacccaa | cattgactgc | acatggaaca | ttgaggtgcc | 1140 |
| caacaaccag | catgtgaagg | tgagcttcaa | attcttctac | ctgctggagc | ccggcgtgcc | 1200 |
| tgcgggcacc | tgccccaagg | actacgtgga | gatcaatggg | gagaaatact | gcggagagag | 1260 |
| gtcccagttc | gtcgtcacca | gcaacagcaa | caagatcaca | gttcgcttcc | actcagatca | 1320 |
| gtcctacacc | gacaccggct | tcttagctga | atacctctcc | tacgactcca | gtgacccatg | 1380 |
| cccggggcag | ttcacgtgcc | gcacggggcg | gtgtatccgg | aaggagctgc | gctgtgatgg | 1440 |
| ctgggccgac | tgcaccgacc | acagcgatga | gctcaactgc | agttgcgacg | ccggccacca | 1500 |
| gttcacgtgc | aagaacaagt | tctgcaagcc | cctcttctgg | gtctgcgaca | gtgtgaacga | 1560 |
| ctgcggagac | aacagcgacg | agcagggtg | cagttgtccg | gcccagacct | tcaggtgttc | 1620 |
| caatgggaag | tgcctctcga | aaagccagca | gtgcaatggg | aaggacgact | gtgggacgg | 1680 |

```
gtccgacgag gcctcctgcc ccaaggtgaa cgtcgtcact tgtaccaaac acacctaccg    1740
ctgcctcaat gggctctgct tgagcaaggg caaccctgag tgtgacggga aggaggactg    1800
tagcgacggc tcagatgaga aggactgcga ctgtgggctg cggtcattca cgagacaggc    1860 tcgt gtt gtt ggg ggc acg gat gcg gat gag ggc gag tgg ccc tgg cag    1909
     Val Val Gly Gly Thr Asp Ala Asp Glu Gly Glu Trp Pro Trp Gln
         1               5              10              15 gta agc ctg cat gct ctg ggc cag ggc cac atc tgc ggt gct tcc ctc    1957
Val Ser Leu His Ala Leu Gly Gln Gly His Ile Cys Gly Ala Ser Leu
         20              25              30 atc tct ccc aac tgg ctg gtc tct gcc gca cac tgc tac atc gat gac    2005
Ile Ser Pro Asn Trp Leu Val Ser Ala Ala His Cys Tyr Ile Asp Asp
             35              40              45 aga gga ttc agg tac tca gac ccc acg cag tgg acg gcc ttc ctg ggc    2053
Arg Gly Phe Arg Tyr Ser Asp Pro Thr Gln Trp Thr Ala Phe Leu Gly
         50              55              60 ttg cac gac cag agc cag cgc agc gcc cct ggg gtg cag gag cgc agg    2101
Leu His Asp Gln Ser Gln Arg Ser Ala Pro Gly Val Gln Glu Arg Arg
65              70              75 ctc aag cgc atc atc tcc cac ccc ttc ttc aat gac ttc acc ttc gac    2149
Leu Lys Arg Ile Ile Ser His Pro Phe Phe Asn Asp Phe Thr Phe Asp
80              85              90              95 tat gac atc gcg ctg ctg gag ctg gag aaa ccg gca gag tac agc tcc    2197
Tyr Asp Ile Ala Leu Leu Glu Leu Glu Lys Pro Ala Glu Tyr Ser Ser
                100             105             110 atg gtg cgg ccc atc tgc ctg ccg gac gcc tcc cat gtc ttc cct gcc    2245
Met Val Arg Pro Ile Cys Leu Pro Asp Ala Ser His Val Phe Pro Ala
            115             120             125 ggc aag gcc atc tgg gtc acg ggc tgg gga cac acc cag tat gga ggc    2293
Gly Lys Ala Ile Trp Val Thr Gly Trp Gly His Thr Gln Tyr Gly Gly
        130             135             140 act ggc gcg ctg atc ctg caa aag ggt gag atc cgc gtc atc aac cag    2341
Thr Gly Ala Leu Ile Leu Gln Lys Gly Glu Ile Arg Val Ile Asn Gln
    145             150             155 acc acc tgc gag aac ctc ctg ccg cag cag atc acg ccg cgc atg atg    2389
Thr Thr Cys Glu Asn Leu Leu Pro Gln Gln Ile Thr Pro Arg Met Met
160             165             170             175 tgc gtg ggc ttc ctc agc ggc ggc gtg gac tcc tgc cag ggt gat tcc    2437
Cys Val Gly Phe Leu Ser Gly Gly Val Asp Ser Cys Gln Gly Asp Ser
            180             185             190 ggg gga ccc ctg tcc agc gtg gag gcg gat ggg cgg atc ttc cag gcc    2485
Gly Gly Pro Leu Ser Ser Val Glu Ala Asp Gly Arg Ile Phe Gln Ala
        195             200             205 ggt gtg gtg agc tgg gga gac ggc tgc gct cag agg aac aag cca ggc    2533
Gly Val Val Ser Trp Gly Asp Gly Cys Ala Gln Arg Asn Lys Pro Gly
    210             215             220 gtg tac aca agg ctc cct ctg ttt cgg gac tgg atc aaa gag aac act    2581
Val Tyr Thr Arg Leu Pro Leu Phe Arg Asp Trp Ile Lys Glu Asn Thr
225             230             235 ggg gta tag gggccggggc cacccaaatg tgtacacctg cggggccacc            2630
Gly Val *
240 catcgtccac cccagtgtgc acgcctgcag gctggagact ggaccgctga ctgcaccagc    2690 gcccccagaa catacactgt gaactcaatc tccaggctc caaatctgcc tagaaaacct    2750 ctcgcttcct cagcctccaa agtggagctg ggaggtagaa ggggaggaca ctggtggttc    2810 tactgaccca actgggggca aaggtttgaa gacacagcct cccccgccag ccccaagctg    2870 ggccgaggcg cgtttgtgta tatctgcctc ccctgtctgt aaggagcagc gggaacggag    2930
```

-continued

```
cttcggagcc tcctcagtga aggtggtggg gctgccggat ctgggctgtg gggcccttgg    2990
gccacgctct tgaggaagcc caggctcgga ggaccctgga aaacagacgg gtctgagact    3050
gaaattgttt taccagctcc cagggtggac ttcagtgtgt gtatttgtgt aaatgggtaa    3110
aacaatttat ttcttttta aaaaaaaaaa aaaaaaa                              3147
```

<210> SEQ ID NO 4
<211> LENGTH: 241
<212> TYPE: PRT
<213> ORGANISM: Homo Sapien

<400> SEQUENCE: 4

```
Val Val Gly Gly Thr Asp Ala Asp Glu Gly Glu Trp Pro Trp Gln Val
  1               5                  10                  15

Ser Leu His Ala Leu Gly Gln Gly His Ile Cys Gly Ala Ser Leu Ile
                 20                  25                  30

Ser Pro Asn Trp Leu Val Ser Ala Ala His Cys Tyr Ile Asp Asp Arg
             35                  40                  45

Gly Phe Arg Tyr Ser Asp Pro Thr Gln Trp Thr Ala Phe Leu Gly Leu
     50                  55                  60

His Asp Gln Ser Gln Arg Ser Ala Pro Gly Val Gln Glu Arg Arg Leu
 65                  70                  75                  80

Lys Arg Ile Ile Ser His Pro Phe Phe Asn Asp Phe Thr Phe Asp Tyr
                 85                  90                  95

Asp Ile Ala Leu Leu Glu Leu Glu Lys Pro Ala Glu Tyr Ser Ser Met
            100                 105                 110

Val Arg Pro Ile Cys Leu Pro Asp Ala Ser His Val Phe Pro Ala Gly
        115                 120                 125

Lys Ala Ile Trp Val Thr Gly Trp Gly His Thr Gln Tyr Gly Gly Thr
    130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
        195                 200                 205

Val Val Ser Trp Gly Asp Gly Cys Ala Gln Arg Asn Lys Pro Gly Val
    210                 215                 220

Tyr Thr Arg Leu Pro Leu Phe Arg Asp Trp Ile Lys Glu Asn Thr Gly
225                 230                 235                 240

Val
```

<210> SEQ ID NO 5
<211> LENGTH: 756
<212> TYPE: DNA
<213> ORGANISM: Homo Sapien
<220> FEATURE:
<221> NAME/KEY: CDS
<222> LOCATION: (1)...(756)
<223> OTHER INFORMATION: Nucleotide sequence encoding CVSP14 protease
      domain

<400> SEQUENCE: 5

```
att ctt gga gga agc caa gtg gag aag ggt tcc tat ccc tgg cag gta    48
Ile Leu Gly Gly Ser Gln Val Glu Lys Gly Ser Tyr Pro Trp Gln Val
```

```
tct ctg aaa caa agg cag aag cat att tgt gga gga agc atc gtc tca      96
Ser Leu Lys Gln Arg Gln Lys His Ile Cys Gly Gly Ser Ile Val Ser
            20                  25                  30 cca cag tgg gtg atc acg gcg gct cac tgc att gca aac aga aac att     144
Pro Gln Trp Val Ile Thr Ala Ala His Cys Ile Ala Asn Arg Asn Ile
        35                  40                  45 gtg tct act ttg aat gtt act gct gga gag tat gac tta agc cag aca     192
Val Ser Thr Leu Asn Val Thr Ala Gly Glu Tyr Asp Leu Ser Gln Thr
    50                  55                  60 gac cca gga gag caa act ctc act att gaa act gtc atc ata cat cca     240
Asp Pro Gly Glu Gln Thr Leu Thr Ile Glu Thr Val Ile Ile His Pro
65                  70                  75                  80 cat ttc tcc acc aag aaa cca atg gac tat gat att gcc ctt ttg aag     288
His Phe Ser Thr Lys Lys Pro Met Asp Tyr Asp Ile Ala Leu Leu Lys
                85                  90                  95 atg gct gga gcc ttc caa ttt ggc cac ttt gtg ggg ccc ata tgt ctt     336
Met Ala Gly Ala Phe Gln Phe Gly His Phe Val Gly Pro Ile Cys Leu
            100                 105                 110 cca gag ctg cgg gag caa ttt gag gct ggt ttt att tgt aca act gca     384
Pro Glu Leu Arg Glu Gln Phe Glu Ala Gly Phe Ile Cys Thr Thr Ala
        115                 120                 125 ggc tgg ggc cgc tta act gaa ggt ggc gtc ctc tca caa gtc ttg cag     432
Gly Trp Gly Arg Leu Thr Glu Gly Gly Val Leu Ser Gln Val Leu Gln
    130                 135                 140 gaa gtg aat ctg cct att ttg acc tgg gaa gag tgt gtg gca gct ctg     480
Glu Val Asn Leu Pro Ile Leu Thr Trp Glu Glu Cys Val Ala Ala Leu
145                 150                 155                 160 tta aca cta aag agg ccc atc agt ggg aag acc ttt ctt tgc aca ggt     528
Leu Thr Leu Lys Arg Pro Ile Ser Gly Lys Thr Phe Leu Cys Thr Gly
                165                 170                 175 ttt cct gat gga ggg aga gac gca tgt cag gga gat tca gga ggt tca     576
Phe Pro Asp Gly Gly Arg Asp Ala Cys Gln Gly Asp Ser Gly Gly Ser
            180                 185                 190 ctc atg tgc cgg aat aag aaa ggg gcc tgg act ctg gct ggt gtg act     624
Leu Met Cys Arg Asn Lys Lys Gly Ala Trp Thr Leu Ala Gly Val Thr
        195                 200                 205 tcc tgg ggt ttg ggc tgt ggt cga ggc tgg aga aac aat gtg agg aaa     672
Ser Trp Gly Leu Gly Cys Gly Arg Gly Trp Arg Asn Asn Val Arg Lys
    210                 215                 220 agt gat caa gga tcc cct ggg atc ttc aca gac att agt aaa gtg ctt     720
Ser Asp Gln Gly Ser Pro Gly Ile Phe Thr Asp Ile Ser Lys Val Leu
225                 230                 235                 240 tcc tgg atc cac gaa cac atc caa act ggt aac taa                     756
Ser Trp Ile His Glu His Ile Gln Thr Gly Asn *
                245                 250
```

<210> SEQ ID NO 6
<211> LENGTH: 251
<212> TYPE: PRT
<213> ORGANISM: Homo Sapien

<400> SEQUENCE: 6

```
Ile Leu Gly Gly Ser Gln Val Glu Lys Gly Ser Tyr Pro Trp Gln Val
1               5                   10                  15

Ser Leu Lys Gln Arg Gln Lys His Ile Cys Gly Gly Ser Ile Val Ser
            20                  25                  30

Pro Gln Trp Val Ile Thr Ala Ala His Cys Ile Ala Asn Arg Asn Ile
        35                  40                  45
```

```
Val Ser Thr Leu Asn Val Thr Ala Gly Glu Tyr Asp Leu Ser Gln Thr
 50                  55                  60

Asp Pro Gly Glu Gln Thr Leu Thr Ile Glu Thr Val Ile Ile His Pro
 65                  70                  75                  80

His Phe Ser Thr Lys Lys Pro Met Asp Tyr Asp Ile Ala Leu Leu Lys
                 85                  90                  95

Met Ala Gly Ala Phe Gln Phe Gly His Phe Val Gly Pro Ile Cys Leu
            100                 105                 110

Pro Glu Leu Arg Glu Gln Phe Glu Ala Gly Phe Ile Cys Thr Thr Ala
            115                 120                 125

Gly Trp Gly Arg Leu Thr Glu Gly Gly Val Leu Ser Gln Val Leu Gln
130                 135                 140

Glu Val Asn Leu Pro Ile Leu Thr Trp Glu Glu Cys Val Ala Ala Leu
145                 150                 155                 160

Leu Thr Leu Lys Arg Pro Ile Ser Gly Lys Thr Phe Leu Cys Thr Gly
                165                 170                 175

Phe Pro Asp Gly Gly Arg Asp Ala Cys Gln Gly Asp Ser Gly Gly Ser
            180                 185                 190

Leu Met Cys Arg Asn Lys Lys Gly Ala Trp Thr Leu Ala Gly Val Thr
            195                 200                 205

Ser Trp Gly Leu Gly Cys Gly Arg Gly Trp Arg Asn Asn Val Arg Lys
210                 215                 220

Ser Asp Gln Gly Ser Pro Gly Ile Phe Thr Asp Ile Ser Lys Val Leu
225                 230                 235                 240

Ser Trp Ile His Glu His Ile Gln Thr Gly Asn
                245                 250

<210> SEQ ID NO 7
<211> LENGTH: 30
<212> TYPE: DNA
<213> ORGANISM: Artificial Sequence
<220> FEATURE:
<223> OTHER INFORMATION: Sense primer:DSSP11
<221> NAME/KEY: modified_base
<222> LOCATION: 7, 12, 17, 20, 24
<223> OTHER INFORMATION: N is Deoxyinosine

<400> SEQUENCE: 7
tgggatnacg tntacgngcn agcncatctg                                     30

<210> SEQ ID NO 8
<211> LENGTH: 34
<212> TYPE: DNA
<213> ORGANISM: Artificial Sequence
<220> FEATURE:
<223> OTHER INFORMATION: antisense primer: DSSP2
<221> NAME/KEY: modified_base
<222> LOCATION: 1, 4, 7, 10, 19, 25, 30
<223> OTHER INFORMATION: N is Deoxyinosine

<400> SEQUENCE: 8
nggnccnccn cgtagatcnc ctctnagcan gtac                                34

<210> SEQ ID NO 9
<211> LENGTH: 28
<212> TYPE: DNA
<213> ORGANISM: Artificial Sequence
<220> FEATURE:
<223> OTHER INFORMATION: CVSP14 specific primer: GX-SP1-1

<400> SEQUENCE: 9
```

| | |
|---|---|
| gacttaagcc agacagaccc aggagagc | 28 |

<210> SEQ ID NO 10
<211> LENGTH: 29
<212> TYPE: DNA
<213> ORGANISM: Artificial Sequence
<220> FEATURE:
<223> OTHER INFORMATION: CVSP14 specific primer: GX-SP1-1-2AS

<400> SEQUENCE: 10

| | |
|---|---|
| ttgtgagagg acgccacctt cagttaagc | 29 |

<210> SEQ ID NO 11
<211> LENGTH: 9276
<212> TYPE: DNA
<213> ORGANISM: Pichia pastoris

<400> SEQUENCE: 11

| | |
|---|---|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcgcca taccgttttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga acacccgct | 660 |
| ttttggatga ttatgcattg tctccacatt gtatgcttcc aagattctgg tgggaatact | 720 |
| gctgatagcc taacgttcat gatcaaaatt taactgttct accccctact tgacagcaat | 780 |
| atataaacag aaggaagctg ccctgtctta accttttttt tttatcatca ttattagctt | 840 |
| actttcataa ttgcgactgg ttccaattga caagcttttg attttaacga cttttaacga | 900 |
| caacttgaga agatcaaaaa acaactaatt attcgaagga tccaaacgat gagatttcct | 960 |
| tcaattttta ctgcagtttt attcgcagca tcctccgcat tagctgctcc agtcaacact | 1020 |
| acaacagaag atgaaacggc acaaattccg gctgaagctg tcatcggtta ctcagattta | 1080 |
| gaagggatt tcgatgttgc tgttttgcca ttttccaaca gcacaaataa cgggttattg | 1140 |
| tttataaata ctactattgc cagcattgct gctaaagaag aaggggtatc tctcgagaaa | 1200 |
| agagaggctg aagcttacgt agaattccct agggcggccg cgaattaatt cgccttagac | 1260 |
| atgactgttc tcagttcaa gttgggcact acgagaaga ccgtcttgc tagattctaa | 1320 |
| tcaagaggat gtcagaatgc catttgcctg agagatgcag gcttcatttt tgatactttt | 1380 |
| ttatttgtaa cctatatagt ataggatttt ttttgtcatt ttgtttcttc tcgtacgagc | 1440 |
| ttgctcctga tcagcctatc tcgcagctga tgaatatctt gtggtagggg tttgggaaaa | 1500 |
| tcattcgagt ttgatgtttt tcttggtatt tcccactcct cttcagagta cagaagatta | 1560 |
| agtgagaagt tcgtttgtgc aagcttatcg ataagcttta atgcggtagt ttatcacagt | 1620 |
| taaattgcta acgcagtcag gcaccgtgta tgaaatctaa caatgcgctc atcgtcatcc | 1680 |
| tcggcaccgt caccctggat gctgtaggca taggcttggt tatgccggta ctgccgggcc | 1740 |

-continued

```
tcttgcggga tatcgtccat tccgacagca tcgccagtca ctatggcgtg ctgctagcgc    1800
tatatgcgtt gatgcaattt ctatgcgcac ccgttctcgg agcactgtcc gaccgctttg    1860
gccgccgccc agtcctgctc gcttcgctac ttggagccac tatcgactac gcgatcatgg    1920
cgaccacacc cgtcctgtgg atctatcgaa tctaaatgta agttaaaatc tctaaataat    1980
taaataagtc ccagtttctc catacgaacc ttaacagcat tgcggtgagc atctagacct    2040
tcaacagcag ccagatccat cactgcttgg ccaatatgtt tcagtccctc aggagttacg    2100
tcttgtgaag tgatgaactt ctggaaggtt gcagtgttaa ctccgctgta ttgacgggca    2160
tatccgtacg ttggcaaagt gtggttggta ccggaggagt aatctccaca actctctgga    2220
gagtaggcac caacaaacac agatccagcg tgttgtactt gatcaacata agaagaagca    2280
ttctcgattt gcaggatcaa gtgttcagga gcgtactgat tggacatttc caaagcctgc    2340
tcgtaggttg caaccgatag ggttgtagag tgtgcaatac acttgcgtac aatttcaacc    2400
cttggcaact gcacagcttg gttgtgaaca gcatcttcaa ttctggcaag ctccttgtct    2460
gtcatatcga cagccaacag aatcacctgg aatcaatac catgttcagc ttgagacaga    2520
aggtctgagg caacgaaatc tggatcagcg tatttatcag caataactag aacttcagaa    2580
ggcccagcag gcatgtcaat actacacagg gctgatgtgt cattttgaac catcatcttg    2640
gcagcagtaa cgaactggtt tcctggacca aatattttgt cacacttagg aacagtttct    2700
gttccgtaag ccatagcagc tactgcctgg gcgcctcctg ctagcacgat acacttagca    2760
ccaaccttgt gggcaacgta gatgacttct ggggtaaggg taccatcctt cttaggtgga    2820
gatgcaaaaa caatttcttt gcaaccagca actttggcag gaacacccag catcagggaa    2880
gtggaaggca gaattgcggt tccaccagga atatagaggc caacttctc aataggtctt    2940
gcaaaacgag agcagactac accagggcaa gtctcaactt gcaacgtctc cgttagttga    3000
gcttcatgga atttcctgac gttatctata gagagatcaa tggctctctt aacgttatct    3060
ggcaattgca taagttcctc tgggaaagga gcttctaaca caggtgtctt caaagcgact    3120
ccatcaaact tggcagttag ttctaaaagg gctttgtcac catttttgacg aacattgtcg    3180
acaattggtt tgactaattc cataatctgt tccgttttct ggataggacg acgaagggca    3240
tcttcaattt cttgtgagga ggccttagaa acgtcaattt tgcacaattc aatacgacct    3300
tcagaaggga cttctttagg tttggattct tctttaggtt gttccttggt gtatcctggc    3360
ttggcatctc ctttccttct agtgaccttt agggacttca tatccaggtt tctctccacc    3420
tcgtccaacg tcacaccgta cttggcacat ctaactaatg caaaataaaa taagtcagca    3480
cattcccagg ctatatcttc cttggattta gcttctgcaa gttcatcagc ttcctcccta    3540
attttagcgt tcaacaaaac ttcgtcgtca ataaccgtt tggtataaga accttctgga    3600
gcattgctct tacgatccca caaggtggct tccatggctc taagacccctt tgattggcca    3660
aaacaggaag tgcgttccaa gtgacagaaa ccaacacctg tttgttcaac cacaaatttc    3720
aagcagtctc catcacaatc caattcgata cccagcaact tttgagttgc tccagatgta    3780
gcacctttat accacaaacc gtgacgacga gattggtaga ctccagtttg tgtccttata    3840
gcctccggaa tagactttttt ggacgagtac accaggccca acgagtaatt agaagagtca    3900
gccaccaaag tagtgaatag accatcgggg cggtcagtag tcaaagacgc caacaaaatt    3960
tcactgacag ggaacttttt gacatcttca gaaagttcgt attcagtagt caattgccga    4020
gcatcaataa tgggattat accagaagca acagtggaag tcacatctac caactttgcg    4080
```

```
gtctcagaaa aagcataaac agttctacta ccgccattag tgaaactttt caaatcgccc      4140
agtggagaag aaaaaggcac agcgatacta gcattagcgg gcaaggatgc aactttatca      4200
accagggtcc tatagataac cctagcgcct gggatcatcc tttggacaac tctttctgcc      4260
aaatctaggt ccaaaatcac ttcattgata ccattattgt acaacttgag caagttgtcg      4320
atcagctcct caaattggtc ctctgtaacg gatgactcaa cttgcacatt aacttgaagc      4380
tcagtcgatt gagtgaactt gatcaggttg tgcagctggt cagcagcata gggaaacacg      4440
gcttttccta ccaaactcaa ggaattatca aactctgcaa cacttgcgta tgcaggtagc      4500
aagggaaatg tcatacttga agtcggacag tgagtgtagt cttgagaaat tctgaagccg      4560 tattttatt atcagtgagt cagtcatcag gagatcctct acgccggacg catcgtggcc       4620
gacctgcagg ggggggggg gcgctgaggt ctgcctcgtg aagaaggtgt tgctgactca       4680
taccaggcct gaatcgcccc atcatccagc cagaaagtga gggagccacg gttgatgaga      4740
gctttgttgt aggtggacca gttggtgatt ttgaactttt gctttgccac ggaacggtct      4800
gcgttgtcgg gaagatgcgt gatctgatcc ttcaactcag caaaagttcg atttattcaa      4860
caaagccgcc gtcccgtcaa gtcagcgtaa tgctctgcca gtgttacaac caattaacca      4920
attctgatta gaaaaactca tcgagcatca aatgaaactg caatttattc atatcaggat      4980
tatcaatacc atattttga aaaagccgtt tctgtaatga aggagaaaac tcaccgaggc       5040
agttccatag gatggcaaga tcctggtatc ggtctgcgat tccgactcgt ccaacatcaa      5100
tacaacctat taatttcccc tcgtcaaaaa taaggttatc aagtgagaaa tcaccatgag      5160
tgacgactga atccggtgag aatggcaaaa gcttatgcat ttctttccag acttgttcaa      5220
caggccagcc attacgctcg tcatcaaaat cactcgcatc aaccaaaccg ttattcattc      5280
gtgattgcgc ctgagcgaga cgaaatacgc gatcgctgtt aaaaggacaa ttacaaacag      5340
gaatcgaatg caaccggcgc aggaacactg ccagcgcatc aacaatattt tcacctgaat      5400
caggatattc ttctaatacc tggaatgctg ttttcccggg gatcgcagtg gtgagtaacc      5460
atgcatcatc aggagtacgg ataaaatgct tgatggtcgg aagaggcata aattccgtca      5520
gccagtttag tctgaccatc tcatctgtaa catcattggc aacgctacct tgccatgtt      5580 tcagaaacaa ctctggcgca tcgggcttcc catacaatcg atagattgtc gcacctgatt      5640
gcccgacatt atcgcgagcc catttatacc catataaatc agcatccatg ttggaattta      5700
atcgcggcct cgagcaagac gtttcccgtt gaatatggct cataacaccc cttgtattac      5760
tgtttatgta agcagacagt tttattgttc atgatgatat ttttatct tgtgcaatgt       5820 aacatcagag attttgagac acaacgtggc tttccccccc cccctgcag gtcggcatca      5880 ccggcgccac aggtgcggtt gctggcgcct atatcgccga catcaccgat ggggaagatc      5940
gggctcgcca cttcgggctc atgagcgctt gtttcggcgt gggtatggtg caggccccg      6000 tggccggggg actgttgggc gccatctcct tgcatgcacc attccttgcg gcggcggtgc      6060
tcaacggcct caacctacta ctgggctgct tcctaatgca ggagtcgcat aagggagagc      6120
gtcgagtatc tatgattgga agtatgggaa tggtgatacc cgcattcttc agtgtcttga      6180
ggtctcctat cagattatgc ccaactaaag caaccggagg aggagatttc atggtaaatt      6240
tctctgactt tggtcatca gtagactcga actgtgagac tatctcggtt atgacagcag       6300
aaatgtcctt cttggagaca gtaaatgaag tcccaccaat aaagaaatcc ttgttatcag      6360
gaacaaactt cttgtttcga actttttcgg tgccttgaac tataaaatgt agagtggata      6420
tgtcgggtag gaatggagcg ggcaaatgct taccttctgg accttcaaga ggtatgtagg      6480
```

```
gtttgtagat actgatgcca acttcagtga caacgttgct atttcgttca aaccattccg    6540
aatccagaga aatcaaagtt gtttgtctac tattgatcca agccagtgcg gtcttgaaac    6600
tgacaatagt gtgctcgtgt tttgaggtca tctttgtatg aataaatcta gtctttgatc    6660
taaataatct tgacgagcca aggcgataaa tacccaaatc taaaactctt ttaaaacgtt    6720
aaaaggacaa gtatgtctgc ctgtattaaa ccccaaatca gctcgtagtc tgatcctcat    6780
caacttgagg ggcactatct tgttttagag aaatttgcgg agatgcgata tcgagaaaaa    6840
ggtacgctga ttttaaacgt gaaatttatc tcaagatctc tgcctcgcgc gtttcggtga    6900
tgacggtgaa aacctctgac acatgcagct cccggagacg gtcacagctt gtctgtaagc    6960
ggatgccggg agcagacaag cccgtcaggg cgcgtcagcg ggtgttggcg ggtgtcgggg    7020
cgcagccatg acccagtcac gtagcgatag cggagtgtat actggcttaa ctatgcggca    7080
tcagagcaga ttgtactgag agtgcaccat atgcggtgtg aaataccgca cagatgcgta    7140
aggagaaaat accgcatcag gcgctcttcc gcttcctcgc tcactgactc gctgcgctcg    7200
gtcgttcggc tgcggcgagc ggtatcagct cactcaaagg cggtaatacg gttatccaca    7260
gaatcagggg ataacgcagg aaagaacatg tgagcaaaag gccagcaaaa ggccaggaac    7320
cgtaaaaagg ccgcgttgct ggcgtttttc cataggctcc gcccccctga cgagcatcac    7380
aaaaatcgac gctcaagtca gaggtggcga aacccgacag gactataaag ataccaggcg    7440
tttccccctg gaagctccct cgtgcgctct cctgttccga ccctgccgct taccggatac    7500
ctgtccgcct ttctcccttc gggaagcgtg gcgctttctc aatgctcacg ctgtaggtat    7560
ctcagttcgg tgtaggtcgt tcgctccaag ctgggctgtg tgcacgaacc ccccgttcag    7620
cccgaccgct gcgccttatc cggtaactat cgtcttgagt ccaacccggt aagacacgac    7680
ttatcgccac tggcagcagc cactggtaac aggattagca gagcgaggta tgtaggcggt    7740
gctacagagt tcttgaagtg gtggcctaac tacggctaca ctagaaggac agtatttggt    7800
atctgcgctc tgctgaagcc agttaccttc ggaaaaagag ttggtagctc ttgatccggc    7860
aaacaaacca ccgctggtag cggtggtttt tttgtttgca agcagcagat tacgcgcaga    7920
aaaaaaggat ctcaagaaga tcctttgatc ttttctacgg ggtctgacgc tcagtggaac    7980
gaaaactcac gttaagggat tttggtcatg agattatcaa aaaggatctt cacctagatc    8040
cttttaaatt aaaaatgaag ttttaaatca atctaaagta tatatgagta aacttggtct    8100
gacagttacc aatgcttaat cagtgaggca cctatctcag cgatctgtct atttcgttca    8160
tccatagttg cctgactccc cgtcgtgtag ataactacga tacgggaggg cttaccatct    8220
ggccccagtg ctgcaatgat accgcgagac ccacgctcac cggctccaga tttatcagca    8280
ataaaccagc cagccggaag ggccgagcgc agaagtggtc ctgcaacttt atccgcctcc    8340
atccagtcta ttaattgttg ccgggaagct agagtaagta gttcgccagt taatagtttg    8400
cgcaacgttg ttgccattgc tgcaggcatc gtggtgtcac gctcgtcgtt tggtatggct    8460
tcattcagct ccggttccca acgatcaagg cgagttacat gatcccccat gttgtgcaaa    8520
aaagcggtta gctccttcgg tcctccgatc gttgtcagaa gtaagttggc cgcagtgtta    8580
tcactcatgg ttatggcagc actgcataat tctcttactg tcatgccatc cgtaagatgc    8640
ttttctgtga ctggtgagta ctcaaccaag tcattctgag aatagtgtat gcggcgaccg    8700
agttgctctt gcccggcgtc aacacgggat aataccgcgc cacatagcag aactttaaaa    8760
gtgctcatca ttggaaaacg ttcttcgggg cgaaaactct caaggatctt accgctgttg    8820
```

-continued

```
agatccagtt cgatgtaacc cactcgtgca cccaactgat cttcagcatc ttttactttc    8880
accagcgttt ctgggtgagc aaaaacagga aggcaaaatg ccgcaaaaaa gggaataagg    8940
gcgacacgga aatgttgaat actcatactc ttcctttttc aatattattg aagcatttat    9000
cagggttatt gtctcatgag cggatacata tttgaatgta tttagaaaaa taaacaaata    9060
ggggttccgc gcacatttcc ccgaaaagtg ccacctgacg tctaagaaac cattattatc    9120
atgacattaa cctataaaaa taggcgtatc acgaggccct ttcgtcttca agaattaatt    9180
ctcatgtttg acagcttatc atcgataagc tgactcatgt tggtattgtg aaatagacgc    9240
agatcgggaa cactgaaaaa taacagttat tattcg                              9276
```

<210> SEQ ID NO 12
<211> LENGTH: 1035
<212> TYPE: DNA
<213> ORGANISM: Homo Sapien
<220> FEATURE:
<221> NAME/KEY: CDS
<222> LOCATION: (115)...(1035)
<223> OTHER INFORMATION: DNA encoding full length CVSP14
<221> NAME/KEY: misc_signal
<222> LOCATION: (115)...(189)
<223> OTHER INFORMATION: signal sequence

<400> SEQUENCE: 12

```
gattcaccac gtcttggtta atgaataaac ttgttttaaa ttggcttatt gctggtctct        60
caaggcttcc tattttttgtt tgctttagtc tctctaaaat ttcagggaaa aact atg       117
                                                               Met
                                                               1 agt ctc aaa atg ctt ata agc agg aac aag ctg att tta cta cta gga        165
Ser Leu Lys Met Leu Ile Ser Arg Asn Lys Leu Ile Leu Leu Leu Gly
        5                  10                  15 ata gtc ttt ttt gaa caa ggt aaa tct gca gct ctt tcg ctc ccc aaa        213
Ile Val Phe Phe Glu Gln Gly Lys Ser Ala Ala Leu Ser Leu Pro Lys
 20                  25                  30 gct ccc agt tgt ggg cag agt ctg gtt aag gta cag cct tgg aat tat        261
Ala Pro Ser Cys Gly Gln Ser Leu Val Lys Val Gln Pro Trp Asn Tyr
             35                  40                  45 ttt aac att ttc agt cgc att ctt gga gga agc caa gtg gag aag ggt        309
Phe Asn Ile Phe Ser Arg Ile Leu Gly Gly Ser Gln Val Glu Lys Gly
 50                  55                  60                  65 tcc tat ccc tgg cag gta tct ctg aaa caa agg cag aag cat att tgt        357
Ser Tyr Pro Trp Gln Val Ser Leu Lys Gln Arg Gln Lys His Ile Cys
                 70                  75                  80 gga gga agc atc gtc tca cca cag tgg gtg atc acg gcg gct cac tgc        405
Gly Gly Ser Ile Val Ser Pro Gln Trp Val Ile Thr Ala Ala His Cys
             85                  90                  95 att gca aac aga aac att gtg tct act ttg aat gtt act gct gga gag        453
Ile Ala Asn Arg Asn Ile Val Ser Thr Leu Asn Val Thr Ala Gly Glu
        100                 105                 110 tat gac tta agc cag aca gac cca gga gag caa act ctc act att gaa        501
Tyr Asp Leu Ser Gln Thr Asp Pro Gly Glu Gln Thr Leu Thr Ile Glu
    115                 120                 125 act gtc atc ata cat cca cat ttc tcc acc aag aaa cca atg gac tat        549
Thr Val Ile Ile His Pro His Phe Ser Thr Lys Lys Pro Met Asp Tyr
130                 135                 140                 145 gat att gcc ctt ttg aag atg gct gga gcc ttc caa ttt ggc cac ttt        597
Asp Ile Ala Leu Leu Lys Met Ala Gly Ala Phe Gln Phe Gly His Phe
                150                 155                 160 gtg ggg ccc ata tgt ctt cca gag ctg cgg gag caa ttt gag gct ggt        645
Val Gly Pro Ile Cys Leu Pro Glu Leu Arg Glu Gln Phe Glu Ala Gly
```

|  |  |
|---|---|
| ttt att tgt aca act gca ggc tgg ggc cgc tta act gaa ggt ggc gtc<br>Phe Ile Cys Thr Thr Ala Gly Trp Gly Arg Leu Thr Glu Gly Gly Val<br>          180                    185                  190 | 693 |
| ctc tca caa gtc ttg cag gaa gtg aat ctg cct att ttg acc tgg gaa<br>Leu Ser Gln Val Leu Gln Glu Val Asn Leu Pro Ile Leu Thr Trp Glu<br>195                    200                    205 | 741 |
| gag tgt gtg gca gct ctg tta aca cta aag agg ccc atc agt ggg aag<br>Glu Cys Val Ala Ala Leu Leu Thr Leu Lys Arg Pro Ile Ser Gly Lys<br>210                    215                    220                  225 | 789 |
| acc ttt ctt tgc aca ggt ttt cct gat gga ggg aga gac gca tgt cag<br>Thr Phe Leu Cys Thr Gly Phe Pro Asp Gly Gly Arg Asp Ala Cys Gln<br>                 230                    235                    240 | 837 |
| gga gat tca gga ggt tca ctc atg tgc cgg aat aag aaa ggg gcc tgg<br>Gly Asp Ser Gly Gly Ser Leu Met Cys Arg Asn Lys Lys Gly Ala Trp<br>          245                    250                    255 | 885 |
| act ctg gct ggt gtg act tcc tgg ggt ttg ggc tgt ggt cga ggc tgg<br>Thr Leu Ala Gly Val Thr Ser Trp Gly Leu Gly Cys Gly Arg Gly Trp<br>260                    265                    270 | 933 |
| aga aac aat gtg agg aaa agt gat caa gga tcc cct ggg atc ttc aca<br>Arg Asn Asn Val Arg Lys Ser Asp Gln Gly Ser Pro Gly Ile Phe Thr<br>275                    280                    285 | 981 |
| gac att agt aaa gtg ctt tcc tgg atc cac gaa cac atc caa act ggt<br>Asp Ile Ser Lys Val Leu Ser Trp Ile His Glu His Ile Gln Thr Gly<br>290                    295                    300                  305 | 1029 |
| aac taa<br>Asn  * | 1035 |

<210> SEQ ID NO 13
<211> LENGTH: 306
<212> TYPE: PRT
<213> ORGANISM: Homo Sapien
<220> FEATURE:
<221> NAME/KEY: SIGNAL
<222> LOCATION: (1)...(25)
<223> OTHER INFORMATION: signal peptide

<400> SEQUENCE: 13

Met Ser Leu Lys Met Leu Ile Ser Arg Asn Lys Leu Ile Leu Leu Leu
 1               5                  10                  15

Gly Ile Val Phe Phe Glu Gln Gly Lys Ser Ala Ala Leu Ser Leu Pro
                20                  25                  30

Lys Ala Pro Ser Cys Gly Gln Ser Leu Val Lys Val Gln Pro Trp Asn
            35                  40                  45

Tyr Phe Asn Ile Phe Ser Arg Ile Leu Gly Gly Ser Gln Val Glu Lys
 50                  55                  60

Gly Ser Tyr Pro Trp Gln Val Ser Leu Lys Gln Arg Gln Lys His Ile
65                   70                  75                  80

Cys Gly Gly Ser Ile Val Ser Pro Gln Trp Val Ile Thr Ala Ala His
                 85                  90                  95

Cys Ile Ala Asn Arg Asn Ile Val Ser Thr Leu Asn Val Thr Ala Gly
            100                 105                 110

Glu Tyr Asp Leu Ser Gln Thr Asp Pro Gly Glu Gln Thr Leu Thr Ile
        115                 120                 125

Glu Thr Val Ile Ile His Pro His Phe Ser Thr Lys Lys Pro Met Asp
    130                 135                 140

Tyr Asp Ile Ala Leu Leu Lys Met Ala Gly Ala Phe Gln Phe Gly His
145                 150                 155                 160

-continued

```
Phe Val Gly Pro Ile Cys Leu Pro Glu Leu Arg Glu Gln Phe Glu Ala
                165                 170                 175
Gly Phe Ile Cys Thr Thr Ala Gly Trp Gly Arg Leu Thr Glu Gly Gly
            180                 185                 190
Val Leu Ser Gln Val Leu Gln Glu Val Asn Leu Pro Ile Leu Thr Trp
        195                 200                 205
Glu Glu Cys Val Ala Ala Leu Leu Thr Leu Lys Arg Pro Ile Ser Gly
    210                 215                 220
Lys Thr Phe Leu Cys Thr Gly Phe Pro Asp Gly Gly Arg Asp Ala Cys
225                 230                 235                 240
Gln Gly Asp Ser Gly Gly Ser Leu Met Cys Arg Asn Lys Lys Gly Ala
                245                 250                 255
Trp Thr Leu Ala Gly Val Thr Ser Trp Gly Leu Gly Cys Gly Arg Gly
            260                 265                 270
Trp Arg Asn Asn Val Arg Lys Ser Asp Gln Gly Ser Pro Gly Ile Phe
        275                 280                 285
Thr Asp Ile Ser Lys Val Leu Ser Trp Ile His Glu His Ile Gln Thr
    290                 295                 300
Gly Asn
305
```

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
tctctcgaga aagaattct tggaggaagc caagtggag                    39

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
tttgtggggc ccataagtct tccagagctg cgg                         33

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
attcgcggcc gcttagttac cagtttggat gtgttcgtg                   39

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
ccgcagctct ggaagactta tgggccccac aaa                         33

```
<210> SEQ ID NO 18
<211> LENGTH: 28
<212> TYPE: DNA
<213> ORGANISM: Artificial Sequence
<220> FEATURE:
<223> OTHER INFORMATION: primer

<400> SEQUENCE: 18
gttaagcggc cccagcctgc agttgtac                                         28

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
gctctcctgg gtctgtctgg cttaagt                                          27

<210> SEQ ID NO 20
<211> LENGTH: 12
<212> TYPE: DNA
<213> ORGANISM: Artificial Sequence
<220> FEATURE:
<223> OTHER INFORMATION: start site

<400> SEQUENCE: 20
aaaactatga gt                                                          12

<210> SEQ ID NO 21
<211> LENGTH: 67
<212> TYPE: DNA
<213> ORGANISM: Artificial Sequence
<220> FEATURE:
<223> OTHER INFORMATION: CVSP14 specific primer

<400> SEQUENCE: 21
ggaattccat atgagcagcg gccatatcga cgacgacgac aaaattcttg gaggaagcca      60
agtggag                                                                67

<210> SEQ ID NO 22
<211> LENGTH: 34
<212> TYPE: DNA
<213> ORGANISM: Artificial Sequence
<220> FEATURE:
<223> OTHER INFORMATION: CVSP14 specific primer

<400> SEQUENCE: 22
ccgctcgagg ttaccagttt ggatgtgttc gtgg                                  34
```